US005612215A

United States Patent [19]
Draper et al.

[11] Patent Number: 5,612,215
[45] Date of Patent: Mar. 18, 1997

[54] STROMELYSIN TARGETED RIBOZYMES

[75] Inventors: Kenneth G. Draper, Boulder; Pamela Pavco, Layfayette; James McSwiggen, Boulder; John Gustofson, Boulder; Dan T. Stinchcomb, Boulder, all of Colo.

[73] Assignee: Ribozyme Pharmaceuticals, Inc., Boulder, Colo.

[21] Appl. No.: 390,850

[22] Filed: Feb. 17, 1995

Related U.S. Application Data

[63] Continuation-in-part of Ser. No. 354,920, Dec. 13, 1994, abandoned, which is a continuation-in-part of Ser. No. 152,487, Nov. 12, 1993, abandoned, which is a continuation-in-part of Ser. No. 989,848, Dec. 7, 1992, abandoned.

[51] Int. Cl.$^6$ .............................. C12N 15/85; C12Q 1/68; A61K 48/00
[52] U.S. Cl. ...................... 435/366; 435/6; 435/91.31; 435/172.3; 435/320.1; 435/325; 536/23.1; 536/23.2; 536/24.5; 514/44
[58] Field of Search .................... 435/6, 91.31, 172.3, 435/240.1, 240.2, 320.1; 514/44; 536/23.1, 23.2, 24.5

[56] References Cited

U.S. PATENT DOCUMENTS

| | | | |
|---|---|---|---|
| 4,987,071 | 1/1991 | Cech et al. | 435/91.31 |
| 5,168,053 | 12/1992 | Altman et al. | 514/44 |
| 5,225,337 | 7/1993 | Robertson et al. | 435/91.31 |
| 5,334,711 | 8/1994 | Sproat et al. | 536/24.5 |

FOREIGN PATENT DOCUMENTS

| | | |
|---|---|---|
| 0360257 | 3/1990 | European Pat. Off. . |
| 9200080 | 1/1990 | WIPO . |
| 9103162 | 3/1991 | WIPO . |
| 9115580 | 10/1991 | WIPO . |
| 9118625 | 12/1991 | WIPO . |
| 9118913 | 12/1991 | WIPO . |
| 9118624 | 12/1991 | WIPO . |
| 9207065 | 4/1992 | WIPO . |
| 0519463 | 12/1992 | WIPO . |
| 9315187 | 8/1993 | WIPO . |
| 9323569 | 11/1993 | WIPO . |
| 9402595 | 2/1994 | WIPO . |
| 9413688 | 6/1994 | WIPO . |

OTHER PUBLICATIONS

Cameron and Jennings, "Specific Gene Expression by Engineered Ribozymes in Monkey Cells," *Proc. Natl. Acad. Sci. USA* 86:9139–9143 (1989).

Carter, "Adeno–Associated Virus Vectors," *Curr Opi. Biotech.* 3:533–539 (1992).

Cech, "Ribozymes and Their Medical Implications," *JAMA* 260:3030–3034 (1988).

Cech, "Ribozymes: Tools for Sequence–Sepcific Cleavage of RNA," *U.S. Biochemical Editoral Comments* 16:1–5 (1989).

Cech, "RNA© Tet 1.0 Kit," *U.S. Biochemical Editoral Comments* 16:8–9 (1989).

Chem. Abstracts 109(7):49622 Docherty et al. WO 8707907 (Dec. 30, 1987).

Chem. Abstracts 117(23):23163—Basset et al., WO 9209701 (Jun. 11, 1992).

Chem. Abstracts 109(23):205926—Sans et al. *J. Biol. Chem.* 263:6742 (1988).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira and Burke, "Extensive Phosphorothioate Substitution Yields Highly Active and Nuclease–Resistant Hairpin Ribozymes," *Nucleic Acids Res.* 20:2835–2840 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Chuat and Galibert, "Can Ribozymes be Used to Regulate Procaryote Gene Expression?" *Biochemical and Biophysical Research Communications* 162:1025 (1989).

Collins and Olive, "Reaction Conditions and Kinetics of Self–Cleavage of a Ribozyme Derived From Neurospora VS RNA," *Biochemistry* 32:2795–2799 (1993).

Dropulic et al., "Functional Characterization of a U5 Ribozyme: Intracellular Suppression of Human Immunodeficiency Virus Type I Expression," *Journal of Virology* 66:1432–1441 (1992).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).

Guerrier–Takada et al., "The RNA Moiety of Ribonuclease P Is the Catalytic Subunit of the Enzyme," *Cell* 35:849–857 (1983).

Hampel et al., "'Hairpin' Catalytic RNA Model: Evidence for Helices and Sequence Requirement for Substrate RNA," *Nucleic Acids Research* 18:299–304 (1990).

Hampel and Tritz, "RNA Catalytic Properties of the Minimum (–)sTRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Hembry et al., *Am. J. Pathol.* 143:628 (1993).

Hertel et al., "Numbering System for the Hammerhead," *Nucleic Acids Res.* 20:3252 (1992).

Jaeger et al., "Improved Predictions of Secondary Structures for RNA," *Proc. Natl. Acad. Sci. USA* 86:7706–7710 (1989).

(List continued on next page.)

*Primary Examiner*—John L. LeGuyader
*Attorney, Agent, or Firm*—Lyon & Lyon

[57] ABSTRACT

An enzymatic RNA molecule which cleaves mRNA associated with development or maintenance of an arthritic condition.

166 Claims, 16 Drawing Sheets

OTHER PUBLICATIONS

Jeffries and Symons, "A Catalytic 13–mer Ribozyme," *Nucleic Acids Research* 17:1371–1377 (1989).

Kashani–Sabet et al., "Reversal of the Malignant Phenotype by an Anti–ras Ribozyme," *Antisense Research & Development* 2:3–15 (1992).

Kim and Cech, "Three–dimensional model of the active site of the self-splicing rRNA precursor of *Tetrahymena*," *Proc. Natl. Acad. Sci. USA* 84:8788 (1987).

Koizumi et al., "Ribozymes Designed to Inhibit Transformation of NIH3T3 Cells by the Activated c–Ha–ras Gene," *Gene* 117:179 (1992).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Mamone et al., "Design of Mannerhead Ribozymes Targeted to Sequences in HIV, HSV, and the RAT ANF GENE," Abstract of Keystone, CO (May 27, 1992).

Martel–Pelletier et al., "Excess of Metalloproteases Over Tissue Inhibitor of Metalloprotease May Contribute to Cartilage Degradation in Osteoarthritis and Rheumaoid Arthritis," *Laboratory Investigation* 70:807 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Okada et al., "Localization of Matrix Metalloproteinase 3 (Stromelysin) in Osteoarthritic Cartilage and Synovium," *Laboratory Investigation* 66:680 (1992).

Pavco et al., "Regulation of Self–Splicing Reactions by Antisense RNA," Abstract of Keystone, CO (May 27, 1992).

Perreault et al., "Mixed Deoxyribo–and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease-Resistant 2'–Modified Hammerhead Ribozymes," *Science* 253:314–317 (1991).

Rossi et al., "Ribozyme Mediated Intracellular Immunity to HIV–1 in CD4," *J. Cell Biochem.* Suppl 14A:D428 (1990).

Rossi et al, "Ribozymes as Anti–HIV–1 Therapeutic Agents: Principles, Applications, and Problems," *Aids Research and Human Retroviruses* 8:183–189 (1992).

Sarver et al., "Catalytic RNAs (Ribozymes): A New Frontier in Biomedical Applications," *AIDS Res. Revs.* 2:259 (1992).

Sarver et al., "Ribozymes as Potential Anti–HIV–1 Therapeutic Agents" *Science* 247:1222–1225 (1990).

Saville and Collins, "RNA–Mediated Ligation of Self–Cleavage Products of a *Neurospora* Mitochondrial Plasmid Transcript," *Proc. Natl. Acad. Sci. USA* 88:8826–8830 (1991).

Saville and Collins, "A Site–Specific Self–Cleavage Reaction Performed by a Novel RNA In Neurospora Mitochondria," *Cell* 61:685–696 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Sioud and Drlica, "Prevention of Human Immunodeficiency Virus Type 1 Integrase Expression in *Escherichia coli* by a Ribozyme," *Proc. Natl. Acad. Sci. USA* 88:7303–7307 (1991).

Taira et al., "Construction of a novel RNA–transcript–trimming plasmid which can be used both in vitro in place of run–off and (G)–free transcriptions and in vivo as multi-sequences transcription vectors," *Nucleic Acids Research* 19:5125–5130 (1991).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman and Cedergren, "Exploiting the chemical synthesis of RNA," *TIBS* 17:334–339 (1992).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme," *Journal of Virology* 65:5531–5534 (1994).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zaug et al., "The *Tetrahymena* ribozyme acts like an RNA restriction endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

Zuker, "On Finding All Suboptimal Foldings of an RNA Molecule," *Science* 244:48–52 (1989).

Zafarullah et al., "Elevated Metalloproteinase and Tissue Inhibitor of Metalloproteinase mRNA in Human Osteoarthritic Synovia," *The Journal of Rheumatology* 20:693 (1993).

● 21 HH Active
▲ 21 HH Inactive

● 463 Active
▲ 463 Inactive

■ 1049 (active)
◇ 1049 (inactive)

● 1366 Active
▲ 1366 Inactive

1410 HH

1049 HH Ribozyme

SEQUENCE LISTING ( 1 ) GENERAL INFORMATION:

( i i i ) NUMBER OF SEQUENCES: 1151

( 2 ) INFORMATION FOR SEQ ID NO:1:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1:

UAGAGCUAAG UAAAGCCAG                                                       19

( 2 ) INFORMATION FOR SEQ ID NO:2:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

ACACCAGCAU GAA                                                             13

( 2 ) INFORMATION FOR SEQ ID NO:3:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:3:

AGAAAUAUCU AGA                                                             13

( 2 ) INFORMATION FOR SEQ ID NO:4:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:4:

ACCUCAAAAA AGAUGUGAAA CAGU                                                 24

( 2 ) INFORMATION FOR SEQ ID NO:5:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:5:

AAAUGCAGAA GUUC                                                            14

( 2 ) INFORMATION FOR SEQ ID NO:6:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

GACACUCUGG AGGUGAUGCG CAAGCCCAGG UGU          33

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CUGAUGUUGG UCACUUCAGA AC          22

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GCAUCCCGAA GUGGAGGAAA ACCCACCUUA CAU          33

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AUUAUACACC AGAUUUGCCA AAAGAUG          27

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CUGUUGAUUC UGCUGUUGAG A          21

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CUGAAAGUCU GGGAAGAGGU GA          22

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
CUGAUAUAAU GA                                                                    12
```

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
UGCCUAUGCC CC                                                                    12
```

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AUGCCCACUU UGAUGAUGAU GAACAAUGGA CA                                              32
```

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
AUUUCUCGUU GCUGCUCAUG                                                            20
```

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
CACUCAGCCA ACACUGA                                                               17
```

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
AAGAUGAUAU AAAUGGCAUU CAGUCC                                                     26
```

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
CUCUAUGGAC CUCCCCUGA CUCCCCU                                                     27
```

( 2 ) INFORMATION FOR SEQ ID NO:19:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CCCCCUGGUA CCCA         14

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

UCCUGCUUUG UCCUUUGAUG CUGUCAGCAC         30

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

AAUCCUGAUC UUUAAAGA         18

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CAGGCACUUU UGGCGCAAAU CCC         23

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

AUUGCAUUUG AUCUCUUCAU UUUGGCCAUC         30

( 2 ) INFORMATION FOR SEQ ID NO:24:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GCAUAUGAAG UUA         13

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

AAAUCGAUGC AGCCAUUUCU GA                                        22

( 2 ) INFORMATION FOR SEQ ID NO:26:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

UUUGAUGAGA AGAGAAAUUC CAUGGAGC                            28

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CAGGCUUUCC CAAGCAAAUA GCUGAAGAC                          29

( 2 ) INFORMATION FOR SEQ ID NO:28:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

CCCAAAUGCA AAG                                                    13

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AUGUAGAAGG CACAAUAUGG GCACUUUAAA                        30

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

UCUUGCCGGU CAUUUUAUG UUAU                                  24

( 2 ) INFORMATION FOR SEQ ID NO:31:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

GCUGCUGCUU AGC                                         13

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CAACAGACAA GUGACUGUAU CU                           22

( 2 ) INFORMATION FOR SEQ ID NO:33:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

CUUAUUUAAU A                                           11

( 2 ) INFORMATION FOR SEQ ID NO:34:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GCAAGGCAUA GAGACAACAU AGAGC                     25

( 2 ) INFORMATION FOR SEQ ID NO:35:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GCAUAGAGAC AACAUAGAGC UAAGUAAAGC C              31

( 2 ) INFORMATION FOR SEQ ID NO:36:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

AGACAACAUA GAGCUAAGUA AAGCCAGUGG A              31

( 2 ) INFORMATION FOR SEQ ID NO:37:

( i ) SEQUENCE CHARACTERISTICS:
        ( A ) LENGTH: 31 base pairs (B) TYPE: nucleic acid
(C) STRANDEDNESS: single
(D) TOPOLOGY: linear (xi) SEQUENCE DESCRIPTION: SEQ ID NO:37:

AACAUAGAGC UAAGUAAAGC CAGUGGAAAU G    31

(2) INFORMATION FOR SEQ ID NO:38:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:38:

GUGGAAAUGA AGAGUCUUCC AAUCCUACUG U    31

(2) INFORMATION FOR SEQ ID NO:39:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:39:

GGAAAUGAAG AGUCUUCCAA UCCUACUGUU G    31

(2) INFORMATION FOR SEQ ID NO:40:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:40:

GAAAUGAAGA GUCUUCCAAU CCUACUGUUG C    31

(2) INFORMATION FOR SEQ ID NO:41:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:41:

GAAGAGUCUU CCAAUCCUAC UGUUGCUGUG C    31

(2) INFORMATION FOR SEQ ID NO:42:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:42:

GAGUCUUCCA AUCCUACUGU UGCUGUGCGU G    31

(2) INFORMATION FOR SEQ ID NO:43:

(i) SEQUENCE CHARACTERISTICS:
(A) LENGTH: 31 base pairs
(B) TYPE: nucleic acid
(C) STRANDEDNESS: single ( D ) TOPOLOGY: linear ( x i ) SEQUENCE DESCRIPTION: SEQ ID NO:43:

UUCCAAUCCU ACUGUUGCUG UGCGUGGCAG U 31

( 2 ) INFORMATION FOR SEQ ID NO:44:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

GCUGUGCGUG GCAGUUUGCU CAGCCUAUCC A 31

( 2 ) INFORMATION FOR SEQ ID NO:45:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

CUGUGCGUGG CAGUUUGCUC AGCCUAUCCA U 31

( 2 ) INFORMATION FOR SEQ ID NO:46:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

GCGUGGCAGU UUGCUCAGCC UAUCCAUUGG A 31

( 2 ) INFORMATION FOR SEQ ID NO:47:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

CAGUUUGCUC AGCCUAUCCA UUGGAUGGAG C 31

( 2 ) INFORMATION FOR SEQ ID NO:48:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GUUUGCUCAG CCUAUCCAUU GGAUGGAGCU G 31

( 2 ) INFORMATION FOR SEQ ID NO:49:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

GCUCAGCCUA UCCAUUGGAU GGAGCUGCAA G                    31

( 2 ) INFORMATION FOR SEQ ID NO:50:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

CACCAGCAUG AACCUUGUUC AGAAAUAUCU A                    31

( 2 ) INFORMATION FOR SEQ ID NO:51:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

CAGCAUGAAC CUUGUUCAGA AAUAUCUAGA A                    31

( 2 ) INFORMATION FOR SEQ ID NO:52:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

AGCAUGAACC UUGUUCAGAA AUAUCUAGAA A                    31

( 2 ) INFORMATION FOR SEQ ID NO:53:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

ACCUUGUUCA GAAAUAUCUA GAAAACUACU A                    31

( 2 ) INFORMATION FOR SEQ ID NO:54:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

CUUGUUCAGA AAUAUCUAGA AAACUACUAC G                    31

( 2 ) INFORMATION FOR SEQ ID NO:55:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

UGUUCAGAAA UAUCUAGAAA ACUACUACGA C 31

(2) INFORMATION FOR SEQ ID NO:56:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:56:

AAUAUCUAGA AAACUACUAC GACCUCAAAA A 31

(2) INFORMATION FOR SEQ ID NO:57:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:57:

AUCUAGAAAA CUACUACGAC CUCAAAAAAG A 31

(2) INFORMATION FOR SEQ ID NO:58:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:58:

AAACUACUAC GACCUCAAAA AAGAUGUGAA A 31

(2) INFORMATION FOR SEQ ID NO:59:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:59:

AAGAUGUGAA ACAGUUUGUU AGGAGAAAGG A 31

(2) INFORMATION FOR SEQ ID NO:60:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:60:

AGAUGUGAAA CAGUUUGUUA GGAGAAAGGA C 31

(2) INFORMATION FOR SEQ ID NO:61:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:61:

UGUGAAACAG UUUGUUAGGA GAAAGGACAG U 31

(2) INFORMATION FOR SEQ ID NO:62:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:62:

GUGAAACAGU UUGUUAGGAG AAAGGACAGU G                   31

(2) INFORMATION FOR SEQ ID NO:63:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:63:

AGAAAGGACA GUGGUCCUGU UGUUAAAAA A                   31

(2) INFORMATION FOR SEQ ID NO:64:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:64:

GGACAGUGGU CCUGUUGUUA AAAAAUCCG A                   31

(2) INFORMATION FOR SEQ ID NO:65:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:65:

CAGUGGUCCU GUUGUUAAAA AAAUCCGAGA A                   31

(2) INFORMATION FOR SEQ ID NO:66:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:66:

AGUGGUCCUG UUGUUAAAAA AAUCCGAGAA A                   31

(2) INFORMATION FOR SEQ ID NO:67:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:67:

UGUUGUUAAA AAAAUCCGAG AAAUGCAGAA G                   31

(2) INFORMATION FOR SEQ ID NO:68:

( i ) SEQUENCE CHARACTERISTICS:
   ( A ) LENGTH: 31 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:68:

GAGAAAUGCA GAAGUUCCUU GGAUUGGAGG U                                31

( 2 ) INFORMATION FOR SEQ ID NO:69:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:69:

AGAAAUGCAG AAGUUCCUUG GAUUGGAGGU G                                31

( 2 ) INFORMATION FOR SEQ ID NO:70:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:70:

AAUGCAGAAG UUCCUUGGAU UGGAGGUGAC G                                31

( 2 ) INFORMATION FOR SEQ ID NO:71:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:71:

AGAAGUUCCU UGGAUUGGAG GUGACGGGGA A                                31

( 2 ) INFORMATION FOR SEQ ID NO:72:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:72:

CGGGGAAGCU GGACUCCGAC ACUCUGGAGG U                                31

( 2 ) INFORMATION FOR SEQ ID NO:73:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:73:

CUGGACUCCG ACACUCUGGA GGUGAUGCGC A                                31

( 2 ) INFORMATION FOR SEQ ID NO:74:

( i ) SEQUENCE CHARACTERISTICS:

(A) LENGTH: 31 base pairs
(B) TYPE: nucleic acid
(C) STRANDEDNESS: single
(D) TOPOLOGY: linear (x i) SEQUENCE DESCRIPTION: SEQ ID NO:74:

GCCCAGGUGU GGAGUUCCUG AUGUUGGUCA C        31

(2) INFORMATION FOR SEQ ID NO:75:

(i) SEQUENCE CHARACTERISTICS:
(A) LENGTH: 31 base pairs
(B) TYPE: nucleic acid
(C) STRANDEDNESS: single
(D) TOPOLOGY: linear (x i) SEQUENCE DESCRIPTION: SEQ ID NO:75:

CCCAGGUGUG GAGUUCCUGA UGUUGGUCAC U        31

(2) INFORMATION FOR SEQ ID NO:76:

(i) SEQUENCE CHARACTERISTICS:
(A) LENGTH: 31 base pairs
(B) TYPE: nucleic acid
(C) STRANDEDNESS: single
(D) TOPOLOGY: linear (x i) SEQUENCE DESCRIPTION: SEQ ID NO:76:

UGGAGUUCCU GAUGUUGGUC ACUUCAGAAC C        31

(2) INFORMATION FOR SEQ ID NO:77:

(i) SEQUENCE CHARACTERISTICS:
(A) LENGTH: 31 base pairs
(B) TYPE: nucleic acid
(C) STRANDEDNESS: single
(D) TOPOLOGY: linear (x i) SEQUENCE DESCRIPTION: SEQ ID NO:77:

GUUCCUGAUG UUGGUCACUU CAGAACCUUU C        31

(2) INFORMATION FOR SEQ ID NO:78:

(i) SEQUENCE CHARACTERISTICS:
(A) LENGTH: 31 base pairs
(B) TYPE: nucleic acid
(C) STRANDEDNESS: single
(D) TOPOLOGY: linear (x i) SEQUENCE DESCRIPTION: SEQ ID NO:78:

CUGAUGUUGG UCACUUCAGA ACCUUUCCUG G        31

(2) INFORMATION FOR SEQ ID NO:79:

(i) SEQUENCE CHARACTERISTICS:
(A) LENGTH: 31 base pairs
(B) TYPE: nucleic acid
(C) STRANDEDNESS: single
(D) TOPOLOGY: linear (x i) SEQUENCE DESCRIPTION: SEQ ID NO:79:

UGAUGUUGGU CACUUCAGAA CCUUUCCUGG C        31

(2) INFORMATION FOR SEQ ID NO:80:

(i) SEQUENCE CHARACTERISTICS:
(A) LENGTH: 31 base pairs
(B) TYPE: nucleic acid (C) STRANDEDNESS: single
(D) TOPOLOGY: linear (xi) SEQUENCE DESCRIPTION: SEQ ID NO:80:

GUCACUUCAG AACCUUUCCU GGCAUCCCGA A  31

(2) INFORMATION FOR SEQ ID NO:81:

(i) SEQUENCE CHARACTERISTICS:
 (A) LENGTH: 31 base pairs
 (B) TYPE: nucleic acid
 (C) STRANDEDNESS: single
 (D) TOPOLOGY: linear (xi) SEQUENCE DESCRIPTION: SEQ ID NO:81:

UCACUUCAGA ACCUUUCCUG GCAUCCCGAA G  31

(2) INFORMATION FOR SEQ ID NO:82:

(i) SEQUENCE CHARACTERISTICS:
 (A) LENGTH: 31 base pairs
 (B) TYPE: nucleic acid
 (C) STRANDEDNESS: single
 (D) TOPOLOGY: linear (xi) SEQUENCE DESCRIPTION: SEQ ID NO:82:

CACUUCAGAA CCUUUCCUGG CAUCCCGAAG U  31

(2) INFORMATION FOR SEQ ID NO:83:

(i) SEQUENCE CHARACTERISTICS:
 (A) LENGTH: 31 base pairs
 (B) TYPE: nucleic acid
 (C) STRANDEDNESS: single
 (D) TOPOLOGY: linear (xi) SEQUENCE DESCRIPTION: SEQ ID NO:83:

AACCUUUCCU GGCAUCCCGA AGUGGAGGAA A  31

(2) INFORMATION FOR SEQ ID NO:84:

(i) SEQUENCE CHARACTERISTICS:
 (A) LENGTH: 31 base pairs
 (B) TYPE: nucleic acid
 (C) STRANDEDNESS: single
 (D) TOPOLOGY: linear (xi) SEQUENCE DESCRIPTION: SEQ ID NO:84:

GAGGAAAACC CACCUUACAU ACAGGAUUGU G  31

(2) INFORMATION FOR SEQ ID NO:85:

(i) SEQUENCE CHARACTERISTICS:
 (A) LENGTH: 31 base pairs
 (B) TYPE: nucleic acid
 (C) STRANDEDNESS: single
 (D) TOPOLOGY: linear (xi) SEQUENCE DESCRIPTION: SEQ ID NO:85:

AGGAAAACCC ACCUUACAUA CAGGAUUGUG A  31

(2) INFORMATION FOR SEQ ID NO:86:

(i) SEQUENCE CHARACTERISTICS:
 (A) LENGTH: 31 base pairs
 (B) TYPE: nucleic acid
 (C) STRANDEDNESS: single
 (D) TOPOLOGY: linear ( x i ) SEQUENCE DESCRIPTION: SEQ ID NO:86:

AAACCCACCU UACAUACAGG AUUGUGAAUU A　　　　　　　　　　　　　　31

( 2 ) INFORMATION FOR SEQ ID NO:87:

( i ) SEQUENCE CHARACTERISTICS:
　　　　( A ) LENGTH: 31 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:87:

CCUUACAUAC AGGAUUGUGA AUUAUACACC A　　　　　　　　　　　　　　31

( 2 ) INFORMATION FOR SEQ ID NO:88:

( i ) SEQUENCE CHARACTERISTICS:
　　　　( A ) LENGTH: 31 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:88:

UACAGGAUUG UGAAUUAUAC ACCAGAUUUG C　　　　　　　　　　　　　　31

( 2 ) INFORMATION FOR SEQ ID NO:89:

( i ) SEQUENCE CHARACTERISTICS:
　　　　( A ) LENGTH: 31 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:89:

ACAGGAUUGU GAAUUAUACA CCAGAUUUGC C　　　　　　　　　　　　　　31

( 2 ) INFORMATION FOR SEQ ID NO:90:

( i ) SEQUENCE CHARACTERISTICS:
　　　　( A ) LENGTH: 31 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:90:

AGGAUUGUGA AUUAUACACC AGAUUUGCCA A　　　　　　　　　　　　　　31

( 2 ) INFORMATION FOR SEQ ID NO:91:

( i ) SEQUENCE CHARACTERISTICS:
　　　　( A ) LENGTH: 31 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:91:

AAUUAUACAC CAGAUUUGCC AAAAGAUGCU G　　　　　　　　　　　　　　31

( 2 ) INFORMATION FOR SEQ ID NO:92:

( i ) SEQUENCE CHARACTERISTICS:
　　　　( A ) LENGTH: 31 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:92:

AUUAUACACC AGAUUUGCCA AAAGAUGCUG U                      31

(2) INFORMATION FOR SEQ ID NO:93:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:93:

GCCAAAAGAU GCUGUUGAUU CUGCUGUUGA G                      31

(2) INFORMATION FOR SEQ ID NO:94:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:94:

AAAGAUGCUG UUGAUUCUGC UGUUGAGAAA G                      31

(2) INFORMATION FOR SEQ ID NO:95:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:95:

AAGAUGCUGU UGAUUCUGCU GUUGAGAAAG C                      31

(2) INFORMATION FOR SEQ ID NO:96:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:96:

UGUUGAUUCU GCUGUUGAGA AAGCUCUGAA A                      31

(2) INFORMATION FOR SEQ ID NO:97:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:97:

GCUGUUGAGA AAGCUCUGAA AGUCUGGGAA G                      31

(2) INFORMATION FOR SEQ ID NO:98:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:98:

GAAAGCUCUG AAAGUCUGGG AAGAGGUGAC U                      31

( 2 ) INFORMATION FOR SEQ ID NO:99:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

UGGGAAGAGG UGACUCCACU CACAUUCUCC A     31

( 2 ) INFORMATION FOR SEQ ID NO:100:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

AGAGGUGACU CCACUCACAU UCUCCAGGCU G     31

( 2 ) INFORMATION FOR SEQ ID NO:101:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:101:

UGACUCCACU CACAUUCUCC AGGCUGUAUG A     31

( 2 ) INFORMATION FOR SEQ ID NO:102:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

GACUCCACUC ACAUUCUCCA GGCUGUAUGA A     31

( 2 ) INFORMATION FOR SEQ ID NO:103:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

CUCCACUCAC AUUCUCCAGG CUGUAUGAAG G     31

( 2 ) INFORMATION FOR SEQ ID NO:104:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

CAUUCUCCAG GCUGUAUGAA GGAGAGGCUG A     31

( 2 ) INFORMATION FOR SEQ ID NO:105:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

GAAGGAGAGG CUGAUAUAAU GAUCUCUUUU G      31

( 2 ) INFORMATION FOR SEQ ID NO:106:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

AGGAGAGGCU GAUAUAAUGA UCUCUUUUGC A      31

( 2 ) INFORMATION FOR SEQ ID NO:107:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

GGCUGAUAUA AUGAUCUCUU UUGCAGUUAG A      31

( 2 ) INFORMATION FOR SEQ ID NO:108:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

CUGAUAUAAU GAUCUCUUUU GCAGUUAGAG A      31

( 2 ) INFORMATION FOR SEQ ID NO:109:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

GAUAUAAUGA UCUCUUUUGC AGUUAGAGAA C      31

( 2 ) INFORMATION FOR SEQ ID NO:110:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

AUAUAAUGAU CUCUUUUGCA GUUAGAGAAC A      31

( 2 ) INFORMATION FOR SEQ ID NO:111:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:111:

UAUAAUGAUC UCUUUUGCAG UUAGAGAACA U  31

( 2 ) INFORMATION FOR SEQ ID NO:112:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:112:

GAUCUCUUUU GCAGUUAGAG AACAUGGAGA C  31

( 2 ) INFORMATION FOR SEQ ID NO:113:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:113:

AUCUCUUUUG CAGUUAGAGA ACAUGGAGAC U  31

( 2 ) INFORMATION FOR SEQ ID NO:114:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:114:

GAGAACAUGG AGACUUUUAC CCUUUUGAUG G  31

( 2 ) INFORMATION FOR SEQ ID NO:115:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:115:

AGAACAUGGA GACUUUACC CUUUUGAUGG A  31

( 2 ) INFORMATION FOR SEQ ID NO:116:

( i ) SEQUENCE CHARACTERISTICS:
 ( A ) LENGTH: 31 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:116:

GAACAUGGAG ACUUUACCC UUUUGAUGGA C  31

( 2 ) INFORMATION FOR SEQ ID NO:117:

( i ) SEQUENCE CHARACTERISTICS:
 ( A ) LENGTH: 31 base pairs ( B ) TYPE: nucleic acid
( C ) STRANDEDNESS: single
( D ) TOPOLOGY: linear ( x i ) SEQUENCE DESCRIPTION: SEQ ID NO:117:

AACAUGGAGA CUUUUACCCU UUUGAUGGAC C  31

( 2 ) INFORMATION FOR SEQ ID NO:118:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:118:

GGAGACUUUU ACCCUUUUGA UGGACCUGGA A  31

( 2 ) INFORMATION FOR SEQ ID NO:119:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:119:

GAGACUUUUA CCCUUUUGAU GGACCUGGAA A  31

( 2 ) INFORMATION FOR SEQ ID NO:120:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:120:

AGACUUUUAC CCUUUUGAUG GACCUGGAAA U  31

( 2 ) INFORMATION FOR SEQ ID NO:121:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:121:

UGGACCUGGA AAUGUUUUGG CCCAUGCCUA U  31

( 2 ) INFORMATION FOR SEQ ID NO:122:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:122:

GGACCUGGAA AUGUUUUGGC CCAUGCCUAU G  31

( 2 ) INFORMATION FOR SEQ ID NO:123:

( i ) SEQUENCE CHARACTERISTICS:
( A ) LENGTH: 31 base pairs
( B ) TYPE: nucleic acid
( C ) STRANDEDNESS: single ( D ) TOPOLOGY: linear ( x i ) SEQUENCE DESCRIPTION: SEQ ID NO:123:

GACCUGGAAA UGUUUGGCC CAUGCCUAUG C 31

( 2 ) INFORMATION FOR SEQ ID NO:124:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:124:

UUUUGGCCCA UGCCUAUGCC CCUGGGCCAG G 31

( 2 ) INFORMATION FOR SEQ ID NO:125:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:125:

CCCUGGGCCA GGGAUUAAUG GAGAUGCCCA C 31

( 2 ) INFORMATION FOR SEQ ID NO:126:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

CCUGGGCCAG GGAUUAAUGG AGAUGCCCAC U 31

( 2 ) INFORMATION FOR SEQ ID NO:127:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

AUGGAGAUGC CCACUUUGAU GAUGAUGAAC A 31

( 2 ) INFORMATION FOR SEQ ID NO:128:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

UGGAGAUGCC CACUUUGAUG AUGAUGAACA A 31

( 2 ) INFORMATION FOR SEQ ID NO:129:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

CAAUGGACAA AGGAUACAAC AGGGACCAAU U                31

( 2 ) INFORMATION FOR SEQ ID NO:130:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:130:

ACAACAGGGA CCAAUUAUU UCUCGUUGCU G                31

( 2 ) INFORMATION FOR SEQ ID NO:131:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:131:

CAACAGGGAC CAAUUUAUUU CUCGUUGCUG C                31

( 2 ) INFORMATION FOR SEQ ID NO:132:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:132:

AACAGGGACC AAUUUAUUUC UCGUUGCUGC U                31

( 2 ) INFORMATION FOR SEQ ID NO:133:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:133:

CAGGGACCAA UUUAUUUCUC GUUGCUGCUC A                31

( 2 ) INFORMATION FOR SEQ ID NO:134:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:134:

AGGGACCAAU UUAUUUCUCG UUGCUGCUCA U                31

( 2 ) INFORMATION FOR SEQ ID NO:135:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:135:

```
GGGACCAAUU UAUUUCUCGU UGCUGCUCAU G                                              31
```

( 2 ) INFORMATION FOR SEQ ID NO:136:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

```
GACCAAUUUA UUUCUCGUUG CUGCUCAUGA A                                              31
```

( 2 ) INFORMATION FOR SEQ ID NO:137:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

```
CAAUUUAUUU CUCGUUGCUG CUCAUGAAAU U                                              31
```

( 2 ) INFORMATION FOR SEQ ID NO:138:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

```
UUUCUCGUUG CUGCUCAUGA AAUUGGCCAC U                                              31
```

( 2 ) INFORMATION FOR SEQ ID NO:139:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

```
UGCUGCUCAU GAAAUUGGCC ACUCCCUGGG U                                              31
```

( 2 ) INFORMATION FOR SEQ ID NO:140:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

```
AUGAAAUUGG CCACUCCCUG GGUCUCUUUC A                                              31
```

( 2 ) INFORMATION FOR SEQ ID NO:141:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

```
GGCCACUCCC UGGGUCUCUU UCACUCAGCC A                                              31
```

( 2 ) INFORMATION FOR SEQ ID NO:142:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

CCACUCCCUG GGUCUCUUUC ACUCAGCCAA C        31

( 2 ) INFORMATION FOR SEQ ID NO:143:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

ACUCCCUGGG UCUCUUUCAC UCAGCCAACA C        31

( 2 ) INFORMATION FOR SEQ ID NO:144:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:144:

CUCCCUGGGU CUCUUUCACU CAGCCAACAC U        31

( 2 ) INFORMATION FOR SEQ ID NO:145:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:145:

UCCCUGGGUC UCUUUCACUC AGCCAACACU G        31

( 2 ) INFORMATION FOR SEQ ID NO:146:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:146:

UGGGUCUCUU UCACUCAGCC AACACUGAAG C        31

( 2 ) INFORMATION FOR SEQ ID NO:147:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:147:

GCCAACACUG AAGCUUUGAU GUACCCACUC U        31

( 2 ) INFORMATION FOR SEQ ID NO:148:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:148:

CCAACACUGA AGCUUUGAUG UACCCACUCU A    31

( 2 ) INFORMATION FOR SEQ ID NO:149:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:149:

CUGAAGCUUU GAUGUACCCA CUCUAUCACU C    31

( 2 ) INFORMATION FOR SEQ ID NO:150:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:150:

UUUGAUGUAC CCACUCUAUC ACUCACUCAC A    31

( 2 ) INFORMATION FOR SEQ ID NO:151:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:151:

UGAUGUACCC ACUCUAUCAC UCACUCACAG A    31

( 2 ) INFORMATION FOR SEQ ID NO:152:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:152:

AUGUACCCAC UCUAUCACUC ACUCACAGAC C    31

( 2 ) INFORMATION FOR SEQ ID NO:153:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:153:

ACCCACUCUA UCACUCACUC ACAGACCUGA C    31

( 2 ) INFORMATION FOR SEQ ID NO:154:

( i ) SEQUENCE CHARACTERISTICS:

(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:154:

ACUCUAUCAC UCACUCACAG ACCUGACUCG G   31

(2) INFORMATION FOR SEQ ID NO:155:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:155:

CUCACAGACC UGACUCGGUU CCGCCUGUCU C   31

(2) INFORMATION FOR SEQ ID NO:156:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:156:

CAGACCUGAC UCGGUUCCGC CUGUCUCAAG A   31

(2) INFORMATION FOR SEQ ID NO:157:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:157:

AGACCUGACU CGGUUCCGCC UGUCUCAAGA U   31

(2) INFORMATION FOR SEQ ID NO:158:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:158:

CUCGGUUCCG CCUGUCUCAA GAUGAUAUAA A   31

(2) INFORMATION FOR SEQ ID NO:159:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:159:

CGGUUCCGCC UGUCUCAAGA UGAUAUAAAU G   31

(2) INFORMATION FOR SEQ ID NO:160:

(i) SEQUENCE CHARACTERISTICS:
(A) LENGTH: 31 base pairs
(B) TYPE: nucleic acid (C) STRANDEDNESS: single
(D) TOPOLOGY: linear ( x i ) SEQUENCE DESCRIPTION: SEQ ID NO:160:

CUGUCUCAAG AUGAUAUAAA UGGCAUUCAG U 31

( 2 ) INFORMATION FOR SEQ ID NO:161:

( i ) SEQUENCE CHARACTERISTICS:
(A) LENGTH: 31 base pairs
(B) TYPE: nucleic acid
(C) STRANDEDNESS: single
(D) TOPOLOGY: linear ( x i ) SEQUENCE DESCRIPTION: SEQ ID NO:161:

GUCUCAAGAU GAUAUAAAUG GCAUUCAGUC C 31

( 2 ) INFORMATION FOR SEQ ID NO:162:

( i ) SEQUENCE CHARACTERISTICS:
(A) LENGTH: 31 base pairs
(B) TYPE: nucleic acid
(C) STRANDEDNESS: single
(D) TOPOLOGY: linear ( x i ) SEQUENCE DESCRIPTION: SEQ ID NO:162:

UGAUAUAAAU GGCAUUCAGU CCCUCUAUGG A 31

( 2 ) INFORMATION FOR SEQ ID NO:163:

( i ) SEQUENCE CHARACTERISTICS:
(A) LENGTH: 31 base pairs
(B) TYPE: nucleic acid
(C) STRANDEDNESS: single
(D) TOPOLOGY: linear ( x i ) SEQUENCE DESCRIPTION: SEQ ID NO:163:

GAUAUAAAUG GCAUUCAGUC CCUCUAUGGA C 31

( 2 ) INFORMATION FOR SEQ ID NO:164:

( i ) SEQUENCE CHARACTERISTICS:
(A) LENGTH: 31 base pairs
(B) TYPE: nucleic acid
(C) STRANDEDNESS: single
(D) TOPOLOGY: linear ( x i ) SEQUENCE DESCRIPTION: SEQ ID NO:164:

UAAAUGGCAU UCAGUCCCUC UAUGGACCUC C 31

( 2 ) INFORMATION FOR SEQ ID NO:165:

( i ) SEQUENCE CHARACTERISTICS:
(A) LENGTH: 31 base pairs
(B) TYPE: nucleic acid
(C) STRANDEDNESS: single
(D) TOPOLOGY: linear ( x i ) SEQUENCE DESCRIPTION: SEQ ID NO:165:

UGGCAUUCAG UCCCUCUAUG GACCUCCCCC U 31

( 2 ) INFORMATION FOR SEQ ID NO:166:

( i ) SEQUENCE CHARACTERISTICS:
(A) LENGTH: 31 base pairs
(B) TYPE: nucleic acid
(C) STRANDEDNESS: single
(D) TOPOLOGY: linear ( x i ) SEQUENCE DESCRIPTION: SEQ ID NO:166:

GCAUUCAGUC CCUCUAUGGA CCUCCCCUG A         31

( 2 ) INFORMATION FOR SEQ ID NO:167:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:167:

UCCCUCUAUG GACCUCCCCC UGACUCCCCU G         31

( 2 ) INFORMATION FOR SEQ ID NO:168:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:168:

GACCUCCCCC UGACUCCCCU GAGACCCCCC U         31

( 2 ) INFORMATION FOR SEQ ID NO:169:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:169:

UGAGACCCCC CUGGUACCCA CGGAACCUGU C         31

( 2 ) INFORMATION FOR SEQ ID NO:170:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:170:

ACCCACGGAA CCUGUCCCUC CAGAACCUGG G         31

( 2 ) INFORMATION FOR SEQ ID NO:171:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:171:

ACGGAACCUG UCCCUCCAGA ACCUGGGACG C         31

( 2 ) INFORMATION FOR SEQ ID NO:172:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:172:

```
CCAGCCAACU GUGAUCCUGC UUUGUCCUUU G                                           31
```

( 2 ) INFORMATION FOR SEQ ID NO:173:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:173:

```
AACUGUGAUC CUGCUUUGUC CUUUGAUGCU G                                           31
```

( 2 ) INFORMATION FOR SEQ ID NO:174:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

```
ACUGUGAUCC UGCUUUGUCC UUUGAUGCUG U                                           31
```

( 2 ) INFORMATION FOR SEQ ID NO:175:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

```
GUGAUCCUGC UUUGUCCUUU GAUGCUGUCA G                                           31
```

( 2 ) INFORMATION FOR SEQ ID NO:176:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

```
AUCCUGCUUU GUCCUUUGAU GCUGUCAGCA C                                           31
```

( 2 ) INFORMATION FOR SEQ ID NO:177:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

```
UCCUGCUUUG UCCUUUGAUG CUGUCAGCAC U                                           31
```

( 2 ) INFORMATION FOR SEQ ID NO:178:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

```
GUCCUUUGAU GCUGUCAGCA CUCUGAGGGG A                                           31
```

( 2 ) INFORMATION FOR SEQ ID NO:179:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

GAUGCUGUCA GCACUCUGAG GGGAGAAAUC C      31

( 2 ) INFORMATION FOR SEQ ID NO:180:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

UCUGAGGGA GAAAUCCUGA UCUUUAAAGA C      31

( 2 ) INFORMATION FOR SEQ ID NO:181:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:181:

GGGAGAAAUC CUGAUCUUUA AAGACAGGCA C      31

( 2 ) INFORMATION FOR SEQ ID NO:182:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:182:

GAGAAAUCCU GAUCUUUAAA GACAGGCACU U      31

( 2 ) INFORMATION FOR SEQ ID NO:183:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:183:

AGAAAUCCUG AUCUUUAAAG ACAGGCACUU U      31

( 2 ) INFORMATION FOR SEQ ID NO:184:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:184:

GAAAUCCUGA UCUUUAAAGA CAGGCACUUU U      31

( 2 ) INFORMATION FOR SEQ ID NO:185:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:185:

UUAAAGACAG GCACUUUGG CGCAAAUCCC U        31

( 2 ) INFORMATION FOR SEQ ID NO:186:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:186:

UAAAGACAGG CACUUUGGC GCAAAUCCCU C        31

( 2 ) INFORMATION FOR SEQ ID NO:187:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:187:

AAAGACAGGC ACUUUGGCG CAAAUCCCUC A        31

( 2 ) INFORMATION FOR SEQ ID NO:188:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:188:

ACUUUGGCG CAAAUCCCUC AGGAAGCUUG A        31

( 2 ) INFORMATION FOR SEQ ID NO:189:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:189:

UUGGCGCAAA UCCCUCAGGA AGCUUGAACC U        31

( 2 ) INFORMATION FOR SEQ ID NO:190:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:190:

AUCCCUCAGG AAGCUUGAAC CUGAAUUGCA U        31

( 2 ) INFORMATION FOR SEQ ID NO:191:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:191:

AGCUUGAACC UGAAUUGCAU UUGAUCUCUU C     31

(2) INFORMATION FOR SEQ ID NO:192:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:192:

GAACCUGAAU UGCAUUUGAU CUCUUCAUUU U     31

(2) INFORMATION FOR SEQ ID NO:193:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:193:

AACCUGAAUU GCAUUUGAUC UCUUCAUUUU G     31

(2) INFORMATION FOR SEQ ID NO:194:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:194:

UGAAUUGCAU UUGAUCUCUU CAUUUGGCC A     31

(2) INFORMATION FOR SEQ ID NO:195:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:195:

AAUUGCAUUU GAUCUCUUCA UUUUGGCCAU C     31

(2) INFORMATION FOR SEQ ID NO:196:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:196:

UUGCAUUUGA UCUCUUCAUU UUGGCCAUCU C     31

(2) INFORMATION FOR SEQ ID NO:197:

(i) SEQUENCE CHARACTERISTICS:
    (A) LENGTH: 31 base pairs ( B ) TYPE: nucleic acid
( C ) STRANDEDNESS: single
( D ) TOPOLOGY: linear ( x i ) SEQUENCE DESCRIPTION: SEQ ID NO:197:

UGCAUUUGAU CUCUUCAUUU UGGCCAUCUC U  31

( 2 ) INFORMATION FOR SEQ ID NO:198:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:198:

AUUUGAUCUC UUCAUUUUGG CCAUCUCUUC C  31

( 2 ) INFORMATION FOR SEQ ID NO:199:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:199:

UUUGAUCUCU UCAUUUGGC CAUCUCUUCC U  31

( 2 ) INFORMATION FOR SEQ ID NO:200:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:200:

UUGAUCUCUU CAUUUGGCC AUCUCUUCCU U  31

( 2 ) INFORMATION FOR SEQ ID NO:201:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:201:

CUUCAUUUG GCCAUCUCUU CCUUCAGGCG U  31

( 2 ) INFORMATION FOR SEQ ID NO:202:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:202:

UCAUUUGGC CAUCUCUUCC UUCAGGCGUG G  31

( 2 ) INFORMATION FOR SEQ ID NO:203:

( i ) SEQUENCE CHARACTERISTICS:
( A ) LENGTH: 31 base pairs
( B ) TYPE: nucleic acid
( C ) STRANDEDNESS: single ( D ) TOPOLOGY: linear ( x i ) SEQUENCE DESCRIPTION: SEQ ID NO:203:

AUUUUGGCCA UCUCUUCCUU CAGGCGUGGA U　　　　　　　　　　　　　31

( 2 ) INFORMATION FOR SEQ ID NO:204:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:204:

UUUUGGCCAU CUCUUCCUUC AGGCGUGGAU G　　　　　　　　　　　　　31

( 2 ) INFORMATION FOR SEQ ID NO:205:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:205:

UGGCCAUCUC UUCCUUCAGG CGUGGAUGCC G　　　　　　　　　　　　　31

( 2 ) INFORMATION FOR SEQ ID NO:206:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:206:

GGCCAUCUCU UCCUUCAGGC GUGGAUGCCG C　　　　　　　　　　　　　31

( 2 ) INFORMATION FOR SEQ ID NO:207:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:207:

GCGUGGAUGC CGCAUAUGAA GUUACUAGCA A　　　　　　　　　　　　　31

( 2 ) INFORMATION FOR SEQ ID NO:208:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:208:

UGCCGCAUAU GAAGUUACUA GCAAGGACCU C　　　　　　　　　　　　　31

( 2 ) INFORMATION FOR SEQ ID NO:209:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:209:

GCCGCAUAUG AAGUUACUAG CAAGGACCUC G                      31

( 2 ) INFORMATION FOR SEQ ID NO:210:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:210:

GCAUAUGAAG UUACUAGCAA GGACCUCGUU U                      31

( 2 ) INFORMATION FOR SEQ ID NO:211:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:211:

UACUAGCAAG GACCUCGUUU UCAUUUUAA A                       31

( 2 ) INFORMATION FOR SEQ ID NO:212:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:212:

UAGCAAGGAC CUCGUUUUCA UUUUUAAAGG A                      31

( 2 ) INFORMATION FOR SEQ ID NO:213:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:213:

AGCAAGGACC UCGUUUUCAU UUUUAAAGGA A                      31

( 2 ) INFORMATION FOR SEQ ID NO:214:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:214:

GCAAGGACCU CGUUUUCAUU UUUAAAGGAA A                      31

( 2 ) INFORMATION FOR SEQ ID NO:215:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:215:

CAAGGACCUC GUUUUCAUUU UUAAAGGAAA U                       31

( 2 ) INFORMATION FOR SEQ ID NO:216:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:216:

GGACCUCGUU UCAUUUUUA AAGGAAAUCA A                        31

( 2 ) INFORMATION FOR SEQ ID NO:217:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

GACCUCGUUU UCAUUUUUAA AGGAAAUCAA U                       31

( 2 ) INFORMATION FOR SEQ ID NO:218:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

ACCUCGUUUU CAUUUUUAAA GGAAAUCAAU U                       31

( 2 ) INFORMATION FOR SEQ ID NO:219:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:219:

CCUCGUUUUC AUUUUUAAAG GAAAUCAAUU C                       31

( 2 ) INFORMATION FOR SEQ ID NO:220:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

CUCGUUUUCA UUUUUAAAGG AAAUCAAUUC U                       31

( 2 ) INFORMATION FOR SEQ ID NO:221:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

AUUUUUAAAG GAAAUCAAUU CUGGGCCAUC A                       31

( 2 ) INFORMATION FOR SEQ ID NO:222:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

UUAAAGGAAA UCAAUUCUGG GCCAUCAGAG G                                      31

( 2 ) INFORMATION FOR SEQ ID NO:223:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

UAAAGGAAAU CAAUUCUGGG CCAUCAGAGG A                                      31

( 2 ) INFORMATION FOR SEQ ID NO:224:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:224:

UCAAUUCUGG GCCAUCAGAG GAAAUGAGGU A                                      31

( 2 ) INFORMATION FOR SEQ ID NO:225:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:225:

CAGAGGAAAU GAGGUACGAG CUGGAUACCC A                                      31

( 2 ) INFORMATION FOR SEQ ID NO:226:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:226:

AGGUACGAGC UGGAUACCCA AGAGGCAUCC A                                      31

( 2 ) INFORMATION FOR SEQ ID NO:227:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:227:

AUACCCAAGA GGCAUCCACA CCCUAGGUUU C                                      31

( 2 ) INFORMATION FOR SEQ ID NO:228:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:228:

AGGCAUCCAC ACCCUAGGUU UCCCUCCAAC C                                                                              31

(2) INFORMATION FOR SEQ ID NO:229:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:229:

AUCCACACCC UAGGUUUCCC UCCAACCGUG A                                                                              31

(2) INFORMATION FOR SEQ ID NO:230:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:230:

UCCACACCCU AGGUUUCCCU CCAACCGUGA G                                                                              31

(2) INFORMATION FOR SEQ ID NO:231:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:231:

CCACACCCUA GGUUUCCCUC CAACCGUGAG G                                                                              31

(2) INFORMATION FOR SEQ ID NO:232:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:232:

ACCCUAGGUU UCCCUCCAAC CGUGAGGAAA A                                                                              31

(2) INFORMATION FOR SEQ ID NO:233:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:233:

AACCGUGAGG AAAAUCGAUG CAGCCAUUUC U                                                                              31

(2) INFORMATION FOR SEQ ID NO:234:

(i) SEQUENCE CHARACTERISTICS:

( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:234:

AAUCGAUGCA GCCAUUUCUG AUAAGGAAAA G 31

( 2 ) INFORMATION FOR SEQ ID NO:235:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:235:

AUCGAUGCAG CCAUUUCUGA UAAGGAAAAG A 31

( 2 ) INFORMATION FOR SEQ ID NO:236:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:236:

UCGAUGCAGC CAUUCUGAU AAGGAAAAGA A 31

( 2 ) INFORMATION FOR SEQ ID NO:237:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:237:

GCAGCCAUUU CUGAUAAGGA AAGAACAAA A 31

( 2 ) INFORMATION FOR SEQ ID NO:238:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:238:

AAAAGAACAA AACAUAUUUC UUUGUAGAGG A 31

( 2 ) INFORMATION FOR SEQ ID NO:239:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:239:

AAGAACAAAA CAUAUUUCUU UGUAGAGGAC A 31

( 2 ) INFORMATION FOR SEQ ID NO:240:

( i ) SEQUENCE CHARACTERISTICS:
( A ) LENGTH: 31 base pairs
( B ) TYPE: nucleic acid ( C ) STRANDEDNESS: single
( D ) TOPOLOGY: linear ( x i ) SEQUENCE DESCRIPTION: SEQ ID NO:240:

AGAACAAAAC AUAUUUCUUU GUAGAGGACA A 31

( 2 ) INFORMATION FOR SEQ ID NO:241:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:241:

GAACAAAACA UAUUUCUUUG UAGAGGACAA A 31

( 2 ) INFORMATION FOR SEQ ID NO:242:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:242:

ACAAAACAUA UUUCUUUGUA GAGGACAAAU A 31

( 2 ) INFORMATION FOR SEQ ID NO:243:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:243:

CAAAACAUAU UUCUUUGUAG AGGACAAAUA C 31

( 2 ) INFORMATION FOR SEQ ID NO:244:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:244:

AACAUAUUUC UUUGUAGAGG ACAAAUACUG G 31

( 2 ) INFORMATION FOR SEQ ID NO:245:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:245:

UUGUAGAGGA CAAAUACUGG AGAUUUGAUG A 31

( 2 ) INFORMATION FOR SEQ ID NO:246:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear (  x i ) SEQUENCE DESCRIPTION: SEQ ID NO:246:

ACAAAUACUG GAGAUUUGAU GAGAAGAGAA A                                31

( 2 ) INFORMATION FOR SEQ ID NO:247:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:247:

CAAAUACUGG AGAUUUGAUG AGAAGAGAAA U                                31

( 2 ) INFORMATION FOR SEQ ID NO:248:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:248:

GAUGAGAAGA GAAAUUCCAU GGAGCCAGGC U                                31

( 2 ) INFORMATION FOR SEQ ID NO:249:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:249:

AUGAGAAGAG AAAUUCCAUG GAGCCAGGCU U                                31

( 2 ) INFORMATION FOR SEQ ID NO:250:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:250:

CCAUGGAGCC AGGCUUUCCC AAGCAAAUAG C                                31

( 2 ) INFORMATION FOR SEQ ID NO:251:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:251:

CAUGGAGCCA GGCUUUCCCA AGCAAAUAGC U                                31

( 2 ) INFORMATION FOR SEQ ID NO:252:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:252:

AUGGAGCCAG GCUUUCCAA GCAAAUAGCU G    31

( 2 ) INFORMATION FOR SEQ ID NO:253:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:253:

CUUUCCCAAG CAAAUAGCUG AAGACUUUCC A    31

( 2 ) INFORMATION FOR SEQ ID NO:254:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

AAAUAGCUGA AGACUUUCCA GGGAUUGACU C    31

( 2 ) INFORMATION FOR SEQ ID NO:255:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:255:

AAUAGCUGAA GACUUUCCAG GGAUUGACUC A    31

( 2 ) INFORMATION FOR SEQ ID NO:256:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:256:

AUAGCUGAAG ACUUUCCAGG GAUUGACUCA A    31

( 2 ) INFORMATION FOR SEQ ID NO:257:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:257:

AGACUUUCCA GGGAUUGACU CAAAGAUUGA U    31

( 2 ) INFORMATION FOR SEQ ID NO:258:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:258:

UUCCAGGGAU UGACUCAAAG AUUGAUGCUG U    31

( 2 ) INFORMATION FOR SEQ ID NO:259:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:259:

GAUUGACUCA AAGAUUGAUG CUGUUUUUGA A      31

( 2 ) INFORMATION FOR SEQ ID NO:260:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:260:

AAAGAUUGAU GCUGUUUUUG AAGAAUUUGG G      31

( 2 ) INFORMATION FOR SEQ ID NO:261:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:261:

AAGAUUGAUG CUGUUUUUGA AGAAUUUGGG U      31

( 2 ) INFORMATION FOR SEQ ID NO:262:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:262:

AGAUUGAUGC UGUUUUUGAA GAAUUUGGGU U      31

( 2 ) INFORMATION FOR SEQ ID NO:263:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:263:

GAUUGAUGCU GUUUUUGAAG AAUUUGGGUU C      31

( 2 ) INFORMATION FOR SEQ ID NO:264:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:264:

CUGUUUUUGA AGAAUUUGGG UUCUUUUAUU U      31

( 2 ) INFORMATION FOR SEQ ID NO:265:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:265:

UGUUUUUGAA GAAUUUGGGU UCUUUUAUUU C           31

( 2 ) INFORMATION FOR SEQ ID NO:266:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:266:

UUGAAGAAUU UGGGUUCUUU UAUUUCUUUA C           31

( 2 ) INFORMATION FOR SEQ ID NO:267:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:267:

UGAAGAAUUU GGGUUCUUUU AUUUCUUUAC U           31

( 2 ) INFORMATION FOR SEQ ID NO:268:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:268:

AAGAAUUUGG GUUCUUUUAU UUCUUUACUG G           31

( 2 ) INFORMATION FOR SEQ ID NO:269:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:269:

AGAAUUUGGG UUCUUUUAUU UCUUUACUGG A           31

( 2 ) INFORMATION FOR SEQ ID NO:270:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:270:

GAAUUUGGGU UCUUUUAUUU CUUUACUGGA U           31

( 2 ) INFORMATION FOR SEQ ID NO:271:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:271:

AAUUUGGGUU CUUUUAUUUC UUUACUGGAU C    31

( 2 ) INFORMATION FOR SEQ ID NO:272:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:272:

UUUGGGUUCU UUUAUUUCUU UACUGGAUCU U    31

( 2 ) INFORMATION FOR SEQ ID NO:273:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:273:

UUGGGUUCUU UUAUUUCUUU ACUGGAUCUU C    31

( 2 ) INFORMATION FOR SEQ ID NO:274:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:274:

UGGGUUCUUU UAUUUCUUUA CUGGAUCUUC A    31

( 2 ) INFORMATION FOR SEQ ID NO:275:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:275:

GGUUCUUUUA UUUCUUUACU GGAUCUUCAC A    31

( 2 ) INFORMATION FOR SEQ ID NO:276:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:276:

GUUCUUUUAU UUCUUUACUG GAUCUUCACA G    31

( 2 ) INFORMATION FOR SEQ ID NO:277:

( i ) SEQUENCE CHARACTERISTICS:
        ( A ) LENGTH: 31 base pairs (B) TYPE: nucleic acid
(C) STRANDEDNESS: single
(D) TOPOLOGY: linear (xi) SEQUENCE DESCRIPTION: SEQ ID NO:277:

UUCUUUUAUU UCUUUACUGG AUCUUCACAG U                                    31

(2) INFORMATION FOR SEQ ID NO:278:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:278:

AUUUCUUUAC UGGAUCUUCA CAGUUGGAGU U                                    31

(2) INFORMATION FOR SEQ ID NO:279:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:279:

UUCUUUACUG GAUCUUCACA GUUGGAGUUU G                                    31

(2) INFORMATION FOR SEQ ID NO:280:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:280:

UCUUUACUGG AUCUUCACAG UUGGAGUUUG A                                    31

(2) INFORMATION FOR SEQ ID NO:281:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:281:

CUGGAUCUUC ACAGUUGGAG UUUGACCCAA A                                    31

(2) INFORMATION FOR SEQ ID NO:282:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:282:

CUUCACAGUU GGAGUUUGAC CCAAAUGCAA A                                    31

(2) INFORMATION FOR SEQ ID NO:283:

(i) SEQUENCE CHARACTERISTICS:
        (A) LENGTH: 31 base pairs
        (B) TYPE: nucleic acid
        (C) STRANDEDNESS: single ( D ) TOPOLOGY: linear ( x i ) SEQUENCE DESCRIPTION: SEQ ID NO:283:

UUCACAGUUG GAGUUUGACC CAAAUGCAAA G    31

( 2 ) INFORMATION FOR SEQ ID NO:284:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:284:

AAAGUGACAC ACACUUUGAA GAGUAACAGC U    31

( 2 ) INFORMATION FOR SEQ ID NO:285:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:285:

AAGUGACACA CACUUUGAAG AGUAACAGCU G    31

( 2 ) INFORMATION FOR SEQ ID NO:286:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:286:

CACACUUUGA AGAGUAACAG CUGGCUUAAU U    31

( 2 ) INFORMATION FOR SEQ ID NO:287:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:287:

GAGUAACAGC UGGCUUAAUU GUUGAAAGAG A    31

( 2 ) INFORMATION FOR SEQ ID NO:288:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:288:

AGUAACAGCU GGCUUAAUUG UUGAAAGAGA U    31

( 2 ) INFORMATION FOR SEQ ID NO:289:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:289:

AACAGCUGGC UUAAUUGUUG AAAGAGAUAU G　　　　　　　　　　　　31

( 2 ) INFORMATION FOR SEQ ID NO:290:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:290:

AGCUGGCUUA AUUGUUGAAA GAGAUAUGUA G　　　　　　　　　　　　31

( 2 ) INFORMATION FOR SEQ ID NO:291:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:291:

AUUGUUGAAA GAGAUAUGUA GAAGGCACAA U　　　　　　　　　　　　31

( 2 ) INFORMATION FOR SEQ ID NO:292:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:292:

UUGAAAGAGA UAUGUAGAAG GCACAAUAUG G　　　　　　　　　　　　31

( 2 ) INFORMATION FOR SEQ ID NO:293:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:293:

UGUAGAAGGC ACAAUAUGGG CACUUUAAAU G　　　　　　　　　　　　31

( 2 ) INFORMATION FOR SEQ ID NO:294:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:294:

CACAAUAUGG GCACUUUAAA UGAAGCUAAU A　　　　　　　　　　　　31

( 2 ) INFORMATION FOR SEQ ID NO:295:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:295:

ACAAUAUGGG CACUUUAAAU GAAGCUAAUA A     31

( 2 ) INFORMATION FOR SEQ ID NO:296:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:296:

CAAUAUGGGC ACUUUAAAUG AAGCUAAUAA U     31

( 2 ) INFORMATION FOR SEQ ID NO:297:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:297:

ACUUUAAAUG AAGCUAAUAA UUCUUCACCU A     31

( 2 ) INFORMATION FOR SEQ ID NO:298:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:298:

UUAAAUGAAG CUAAUAAUUC UUCACCUAAG U     31

( 2 ) INFORMATION FOR SEQ ID NO:299:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:299:

AAUGAAGCUA AUAAUUCUUC ACCUAAGUCU C     31

( 2 ) INFORMATION FOR SEQ ID NO:300:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:300:

AUGAAGCUAA UAAUUCUUCA CCUAAGUCUC U     31

( 2 ) INFORMATION FOR SEQ ID NO:301:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:301:

GAAGCUAAUA AUUCUUCACC UAAGUCUCUG U     31

( 2 ) INFORMATION FOR SEQ ID NO:302:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:302:

AAGCUAAUAA UUCUUCACCU AAGUCUCUGU G     31

( 2 ) INFORMATION FOR SEQ ID NO:303:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:303:

AAUAAUUCUU CACCUAAGUC UCUGUGAAUU G     31

( 2 ) INFORMATION FOR SEQ ID NO:304:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:304:

AUUCUUCACC UAAGUCUCUG UGAAUUGAAA U     31

( 2 ) INFORMATION FOR SEQ ID NO:305:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

UCUUCACCUA AGUCUCUGUG AAUUGAAAUG U     31

( 2 ) INFORMATION FOR SEQ ID NO:306:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:306:

UAAGUCUCUG UGAAUUGAAA UGUUCGUUUU C     31

( 2 ) INFORMATION FOR SEQ ID NO:307:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:307:

UGUGAAUUGA AAUGUUCGUU UUCUCCUGCC U     31

( 2 ) INFORMATION FOR SEQ ID NO:308:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:308:

GUGAAUUGAA AUGUUCGUUU UCUCCUGCCU G    31

( 2 ) INFORMATION FOR SEQ ID NO:309:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:309:

AAUUGAAAUG UUCGUUUUCU CCUGCCUGUG C    31

( 2 ) INFORMATION FOR SEQ ID NO:310:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:310:

AUUGAAAUGU UCGUUUCUC CUGCCUGUGC U    31

( 2 ) INFORMATION FOR SEQ ID NO:311:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:311:

UUGAAAUGUU CGUUUCUCC UGCCUGUGCU G    31

( 2 ) INFORMATION FOR SEQ ID NO:312:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:312:

UGAAAUGUUC GUUUCUCCU GCCUGUGCUG U    31

( 2 ) INFORMATION FOR SEQ ID NO:313:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:313:

AAAUGUUCGU UUCUCCUGC CUGUGCUGUG A    31

( 2 ) INFORMATION FOR SEQ ID NO:314:

( i ) SEQUENCE CHARACTERISTICS:

(A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:314:

GCCUGUGCUG UGACUCGAGU CACACUCAAG G                                31

(2) INFORMATION FOR SEQ ID NO:315:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:315:

UGCUGUGACU CGAGUCACAC UCAAGGGAAC U                                31

(2) INFORMATION FOR SEQ ID NO:316:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:316:

GACUCGAGUC ACACUCAAGG GAACUUGAGC G                                31

(2) INFORMATION FOR SEQ ID NO:317:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:317:

ACACUCAAGG GAACUUGAGC GUGAAUCUGU A                                31

(2) INFORMATION FOR SEQ ID NO:318:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:318:

AACUUGAGCG UGAAUCUGUA UCUUGCCGGU C                                31

(2) INFORMATION FOR SEQ ID NO:319:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:319:

UGAGCGUGAA UCUGUAUCUU GCCGGUCAUU U                                31

(2) INFORMATION FOR SEQ ID NO:320:

(i) SEQUENCE CHARACTERISTICS:
        (A) LENGTH: 31 base pairs
        (B) TYPE: nucleic acid

```
        ( C ) STRANDEDNESS: single
        ( D ) TOPOLOGY: linear ( x i ) SEQUENCE DESCRIPTION: SEQ ID NO:320:

AGCGUGAAUC UGUAUCUUGC CGGUCAUUUU U                              31
```

( 2 ) INFORMATION FOR SEQ ID NO:321:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:321:

```
CGUGAAUCUG UAUCUUGCCG GUCAUUUUUA U                              31
```

( 2 ) INFORMATION FOR SEQ ID NO:322:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:322:

```
CUGUAUCUUG CCGGUCAUUU UUAUGUUAUU A                              31
```

( 2 ) INFORMATION FOR SEQ ID NO:323:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:323:

```
UAUCUUGCCG GUCAUUUUUA UGUUAUUACA G                              31
```

( 2 ) INFORMATION FOR SEQ ID NO:324:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:324:

```
AUCUUGCCGG UCAUUUUUAU GUUAUUACAG G                              31
```

( 2 ) INFORMATION FOR SEQ ID NO:325:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:325:

```
UCUUGCCGGU CAUUUUUAUG UUAUUACAGG G                              31
```

( 2 ) INFORMATION FOR SEQ ID NO:326:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:326:

CUUGCCGGUC AUUUUUAUGU UAUUACAGGG C                                    31

( 2 ) INFORMATION FOR SEQ ID NO:327:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:327:

UUGCCGGUCA UUUUUAUGUU AUUACAGGGC A                                    31

( 2 ) INFORMATION FOR SEQ ID NO:328:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:328:

CGGUCAUUUU UAUGUUAUUA CAGGGCAUUC A                                    31

( 2 ) INFORMATION FOR SEQ ID NO:329:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:329:

GGUCAUUUUU AUGUUAUUAC AGGGCAUUCA A                                    31

( 2 ) INFORMATION FOR SEQ ID NO:330:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:330:

UCAUUUUUAU GUUAUUACAG GCAUUCAAA U                                     31

( 2 ) INFORMATION FOR SEQ ID NO:331:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:331:

CAUUUUUAUG UUAUUACAGG GCAUUCAAAU G                                    31

( 2 ) INFORMATION FOR SEQ ID NO:332:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:332:

GUUAUUACAG GGCAUUCAAA UGGGCUGCUG C    31

( 2 ) INFORMATION FOR SEQ ID NO:333:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:333:

UUAUUACAGG GCAUUCAAAU GGGCUGCUGC U    31

( 2 ) INFORMATION FOR SEQ ID NO:334:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:334:

AAAUGGGCUG CUGCUUAGCU UGCACCUUGU C    31

( 2 ) INFORMATION FOR SEQ ID NO:335:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:335:

AAUGGGCUGC UGCUUAGCUU GCACCUUGUC A    31

( 2 ) INFORMATION FOR SEQ ID NO:336:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

GGCUGCUGCU UAGCUUGCAC CUUGUCACAU A    31

( 2 ) INFORMATION FOR SEQ ID NO:337:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:337:

GCUUAGCUUG CACCUUGUCA CAUAGAGUGA U    31

( 2 ) INFORMATION FOR SEQ ID NO:338:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:338:

UAGCUUGCAC CUUGUCACAU AGAGUGAUCU U    31

( 2 ) INFORMATION FOR SEQ ID NO:339:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:339:

UGCACCUUGU CACAUAGAGU GAUCUUCCC A      31

( 2 ) INFORMATION FOR SEQ ID NO:340:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

GUCACAUAGA GUGAUCUUUC CCAAGAGAAG G      31

( 2 ) INFORMATION FOR SEQ ID NO:341:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:341:

CACAUAGAGU GAUCUUUCCC AAGAGAAGGG G      31

( 2 ) INFORMATION FOR SEQ ID NO:342:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:342:

ACAUAGAGUG AUCUUUCCCA AGAGAAGGGG A      31

( 2 ) INFORMATION FOR SEQ ID NO:343:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:343:

CAUAGAGUGA UCUUUCCCAA GAGAAGGGGA A      31

( 2 ) INFORMATION FOR SEQ ID NO:344:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:344:

AGAAGGGGAA GCACUCGUGU GCAACAGACA A      31

( 2 ) INFORMATION FOR SEQ ID NO:345:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:345:

CAGACAAGUG ACUGUAUCUG UGUAGACUAU U        31

( 2 ) INFORMATION FOR SEQ ID NO:346:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:346:

GACAAGUGAC UGUAUCUGUG UAGACUAUUU G        31

( 2 ) INFORMATION FOR SEQ ID NO:347:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:347:

UGACUGUAUC UGUGUAGACU AUUUGCUUAU U        31

( 2 ) INFORMATION FOR SEQ ID NO:348:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:348:

GUAUCUGUGU AGACUAUUUG CUUAUUUAAU A        31

( 2 ) INFORMATION FOR SEQ ID NO:349:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:349:

AUCUGUGUAG ACUAUUUGCU UAUUUAAUAA A        31

( 2 ) INFORMATION FOR SEQ ID NO:350:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:350:

UCUGUGUAGA CUAUUUGCUU AUUUAAUAAA G        31

( 2 ) INFORMATION FOR SEQ ID NO:351:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:351:

UGUAGACUAU UUGCUUAUUU AAUAAAGACG A          31

( 2 ) INFORMATION FOR SEQ ID NO:352:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:352:

GUAGACUAUU UGCUUAUUUA AUAAAGACGA U          31

( 2 ) INFORMATION FOR SEQ ID NO:353:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:353:

AGACUAUUUG CUUAUUUAAU AAAGACGAUU U          31

( 2 ) INFORMATION FOR SEQ ID NO:354:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:354:

GACUAUUUGC UUAUUUAAUA AAGACGAUUU G          31

( 2 ) INFORMATION FOR SEQ ID NO:355:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:355:

ACUAUUUGCU UAUUUAAUAA AGACGAUUUG U          31

( 2 ) INFORMATION FOR SEQ ID NO:356:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:356:

AUUUGCUUAU UUAAUAAAGA CGAUUUGUCA G          31

( 2 ) INFORMATION FOR SEQ ID NO:357:

( i ) SEQUENCE CHARACTERISTICS:
    ( A ) LENGTH: 29 base pairs ( B ) TYPE: nucleic acid
( C ) STRANDEDNESS: single
( D ) TOPOLOGY: linear ( x i ) SEQUENCE DESCRIPTION: SEQ ID NO:357:

UUUAAUAAAG ACGAUUUGUC AGUUGUUUU    29

( 2 ) INFORMATION FOR SEQ ID NO:358:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:358:

UUAAUAAAGA CGAUUUGUCA GUUGUUUU    28

( 2 ) INFORMATION FOR SEQ ID NO:359:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:359:

AUAAAGACGA UUUGUCAGUU GUUUU    25

( 2 ) INFORMATION FOR SEQ ID NO:360:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:360:

CUACUGUUGC UGUGCGUGGC AGU    23

( 2 ) INFORMATION FOR SEQ ID NO:361:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:361:

UGGCAGUUUG CUCAGCCUAU CCA    23

( 2 ) INFORMATION FOR SEQ ID NO:362:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:362:

AAACAGUUUG UUAGGAGAAA GGA    23

( 2 ) INFORMATION FOR SEQ ID NO:363:

( i ) SEQUENCE CHARACTERISTICS:
( A ) LENGTH: 23 base pairs
( B ) TYPE: nucleic acid
( C ) STRANDEDNESS: single ( D ) TOPOLOGY: linear ( x i ) SEQUENCE DESCRIPTION: SEQ ID NO:363:

AUGCUGUUGA UUCUGCUGUU GAG  23

( 2 ) INFORMATION FOR SEQ ID NO:364:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:364:

CUGCUGUUGA GAAAGCUCUG AAA  23

( 2 ) INFORMATION FOR SEQ ID NO:365:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:365:

UCACAGACCU GACUCGGUUC CGC  23

( 2 ) INFORMATION FOR SEQ ID NO:366:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:366:

AUGCUGUUUU UGAAGAAUUU GGG  23

( 2 ) INFORMATION FOR SEQ ID NO:367:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:367:

UCACAGUUGG AGUUUGACCC AAA  23

( 2 ) INFORMATION FOR SEQ ID NO:368:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for any
base. The letter "H" stands
for A, U, or C.

( x i ) SEQUENCE DESCRIPTION: SEQ ID NO:368:

NNNNUHNNNN N  11

( 2 ) INFORMATION FOR SEQ ID NO:369:

( i ) SEQUENCE CHARACTERISTICS:

( A ) LENGTH: 28 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for any
base.

( x i ) SEQUENCE DESCRIPTION: SEQ ID NO:369:

NNNNNCUGAN GAGNNNNNC GAAANNNN   28

( 2 ) INFORMATION FOR SEQ ID NO:370:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for any
base. The letter "Y"stands for
U or C. The letter "H"stands
for A, U, or C.

( x i ) SEQUENCE DESCRIPTION: SEQ ID NO:370:

NNNNNNN Y NG H Y NNN   15

( 2 ) INFORMATION FOR SEQ ID NO:371:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for any
base.

( x i ) SEQUENCE DESCRIPTION: SEQ ID NO:371:

NNNNGAAGNN NNNNNNNNA AAHANNNNNN NACAUUACNN NNNNNNN   47

( 2 ) INFORMATION FOR SEQ ID NO:372:

( i ) SEQUENCE CHARACTERISTICS:
( A ) LENGTH: 85 base pairs
( B ) TYPE: nucleic acid
( C ) STRANDEDNESS: single
( D ) TOPOLOGY: linear ( x i ) SEQUENCE DESCRIPTION: SEQ ID NO:372:

UGGCCGGCAU GGUCCCAGCC UCCUCGCUGG CGCCGGCUGG GCAACAUUCC GAGGGGACCG   60

UCCCCUCGGU AAUGGCGAAU GGGAC   85

( 2 ) INFORMATION FOR SEQ ID NO:373:

( i ) SEQUENCE CHARACTERISTICS:
( A ) LENGTH: 176 base pairs
( B ) TYPE: nucleic acid
( C ) STRANDEDNESS: single
( D ) TOPOLOGY: linear ( x i ) SEQUENCE DESCRIPTION: SEQ ID NO:373:

GGGAAAGCUU GCGAAGGGCG UCGUCGCCCC GAGCGGUAGU AAGCAGGGAA CUCACCUCCA   60

AUUUCAGUAC UGAAAUUGUC GUAGCAGUUG ACUACUGUUA UGUGAUUGGU AGAGGCUAAG   120

UGACGGUAUU GGCGUAAGUC AGUAUUGCAG CACAGCACAA GCCCGCUUGC GAGAAU   176

( 2 ) INFORMATION FOR SEQ ID NO:374:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:374:

GGCCGAAAGG CC                                      1 2

( 2 ) INFORMATION FOR SEQ ID NO:375:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:375:

GUUGUCUCCU GAAGAGCACG AAAGUGCGAA AUGCCUUG            3 8

( 2 ) INFORMATION FOR SEQ ID NO:376:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:376:

UUAGCUCCUG AUGAGGCCGA AAGGCCGAAA UGUUGU             3 6

( 2 ) INFORMATION FOR SEQ ID NO:377:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:377:

GAGGUCGCUG AUGAGGCCGA AAGGCCGAAA GUAGUU             3 6

( 2 ) INFORMATION FOR SEQ ID NO:378:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:378:

CUCCAUUCUG AUGAGGCCGA AAGGCCGAAA UCCCUG             3 6

( 2 ) INFORMATION FOR SEQ ID NO:379:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:379:

UCUCCAUCUG AUGAGGCCGA AAGGCCGAAA AUCCCU             3 6

( 2 ) INFORMATION FOR SEQ ID NO:380:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:380:

CAUCAUCACU GAAGAGCACG AAAGUGCGAA AGUGGGCA    3 8

( 2 ) INFORMATION FOR SEQ ID NO:381:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:381:

UCAUCAUCCU GAAGAGCACG AAAGUGCGAA AAGUGGGC    3 8

( 2 ) INFORMATION FOR SEQ ID NO:382:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:382:

CCUGUUGCUG AUGAGGCCGA AAGGCCGAAA UCCUUU    3 6

( 2 ) INFORMATION FOR SEQ ID NO:383:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:383:

ACCCAGGCUG AUGAGGCCGA AAGGCCGAAA GUGGCC    3 6

( 2 ) INFORMATION FOR SEQ ID NO:384:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:384:

GGGACUGCUG AUGAGGCCGA AAGGCCGAAA UGCCAU    3 6

( 2 ) INFORMATION FOR SEQ ID NO:385:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:385:

UCUGGAGGCU GAAGAGCACG AAAGUGCGAA ACAGGUUC    3 8

( 2 ) INFORMATION FOR SEQ ID NO:386:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:386:

CCCCUCACUG AUGAGGCCGA AAGGCCGAAA GUGCUG                    36

( 2 ) INFORMATION FOR SEQ ID NO:387:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:387:

CCUGAGGCUG AUGAGGCCGA AAGGCCGAAA UUUGCG                    36

( 2 ) INFORMATION FOR SEQ ID NO:388:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:388:

UGGCCCACUG AUGAGGCCGA AAGGCCGAAA AUUGAU                    36

( 2 ) INFORMATION FOR SEQ ID NO:389:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:389:

UUUCCUCUCU GAUGAGCACG AAAGUGCGAA AUGGCCCA                  38

( 2 ) INFORMATION FOR SEQ ID NO:390:

( i ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:390:

CCUUAUCACU GAAGAGCACG AAAGUGCGAA AAAUGGCU                  38

( 2 ) INFORMATION FOR SEQ ID NO:391:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:391:

UCUCCAGCUG AUGAGGCCGA AAGGCCGAAA UUUGUC                    36

( 2 ) INFORMATION FOR SEQ ID NO:392:

( i ) SEQUENCE CHARACTERISTICS:
          ( A ) LENGTH: 38 base pairs ( B ) TYPE: nucleic acid
( C ) STRANDEDNESS: single
( D ) TOPOLOGY: linear ( x i ) SEQUENCE DESCRIPTION: SEQ ID NO:392:

UCUCAUCACU GAAGAGCACG AAAGUGCGAA AUCUCCAG     38

( 2 ) INFORMATION FOR SEQ ID NO:393:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:393:

AUCCCUGCUG AUGAGGCCGA AAGGCCGAAA AAGUCU     36

( 2 ) INFORMATION FOR SEQ ID NO:394:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:394:

CAGCAUCCUG AUGAGGCCGA AAGGCCGAAA UCUUUG     36

( 2 ) INFORMATION FOR SEQ ID NO:395:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:395:

UCUUCAAACU GAUGAGCACG AAAGUGCGAA ACAGCAUC     38

( 2 ) INFORMATION FOR SEQ ID NO:396:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:396:

AAACUCCCUG AUGAGGCCGA AAGGCCGAAA CUGUGA     36

( 2 ) INFORMATION FOR SEQ ID NO:397:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:397:

CAAGGCAUCA AGACAGC     17

( 2 ) INFORMATION FOR SEQ ID NO:398:

( i ) SEQUENCE CHARACTERISTICS:
( A ) LENGTH: 17 base pairs
( B ) TYPE: nucleic acid
( C ) STRANDEDNESS: single ( D ) TOPOLOGY: linear ( x i ) SEQUENCE DESCRIPTION: SEQ ID NO:398:

GACAGCAUAG AGCUGAG 17

( 2 ) INFORMATION FOR SEQ ID NO:399:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:399:

AGCUGAGUAA AGCCAAU 17

( 2 ) INFORMATION FOR SEQ ID NO:400:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:400:

UGAAAACUCU UCCAACC 17

( 2 ) INFORMATION FOR SEQ ID NO:401:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:401:

AAAACUCUUC CAACCCU 17

( 2 ) INFORMATION FOR SEQ ID NO:402:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:402:

AAACUCUUCC AACCCUG 17

( 2 ) INFORMATION FOR SEQ ID NO:403:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:403:

ACCCUGCUAC UGCUGUG 17

( 2 ) INFORMATION FOR SEQ ID NO:404:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear -continued ( x i ) SEQUENCE DESCRIPTION: SEQ ID NO:404:

GUGGCGCUUU GCUCAGC     17

( 2 ) INFORMATION FOR SEQ ID NO:405:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:405:

UGGCGCUUUG CUCAGCC     17

( 2 ) INFORMATION FOR SEQ ID NO:406:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:406:

GCUUUGCUCA GCCUAUC     17

( 2 ) INFORMATION FOR SEQ ID NO:407:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:407:

CUCAGCCUAU CCACUGG     17

( 2 ) INFORMATION FOR SEQ ID NO:408:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:408:

CAGCCUAUCC ACUGGAU     17

( 2 ) INFORMATION FOR SEQ ID NO:409:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:409:

UGGAGCCUCA AGGGAUG     17

( 2 ) INFORMATION FOR SEQ ID NO:410:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:410:

AUGGACCUUC UUCAGCA                                                              17

( 2 ) INFORMATION FOR SEQ ID NO:411:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:411:

UGGACCUUCU UCAGCAA                                                              17

( 2 ) INFORMATION FOR SEQ ID NO:412:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:412:

GACCUUCUUC AGCAAUA                                                              17

( 2 ) INFORMATION FOR SEQ ID NO:413:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:413:

ACCUUCUUCA GCAAUAU                                                              17

( 2 ) INFORMATION FOR SEQ ID NO:414:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:414:

UCAGCAAUAU CUGGAAA                                                              17

( 2 ) INFORMATION FOR SEQ ID NO:415:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:415:

AGCAAUAUCU GGAAAAC                                                              17

( 2 ) INFORMATION FOR SEQ ID NO:416:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:416:

GGAAAACUAC UACAACC                                                              17

( 2 ) INFORMATION FOR SEQ ID NO:417:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:417:

AAACUACUAC AACCUUG                      17

( 2 ) INFORMATION FOR SEQ ID NO:418:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:418:

UACAACCUUG AAAAAGA                      17

( 2 ) INFORMATION FOR SEQ ID NO:419:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:419:

GAAACAGUUU GUUAAAA                      17

( 2 ) INFORMATION FOR SEQ ID NO:420:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:420:

AAACAGUUUG UUAAAAG                      17

( 2 ) INFORMATION FOR SEQ ID NO:421:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:421:

CAGUUUGUUA AAAGAAA                      17

( 2 ) INFORMATION FOR SEQ ID NO:422:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:422:

AGUUUGUUAA AAGAAAG                      17

( 2 ) INFORMATION FOR SEQ ID NO:423:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:423:

AGGACAGUAG UCCUGUU                                                                                17

( 2 ) INFORMATION FOR SEQ ID NO:424:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:424:

ACAGUAGUCC UGUUGUU                                                                                17

( 2 ) INFORMATION FOR SEQ ID NO:425:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:425:

AGUCCUGUUG UUAAAAA                                                                                17

( 2 ) INFORMATION FOR SEQ ID NO:426:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:426:

CCUGUUGUUA AAAAAAU                                                                                17

( 2 ) INFORMATION FOR SEQ ID NO:427:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:427:

CUGUUGUUAA AAAAAUC                                                                                17

( 2 ) INFORMATION FOR SEQ ID NO:428:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:428:

AAAAAAAUCC AAGAAAU                                                                                17

( 2 ) INFORMATION FOR SEQ ID NO:429:

( i ) SEQUENCE CHARACTERISTICS:

( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:429:

GCAGAAGUUC CUUGGCU                17

( 2 ) INFORMATION FOR SEQ ID NO:430:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:430:

CAGAAGUUCC UUGGCUU                17

( 2 ) INFORMATION FOR SEQ ID NO:431:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:431:

AAGUUCCUUG GCUUGGA                17

( 2 ) INFORMATION FOR SEQ ID NO:432:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:432:

CCUUGGCUUG GAGGUGA                17

( 2 ) INFORMATION FOR SEQ ID NO:433:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:433:

GCUGGACUCC AACACCC                17

( 2 ) INFORMATION FOR SEQ ID NO:434:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:434:

GAGGUGAUAC GCAAGCC                17

( 2 ) INFORMATION FOR SEQ ID NO:435:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (xi) SEQUENCE DESCRIPTION: SEQ ID NO:435:

UGUGGCGUUC CUGAUGU 17

(2) INFORMATION FOR SEQ ID NO:436:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:436:

GUGGCGUUCC UGAUGUU 17

(2) INFORMATION FOR SEQ ID NO:437:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:437:

CCUGAUGUUG GUCACUU 17

(2) INFORMATION FOR SEQ ID NO:438:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:438:

AUGUUGGUCA CUUCAGU 17

(2) INFORMATION FOR SEQ ID NO:439:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:439:

UGGUCACUUC AGUACCU 17

(2) INFORMATION FOR SEQ ID NO:440:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:440:

GGUCACUUCA GUACCUU 17

(2) INFORMATION FOR SEQ ID NO:441:

(i) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO:441:

ACUUCAGUAC CUUCCCU                                                                                          17

( 2 ) INFORMATION FOR SEQ ID NO:442:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:442:

CAGUACCUUC CCUGGCA                                                                                          17

( 2 ) INFORMATION FOR SEQ ID NO:443:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:443:

AGUACCUUCC CUGGCAC                                                                                          17

( 2 ) INFORMATION FOR SEQ ID NO:444:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:444:

CAAAAACUCA CCUAACU                                                                                          17

( 2 ) INFORMATION FOR SEQ ID NO:445:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:445:

ACUCACCUAA CUUACAG                                                                                          17

( 2 ) INFORMATION FOR SEQ ID NO:446:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:446:

ACCUAACUUA CAGGAUU                                                                                          17

( 2 ) INFORMATION FOR SEQ ID NO:447:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:447:

CCUAACUUAC AGGAUUG                                                                    17

( 2 ) INFORMATION FOR SEQ ID NO:448:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:448:

UACAGGAUUG UGAAUUA                                                                    17

( 2 ) INFORMATION FOR SEQ ID NO:449:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:449:

UUGUGAAUUA CACACCG                                                                    17

( 2 ) INFORMATION FOR SEQ ID NO:450:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:450:

UGUGAAUUAC ACACCGG                                                                    17

( 2 ) INFORMATION FOR SEQ ID NO:451:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:451:

CACCGGAUCU GCCAAGA                                                                    17

( 2 ) INFORMATION FOR SEQ ID NO:452:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:452:

GAUGCUGUUG AUGCUGC                                                                    17

( 2 ) INFORMATION FOR SEQ ID NO:453:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:453:

GCUGCCAUUG AGAAAGC                                                                    17

( 2 ) INFORMATION FOR SEQ ID NO:454:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:454:

AGAAAGCUCU GAAGGUC    17

( 2 ) INFORMATION FOR SEQ ID NO:455:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:455:

CUGAAGGUCU GGGAGGA    17

( 2 ) INFORMATION FOR SEQ ID NO:456:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:456:

AGGUGACUCC ACUCACG    17

( 2 ) INFORMATION FOR SEQ ID NO:457:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:457:

ACUCCACUCA CGUUCUC    17

( 2 ) INFORMATION FOR SEQ ID NO:458:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:458:

ACUCACGUUC UCCAGGA    17

( 2 ) INFORMATION FOR SEQ ID NO:459:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:459:

CUCACGUUCU CCAGGAA    17

( 2 ) INFORMATION FOR SEQ ID NO:460:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:460:

CACGUUCUCC AGGAAGU    17

( 2 ) INFORMATION FOR SEQ ID NO:461:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:461:

CAGGAAGUAU GAAGGAG    17

( 2 ) INFORMATION FOR SEQ ID NO:462:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:462:

GCUGACAUAA UGAUCUC    17

( 2 ) INFORMATION FOR SEQ ID NO:463:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:463:

AUAAUGAUCU CUUUUGG    17

( 2 ) INFORMATION FOR SEQ ID NO:464:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:464:

AAUGAUCUCU UUUGGAG    17

( 2 ) INFORMATION FOR SEQ ID NO:465:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:465:

UGAUCUCUUU UGGAGUC    17

( 2 ) INFORMATION FOR SEQ ID NO:466:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:466:

GAUCUCUUUU GGAGUCC 17

( 2 ) INFORMATION FOR SEQ ID NO:467:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:467:

AUCUCUUUUG GAGUCCG 17

( 2 ) INFORMATION FOR SEQ ID NO:468:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:468:

UUUGGAGUCC GAGAACA 17

( 2 ) INFORMATION FOR SEQ ID NO:469:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:469:

AUGGAGAUUU UAUUCCU 17

( 2 ) INFORMATION FOR SEQ ID NO:470:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:470:

UGGAGAUUUU AUUCCUU 17

( 2 ) INFORMATION FOR SEQ ID NO:471:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:471:

GGAGAUUUUA UUCCUUU 17

( 2 ) INFORMATION FOR SEQ ID NO:472:

( i ) SEQUENCE CHARACTERISTICS:
    ( A ) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO:472:

GAGAUUUUAU UCCUUUU                          17

( 2 ) INFORMATION FOR SEQ ID NO:473:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:473:

GAUUUUAUUC CUUUUGA                          17

( 2 ) INFORMATION FOR SEQ ID NO:474:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:474:

AUUUUAUUCC UUUUGAU                          17

( 2 ) INFORMATION FOR SEQ ID NO:475:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:475:

UUAUUCCUUU UGAUGGA                          17

( 2 ) INFORMATION FOR SEQ ID NO:476:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:476:

UAUUCCUUUU GAUGGAC                          17

( 2 ) INFORMATION FOR SEQ ID NO:477:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:477:

AUUCCUUUUG AUGGACC                          17

( 2 ) INFORMATION FOR SEQ ID NO:478:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( x i ) SEQUENCE DESCRIPTION: SEQ ID NO:478:

GGAAAUGUUU UGGCUCA                                                    17

( 2 ) INFORMATION FOR SEQ ID NO:479:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:479:

GAAAUGUUUU GGCUCAU                                                    17

( 2 ) INFORMATION FOR SEQ ID NO:480:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:480:

AAAUGUUUUG GCUCAUG                                                    17

( 2 ) INFORMATION FOR SEQ ID NO:481:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:481:

UUUUGGCUCA UGCUUAU                                                    17

( 2 ) INFORMATION FOR SEQ ID NO:482:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:482:

CUCAUGCUUA UGCACCU                                                    17

( 2 ) INFORMATION FOR SEQ ID NO:483:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:483:

UCAUGCUUAU GCACCUG                                                    17

( 2 ) INFORMATION FOR SEQ ID NO:484:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:484:

CCAGGAAUUA AUGGAGA 17

( 2 ) INFORMATION FOR SEQ ID NO:485:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:485:

CAGGAAUUAA UGGAGAU 17

( 2 ) INFORMATION FOR SEQ ID NO:486:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:486:

UGCCCACUUU GAUGAUG 17

( 2 ) INFORMATION FOR SEQ ID NO:487:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:487:

GCCCACUUUG AUGAUGA 17

( 2 ) INFORMATION FOR SEQ ID NO:488:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:488:

CAAAGGAUAC AACAGGA 17

( 2 ) INFORMATION FOR SEQ ID NO:489:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:489:

GAACCAAUUU AUUCCUU 17

( 2 ) INFORMATION FOR SEQ ID NO:490:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:490:

```
AACCAAUUUA UUCCUUG                                                    17
```

(2) INFORMATION FOR SEQ ID NO:491:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:491:

```
ACCAAUUUAU UCCUUGU                                                    17
```

(2) INFORMATION FOR SEQ ID NO:492:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:492:

```
CAAUUUAUUC CUUGUUG                                                    17
```

(2) INFORMATION FOR SEQ ID NO:493:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:493:

```
AAUUUAUUCC UUGUUGC                                                    17
```

(2) INFORMATION FOR SEQ ID NO:494:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:494:

```
UUAUUCCUUG UUGCUGC                                                    17
```

(2) INFORMATION FOR SEQ ID NO:495:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:495:

```
UUCCUUGUUG CUGCUCA                                                    17
```

(2) INFORMATION FOR SEQ ID NO:496:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:496:

```
UUGCUGCUCA UGAGCUU                                                    17
```

( 2 ) INFORMATION FOR SEQ ID NO:497:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:497:

CAUGAGCUUG GCCACUC 17

( 2 ) INFORMATION FOR SEQ ID NO:498:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:498:

UGGCCACUCC CUGGGUC 17

( 2 ) INFORMATION FOR SEQ ID NO:499:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:499:

CCCUGGGUCU GUUUCAC 17

( 2 ) INFORMATION FOR SEQ ID NO:500:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:500:

GGGUCUGUUU CACUCGG 17

( 2 ) INFORMATION FOR SEQ ID NO:501:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:501:

GGUCUGUUUC ACUCGGC 17

( 2 ) INFORMATION FOR SEQ ID NO:502:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:502:

GUCUGUUUCA CUCGGCC 17

( 2 ) INFORMATION FOR SEQ ID NO:503:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:503:

GUUCACUCG GCCAACC                                                                    17

(2) INFORMATION FOR SEQ ID NO:504:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:504:

GCUGAUGUAC CCAGUCU                                                                   17

(2) INFORMATION FOR SEQ ID NO:505:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:505:

UACCCAGUCU ACAACGC                                                                   17

(2) INFORMATION FOR SEQ ID NO:506:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:506:

CCCAGUCUAC AACGCCU                                                                   17

(2) INFORMATION FOR SEQ ID NO:507:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:507:

CAACGCCUUC ACAGACC                                                                   17

(2) INFORMATION FOR SEQ ID NO:508:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:508:

AACGCCUUCA CAGACCU                                                                   17

(2) INFORMATION FOR SEQ ID NO:509:

(i) SEQUENCE CHARACTERISTICS:

( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:509:

GGCCCGGUUC CGCCUUU                                                              17

( 2 ) INFORMATION FOR SEQ ID NO:510:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:510:

GCCCGGUUCC GCCUUUC                                                              17

( 2 ) INFORMATION FOR SEQ ID NO:511:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:511:

UUCCGCCUUU CUCAAGA                                                              17

( 2 ) INFORMATION FOR SEQ ID NO:512:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:512:

UCCGCCUUUC UCAAGAU                                                              17

( 2 ) INFORMATION FOR SEQ ID NO:513:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:513:

CCGCCUUUCU CAAGAUG                                                              17

( 2 ) INFORMATION FOR SEQ ID NO:514:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:514:

GCCUUUCUCA AGAUGAU                                                              17

( 2 ) INFORMATION FOR SEQ ID NO:515:

( i ) SEQUENCE CHARACTERISTICS:
            ( A ) LENGTH: 17 base pairs
            ( B ) TYPE: nucleic acid (C) STRANDEDNESS: single
        (D) TOPOLOGY: linear (xi) SEQUENCE DESCRIPTION: SEQ ID NO:515:

GAUGGCAUCC AAUCCCU                            17

(2) INFORMATION FOR SEQ ID NO:516:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:516:

CAUCCAAUCC CUCUAUG                            17

(2) INFORMATION FOR SEQ ID NO:517:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:517:

CAAUCCCUCU AUGGACC                            17

(2) INFORMATION FOR SEQ ID NO:518:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:518:

AUCCCUCUAU GGACCGG                            17

(2) INFORMATION FOR SEQ ID NO:519:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:519:

CCCUGCCUCU CCUGAUA                            17

(2) INFORMATION FOR SEQ ID NO:520:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:520:

CUGCCUCUCC UGAUAAC                            17

(2) INFORMATION FOR SEQ ID NO:521:

(i) SEQUENCE CHARACTERISTICS:
        (A) LENGTH: 17 base pairs
        (B) TYPE: nucleic acid
        (C) STRANDEDNESS: single
        (D) TOPOLOGY: linear ( x i ) SEQUENCE DESCRIPTION: SEQ ID NO:521:

CUCCUGAUAA CUCUGGA 17

( 2 ) INFORMATION FOR SEQ ID NO:522:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:522:

UGAUAACUCU GGAGUGC 17

( 2 ) INFORMATION FOR SEQ ID NO:523:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:523:

GAGUGCCUAU GGAACCU 17

( 2 ) INFORMATION FOR SEQ ID NO:524:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:524:

GAACCUGUCC CUCCAGG 17

( 2 ) INFORMATION FOR SEQ ID NO:525:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:525:

CUGUCCCUCC AGGAUCU 17

( 2 ) INFORMATION FOR SEQ ID NO:526:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:526:

UCCAGGAUCU GGGACCC 17

( 2 ) INFORMATION FOR SEQ ID NO:527:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:527:

ACCCCAGUCA UGUGUGA                                                              17

(2) INFORMATION FOR SEQ ID NO:528:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:528:

UGUGUGAUCC AGAUCUG                                                              17

(2) INFORMATION FOR SEQ ID NO:529:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:529:

AUCCAGAUCU GUCCUUC                                                              17

(2) INFORMATION FOR SEQ ID NO:530:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:530:

AGAUCUGUCC UUCGAUG                                                              17

(2) INFORMATION FOR SEQ ID NO:531:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:531:

UCUGUCCUUC GAUGCAA                                                              17

(2) INFORMATION FOR SEQ ID NO:532:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:532:

CUGUCCUUCG AUGCAAU                                                              17

(2) INFORMATION FOR SEQ ID NO:533:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:533:

GAUGCAAUCA GCACUCU                                                              17

( 2 ) INFORMATION FOR SEQ ID NO:534:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:534:

UCAGCACUCU GAGGGGA 17

( 2 ) INFORMATION FOR SEQ ID NO:535:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:535:

GGAGAAAUUC UGUUCUU 17

( 2 ) INFORMATION FOR SEQ ID NO:536:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:536:

GAGAAAUUCU GUUCUUU 17

( 2 ) INFORMATION FOR SEQ ID NO:537:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:537:

AAUUCUGUUC UUUAAAG 17

( 2 ) INFORMATION FOR SEQ ID NO:538:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:538:

AUUCUGUUCU UUAAAGA 17

( 2 ) INFORMATION FOR SEQ ID NO:539:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:539:

UCUGUUCUUU AAAGACA 17

( 2 ) INFORMATION FOR SEQ ID NO:540:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:540:

CUGUUCUUUA AAGACAG                                                  17

( 2 ) INFORMATION FOR SEQ ID NO:541:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:541:

UGUUCUUUAA AGACAGG                                                  17

( 2 ) INFORMATION FOR SEQ ID NO:542:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:542:

AGACAGGUAU UUCUGGC                                                  17

( 2 ) INFORMATION FOR SEQ ID NO:543:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:543:

ACAGGUAUUU CUGGCGC                                                  17

( 2 ) INFORMATION FOR SEQ ID NO:544:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:544:

CAGGUAUUUC UGGCGCA                                                  17

( 2 ) INFORMATION FOR SEQ ID NO:545:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:545:

AGGUAUUUCU GGCGCAA                                                  17

( 2 ) INFORMATION FOR SEQ ID NO:546:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:546:

GCGCAAGUCC CUCAGGA 17

( 2 ) INFORMATION FOR SEQ ID NO:547:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:547:

AAGUCCCUCA GGAUUCU 17

( 2 ) INFORMATION FOR SEQ ID NO:548:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:548:

CUCAGGAUUC UCGAACC 17

( 2 ) INFORMATION FOR SEQ ID NO:549:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:549:

UCAGGAUUCU CGAACCU 17

( 2 ) INFORMATION FOR SEQ ID NO:550:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:550:

AGGAUUCUCG AACCUGA 17

( 2 ) INFORMATION FOR SEQ ID NO:551:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:551:

ACCUGAGUUU CAUUUGA 17

( 2 ) INFORMATION FOR SEQ ID NO:552:

( i ) SEQUENCE CHARACTERISTICS:
    ( A ) LENGTH: 17 base pairs (B) TYPE: nucleic acid
        (C) STRANDEDNESS: single
        (D) TOPOLOGY: linear (xi) SEQUENCE DESCRIPTION: SEQ ID NO:552:

CCUGAGUUUC AUUUGAU 17

(2) INFORMATION FOR SEQ ID NO:553:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:553:

CUGAGUUUCA UUUGAUC 17

(2) INFORMATION FOR SEQ ID NO:554:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:554:

AGUUUCAUUU GAUCUCU 17

(2) INFORMATION FOR SEQ ID NO:555:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:555:

GUUUCAUUUG AUCUCUU 17

(2) INFORMATION FOR SEQ ID NO:556:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:556:

CAUUUGAUCU CUUCAUU 17

(2) INFORMATION FOR SEQ ID NO:557:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:557:

UUUGAUCUCU UCAUUCU 17

(2) INFORMATION FOR SEQ ID NO:558:

(i) SEQUENCE CHARACTERISTICS:
        (A) LENGTH: 17 base pairs
        (B) TYPE: nucleic acid
        (C) STRANDEDNESS: single ( D ) TOPOLOGY: linear ( x i ) SEQUENCE DESCRIPTION: SEQ ID NO:558:

UGAUCUCUUC AUUCUGG 17

( 2 ) INFORMATION FOR SEQ ID NO:559:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:559:

GAUCUCUUCA UUCUGGC 17

( 2 ) INFORMATION FOR SEQ ID NO:560:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:560:

CUCUUCAUUC UGGCCAU 17

( 2 ) INFORMATION FOR SEQ ID NO:561:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:561:

UCUUCAUUCU GGCCAUC 17

( 2 ) INFORMATION FOR SEQ ID NO:562:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:562:

CUGGCCAUCU CUUCCUU 17

( 2 ) INFORMATION FOR SEQ ID NO:563:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:563:

GGCCAUCUCU UCCUUCA 17

( 2 ) INFORMATION FOR SEQ ID NO:564:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:564:

CCAUCUCUUC CUUCAGC 17

( 2 ) INFORMATION FOR SEQ ID NO:565:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:565:

CAUCUCUUCC UUCAGCA 17

( 2 ) INFORMATION FOR SEQ ID NO:566:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:566:

CUCUUCCUUC AGCAGUG 17

( 2 ) INFORMATION FOR SEQ ID NO:567:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:567:

UCUUCCUUCA GCAGUGG 17

( 2 ) INFORMATION FOR SEQ ID NO:568:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:568:

UGCUGCAUAU GAAGUUA 17

( 2 ) INFORMATION FOR SEQ ID NO:569:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:569:

UAUGAAGUUA UUAGCAG 17

( 2 ) INFORMATION FOR SEQ ID NO:570:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:570:

AUGAAGUUAU UAGCAGG 17

( 2 ) INFORMATION FOR SEQ ID NO:571:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:571:

GAAGUUAUUA GCAGGGA 17

( 2 ) INFORMATION FOR SEQ ID NO:572:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:572:

AAGUUAUUAG CAGGGAU 17

( 2 ) INFORMATION FOR SEQ ID NO:573:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:573:

GCAGGGAUAC UGUUUUC 17

( 2 ) INFORMATION FOR SEQ ID NO:574:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:574:

GAUACUGUUU UCAUUUU 17

( 2 ) INFORMATION FOR SEQ ID NO:575:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:575:

AUACUGUUUU CAUUUUU 17

( 2 ) INFORMATION FOR SEQ ID NO:576:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:576:

UACUGUUUUC AUUUUA 17

( 2 ) INFORMATION FOR SEQ ID NO:577:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:577:

ACUGUUUUCA UUUUUAA 17

( 2 ) INFORMATION FOR SEQ ID NO:578:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:578:

GUUUCAUUU UUAAAGG 17

( 2 ) INFORMATION FOR SEQ ID NO:579:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:579:

UUUCAUUUU UAAAGGA 17

( 2 ) INFORMATION FOR SEQ ID NO:580:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:580:

UUUCAUUUUU AAAGGAA 17

( 2 ) INFORMATION FOR SEQ ID NO:581:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:581:

UUCAUUUUA AAGGAAC 17

( 2 ) INFORMATION FOR SEQ ID NO:582:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:582:

UCAUUUUAA AGGAACU 17

( 2 ) INFORMATION FOR SEQ ID NO:583:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:583:

AAGGAACUCA GUUCUGG                                              17

( 2 ) INFORMATION FOR SEQ ID NO:584:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:584:

AACUCAGUUC UGGGCCA                                              17

( 2 ) INFORMATION FOR SEQ ID NO:585:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:585:

ACUCAGUUCU GGGCCAU                                              17

( 2 ) INFORMATION FOR SEQ ID NO:586:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:586:

UGGGCCAUUA GAGGAAA                                              17

( 2 ) INFORMATION FOR SEQ ID NO:587:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:587:

GGGCCAUUAG AGGAAAU                                              17

( 2 ) INFORMATION FOR SEQ ID NO:588:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:588:

AAUGAGGUAC AAGCUGG                                              17

( 2 ) INFORMATION FOR SEQ ID NO:589:

( i ) SEQUENCE CHARACTERISTICS:

( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:589:

AAGCUGGUUA CCCAAGA                                                                 17

( 2 ) INFORMATION FOR SEQ ID NO:590:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:590:

AGCUGGUUAC CCAAGAA                                                                 17

( 2 ) INFORMATION FOR SEQ ID NO:591:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:591:

AGAAGCAUCC ACACCCU                                                                 17

( 2 ) INFORMATION FOR SEQ ID NO:592:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:592:

CCCUGGGUUU CCCUUCA                                                                 17

( 2 ) INFORMATION FOR SEQ ID NO:593:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:593:

CCUGGGUUUC CCUUCAA                                                                 17

( 2 ) INFORMATION FOR SEQ ID NO:594:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:594:

CUGGGUUUCC CUUCAAC                                                                 17

( 2 ) INFORMATION FOR SEQ ID NO:595:

( i ) SEQUENCE CHARACTERISTICS:
                    ( A ) LENGTH: 17 base pairs
                    ( B ) TYPE: nucleic acid ( C ) STRANDEDNESS: single
( D ) TOPOLOGY: linear ( x i ) SEQUENCE DESCRIPTION: SEQ ID NO:595:

GUUCCCUUC AACCAUA 17

( 2 ) INFORMATION FOR SEQ ID NO:596:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:596:

UUUCCCUUCA ACCAUAA 17

( 2 ) INFORMATION FOR SEQ ID NO:597:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:597:

UCAACCAUAA GAAAAAU 17

( 2 ) INFORMATION FOR SEQ ID NO:598:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:598:

AGAAAAAUUG AUGCUGC 17

( 2 ) INFORMATION FOR SEQ ID NO:599:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:599:

GCUGCCAUUU CUGAUAA 17

( 2 ) INFORMATION FOR SEQ ID NO:600:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:600:

CUGCCAUUUC UGAUAAG 17

( 2 ) INFORMATION FOR SEQ ID NO:601:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:601:

UGCCAUUUCU GAUAAGG 17

( 2 ) INFORMATION FOR SEQ ID NO:602:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:602:

UUUCUGAUAA GGAAAGG 17

( 2 ) INFORMATION FOR SEQ ID NO:603:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:603:

GAAAACAUAC UUCUUUG 17

( 2 ) INFORMATION FOR SEQ ID NO:604:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:604:

AACAUACUUC UUUGUGG 17

( 2 ) INFORMATION FOR SEQ ID NO:605:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:605:

ACAUACUUCU UUGUGGA 17

( 2 ) INFORMATION FOR SEQ ID NO:606:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:606:

AUACUUCUUU GUGGAAG 17

( 2 ) INFORMATION FOR SEQ ID NO:607:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:607:

UACUUCUUUG UGGAAGA                                                              17

(2) INFORMATION FOR SEQ ID NO:608:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:608:

AGACAAAUAC UGGAGGU                                                              17

(2) INFORMATION FOR SEQ ID NO:609:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:609:

CUGGAGGUUU GAUGAGA                                                              17

(2) INFORMATION FOR SEQ ID NO:610:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:610:

UGGAGGUUUG AUGAGAA                                                              17

(2) INFORMATION FOR SEQ ID NO:611:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:611:

GAGACAGUCC CUGGAGC                                                              17

(2) INFORMATION FOR SEQ ID NO:612:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:612:

GCCAGGCUUU CCCAGAC                                                              17

(2) INFORMATION FOR SEQ ID NO:613:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:613:

CCAGGCUUUC CCAGACA                                                              17

( 2 ) INFORMATION FOR SEQ ID NO:614:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:614:

CAGGCUUUCC CAGACAU          17

( 2 ) INFORMATION FOR SEQ ID NO:615:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:615:

CCAGACAUAU AGCAGAA          17

( 2 ) INFORMATION FOR SEQ ID NO:616:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:616:

AGACAUAUAG CAGAAGA          17

( 2 ) INFORMATION FOR SEQ ID NO:617:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:617:

AGAAGACUUU CCAGGAA          17

( 2 ) INFORMATION FOR SEQ ID NO:618:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:618:

GAAGACUUUC CAGGAAU          17

( 2 ) INFORMATION FOR SEQ ID NO:619:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:619:

AAGACUUUCC AGGAAUU          17

( 2 ) INFORMATION FOR SEQ ID NO:620:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:620:

CCAGGAAUUA AUCCAAA   17

( 2 ) INFORMATION FOR SEQ ID NO:621:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:621:

CAGGAAUUAA UCCAAAG   17

( 2 ) INFORMATION FOR SEQ ID NO:622:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:622:

GAAUUAAUCC AAAGAUC   17

( 2 ) INFORMATION FOR SEQ ID NO:623:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:623:

CCAAAGAUCG AUGCUGU   17

( 2 ) INFORMATION FOR SEQ ID NO:624:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:624:

GAUGCUGUUU UUGAAGC   17

( 2 ) INFORMATION FOR SEQ ID NO:625:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:625:

AUGCUGUUUU UGAAGCA   17

( 2 ) INFORMATION FOR SEQ ID NO:626:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:626:

UGCUGUUUUU GAAGCAU 17

(2) INFORMATION FOR SEQ ID NO:627:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:627:

GCUGUUUUUG AAGCAUU 17

(2) INFORMATION FOR SEQ ID NO:628:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:628:

UGAAGCAUUU GGGUUUU 17

(2) INFORMATION FOR SEQ ID NO:629:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:629:

GAAGCAUUUG GGUUUUU 17

(2) INFORMATION FOR SEQ ID NO:630:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:630:

AUUUGGGUUU UUCUAUU 17

(2) INFORMATION FOR SEQ ID NO:631:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:631:

UUUGGGUUUU UCUAUUU 17

(2) INFORMATION FOR SEQ ID NO:632:

(i) SEQUENCE CHARACTERISTICS:
    (A) LENGTH: 17 base pairs ( B ) TYPE: nucleic acid
            ( C ) STRANDEDNESS: single
            ( D ) TOPOLOGY: linear ( x i ) SEQUENCE DESCRIPTION: SEQ ID NO:632:

UUGGGUUUUU CUAUUUC                                                                              17

( 2 ) INFORMATION FOR SEQ ID NO:633:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:633:

UGGGUUUUUC UAUUCU                                                                               17

( 2 ) INFORMATION FOR SEQ ID NO:634:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:634:

GGGUUUUUCU AUUCUU                                                                               17

( 2 ) INFORMATION FOR SEQ ID NO:635:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:635:

GUUUUCUAU UUCUUCA                                                                               17

( 2 ) INFORMATION FOR SEQ ID NO:636:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:636:

UUUUCUAUUU CUUCAGU                                                                              17

( 2 ) INFORMATION FOR SEQ ID NO:637:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:637:

UUUCUAUUUC UUCAGUG                                                                              17

( 2 ) INFORMATION FOR SEQ ID NO:638:

( i ) SEQUENCE CHARACTERISTICS:
            ( A ) LENGTH: 17 base pairs
            ( B ) TYPE: nucleic acid
            ( C ) STRANDEDNESS: single ( D ) TOPOLOGY: linear ( x i ) SEQUENCE DESCRIPTION: SEQ ID NO:638:

UUCUAUUUCU UCAGUGG                                                                              17

( 2 ) INFORMATION FOR SEQ ID NO:639:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:639:

CUAUUUCUUC AGUGGAU                                                                              17

( 2 ) INFORMATION FOR SEQ ID NO:640:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:640:

UAUUUCUUCA GUGGAUC                                                                              17

( 2 ) INFORMATION FOR SEQ ID NO:641:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:641:

CAGUGGAUCU UCACAGU                                                                              17

( 2 ) INFORMATION FOR SEQ ID NO:642:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:642:

GUGGAUCUUC ACAGUCG                                                                              17

( 2 ) INFORMATION FOR SEQ ID NO:643:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:643:

UGGAUCUUCA CAGUCGG                                                                              17

( 2 ) INFORMATION FOR SEQ ID NO:644:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:644:

UUCACAGUCG GAGUUUG    17

( 2 ) INFORMATION FOR SEQ ID NO:645:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:645:

GUCGGAGUUU GACCCAA    17

( 2 ) INFORMATION FOR SEQ ID NO:646:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:646:

UCGGAGUUUG ACCCAAA    17

( 2 ) INFORMATION FOR SEQ ID NO:647:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:647:

ACACAUGUUU UGAAGAG    17

( 2 ) INFORMATION FOR SEQ ID NO:648:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:648:

CACAUGUUUU GAAGAGC    17

( 2 ) INFORMATION FOR SEQ ID NO:649:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:649:

ACAUGUUUUG AAGAGCA    17

( 2 ) INFORMATION FOR SEQ ID NO:650:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:650:

CAGCUGGUUU CAGUGUU                                                                              17

( 2 ) INFORMATION FOR SEQ ID NO:651:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:651:

AGCUGGUUUC AGUGUUA                                                                              17

( 2 ) INFORMATION FOR SEQ ID NO:652:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:652:

GCUGGUUUCA GUGUUAG                                                                              17

( 2 ) INFORMATION FOR SEQ ID NO:653:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:653:

UUCAGUGUUA GGAGGGG                                                                              17

( 2 ) INFORMATION FOR SEQ ID NO:654:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:654:

UCAGUGUUAG GAGGGGU                                                                              17

( 2 ) INFORMATION FOR SEQ ID NO:655:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:655:

AGGGGUGUAU AGAAGGC                                                                              17

( 2 ) INFORMATION FOR SEQ ID NO:656:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:656:

GGGUGUAUAG AAGGCAC                                                                              17

( 2 ) INFORMATION FOR SEQ ID NO:657:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:657:

AUGAAUGUUU UAAAUGA     17

( 2 ) INFORMATION FOR SEQ ID NO:658:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:658:

UGAAUGUUUU AAAUGAA     17

( 2 ) INFORMATION FOR SEQ ID NO:659:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:659:

GAAUGUUUA AAUGAAC     17

( 2 ) INFORMATION FOR SEQ ID NO:660:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:660:

AAUGUUUUAA AUGAACC     17

( 2 ) INFORMATION FOR SEQ ID NO:661:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:661:

AUGAACCUAA UUGUUCA     17

( 2 ) INFORMATION FOR SEQ ID NO:662:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:662:

AACCUAAUUG UUCAACA     17

( 2 ) INFORMATION FOR SEQ ID NO:663:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:663:

CUAAUUGUUC AACACUU                17

( 2 ) INFORMATION FOR SEQ ID NO:664:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:664:

UAAUUGUUCA ACACUUA                17

( 2 ) INFORMATION FOR SEQ ID NO:665:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:665:

UCAACACUUA GGACUUU                17

( 2 ) INFORMATION FOR SEQ ID NO:666:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:666:

CAACACUUAG GACUUUG                17

( 2 ) INFORMATION FOR SEQ ID NO:667:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:667:

UUAGGACUUU GUGAGUU                17

( 2 ) INFORMATION FOR SEQ ID NO:668:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:668:

UAGGACUUUG UGAGUUG                17

( 2 ) INFORMATION FOR SEQ ID NO:669:

( i ) SEQUENCE CHARACTERISTICS:

( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:669:

UUGUGAGUUG AAGUGGC                                                                  17

( 2 ) INFORMATION FOR SEQ ID NO:670:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:670:

AAGUGGCUCA UUUUCUC                                                                  17

( 2 ) INFORMATION FOR SEQ ID NO:671:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:671:

UGGCUCAUUU UCUCCUG                                                                  17

( 2 ) INFORMATION FOR SEQ ID NO:672:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:672:

GGCUCAUUUU CUCCUGC                                                                  17

( 2 ) INFORMATION FOR SEQ ID NO:673:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:673:

GCUCAUUUC UCCUGCA                                                                   17

( 2 ) INFORMATION FOR SEQ ID NO:674:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:674:

CUCAUUUUCU CCUGCAU                                                                  17

( 2 ) INFORMATION FOR SEQ ID NO:675:

( i ) SEQUENCE CHARACTERISTICS:
            ( A ) LENGTH: 17 base pairs
            ( B ) TYPE: nucleic acid

```
            ( C ) STRANDEDNESS: single
            ( D ) TOPOLOGY: linear ( x i ) SEQUENCE DESCRIPTION: SEQ ID NO:675:

CAUUUUCUCC UGCAUAU                                                              17

( 2 ) INFORMATION FOR SEQ ID NO:676:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:676:

UCCUGCAUAU GCUGUGA                                                              17

( 2 ) INFORMATION FOR SEQ ID NO:677:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:677:

AUGGGAAUCU CGAGCAU                                                              17

( 2 ) INFORMATION FOR SEQ ID NO:678:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:678:

GGGAAUCUCG AGCAUGA                                                              17

( 2 ) INFORMATION FOR SEQ ID NO:679:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:679:

AACUGUGUAU CUAACUG                                                              17

( 2 ) INFORMATION FOR SEQ ID NO:680:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:680:

CUGUGUAUCU AACUGGA                                                              17

( 2 ) INFORMATION FOR SEQ ID NO:681:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear
```

( x i ) SEQUENCE DESCRIPTION: SEQ ID NO:681:

GUGUAUCUAA CUGGACU 17

( 2 ) INFORMATION FOR SEQ ID NO:682:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:682:

ACUGGACUUU GCACAUC 17

( 2 ) INFORMATION FOR SEQ ID NO:683:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:683:

CUGGACUUUG CACAUCG 17

( 2 ) INFORMATION FOR SEQ ID NO:684:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:684:

UUGCACAUCG UUACGGG 17

( 2 ) INFORMATION FOR SEQ ID NO:685:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:685:

CACAUCGUUA CGGGUGU 17

( 2 ) INFORMATION FOR SEQ ID NO:686:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:686:

ACAUCGUUAC GGGUGUU 17

( 2 ) INFORMATION FOR SEQ ID NO:687:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:687:

ACGGGUGUUC AAACAGG 17

(2) INFORMATION FOR SEQ ID NO:688:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:688:

CGGGUGUUCA AACAGGC 17

(2) INFORMATION FOR SEQ ID NO:689:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:689:

CUGCUGCUUA GCUUGCA 17

(2) INFORMATION FOR SEQ ID NO:690:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:690:

UGCUGCUUAG CUUGCAC 17

(2) INFORMATION FOR SEQ ID NO:691:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:691:

GCUUAGCUUG CACUUGA 17

(2) INFORMATION FOR SEQ ID NO:692:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:692:

CUUGCACUUG AUCACAU 17

(2) INFORMATION FOR SEQ ID NO:693:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:693:

CACUUGAUCA CAUGGAA 17

( 2 ) INFORMATION FOR SEQ ID NO:694:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:694:

AGGGAGCUUC CACGAGA     17

( 2 ) INFORMATION FOR SEQ ID NO:695:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:695:

GGGAGCUUCC ACGAGAC     17

( 2 ) INFORMATION FOR SEQ ID NO:696:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:696:

GGGGAAGUAC UCAUGUG     17

( 2 ) INFORMATION FOR SEQ ID NO:697:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:697:

GAAGUACUCA UGUGUGA     17

( 2 ) INFORMATION FOR SEQ ID NO:698:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:698:

CGAGUGAUUG UGUCUAU     17

( 2 ) INFORMATION FOR SEQ ID NO:699:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:699:

GAUUGUGUCU AUGUGGA     17

( 2 ) INFORMATION FOR SEQ ID NO:700:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:700:

UUGUGUCUAU GUGGAUU　　　　　　　　　　　　　　　　　　　　　　　　　　　17

( 2 ) INFORMATION FOR SEQ ID NO:701:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:701:

AUGUGGAUUA UUUGCCC　　　　　　　　　　　　　　　　　　　　　　　　　　　17

( 2 ) INFORMATION FOR SEQ ID NO:702:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:702:

UGUGGAUUAU UUGCCCA　　　　　　　　　　　　　　　　　　　　　　　　　　　17

( 2 ) INFORMATION FOR SEQ ID NO:703:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:703:

UGGAUUAUUU GCCCAUU　　　　　　　　　　　　　　　　　　　　　　　　　　　17

( 2 ) INFORMATION FOR SEQ ID NO:704:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:704:

GGAUUAUUUG CCCAUUA　　　　　　　　　　　　　　　　　　　　　　　　　　　17

( 2 ) INFORMATION FOR SEQ ID NO:705:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:705:

UUGCCCAUUA UUUAAUA　　　　　　　　　　　　　　　　　　　　　　　　　　　17

( 2 ) INFORMATION FOR SEQ ID NO:706:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:706:

UGCCCAUUAU UUAAUAA                                                                    17

( 2 ) INFORMATION FOR SEQ ID NO:707:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:707:

CCCAUUAUUU AAUAAAG                                                        17

( 2 ) INFORMATION FOR SEQ ID NO:708:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:708:

CCAUUAUUUA AUAAAGA                                                       17

( 2 ) INFORMATION FOR SEQ ID NO:709:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:709:

CAUUAUUUAA UAAAGAG                                                      17

( 2 ) INFORMATION FOR SEQ ID NO:710:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:710:

UAUUUAAUAA AGAGGAU                                                      17

( 2 ) INFORMATION FOR SEQ ID NO:711:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:711:

AAGAGGAUUU GUCAAUU                                                     17

( 2 ) INFORMATION FOR SEQ ID NO:712:

( i ) SEQUENCE CHARACTERISTICS:
        ( A ) LENGTH: 38 base pairs ( B ) TYPE: nucleic acid
( C ) STRANDEDNESS: single
( D ) TOPOLOGY: linear ( x i ) SEQUENCE DESCRIPTION: SEQ ID NO:712:

GCUGUCUUCU GAUGAGGCCG AAAGGCCGAA AUGCCUUG            38

( 2 ) INFORMATION FOR SEQ ID NO:713:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:713:

CUCAGCUCCU GAUGAGGCCG AAAGGCCGAA AUGCUGUC            38

( 2 ) INFORMATION FOR SEQ ID NO:714:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:714:

AUUGGCUUCU GAUGAGGCCG AAAGGCCGAA ACUCAGCU            38

( 2 ) INFORMATION FOR SEQ ID NO:715:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:715:

GGUUGGAACU GAUGAGGCCG AAAGGCCGAA AGUUUUCA            38

( 2 ) INFORMATION FOR SEQ ID NO:716:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:716:

AGGGUUGGCU GAUGAGGCCG AAAGGCCGAA AGAGUUUU            38

( 2 ) INFORMATION FOR SEQ ID NO:717:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:717:

CAGGGUUGCU GAUGAGGCCG AAAGGCCGAA AAGAGUUU            38

( 2 ) INFORMATION FOR SEQ ID NO:718:

( i ) SEQUENCE CHARACTERISTICS:
( A ) LENGTH: 38 base pairs
( B ) TYPE: nucleic acid
( C ) STRANDEDNESS: single ( D ) TOPOLOGY: linear ( x i ) SEQUENCE DESCRIPTION: SEQ ID NO:718:

CACAGCAGCU GAUGAGGCCG AAAGGCCGAA AGCAGGGU  38

( 2 ) INFORMATION FOR SEQ ID NO:719:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:719:

GCUGAGCACU GAUGAGGCCG AAAGGCCGAA AGCGCCAC  38

( 2 ) INFORMATION FOR SEQ ID NO:720:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:720:

GGCUGAGCCU GAUGAGGCCG AAAGGCCGAA AAGCGCCA  38

( 2 ) INFORMATION FOR SEQ ID NO:721:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:721:

GAUAGGCUCU GAUGAGGCCG AAAGGCCGAA AGCAAAGC  38

( 2 ) INFORMATION FOR SEQ ID NO:722:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:722:

CCAGUGGACU GAUGAGGCCG AAAGGCCGAA AGGCUGAG  38

( 2 ) INFORMATION FOR SEQ ID NO:723:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:723:

AUCCAGUGCU GAUGAGGCCG AAAGGCCGAA AUAGGCUG  38

( 2 ) INFORMATION FOR SEQ ID NO:724:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:724:

CAUCCCUUCU GAUGAGGCCG AAAGGCCGAA AGGCUCCA                    38

( 2 ) INFORMATION FOR SEQ ID NO:725:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:725:

UGCUGAAGCU GAUGAGGCCG AAAGGCCGAA AGGUCCAU                    38

( 2 ) INFORMATION FOR SEQ ID NO:726:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:726:

UUGCUGAACU GAUGAGGCCG AAAGGCCGAA AAGGUCCA                    38

( 2 ) INFORMATION FOR SEQ ID NO:727:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:727:

UAUUGCUGCU GAUGAGGCCG AAAGGCCGAA AGAAGGUC                    38

( 2 ) INFORMATION FOR SEQ ID NO:728:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:728:

AUAUUGCUCU GAUGAGGCCG AAAGGCCGAA AAGAAGGU                    38

( 2 ) INFORMATION FOR SEQ ID NO:729:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:729:

UUUCCAGACU GAUGAGGCCG AAAGGCCGAA AUUGCUGA                    38

( 2 ) INFORMATION FOR SEQ ID NO:730:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:730:

GUUUUCCACU GAUGAGGCCG AAAGGCCGAA AUAUUGCU 38

(2) INFORMATION FOR SEQ ID NO:731:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:731:

GGUUGUAGCU GAUGAGGCCG AAAGGCCGAA AGUUUCC 38

(2) INFORMATION FOR SEQ ID NO:732:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:732:

CAAGGUUGCU GAUGAGGCCG AAAGGCCGAA AGUAGUUU 38

(2) INFORMATION FOR SEQ ID NO:733:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:733:

UCUUUUUCCU GAUGAGGCCG AAAGGCCGAA AGGUUGUA 38

(2) INFORMATION FOR SEQ ID NO:734:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:734:

UUUUAACACU GAUGAGGCCG AAAGGCCGAA ACUGUUUC 38

(2) INFORMATION FOR SEQ ID NO:735:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:735:

CUUUUAACCU GAUGAGGCCG AAAGGCCGAA AACUGUUU 38

(2) INFORMATION FOR SEQ ID NO:736:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:736:

UUUCUUUUCU GAUGAGGCCG AAAGGCCGAA ACAAACUG 38

( 2 ) INFORMATION FOR SEQ ID NO:737:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:737:

CUUUCUUUCU GAUGAGGCCG AAAGGCCGAA AACAAACU                    38

( 2 ) INFORMATION FOR SEQ ID NO:738:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:738:

AACAGGACCU GAUGAGGCCG AAAGGCCGAA ACUGUCCU                    38

( 2 ) INFORMATION FOR SEQ ID NO:739:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:739:

AACAACAGCU GAUGAGGCCG AAAGGCCGAA ACUACUGU                    38

( 2 ) INFORMATION FOR SEQ ID NO:740:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:740:

UUUUUAACCU GAUGAGGCCG AAAGGCCGAA ACAGGACU                    38

( 2 ) INFORMATION FOR SEQ ID NO:741:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:741:

AUUUUUUCU GAUGAGGCCG AAAGGCCGAA ACAACAGG                     38

( 2 ) INFORMATION FOR SEQ ID NO:742:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:742:

GAUUUUUCU GAUGAGGCCG AAAGGCCGAA AACAACAG                     38

( 2 ) INFORMATION FOR SEQ ID NO:743:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:743:

AUUCUUGCU GAUGAGGCCG AAAGGCCGAA AUUUUUU    38

( 2 ) INFORMATION FOR SEQ ID NO:744:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:744:

AGCCAAGGCU GAUGAGGCCG AAAGGCCGAA ACUUCUGC    38

( 2 ) INFORMATION FOR SEQ ID NO:745:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:745:

AAGCCAAGCU GAUGAGGCCG AAAGGCCGAA AACUUCUG    38

( 2 ) INFORMATION FOR SEQ ID NO:746:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:746:

UCCAAGCCCU GAUGAGGCCG AAAGGCCGAA AGGAACUU    38

( 2 ) INFORMATION FOR SEQ ID NO:747:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:747:

UCACCUCCCU GAUGAGGCCG AAAGGCCGAA AGCCAAGG    38

( 2 ) INFORMATION FOR SEQ ID NO:748:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:748:

GGGUGUUGCU GAUGAGGCCG AAAGGCCGAA AGUCCAGC    38

( 2 ) INFORMATION FOR SEQ ID NO:749:

( i ) SEQUENCE CHARACTERISTICS:

( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:749:

GGCUUGCGCU GAUGAGGCCG AAAGGCCGAA AUCACCUC                                    38

( 2 ) INFORMATION FOR SEQ ID NO:750:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:750:

ACAUCAGGCU GAUGAGGCCG AAAGGCCGAA ACGCCACA                                    38

( 2 ) INFORMATION FOR SEQ ID NO:751:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:751:

AACAUCAGCU GAUGAGGCCG AAAGGCCGAA AACGCCAC                                    38

( 2 ) INFORMATION FOR SEQ ID NO:752:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:752:

AAGUGACCCU GAUGAGGCCG AAAGGCCGAA ACAUCAGG                                    38

( 2 ) INFORMATION FOR SEQ ID NO:753:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:753:

ACUGAAGUCU GAUGAGGCCG AAAGGCCGAA ACCAACAU                                    38

( 2 ) INFORMATION FOR SEQ ID NO:754:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:754:

AGGUACUGCU GAUGAGGCCG AAAGGCCGAA AGUGACCA                                    38

( 2 ) INFORMATION FOR SEQ ID NO:755:

( i ) SEQUENCE CHARACTERISTICS:
( A ) LENGTH: 38 base pairs
( B ) TYPE: nucleic acid (C) STRANDEDNESS: single
(D) TOPOLOGY: linear (xi) SEQUENCE DESCRIPTION: SEQ ID NO:755:

AAGGUACUCU GAUGAGGCCG AAAGGCCGAA AAGUGACC 38

(2) INFORMATION FOR SEQ ID NO:756:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:756:

AGGGAAGGCU GAUGAGGCCG AAAGGCCGAA ACUGAAGU 38

(2) INFORMATION FOR SEQ ID NO:757:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:757:

UGCCAGGGCU GAUGAGGCCG AAAGGCCGAA AGGUACUG 38

(2) INFORMATION FOR SEQ ID NO:758:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:758:

GUGCCAGGCU GAUGAGGCCG AAAGGCCGAA AAGGUACU 38

(2) INFORMATION FOR SEQ ID NO:759:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:759:

AGUUAGGUCU GAUGAGGCCG AAAGGCCGAA AGUUUUUG 38

(2) INFORMATION FOR SEQ ID NO:760:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:760:

CUGUAAGUCU GAUGAGGCCG AAAGGCCGAA AGGUGAGU 38

(2) INFORMATION FOR SEQ ID NO:761:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO:761:

AAUCCUGUCU GAUGAGGCCG AAAGGCCGAA AGUUAGGU                    38

( 2 ) INFORMATION FOR SEQ ID NO:762:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:762:

CAAUCCUGCU GAUGAGGCCG AAAGGCCGAA AAGUUAGG                    38

( 2 ) INFORMATION FOR SEQ ID NO:763:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:763:

UAAUUCACCU GAUGAGGCCG AAAGGCCGAA AUCCUGUA                    38

( 2 ) INFORMATION FOR SEQ ID NO:764:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:764:

CGGUGUGUCU GAUGAGGCCG AAAGGCCGAA AUUCACAA                    38

( 2 ) INFORMATION FOR SEQ ID NO:765:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:765:

CCGGUGUGCU GAUGAGGCCG AAAGGCCGAA AAUUCACA                    38

( 2 ) INFORMATION FOR SEQ ID NO:766:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:766:

UCUUGGCACU GAUGAGGCCG AAAGGCCGAA AUCCGGUG                    38

( 2 ) INFORMATION FOR SEQ ID NO:767:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:767:

GCAGCAUCCU GAUGAGGCCG AAAGGCCGAA ACAGCAUC                                    38

( 2 ) INFORMATION FOR SEQ ID NO:768:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:768:

GCUUUCUCCU GAUGAGGCCG AAAGGCCGAA AUGGCAGC                                    38

( 2 ) INFORMATION FOR SEQ ID NO:769:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:769:

GACCUUCACU GAUGAGGCCG AAAGGCCGAA AGCUUUCU                                    38

( 2 ) INFORMATION FOR SEQ ID NO:770:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:770:

UCCUCCCACU GAUGAGGCCG AAAGGCCGAA ACCUUCAG                                    38

( 2 ) INFORMATION FOR SEQ ID NO:771:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:771:

CGUGAGUGCU GAUGAGGCCG AAAGGCCGAA AGUCACCU                                    38

( 2 ) INFORMATION FOR SEQ ID NO:772:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:772:

GAGAACGUCU GAUGAGGCCG AAAGGCCGAA AGUGGAGU                                    38

( 2 ) INFORMATION FOR SEQ ID NO:773:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:773:

UCCUGGAGCU GAUGAGGCCG AAAGGCCGAA ACGUGAGU                                    38

( 2 ) INFORMATION FOR SEQ ID NO:774:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:774:

UUCCUGGACU GAUGAGGCCG AAAGGCCGAA AACGUGAG        38

( 2 ) INFORMATION FOR SEQ ID NO:775:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:775:

ACUUCCUGCU GAUGAGGCCG AAAGGCCGAA AGAACGUG        38

( 2 ) INFORMATION FOR SEQ ID NO:776:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:776:

CUCCUUCACU GAUGAGGCCG AAAGGCCGAA ACUUCCUG        38

( 2 ) INFORMATION FOR SEQ ID NO:777:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:777:

GAGAUCAUCU GAUGAGGCCG AAAGGCCGAA AUGUCAGC        38

( 2 ) INFORMATION FOR SEQ ID NO:778:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:778:

CCAAAAGACU GAUGAGGCCG AAAGGCCGAA AUCAUUAU        38

( 2 ) INFORMATION FOR SEQ ID NO:779:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:779:

CUCCAAAACU GAUGAGGCCG AAAGGCCGAA AGAUCAUU        38

( 2 ) INFORMATION FOR SEQ ID NO:780:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:780:

GACUCCAACU GAUGAGGCCG AAAGGCCGAA AGAGAUCA 38

( 2 ) INFORMATION FOR SEQ ID NO:781:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:781:

GGACUCCACU GAUGAGGCCG AAAGGCCGAA AAGAGAUC 38

( 2 ) INFORMATION FOR SEQ ID NO:782:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:782:

CGGACUCCCU GAUGAGGCCG AAAGGCCGAA AAAGAGAU 38

( 2 ) INFORMATION FOR SEQ ID NO:783:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:783:

UGUUCUCGCU GAUGAGGCCG AAAGGCCGAA ACUCCAAA 38

( 2 ) INFORMATION FOR SEQ ID NO:784:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:784:

AGGAAUAACU GAUGAGGCCG AAAGGCCGAA AUCUCCAU 38

( 2 ) INFORMATION FOR SEQ ID NO:785:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:785:

AAGGAAUACU GAUGAGGCCG AAAGGCCGAA AAUCUCCA 38

( 2 ) INFORMATION FOR SEQ ID NO:786:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:786:

AAAGGAAUCU GAUGAGGCCG AAAGGCCGAA AAAUCUCC     38

( 2 ) INFORMATION FOR SEQ ID NO:787:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:787:

AAAAGGAACU GAUGAGGCCG AAAGGCCGAA AAAAUCUC     38

( 2 ) INFORMATION FOR SEQ ID NO:788:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:788:

UCAAAAGGCU GAUGAGGCCG AAAGGCCGAA AUAAAAUC     38

( 2 ) INFORMATION FOR SEQ ID NO:789:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:789:

AUCAAAAGCU GAUGAGGCCG AAAGGCCGAA AAUAAAAU     38

( 2 ) INFORMATION FOR SEQ ID NO:790:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:790:

UCCAUCAACU GAUGAGGCCG AAAGGCCGAA AGGAAUAA     38

( 2 ) INFORMATION FOR SEQ ID NO:791:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:791:

GUCCAUCACU GAUGAGGCCG AAAGGCCGAA AAGGAAUA     38

( 2 ) INFORMATION FOR SEQ ID NO:792:

( i ) SEQUENCE CHARACTERISTICS:
        ( A ) LENGTH: 38 base pairs ( B ) TYPE: nucleic acid
        ( C ) STRANDEDNESS: single
        ( D ) TOPOLOGY: linear ( x i ) SEQUENCE DESCRIPTION: SEQ ID NO:792:

GGUCCAUCCU GAUGAGGCCG AAAGGCCGAA AAAGGAAU 38

( 2 ) INFORMATION FOR SEQ ID NO:793:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:793:

UGAGCCAACU GAUGAGGCCG AAAGGCCGAA ACAUUCC 38

( 2 ) INFORMATION FOR SEQ ID NO:794:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:794:

AUGAGCCACU GAUGAGGCCG AAAGGCCGAA AACAUUUC 38

( 2 ) INFORMATION FOR SEQ ID NO:795:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:795:

CAUGAGCCCU GAUGAGGCCG AAAGGCCGAA AAACAUUU 38

( 2 ) INFORMATION FOR SEQ ID NO:796:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:796:

AUAAGCAUCU GAUGAGGCCG AAAGGCCGAA AGCCAAAA 38

( 2 ) INFORMATION FOR SEQ ID NO:797:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:797:

AGGUGCAUCU GAUGAGGCCG AAAGGCCGAA AGCAUGAG 38

( 2 ) INFORMATION FOR SEQ ID NO:798:

( i ) SEQUENCE CHARACTERISTICS:
        ( A ) LENGTH: 38 base pairs
        ( B ) TYPE: nucleic acid
        ( C ) STRANDEDNESS: single ( D ) TOPOLOGY: linear ( x i ) SEQUENCE DESCRIPTION: SEQ ID NO:798:

CAGGUGCACU GAUGAGGCCG AAAGGCCGAA AAGCAUGA     38

( 2 ) INFORMATION FOR SEQ ID NO:799:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:799:

UCUCCAUUCU GAUGAGGCCG AAAGGCCGAA AUUCCUGG     38

( 2 ) INFORMATION FOR SEQ ID NO:800:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:800:

AUCUCCAUCU GAUGAGGCCG AAAGGCCGAA AAUUCCUG     38

( 2 ) INFORMATION FOR SEQ ID NO:801:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:801:

CAUCAUCACU GAUGAGGCCG AAAGGCCGAA AGUGGGCA     38

( 2 ) INFORMATION FOR SEQ ID NO:802:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:802:

UCAUCAUCCU GAUGAGGCCG AAAGGCCGAA AAGUGGGC     38

( 2 ) INFORMATION FOR SEQ ID NO:803:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:803:

UCCUGUUGCU GAUGAGGCCG AAAGGCCGAA AUCCUUUG     38

( 2 ) INFORMATION FOR SEQ ID NO:804:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:804:

AAGGAAUACU GAUGAGGCCG AAAGGCCGAA AUUGGUUC 38

( 2 ) INFORMATION FOR SEQ ID NO:805:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:805:

CAAGGAAUCU GAUGAGGCCG AAAGGCCGAA AAUUGGUU 38

( 2 ) INFORMATION FOR SEQ ID NO:806:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:806:

ACAAGGAACU GAUGAGGCCG AAAGGCCGAA AAAUUGGU 38

( 2 ) INFORMATION FOR SEQ ID NO:807:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:807:

CAACAAGGCU GAUGAGGCCG AAAGGCCGAA AUAAAUUG 38

( 2 ) INFORMATION FOR SEQ ID NO:808:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:808:

GCAACAAGCU GAUGAGGCCG AAAGGCCGAA AAUAAAUU 38

( 2 ) INFORMATION FOR SEQ ID NO:809:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:809:

GCAGCAACCU GAUGAGGCCG AAAGGCCGAA AGGAAUAA 38

( 2 ) INFORMATION FOR SEQ ID NO:810:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:810:

```
UGAGCAGCCU GAUGAGGCCG AAAGGCCGAA ACAAGGAA                    38
```

( 2 ) INFORMATION FOR SEQ ID NO:811:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:811:

```
AAGCUCAUCU GAUGAGGCCG AAAGGCCGAA AGCAGCAA                    38
```

( 2 ) INFORMATION FOR SEQ ID NO:812:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:812:

```
GAGUGGCCCU GAUGAGGCCG AAAGGCCGAA AGCUCAUG                    38
```

( 2 ) INFORMATION FOR SEQ ID NO:813:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:813:

```
GACCCAGGCU GAUGAGGCCG AAAGGCCGAA AGUGGCCA                    38
```

( 2 ) INFORMATION FOR SEQ ID NO:814:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:814:

```
GUGAAACACU GAUGAGGCCG AAAGGCCGAA ACCCAGGG                    38
```

( 2 ) INFORMATION FOR SEQ ID NO:815:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:815:

```
CCGAGUGACU GAUGAGGCCG AAAGGCCGAA ACAGACCC                    38
```

( 2 ) INFORMATION FOR SEQ ID NO:816:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:816:

```
GCCGAGUGCU GAUGAGGCCG AAAGGCCGAA AACAGACC                    38
```

( 2 ) INFORMATION FOR SEQ ID NO:817:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:817:

GGCCGAGUCU GAUGAGGCCG AAAGGCCGAA AAACAGAC     38

( 2 ) INFORMATION FOR SEQ ID NO:818:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:818:

GGUUGGCCCU GAUGAGGCCG AAAGGCCGAA AGUGAAAC     38

( 2 ) INFORMATION FOR SEQ ID NO:819:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:819:

AGACUGGGCU GAUGAGGCCG AAAGGCCGAA ACAUCAGC     38

( 2 ) INFORMATION FOR SEQ ID NO:820:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:820:

GCGUUGUACU GAUGAGGCCG AAAGGCCGAA ACUGGGUA     38

( 2 ) INFORMATION FOR SEQ ID NO:821:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:821:

AGGCGUUGCU GAUGAGGCCG AAAGGCCGAA AGACUGGG     38

( 2 ) INFORMATION FOR SEQ ID NO:822:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:822:

GGUCUGUGCU GAUGAGGCCG AAAGGCCGAA AGGCGUUG     38

( 2 ) INFORMATION FOR SEQ ID NO:823:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:823:

AGGUCUGUCU GAUGAGGCCG AAAGGCCGAA AAGGCGUU　　　　　　　　　　　38

( 2 ) INFORMATION FOR SEQ ID NO:824:

( i ) SEQUENCE CHARACTERISTICS:
　　( A ) LENGTH: 38 base pairs
　　( B ) TYPE: nucleic acid
　　( C ) STRANDEDNESS: single
　　( D ) TOPOLOGY: linear ( x i ) SEQUENCE DESCRIPTION: SEQ ID NO:824:

AAAGGCGGCU GAUGAGGCCG AAAGGCCGAA ACCGGGCC　　　　　　　　　　　38

( 2 ) INFORMATION FOR SEQ ID NO:825:

( i ) SEQUENCE CHARACTERISTICS:
　　( A ) LENGTH: 38 base pairs
　　( B ) TYPE: nucleic acid
　　( C ) STRANDEDNESS: single
　　( D ) TOPOLOGY: linear ( x i ) SEQUENCE DESCRIPTION: SEQ ID NO:825:

GAAAGGCGCU GAUGAGGCCG AAAGGCCGAA AACCGGGC　　　　　　　　　　　38

( 2 ) INFORMATION FOR SEQ ID NO:826:

( i ) SEQUENCE CHARACTERISTICS:
　　( A ) LENGTH: 38 base pairs
　　( B ) TYPE: nucleic acid
　　( C ) STRANDEDNESS: single
　　( D ) TOPOLOGY: linear ( x i ) SEQUENCE DESCRIPTION: SEQ ID NO:826:

UCUUGAGACU GAUGAGGCCG AAAGGCCGAA AGGCGGAA　　　　　　　　　　　38

( 2 ) INFORMATION FOR SEQ ID NO:827:

( i ) SEQUENCE CHARACTERISTICS:
　　( A ) LENGTH: 38 base pairs
　　( B ) TYPE: nucleic acid
　　( C ) STRANDEDNESS: single
　　( D ) TOPOLOGY: linear ( x i ) SEQUENCE DESCRIPTION: SEQ ID NO:827:

AUCUUGAGCU GAUGAGGCCG AAAGGCCGAA AAGGCGGA　　　　　　　　　　　38

( 2 ) INFORMATION FOR SEQ ID NO:828:

( i ) SEQUENCE CHARACTERISTICS:
　　( A ) LENGTH: 38 base pairs
　　( B ) TYPE: nucleic acid
　　( C ) STRANDEDNESS: single
　　( D ) TOPOLOGY: linear ( x i ) SEQUENCE DESCRIPTION: SEQ ID NO:828:

CAUCUUGACU GAUGAGGCCG AAAGGCCGAA AAAGGCGG　　　　　　　　　　　38

( 2 ) INFORMATION FOR SEQ ID NO:829:

( i ) SEQUENCE CHARACTERISTICS:

(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:829:

AUCAUCUUCU GAUGAGGCCG AAAGGCCGAA AGAAAGGC                    38

(2) INFORMATION FOR SEQ ID NO:830:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:830:

AGGGAUUGCU GAUGAGGCCG AAAGGCCGAA AUGCCAUC                    38

(2) INFORMATION FOR SEQ ID NO:831:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:831:

CAUAGAGGCU GAUGAGGCCG AAAGGCCGAA AUUGGAUG                    38

(2) INFORMATION FOR SEQ ID NO:832:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:832:

GGUCCAUACU GAUGAGGCCG AAAGGCCGAA AGGGAUUG                    38

(2) INFORMATION FOR SEQ ID NO:833:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:833:

CCGGUCCACU GAUGAGGCCG AAAGGCCGAA AGAGGGAU                    38

(2) INFORMATION FOR SEQ ID NO:834:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:834:

UAUCAGGACU GAUGAGGCCG AAAGGCCGAA AGGCAGGG                    38

(2) INFORMATION FOR SEQ ID NO:835:

(i) SEQUENCE CHARACTERISTICS:
    (A) LENGTH: 38 base pairs
    (B) TYPE: nucleic acid (C) STRANDEDNESS: single
(D) TOPOLOGY: linear (x i) SEQUENCE DESCRIPTION: SEQ ID NO:835:

GUUAUCAGCU GAUGAGGCCG AAAGGCCGAA AGAGGCAG        38

(2) INFORMATION FOR SEQ ID NO:836:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:836:

UCCAGAGUCU GAUGAGGCCG AAAGGCCGAA AUCAGGAG        38

(2) INFORMATION FOR SEQ ID NO:837:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:837:

GCACUCCACU GAUGAGGCCG AAAGGCCGAA AGUUAUCA        38

(2) INFORMATION FOR SEQ ID NO:838:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:838:

AGGUUCCACU GAUGAGGCCG AAAGGCCGAA AGGCACUC        38

(2) INFORMATION FOR SEQ ID NO:839:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:839:

CCUGGAGGCU GAUGAGGCCG AAAGGCCGAA ACAGGUUC        38

(2) INFORMATION FOR SEQ ID NO:840:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:840:

AGAUCCUGCU GAUGAGGCCG AAAGGCCGAA AGGGACAG        38

(2) INFORMATION FOR SEQ ID NO:841:

(i) SEQUENCE CHARACTERISTICS:
(A) LENGTH: 38 base pairs
(B) TYPE: nucleic acid
(C) STRANDEDNESS: single
(D) TOPOLOGY: linear ( x i ) SEQUENCE DESCRIPTION: SEQ ID NO:841:

GGGUCCCACU GAUGAGGCCG AAAGGCCGAA AUCCUGGA 38

( 2 ) INFORMATION FOR SEQ ID NO:842:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:842:

UCACACAUCU GAUGAGGCCG AAAGGCCGAA ACUGGGGU 38

( 2 ) INFORMATION FOR SEQ ID NO:843:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:843:

CAGAUCUGCU GAUGAGGCCG AAAGGCCGAA AUCACACA 38

( 2 ) INFORMATION FOR SEQ ID NO:844:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:844:

GAAGGACACU GAUGAGGCCG AAAGGCCGAA AUCUGGAU 38

( 2 ) INFORMATION FOR SEQ ID NO:845:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:845:

CAUCGAAGCU GAUGAGGCCG AAAGGCCGAA ACAGAUCU 38

( 2 ) INFORMATION FOR SEQ ID NO:846:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:846:

UUGCAUCGCU GAUGAGGCCG AAAGGCCGAA AGGACAGA 38

( 2 ) INFORMATION FOR SEQ ID NO:847:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:847:

AUUGCAUCCU GAUGAGGCCG AAAGGCCGAA AAGGACAG 38

(2) INFORMATION FOR SEQ ID NO:848:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:848:

AGAGUGCUCU GAUGAGGCCG AAAGGCCGAA AUUGCAUC 38

(2) INFORMATION FOR SEQ ID NO:849:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:849:

UCCCCUCACU GAUGAGGCCG AAAGGCCGAA AGUGCUGA 38

(2) INFORMATION FOR SEQ ID NO:850:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:850:

AAGAACAGCU GAUGAGGCCG AAAGGCCGAA AUUUCUCC 38

(2) INFORMATION FOR SEQ ID NO:851:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:851:

AAAGAACACU GAUGAGGCCG AAAGGCCGAA AAUUUCUC 38

(2) INFORMATION FOR SEQ ID NO:852:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:852:

CUUUAAAGCU GAUGAGGCCG AAAGGCCGAA ACAGAAUU 38

(2) INFORMATION FOR SEQ ID NO:853:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:853:

UCUUUAAACU GAUGAGGCCG AAAGGCCGAA AACAGAAU 38

( 2 ) INFORMATION FOR SEQ ID NO:854:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:854:

UGUCUUUACU GAUGAGGCCG AAAGGCCGAA AGAACAGA        38

( 2 ) INFORMATION FOR SEQ ID NO:855:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:855:

CUGUCUUUCU GAUGAGGCCG AAAGGCCGAA AAGAACAG        38

( 2 ) INFORMATION FOR SEQ ID NO:856:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:856:

CCUGUCUUCU GAUGAGGCCG AAAGGCCGAA AAAGAACA        38

( 2 ) INFORMATION FOR SEQ ID NO:857:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:857:

GCCAGAAACU GAUGAGGCCG AAAGGCCGAA ACCUGUCU        38

( 2 ) INFORMATION FOR SEQ ID NO:858:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:858:

GCGCCAGACU GAUGAGGCCG AAAGGCCGAA AUACCUGU        38

( 2 ) INFORMATION FOR SEQ ID NO:859:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:859:

UGCGCCAGCU GAUGAGGCCG AAAGGCCGAA AAUACCUG        38

( 2 ) INFORMATION FOR SEQ ID NO:860:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:860:

UUGCGCCACU GAUGAGGCCG AAAGGCCGAA AAAUACCU     38

( 2 ) INFORMATION FOR SEQ ID NO:861:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:861:

UCCUGAGGCU GAUGAGGCCG AAAGGCCGAA ACUUGCGC     38

( 2 ) INFORMATION FOR SEQ ID NO:862:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:862:

AGAAUCCUCU GAUGAGGCCG AAAGGCCGAA AGGGACUU     38

( 2 ) INFORMATION FOR SEQ ID NO:863:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:863:

GGUUCGAGCU GAUGAGGCCG AAAGGCCGAA AUCCUGAG     38

( 2 ) INFORMATION FOR SEQ ID NO:864:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:864:

AGGUUCGACU GAUGAGGCCG AAAGGCCGAA AAUCCUGA     38

( 2 ) INFORMATION FOR SEQ ID NO:865:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:865:

UCAGGUUCCU GAUGAGGCCG AAAGGCCGAA AGAAUCCU     38

( 2 ) INFORMATION FOR SEQ ID NO:866:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:866:

UCAAAUGACU GAUGAGGCCG AAAGGCCGAA ACUCAGGU    38

( 2 ) INFORMATION FOR SEQ ID NO:867:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:867:

AUCAAAUGCU GAUGAGGCCG AAAGGCCGAA AACUCAGG    38

( 2 ) INFORMATION FOR SEQ ID NO:868:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:868:

GAUCAAAUCU GAUGAGGCCG AAAGGCCGAA AAACUCAG    38

( 2 ) INFORMATION FOR SEQ ID NO:869:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:869:

AGAGAUCACU GAUGAGGCCG AAAGGCCGAA AUGAAACU    38

( 2 ) INFORMATION FOR SEQ ID NO:870:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:870:

AAGAGAUCCU GAUGAGGCCG AAAGGCCGAA AAUGAAAC    38

( 2 ) INFORMATION FOR SEQ ID NO:871:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:871:

AAUGAAGACU GAUGAGGCCG AAAGGCCGAA AUCAAAUG    38

( 2 ) INFORMATION FOR SEQ ID NO:872:

( i ) SEQUENCE CHARACTERISTICS:
        ( A ) LENGTH: 38 base pairs (B) TYPE: nucleic acid
(C) STRANDEDNESS: single
(D) TOPOLOGY: linear (xi) SEQUENCE DESCRIPTION: SEQ ID NO:872:

AGAAUGAACU GAUGAGGCCG AAAGGCCGAA AGAUCAAA　　　　　　　　　　　　38

(2) INFORMATION FOR SEQ ID NO:873:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:873:

CCAGAAUGCU GAUGAGGCCG AAAGGCCGAA AGAGAUCA　　　　　　　　　　　　38

(2) INFORMATION FOR SEQ ID NO:874:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:874:

GCCAGAAUCU GAUGAGGCCG AAAGGCCGAA AAGAGAUC　　　　　　　　　　　　38

(2) INFORMATION FOR SEQ ID NO:875:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:875:

AUGGCCAGCU GAUGAGGCCG AAAGGCCGAA AUGAAGAG　　　　　　　　　　　　38

(2) INFORMATION FOR SEQ ID NO:876:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:876:

GAUGGCCACU GAUGAGGCCG AAAGGCCGAA AAUGAAGA　　　　　　　　　　　　38

(2) INFORMATION FOR SEQ ID NO:877:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (xi) SEQUENCE DESCRIPTION: SEQ ID NO:877:

AAGGAAGACU GAUGAGGCCG AAAGGCCGAA AUGGCCAG　　　　　　　　　　　　38

(2) INFORMATION FOR SEQ ID NO:878:

(i) SEQUENCE CHARACTERISTICS:
    (A) LENGTH: 38 base pairs
    (B) TYPE: nucleic acid
    (C) STRANDEDNESS: single ( D ) TOPOLOGY: linear ( x i ) SEQUENCE DESCRIPTION: SEQ ID NO:878:

UGAAGGAACU GAUGAGGCCG AAAGGCCGAA AGAUGGCC 38

( 2 ) INFORMATION FOR SEQ ID NO:879:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:879:

GCUGAAGGCU GAUGAGGCCG AAAGGCCGAA AGAGAUGG 38

( 2 ) INFORMATION FOR SEQ ID NO:880:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:880:

UGCUGAAGCU GAUGAGGCCG AAAGGCCGAA AAGAGAUG 38

( 2 ) INFORMATION FOR SEQ ID NO:881:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:881:

CACUGCUGCU GAUGAGGCCG AAAGGCCGAA AGGAAGAG 38

( 2 ) INFORMATION FOR SEQ ID NO:882:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:882:

CCACUGCUCU GAUGAGGCCG AAAGGCCGAA AAGGAAGA 38

( 2 ) INFORMATION FOR SEQ ID NO:883:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:883:

UAACUUCACU GAUGAGGCCG AAAGGCCGAA AUGCAGCA 38

( 2 ) INFORMATION FOR SEQ ID NO:884:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:884:

CUGCUAAUCU GAUGAGGCCG AAAGGCCGAA ACUUCAUA 38

( 2 ) INFORMATION FOR SEQ ID NO:885:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:885:

CCUGCUAACU GAUGAGGCCG AAAGGCCGAA AACUUCAU 38

( 2 ) INFORMATION FOR SEQ ID NO:886:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:886:

UCCCUGCUCU GAUGAGGCCG AAAGGCCGAA AUAACUUC 38

( 2 ) INFORMATION FOR SEQ ID NO:887:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:887:

AUCCCUGCCU GAUGAGGCCG AAAGGCCGAA AAUAACUU 38

( 2 ) INFORMATION FOR SEQ ID NO:888:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:888:

GAAAACAGCU GAUGAGGCCG AAAGGCCGAA AUCCCUGC 38

( 2 ) INFORMATION FOR SEQ ID NO:889:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:889:

AAAAUGAACU GAUGAGGCCG AAAGGCCGAA ACAGUAUC 38

( 2 ) INFORMATION FOR SEQ ID NO:890:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:890:

AAAAAUGACU GAUGAGGCCG AAAGGCCGAA AACAGUAU 38

(2) INFORMATION FOR SEQ ID NO:891:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:891:

UAAAAAUGCU GAUGAGGCCG AAAGGCCGAA AAACAGUA 38

(2) INFORMATION FOR SEQ ID NO:892:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:892:

UUAAAAAUCU GAUGAGGCCG AAAGGCCGAA AAAACAGU 38

(2) INFORMATION FOR SEQ ID NO:893:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:893:

CCUUUAAACU GAUGAGGCCG AAAGGCCGAA AUGAAAAC 38

(2) INFORMATION FOR SEQ ID NO:894:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:894:

UCCUUUAACU GAUGAGGCCG AAAGGCCGAA AAUGAAAA 38

(2) INFORMATION FOR SEQ ID NO:895:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:895:

UUCCUUUACU GAUGAGGCCG AAAGGCCGAA AAAUGAAA 38

(2) INFORMATION FOR SEQ ID NO:896:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:896:

GUUCCUUUCU GAUGAGGCCG AAAGGCCGAA AAAAUGAA 38

( 2 ) INFORMATION FOR SEQ ID NO:897:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:897:

AGUUCCUUCU GAUGAGGCCG AAAGGCCGAA AAAAAUGA    38

( 2 ) INFORMATION FOR SEQ ID NO:898:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:898:

CCAGAACUCU GAUGAGGCCG AAAGGCCGAA AGUUCCUU    38

( 2 ) INFORMATION FOR SEQ ID NO:899:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:899:

UGGCCCAGCU GAUGAGGCCG AAAGGCCGAA ACUGAGUU    38

( 2 ) INFORMATION FOR SEQ ID NO:900:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:900:

AUGGCCCACU GAUGAGGCCG AAAGGCCGAA AACUGAGU    38

( 2 ) INFORMATION FOR SEQ ID NO:901:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:901:

UUUCCUCUCU GAUGAGGCCG AAAGGCCGAA AUGGCCCA    38

( 2 ) INFORMATION FOR SEQ ID NO:902:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:902:

AUUCCUCCU GAUGAGGCCG AAAGGCCGAA AAUGGCCC    38

( 2 ) INFORMATION FOR SEQ ID NO:903:

( i ) SEQUENCE CHARACTERISTICS:
   ( A ) LENGTH: 38 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:903:

CCAGCUUGCU GAUGAGGCCG AAAGGCCGAA ACCUCAUU 38

( 2 ) INFORMATION FOR SEQ ID NO:904:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:904:

UCUUGGGUCU GAUGAGGCCG AAAGGCCGAA ACCAGCUU 38

( 2 ) INFORMATION FOR SEQ ID NO:905:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:905:

UUCUUGGGCU GAUGAGGCCG AAAGGCCGAA AACCAGCU 38

( 2 ) INFORMATION FOR SEQ ID NO:906:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:906:

AGGGUGUGCU GAUGAGGCCG AAAGGCCGAA AUGCUUCU 38

( 2 ) INFORMATION FOR SEQ ID NO:907:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:907:

UGAAGGGACU GAUGAGGCCG AAAGGCCGAA ACCCAGGG 38

( 2 ) INFORMATION FOR SEQ ID NO:908:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:908:

UUGAAGGGCU GAUGAGGCCG AAAGGCCGAA AACCCAGG 38

( 2 ) INFORMATION FOR SEQ ID NO:909:

( i ) SEQUENCE CHARACTERISTICS:

(A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:909:

GUUGAAGGCU GAUGAGGCCG AAAGGCCGAA AAACCCAG 38

(2) INFORMATION FOR SEQ ID NO:910:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:910:

UAUGGUUGCU GAUGAGGCCG AAAGGCCGAA AGGGAAAC 38

(2) INFORMATION FOR SEQ ID NO:911:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:911:

UUAUGGUUCU GAUGAGGCCG AAAGGCCGAA AAGGGAAA 38

(2) INFORMATION FOR SEQ ID NO:912:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:912:

AUUUUCUCU GAUGAGGCCG AAAGGCCGAA AUGGUUGA 38

(2) INFORMATION FOR SEQ ID NO:913:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:913:

GCAGCAUCCU GAUGAGGCCG AAAGGCCGAA AUUUUUCU 38

(2) INFORMATION FOR SEQ ID NO:914:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:914:

UUAUCAGACU GAUGAGGCCG AAAGGCCGAA AUGGCAGC 38

(2) INFORMATION FOR SEQ ID NO:915:

(i) SEQUENCE CHARACTERISTICS:
        (A) LENGTH: 38 base pairs
        (B) TYPE: nucleic acid (C) STRANDEDNESS: single
        (D) TOPOLOGY: linear (xi) SEQUENCE DESCRIPTION: SEQ ID NO:915:

CUUAUCAGCU GAUGAGGCCG AAAGGCCGAA AAUGGCAG 38

(2) INFORMATION FOR SEQ ID NO:916:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:916:

CCUUAUCACU GAUGAGGCCG AAAGGCCGAA AAAUGGCA 38

(2) INFORMATION FOR SEQ ID NO:917:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:917:

CCUUUCCUCU GAUGAGGCCG AAAGGCCGAA AUCAGAAA 38

(2) INFORMATION FOR SEQ ID NO:918:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:918:

CAAAGAAGCU GAUGAGGCCG AAAGGCCGAA AUGUUUC 38

(2) INFORMATION FOR SEQ ID NO:919:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:919:

CCACAAAGCU GAUGAGGCCG AAAGGCCGAA AGUAUGUU 38

(2) INFORMATION FOR SEQ ID NO:920:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:920:

UCCACAAACU GAUGAGGCCG AAAGGCCGAA AAGUAUGU 38

(2) INFORMATION FOR SEQ ID NO:921:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:921:

CUUCCACACU GAUGAGGCCG AAAGGCCGAA AGAAGUAU　　　　　38

( 2 ) INFORMATION FOR SEQ ID NO:922:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:922:

UCUUCCACCU GAUGAGGCCG AAAGGCCGAA AAGAAGUA　　　　　38

( 2 ) INFORMATION FOR SEQ ID NO:923:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:923:

ACCUCCAGCU GAUGAGGCCG AAAGGCCGAA AUUUGUCU　　　　　38

( 2 ) INFORMATION FOR SEQ ID NO:924:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:924:

UCUCAUCACU GAUGAGGCCG AAAGGCCGAA ACCUCCAG　　　　　38

( 2 ) INFORMATION FOR SEQ ID NO:925:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:925:

UUCUCAUCCU GAUGAGGCCG AAAGGCCGAA AACCUCCA　　　　　38

( 2 ) INFORMATION FOR SEQ ID NO:926:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:926:

GCUCCAGGCU GAUGAGGCCG AAAGGCCGAA ACUGUCUC　　　　　38

( 2 ) INFORMATION FOR SEQ ID NO:927:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:927:

GUCUGGGACU GAUGAGGCCG AAAGGCCGAA AGCCUGGC    38

(2) INFORMATION FOR SEQ ID NO:928:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:928:

UGUCUGGGCU GAUGAGGCCG AAAGGCCGAA AAGCCUGG    38

(2) INFORMATION FOR SEQ ID NO:929:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:929:

AUGUCUGGCU GAUGAGGCCG AAAGGCCGAA AAAGCCUG    38

(2) INFORMATION FOR SEQ ID NO:930:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:930:

UUCUGCUACU GAUGAGGCCG AAAGGCCGAA AUGUCUGG    38

(2) INFORMATION FOR SEQ ID NO:931:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:931:

UCUUCUGCCU GAUGAGGCCG AAAGGCCGAA AUAUGUCU    38

(2) INFORMATION FOR SEQ ID NO:932:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:932:

UUCCUGGACU GAUGAGGCCG AAAGGCCGAA AGUCUUCU    38

(2) INFORMATION FOR SEQ ID NO:933:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:933:

AUUCCUGGCU GAUGAGGCCG AAAGGCCGAA AAGUCUUC    38

( 2 ) INFORMATION FOR SEQ ID NO:934:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:934:

AAUCCUGCU GAUGAGGCCG AAAGGCCGAA AAAGUCUU       38

( 2 ) INFORMATION FOR SEQ ID NO:935:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:935:

UUUGGAUUCU GAUGAGGCCG AAAGGCCGAA AUUCCUGG       38

( 2 ) INFORMATION FOR SEQ ID NO:936:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:936:

CUUUGGAUCU GAUGAGGCCG AAAGGCCGAA AAUUCCUG       38

( 2 ) INFORMATION FOR SEQ ID NO:937:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:937:

GAUCUUUGCU GAUGAGGCCG AAAGGCCGAA AUUAAUUC       38

( 2 ) INFORMATION FOR SEQ ID NO:938:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:938:

ACAGCAUCCU GAUGAGGCCG AAAGGCCGAA AUCUUUGG       38

( 2 ) INFORMATION FOR SEQ ID NO:939:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:939:

GCUUCAAACU GAUGAGGCCG AAAGGCCGAA ACAGCAUC       38

( 2 ) INFORMATION FOR SEQ ID NO:940:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:940:

UGCUUCAACU GAUGAGGCCG AAAGGCCGAA AACAGCAU       38

( 2 ) INFORMATION FOR SEQ ID NO:941:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:941:

AUGCUUCACU GAUGAGGCCG AAAGGCCGAA AAACAGCA       38

( 2 ) INFORMATION FOR SEQ ID NO:942:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:942:

AAUGCUUCCU GAUGAGGCCG AAAGGCCGAA AAAACAGC       38

( 2 ) INFORMATION FOR SEQ ID NO:943:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:943:

AAAACCCACU GAUGAGGCCG AAAGGCCGAA AUGCUUCA       38

( 2 ) INFORMATION FOR SEQ ID NO:944:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:944:

AAAAACCCCU GAUGAGGCCG AAAGGCCGAA AAUGCUUC       38

( 2 ) INFORMATION FOR SEQ ID NO:945:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:945:

AAUAGAAACU GAUGAGGCCG AAAGGCCGAA ACCCAAAU       38

( 2 ) INFORMATION FOR SEQ ID NO:946:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:946:

AAAUAGAACU GAUGAGGCCG AAAGGCCGAA AACCCAAA    38

( 2 ) INFORMATION FOR SEQ ID NO:947:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:947:

GAAAUAGACU GAUGAGGCCG AAAGGCCGAA AAACCCAA    38

( 2 ) INFORMATION FOR SEQ ID NO:948:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:948:

AGAAAUAGCU GAUGAGGCCG AAAGGCCGAA AAAACCCA    38

( 2 ) INFORMATION FOR SEQ ID NO:949:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:949:

AAGAAAUACU GAUGAGGCCG AAAGGCCGAA AAAAACCC    38

( 2 ) INFORMATION FOR SEQ ID NO:950:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:950:

UGAAGAAACU GAUGAGGCCG AAAGGCCGAA AGAAAAAC    38

( 2 ) INFORMATION FOR SEQ ID NO:951:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:951:

ACUGAAGACU GAUGAGGCCG AAAGGCCGAA AUAGAAAA    38

( 2 ) INFORMATION FOR SEQ ID NO:952:

( i ) SEQUENCE CHARACTERISTICS:
    ( A ) LENGTH: 38 base pairs (B) TYPE: nucleic acid
        (C) STRANDEDNESS: single
        (D) TOPOLOGY: linear (xi) SEQUENCE DESCRIPTION: SEQ ID NO:952:

CACUGAAGCU GAUGAGGCCG AAAGGCCGAA AAUAGAAA 38

(2) INFORMATION FOR SEQ ID NO:953:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:953:

CCACUGAACU GAUGAGGCCG AAAGGCCGAA AAAUAGAA 38

(2) INFORMATION FOR SEQ ID NO:954:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:954:

AUCCACUGCU GAUGAGGCCG AAAGGCCGAA AGAAAUAG 38

(2) INFORMATION FOR SEQ ID NO:955:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:955:

GAUCCACUCU GAUGAGGCCG AAAGGCCGAA AAGAAAUA 38

(2) INFORMATION FOR SEQ ID NO:956:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:956:

ACUGUGAACU GAUGAGGCCG AAAGGCCGAA AUCCACUG 38

(2) INFORMATION FOR SEQ ID NO:957:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:957:

CGACUGUGCU GAUGAGGCCG AAAGGCCGAA AGAUCCAC 38

(2) INFORMATION FOR SEQ ID NO:958:

(i) SEQUENCE CHARACTERISTICS:
        (A) LENGTH: 38 base pairs
        (B) TYPE: nucleic acid
        (C) STRANDEDNESS: single ( D ) TOPOLOGY: linear ( x i ) SEQUENCE DESCRIPTION: SEQ ID NO:958:

CCGACUGUCU GAUGAGGCCG AAAGGCCGAA AAGAUCCA 38

( 2 ) INFORMATION FOR SEQ ID NO:959:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:959:

CAAACUCCCU GAUGAGGCCG AAAGGCCGAA ACUGUGAA 38

( 2 ) INFORMATION FOR SEQ ID NO:960:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:960:

UUGGGUCACU GAUGAGGCCG AAAGGCCGAA ACUCCGAC 38

( 2 ) INFORMATION FOR SEQ ID NO:961:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:961:

UUUGGGUCCU GAUGAGGCCG AAAGGCCGAA AACUCCGA 38

( 2 ) INFORMATION FOR SEQ ID NO:962:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:962:

CUCUUCAACU GAUGAGGCCG AAAGGCCGAA ACAUGUGU 38

( 2 ) INFORMATION FOR SEQ ID NO:963:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:963:

GCUCUUCACU GAUGAGGCCG AAAGGCCGAA AACAUGUG 38

( 2 ) INFORMATION FOR SEQ ID NO:964:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:964:

UGCUCUUCCU GAUGAGGCCG AAAGGCCGAA AAACAUGU 38

( 2 ) INFORMATION FOR SEQ ID NO:965:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:965:

AACACUGACU GAUGAGGCCG AAAGGCCGAA ACCAGCUG 38

( 2 ) INFORMATION FOR SEQ ID NO:966:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:966:

UAACACUGCU GAUGAGGCCG AAAGGCCGAA AACCAGCU 38

( 2 ) INFORMATION FOR SEQ ID NO:967:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:967:

CUAACACUCU GAUGAGGCCG AAAGGCCGAA AAACCAGC 38

( 2 ) INFORMATION FOR SEQ ID NO:968:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:968:

CCCCUCCUCU GAUGAGGCCG AAAGGCCGAA ACACUGAA 38

( 2 ) INFORMATION FOR SEQ ID NO:969:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:969:

ACCCCUCCCU GAUGAGGCCG AAAGGCCGAA AACACUGA 38

( 2 ) INFORMATION FOR SEQ ID NO:970:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:970:

GCCUUCUACU GAUGAGGCCG AAAGGCCGAA ACACCCCU 38

( 2 ) INFORMATION FOR SEQ ID NO:971:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:971:

GUGCCUUCCU GAUGAGGCCG AAAGGCCGAA AUACACCC 38

( 2 ) INFORMATION FOR SEQ ID NO:972:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:972:

UCAUUUAACU GAUGAGGCCG AAAGGCCGAA ACAUUCAU 38

( 2 ) INFORMATION FOR SEQ ID NO:973:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:973:

UUCAUUUACU GAUGAGGCCG AAAGGCCGAA AACAUUCA 38

( 2 ) INFORMATION FOR SEQ ID NO:974:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:974:

GUUCAUUUCU GAUGAGGCCG AAAGGCCGAA AAACAUUC 38

( 2 ) INFORMATION FOR SEQ ID NO:975:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:975:

GGUUCAUUCU GAUGAGGCCG AAAGGCCGAA AAAACAUU 38

( 2 ) INFORMATION FOR SEQ ID NO:976:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:976:

UGAACAAUCU GAUGAGGCCG AAAGGCCGAA AGGUUCAU 38

( 2 ) INFORMATION FOR SEQ ID NO:977:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:977:

UGUUGAACCU GAUGAGGCCG AAAGGCCGAA AUUAGGUU        38

( 2 ) INFORMATION FOR SEQ ID NO:978:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:978:

AAGUGUUGCU GAUGAGGCCG AAAGGCCGAA ACAAUUAG        38

( 2 ) INFORMATION FOR SEQ ID NO:979:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:979:

UAAGUGUUCU GAUGAGGCCG AAAGGCCGAA AACAAUUA        38

( 2 ) INFORMATION FOR SEQ ID NO:980:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:980:

AAAGUCCUCU GAUGAGGCCG AAAGGCCGAA AGUGUUGA        38

( 2 ) INFORMATION FOR SEQ ID NO:981:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:981:

CAAAGUCCCU GAUGAGGCCG AAAGGCCGAA AAGUGUUG        38

( 2 ) INFORMATION FOR SEQ ID NO:982:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:982:

AACUCACACU GAUGAGGCCG AAAGGCCGAA AGUCCUAA        38

( 2 ) INFORMATION FOR SEQ ID NO:983:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:983:

CAACUCACCU GAUGAGGCCG AAAGGCCGAA AAGUCCUA 38

( 2 ) INFORMATION FOR SEQ ID NO:984:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:984:

GCCACUUCCU GAUGAGGCCG AAAGGCCGAA ACUCACAA 38

( 2 ) INFORMATION FOR SEQ ID NO:985:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:985:

GAGAAAAUCU GAUGAGGCCG AAAGGCCGAA AGCCACUU 38

( 2 ) INFORMATION FOR SEQ ID NO:986:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:986:

CAGGAGAACU GAUGAGGCCG AAAGGCCGAA AUGAGCCA 38

( 2 ) INFORMATION FOR SEQ ID NO:987:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:987:

GCAGGAGACU GAUGAGGCCG AAAGGCCGAA AAUGAGCC 38

( 2 ) INFORMATION FOR SEQ ID NO:988:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:988:

UGCAGGAGCU GAUGAGGCCG AAAGGCCGAA AAAUGAGC 38

( 2 ) INFORMATION FOR SEQ ID NO:989:

( i ) SEQUENCE CHARACTERISTICS:

(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:989:

AUGCAGGACU GAUGAGGCCG AAAGGCCGAA AAAAUGAG 38

(2) INFORMATION FOR SEQ ID NO:990:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:990:

AUAUGCAGCU GAUGAGGCCG AAAGGCCGAA AGAAAAUG 38

(2) INFORMATION FOR SEQ ID NO:991:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:991:

UCACAGCACU GAUGAGGCCG AAAGGCCGAA AUGCAGGA 38

(2) INFORMATION FOR SEQ ID NO:992:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:992:

AUGCUCGACU GAUGAGGCCG AAAGGCCGAA AUUCCCAU 38

(2) INFORMATION FOR SEQ ID NO:993:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:993:

UCAUGCUCCU GAUGAGGCCG AAAGGCCGAA AGAUUCCC 38

(2) INFORMATION FOR SEQ ID NO:994:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:994:

CAGUUAGACU GAUGAGGCCG AAAGGCCGAA ACACAGUU 38

(2) INFORMATION FOR SEQ ID NO:995:

(i) SEQUENCE CHARACTERISTICS:
(A) LENGTH: 38 base pairs
(B) TYPE: nucleic acid (C) STRANDEDNESS: single
(D) TOPOLOGY: linear (x i) SEQUENCE DESCRIPTION: SEQ ID NO:995:

UCCAGUUACU GAUGAGGCCG AAAGGCCGAA AUACACAG 38

(2) INFORMATION FOR SEQ ID NO:996:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:996:

AGUCCAGUCU GAUGAGGCCG AAAGGCCGAA AGAUACAC 38

(2) INFORMATION FOR SEQ ID NO:997:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:997:

GAUGUGCACU GAUGAGGCCG AAAGGCCGAA AGUCCAGU 38

(2) INFORMATION FOR SEQ ID NO:998:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:998:

CGAUGUGCCU GAUGAGGCCG AAAGGCCGAA AAGUCCAG 38

(2) INFORMATION FOR SEQ ID NO:999:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:999:

CCCGUAACCU GAUGAGGCCG AAAGGCCGAA AUGUGCAA 38

(2) INFORMATION FOR SEQ ID NO:1000:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (x i) SEQUENCE DESCRIPTION: SEQ ID NO:1000:

ACACCCGUCU GAUGAGGCCG AAAGGCCGAA ACGAUGUG 38

(2) INFORMATION FOR SEQ ID NO:1001:

(i) SEQUENCE CHARACTERISTICS:
        (A) LENGTH: 38 base pairs
        (B) TYPE: nucleic acid
        (C) STRANDEDNESS: single
        (D) TOPOLOGY: linear ( x i ) SEQUENCE DESCRIPTION: SEQ ID NO:1001:

AACACCCGCU GAUGAGGCCG AAAGGCCGAA AACGAUGU                     38

( 2 ) INFORMATION FOR SEQ ID NO:1002:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1002:

CCUGUUUGCU GAUGAGGCCG AAAGGCCGAA ACACCCGU                     38

( 2 ) INFORMATION FOR SEQ ID NO:1003:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1003:

GCCUGUUUCU GAUGAGGCCG AAAGGCCGAA AACACCCG                     38

( 2 ) INFORMATION FOR SEQ ID NO:1004:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1004:

UGCAAGCUCU GAUGAGGCCG AAAGGCCGAA AGCAGCAG                     38

( 2 ) INFORMATION FOR SEQ ID NO:1005:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1005:

GUGCAAGCCU GAUGAGGCCG AAAGGCCGAA AAGCAGCA                     38

( 2 ) INFORMATION FOR SEQ ID NO:1006:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1006:

UCAAGUGCCU GAUGAGGCCG AAAGGCCGAA AGCUAAGC                     38

( 2 ) INFORMATION FOR SEQ ID NO:1007:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1007:

```
AUGUGAUCCU GAUGAGGCCG AAAGGCCGAA AGUGCAAG                               38
```

( 2 ) INFORMATION FOR SEQ ID NO:1008:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1008:

```
UUCCAUGUCU GAUGAGGCCG AAAGGCCGAA AUCAAGUG                               38
```

( 2 ) INFORMATION FOR SEQ ID NO:1009:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1009:

```
UCUCGUGGCU GAUGAGGCCG AAAGGCCGAA AGCUCCCU                               38
```

( 2 ) INFORMATION FOR SEQ ID NO:1010:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1010:

```
GUCUCGUGCU GAUGAGGCCG AAAGGCCGAA AAGCUCCC                               38
```

( 2 ) INFORMATION FOR SEQ ID NO:1011:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1011:

```
CACAUGAGCU GAUGAGGCCG AAAGGCCGAA ACUUCCCC                               38
```

( 2 ) INFORMATION FOR SEQ ID NO:1012:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1012:

```
UCACACAUCU GAUGAGGCCG AAAGGCCGAA AGUACUUC                               38
```

( 2 ) INFORMATION FOR SEQ ID NO:1013:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1013:

```
AUAGACACCU GAUGAGGCCG AAAGGCCGAA AUCACUCG                               38
```

( 2 ) INFORMATION FOR SEQ ID NO:1014:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1014:

UCCACAUACU GAUGAGGCCG AAAGGCCGAA ACACAAUC     38

( 2 ) INFORMATION FOR SEQ ID NO:1015:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1015:

AAUCCACACU GAUGAGGCCG AAAGGCCGAA AGACACAA     38

( 2 ) INFORMATION FOR SEQ ID NO:1016:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1016:

GGGCAAAUCU GAUGAGGCCG AAAGGCCGAA AUCCACAU     38

( 2 ) INFORMATION FOR SEQ ID NO:1017:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1017:

UGGGCAAACU GAUGAGGCCG AAAGGCCGAA AAUCCACA     38

( 2 ) INFORMATION FOR SEQ ID NO:1018:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1018:

AAUGGGCACU GAUGAGGCCG AAAGGCCGAA AUAAUCCA     38

( 2 ) INFORMATION FOR SEQ ID NO:1019:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1019:

UAAUGGGCCU GAUGAGGCCG AAAGGCCGAA AAUAAUCC     38

( 2 ) INFORMATION FOR SEQ ID NO:1020:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1020:

UAUUAAAUCU GAUGAGGCCG AAAGGCCGAA AUGGGCAA    38

( 2 ) INFORMATION FOR SEQ ID NO:1021:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1021:

UUAUUAAACU GAUGAGGCCG AAAGGCCGAA AAUGGGCA    38

( 2 ) INFORMATION FOR SEQ ID NO:1022:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1022:

CUUUAUUACU GAUGAGGCCG AAAGGCCGAA AUAAUGGG    38

( 2 ) INFORMATION FOR SEQ ID NO:1023:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1023:

UCUUUAUUCU GAUGAGGCCG AAAGGCCGAA AAUAAUGG    38

( 2 ) INFORMATION FOR SEQ ID NO:1024:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1024:

CUCUUUAUCU GAUGAGGCCG AAAGGCCGAA AAAUAAUG    38

( 2 ) INFORMATION FOR SEQ ID NO:1025:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1025:

AUCCUCUUCU GAUGAGGCCG AAAGGCCGAA AUUAAAUA    38

( 2 ) INFORMATION FOR SEQ ID NO:1026:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1026:

AAUUGACACU GAUGAGGCCG AAAGGCCGAA AUCCUCUU 38

( 2 ) INFORMATION FOR SEQ ID NO:1027:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1027:

CGCACAGCAG AAGUAGGAAC CAGAGAAACA CACGUUGUGG UACAUUACCU GGUA 54

( 2 ) INFORMATION FOR SEQ ID NO:1028:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1028:

GCUGAGCAAG AAGCCACGAC CAGAGAAACA CACGUUGUGG UACAUUACCU GGUA 54

( 2 ) INFORMATION FOR SEQ ID NO:1029:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1029:

AAUGGAUAAG AAGAGCAAAC CAGAGAAACA CACGUUGUGG UACAUUACCU GGUA 54

( 2 ) INFORMATION FOR SEQ ID NO:1030:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1030:

UCCUAACAAG AAGUUUCAAC CAGAGAAACA CACGUUGUGG UACAUUACCU GGUA 54

( 2 ) INFORMATION FOR SEQ ID NO:1031:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1031:

UUUUUAACAG AAGGACCAAC CAGAGAAACA CACGUUGUGG UACAUUACCU GGUA 54

( 2 ) INFORMATION FOR SEQ ID NO:1032:

( i ) SEQUENCE CHARACTERISTICS:
    ( A ) LENGTH: 54 base pairs

```
        ( B ) TYPE: nucleic acid
        ( C ) STRANDEDNESS: single
        ( D ) TOPOLOGY: linear ( x i ) SEQUENCE DESCRIPTION: SEQ ID NO:1032:

UGACCAACAG   AAGGAACUAC   CAGAGAAACA   CACGUUGUGG   UACAUUACCU   GGUA            5 4

( 2 ) INFORMATION FOR SEQ ID NO:1033:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1033:

UUUGGCAAAG   AAGGUGUAAC   CAGAGAAACA   CACGUUGUGG   UACAUUACCU   GGUA            5 4

( 2 ) INFORMATION FOR SEQ ID NO:1034:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1034:

GCAGAAUCAG   AAGCAUCUAC   CAGAGAAACA   CACGUUGUGG   UACAUUACCU   GGUA            5 4

( 2 ) INFORMATION FOR SEQ ID NO:1035:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1035:

UUCUCAACAG   AAGAAUCAAC   CAGAGAAACA   CACGUUGUGG   UACAUUACCU   GGUA            5 4

( 2 ) INFORMATION FOR SEQ ID NO:1036:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1036:

GCUUUCUCAG   AAGCAGAAAC   CAGAGAAACA   CACGUUGUGG   UACAUUACCU   GGUA            5 4

( 2 ) INFORMATION FOR SEQ ID NO:1037:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1037:

AUUUCAUGAG   AAGCAACGAC   CAGAGAAACA   CACGUUGUGG   UACAUUACCU   GGUA            5 4

( 2 ) INFORMATION FOR SEQ ID NO:1038:

( i ) SEQUENCE CHARACTERISTICS:
        ( A ) LENGTH: 54 base pairs
        ( B ) TYPE: nucleic acid
        ( C ) STRANDEDNESS: single
```

(D) TOPOLOGY: linear (xi) SEQUENCE DESCRIPTION: SEQ ID NO:1038:

CGAGUCAGAG AAGUGAGUAC CAGAGAAACA CACGUUGUGG UACAUUACCU GGUA   54

(2) INFORMATION FOR SEQ ID NO:1039:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (xi) SEQUENCE DESCRIPTION: SEQ ID NO:1039:

GGAACCGAAG AAGGUCUGAC CAGAGAAACA CACGUUGUGG UACAUUACCU GGUA   54

(2) INFORMATION FOR SEQ ID NO:1040:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (xi) SEQUENCE DESCRIPTION: SEQ ID NO:1040:

ACAGGCGGAG AAGAGUCAAC CAGAGAAACA CACGUUGUGG UACAUUACCU GGUA   54

(2) INFORMATION FOR SEQ ID NO:1041:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (xi) SEQUENCE DESCRIPTION: SEQ ID NO:1041:

UUGAGACAAG AAGAACCGAC CAGAGAAACA CACGUUGUGG UACAUUACCU GGUA   54

(2) INFORMATION FOR SEQ ID NO:1042:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (xi) SEQUENCE DESCRIPTION: SEQ ID NO:1042:

CAUCUUGAAG AAGGCGGAAC CAGAGAAACA CACGUUGUGG UACAUUACCU GGUA   54

(2) INFORMATION FOR SEQ ID NO:1043:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (xi) SEQUENCE DESCRIPTION: SEQ ID NO:1043:

CAUAGAGGAG AAGAAUGCAC CAGAGAAACA CACGUUGUGG UACAUUACCU GGUA   54

(2) INFORMATION FOR SEQ ID NO:1044:

(i) SEQUENCE CHARACTERISTICS:
      (A) LENGTH: 54 base pairs
      (B) TYPE: nucleic acid
      (C) STRANDEDNESS: single
      (D) TOPOLOGY: linear ( x i ) SEQUENCE DESCRIPTION: SEQ ID NO:1044:

UCAGGGGAAG AAGGGGAAC CAGAGAAACA CACGUUGUGG UACAUUACCU GGUA      54

( 2 ) INFORMATION FOR SEQ ID NO:1045:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1045:

UCUGGAGGAG AAGGUUCCAC CAGAGAAACA CACGUUGUGG UACAUUACCU GGUA      54

( 2 ) INFORMATION FOR SEQ ID NO:1046:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1046:

AAGGACAAAG AAGGAUCAAC CAGAGAAACA CACGUUGUGG UACAUUACCU GGUA      54

( 2 ) INFORMATION FOR SEQ ID NO:1047:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1047:

CUUUAAAGAG AAGGAUUUAC CAGAGAAACA CACGUUGUGG UACAUUACCU GGUA      54

( 2 ) INFORMATION FOR SEQ ID NO:1048:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1048:

UCUUCAAAAG AAGCAUCAAC CAGAGAAACA CACGUUGUGG UACAUUACCU GGUA      54

( 2 ) INFORMATION FOR SEQ ID NO:1049:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1049:

CAAACUCCAG AAGUGAAGAC CAGAGAAACA CACGUUGUGG UACAUUACCU GGUA      54

( 2 ) INFORMATION FOR SEQ ID NO:1050:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1050:

```
AUUAAGCCAG  AAGUUACUAC  CAGAGAAACA  CACGUUGUGG  UACAUUACCU  GGUA         54
```

( 2 ) INFORMATION FOR SEQ ID NO:1051:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1051:

```
ACAGCACAAG  AAGGAGAAAC  CAGAGAAACA  CACGUUGUGG  UACAUUACCU  GGUA         54
```

( 2 ) INFORMATION FOR SEQ ID NO:1052:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1052:

```
AGCUAAGCAG  AAGCCCAUAC  CAGAGAAACA  CACGUUGUGG  UACAUUACCU  GGUA         54
```

( 2 ) INFORMATION FOR SEQ ID NO:1053:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1053:

```
GCAAGCUAAG  AAGCAGCCAC  CAGAGAAACA  CACGUUGUGG  UACAUUACCU  GGUA         54
```

( 2 ) INFORMATION FOR SEQ ID NO:1054:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1054:

```
UCCUACUGUU  GCUGUGCG                                                    18
```

( 2 ) INFORMATION FOR SEQ ID NO:1055:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1055:

```
CGUGGCAGUU  UGCUCAGC                                                    18
```

( 2 ) INFORMATION FOR SEQ ID NO:1056:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1056:

```
UUGCUCAGCC  UAUCCAUU                                                    18
```

( 2 ) INFORMATION FOR SEQ ID NO:1057:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1057:

UGAAACAGUU UGUUAGGA     18

( 2 ) INFORMATION FOR SEQ ID NO:1058:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1058:

UGGUCCUGUU GUUAAAAA     18

( 2 ) INFORMATION FOR SEQ ID NO:1059:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1059:

AGUUCCUGAU GUUGGUCA     18

( 2 ) INFORMATION FOR SEQ ID NO:1060:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1060:

UACACCAGAU UUGCCAAA     18

( 2 ) INFORMATION FOR SEQ ID NO:1061:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1061:

AGAUGCUGUU GAUUCUGC     18

( 2 ) INFORMATION FOR SEQ ID NO:1062:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1062:

UGAUUCUGCU GUUGAGAA     18

( 2 ) INFORMATION FOR SEQ ID NO:1063:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1063:

UUCUGCUGUU GAGAAAGC 18

( 2 ) INFORMATION FOR SEQ ID NO:1064:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1064:

CGUUGCUGCU CAUGAAAU 18

( 2 ) INFORMATION FOR SEQ ID NO:1065:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1065:

ACUCACAGAC CUGACUCG 18

( 2 ) INFORMATION FOR SEQ ID NO:1066:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1066:

CAGACCUGAC UCGGUUCC 18

( 2 ) INFORMATION FOR SEQ ID NO:1067:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1067:

UGACUCGGUU CCGCCUGU 18

( 2 ) INFORMATION FOR SEQ ID NO:1068:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1068:

CGGUUCCGCC UGUCUCAA 18

( 2 ) INFORMATION FOR SEQ ID NO:1069:

( i ) SEQUENCE CHARACTERISTICS:

( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1069:

UCCGCCUGUC UCAAGAUG 18

( 2 ) INFORMATION FOR SEQ ID NO:1070:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1070:

GCAUUCAGUC CCUCUAUG 18

( 2 ) INFORMATION FOR SEQ ID NO:1071:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1071:

UCCCCCUGAC UCCCCUGA 18

( 2 ) INFORMATION FOR SEQ ID NO:1072:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1072:

GGAACCUGUC CCUCCAGA 18

( 2 ) INFORMATION FOR SEQ ID NO:1073:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1073:

UGAUCCUGCU UUGUCCUU 18

( 2 ) INFORMATION FOR SEQ ID NO:1074:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1074:

AAAUCCUGAU CUUUAAAG 18

( 2 ) INFORMATION FOR SEQ ID NO:1075:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (xi) SEQUENCE DESCRIPTION: SEQ ID NO:1075:

UGAUGCUGUU UUUGAAGA  18

(2) INFORMATION FOR SEQ ID NO:1076:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1076:

CUUCACAGUU GGAGUUUG  18

(2) INFORMATION FOR SEQ ID NO:1077:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1077:

AGUAACAGCU GGCUUAAU  18

(2) INFORMATION FOR SEQ ID NO:1078:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1078:

UUCUCCUGCC UGUGCUGU  18

(2) INFORMATION FOR SEQ ID NO:1079:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1079:

AUGGGCUGCU GCUUAGCU  18

(2) INFORMATION FOR SEQ ID NO:1080:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1080:

GGCUGCUGCU UAGCUUGC  18

(2) INFORMATION FOR SEQ ID NO:1081:

(i) SEQUENCE CHARACTERISTICS:
(A) LENGTH: 54 base pairs
(B) TYPE: nucleic acid
(C) STRANDEDNESS: single
(D) TOPOLOGY: linear ( x i ) SEQUENCE DESCRIPTION: SEQ ID NO:1081:

CCACGCACAG AAGUAGCAAC CAGAGAAACA CACGUUGUGG UACAUUACCU GGUA 54

( 2 ) INFORMATION FOR SEQ ID NO:1082:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1082:

AGUGGAUAAG AAGAGCAAAC CAGAGAAACA CACGUUGUGG UACAUUACCU GGUA 54

( 2 ) INFORMATION FOR SEQ ID NO:1083:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1083:

UUUUAACAAG AAGUUCAAC CAGAGAAACA CACGUUGUGG UACAUUACCU GGUA 54

( 2 ) INFORMATION FOR SEQ ID NO:1084:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1084:

UUUUUAACAG AAGGACUAAC CAGAGAAACA CACGUUGUGG UACAUUACCU GGUA 54

( 2 ) INFORMATION FOR SEQ ID NO:1085:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1085:

UGACCAACAG AAGGAACGAC CAGAGAAACA CACGUUGUGG UACAUUACCU GGUA 54

( 2 ) INFORMATION FOR SEQ ID NO:1086:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1086:

CUUGGCAGAG AAGGUGUGAC CAGAGAAACA CACGUUGUGG UACAUUACCU GGUA 54

( 2 ) INFORMATION FOR SEQ ID NO:1087:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1087:

```
GCAGCAUCAG  AAGCAUCUAC  CAGAGAAACA  CACGUUGUGG  UACAUUACCU  GGUA                    5 4
```

( 2 ) INFORMATION FOR SEQ ID NO:1088:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1088:

```
AGCUCAUGAG  AAGCAACAAC  CAGAGAAACA  CACGUUGUGG  UACAUUACCU  GGUA                    5 4
```

( 2 ) INFORMATION FOR SEQ ID NO:1089:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1089:

```
CCGAGUGAAG  AAGACCCAAC  CAGAGAAACA  CACGUUGUGG  UACAUUACCU  GGUA                    5 4
```

( 2 ) INFORMATION FOR SEQ ID NO:1090:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1090:

```
CUGGGUACAG  AAGCGCUUAC  CAGAGAAACA  CACGUUGUGG  UACAUUACCU  GGUA                    5 4
```

( 2 ) INFORMATION FOR SEQ ID NO:1091:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1091:

```
GCGUUGUAAG  AAGGGUACAC  CAGAGAAACA  CACGUUGUGG  UACAUUACCU  GGUA                    5 4
```

( 2 ) INFORMATION FOR SEQ ID NO:1092:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1092:

```
CGGGCCAGAG  AAGUGAAGAC  CAGAGAAACA  CACGUUGUGG  UACAUUACCU  GGUA                    5 4
```

( 2 ) INFORMATION FOR SEQ ID NO:1093:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1093:

```
AAAGGCGGAG  AAGGGCCAAC  CAGAGAAACA  CACGUUGUGG  UACAUUACCU  GGUA                    5 4
```

( 2 ) INFORMATION FOR SEQ ID NO:1094:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1094:

UUGAGAAAAG AAGAACCGAC CAGAGAAACA CACGUUGUGG UACAUUACCU GGUA     54

( 2 ) INFORMATION FOR SEQ ID NO:1095:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1095:

GAGGCAGGAG AAGGUCCAAC CAGAGAAACA CACGUUGUGG UACAUUACCU GGUA     54

( 2 ) INFORMATION FOR SEQ ID NO:1096:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1096:

UCAGGAGAAG AAGGGGCCAC CAGAGAAACA CACGUUGUGG UACAUUACCU GGUA     54

( 2 ) INFORMATION FOR SEQ ID NO:1097:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1097:

CCUGGAGGAG AAGGUUCCAC CAGAGAAACA CACGUUGUGG UACAUUACCU GGUA     54

( 2 ) INFORMATION FOR SEQ ID NO:1098:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1098:

AAGGACAGAG AAGGAUCAAC CAGAGAAACA CACGUUGUGG UACAUUACCU GGUA     54

( 2 ) INFORMATION FOR SEQ ID NO:1099:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1099:

CAUCGAAGAG AAGAUCUGAC CAGAGAAACA CACGUUGUGG UACAUUACCU GGUA     54

( 2 ) INFORMATION FOR SEQ ID NO:1100:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1100:

CUUUAAGAG AAGAAUUUAC CAGAGAAACA CACGUUGUGG UACAUUACCU GGUA    54

( 2 ) INFORMATION FOR SEQ ID NO:1101:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1101:

AAAAUGAAAG AAGUACCAC CAGAGAAACA CACGUUGUGG UACAUUACCU GGUA    54

( 2 ) INFORMATION FOR SEQ ID NO:1102:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1102:

UGGCCCAGAG AAGAGUUCAC CAGAGAAACA CACGUUGUGG UACAUUACCU GGUA    54

( 2 ) INFORMATION FOR SEQ ID NO:1103:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1103:

GCUCCAGGAG AAGUCUCUAC CAGAGAAACA CACGUUGUGG UACAUUACCU GGUA    54

( 2 ) INFORMATION FOR SEQ ID NO:1104:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1104:

GCUUCAAAAG AAGCAUCGAC CAGAGAAACA CACGUUGUGG UACAUUACCU GGUA    54

( 2 ) INFORMATION FOR SEQ ID NO:1105:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1105:

CAAACUCCAG AAGUGAAGAC CAGAGAAACA CACGUUGUGG UACAUUACCU GGUA    54

( 2 ) INFORMATION FOR SEQ ID NO:1106:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1106:

CUGAAACCAG AAGUUGCUAC CAGAGAAACA CACGUUGUGG UACAUUACCU GGUA    54

( 2 ) INFORMATION FOR SEQ ID NO:1107:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1107:

AGCUAAGCAG AAGCCUGUAC CAGAGAAACA CACGUUGUGG UACAUUACCU GGUA    54

( 2 ) INFORMATION FOR SEQ ID NO:1108:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1108:

GCAAGCUAAG AAGCAGCCAC CAGAGAAACA CACGUUGUGG UACAUUACCU GGUA    54

( 2 ) INFORMATION FOR SEQ ID NO:1109:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1109:

AAUCACUCAG AAGUCACAAC CAGAGAAACA CACGUUGUGG UACAUUACCU GGUA    54

( 2 ) INFORMATION FOR SEQ ID NO:1110:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1110:

UGCUACUGCU GUGCGUGG    18

( 2 ) INFORMATION FOR SEQ ID NO:1111:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1111:

UUGCUCAGCC UAUCCACU    18

( 2 ) INFORMATION FOR SEQ ID NO:1112:

( i ) SEQUENCE CHARACTERISTICS:
        ( A ) LENGTH: 18 base pairs ( B ) TYPE: nucleic acid
            ( C ) STRANDEDNESS: single
            ( D ) TOPOLOGY: linear ( x i ) SEQUENCE DESCRIPTION: SEQ ID NO:1112:

UGAAACAGUU UGUUAAAA                                                                          18

( 2 ) INFORMATION FOR SEQ ID NO:1113:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1113:

UAGUCCUGUU GUUAAAAA                                                                          18

( 2 ) INFORMATION FOR SEQ ID NO:1114:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1114:

CGUUCCUGAU GUUGGUCA                                                                          18

( 2 ) INFORMATION FOR SEQ ID NO:1115:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1115:

CACACCGGAU CUGCCAAG                                                                          18

( 2 ) INFORMATION FOR SEQ ID NO:1116:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1116:

AGAUGCUGUU GAUGCUGC                                                                          18

( 2 ) INFORMATION FOR SEQ ID NO:1117:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1117:

UGUUGCUGCU CAUGAGCU                                                                          18

( 2 ) INFORMATION FOR SEQ ID NO:1118:

( i ) SEQUENCE CHARACTERISTICS:
            ( A ) LENGTH: 18 base pairs
            ( B ) TYPE: nucleic acid
            ( C ) STRANDEDNESS: single (D) TOPOLOGY: linear (x i) SEQUENCE DESCRIPTION: SEQ ID NO:1118:

UGGGUCUGUU UCACUCGG                             18

(2) INFORMATION FOR SEQ ID NO:1119:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO:1119:

AAGCGCUGAU GUACCCAG                             18

(2) INFORMATION FOR SEQ ID NO:1120:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO:1120:

GUACCCAGUC UACAACGC                             18

(2) INFORMATION FOR SEQ ID NO:1121:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO:1121:

CUUCACAGAC CUGGCCCG                             18

(2) INFORMATION FOR SEQ ID NO:1122:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO:1122:

UGGCCCGGUU CCGCCUUU                             18

(2) INFORMATION FOR SEQ ID NO:1123:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO:1123:

CGGUUCCGCC UUUCUCAA                             18

(2) INFORMATION FOR SEQ ID NO:1124:

(i) SEQUENCE CHARACTERISTICS:
      (A) LENGTH: 18 base pairs
      (B) TYPE: nucleic acid
      (C) STRANDEDNESS: single
      (D) TOPOLOGY: linear ( x i ) SEQUENCE DESCRIPTION: SEQ ID NO:1124:

UGGACCGGCC CCUGCCUC                                                                                    18

( 2 ) INFORMATION FOR SEQ ID NO:1125:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1125:

GGCCCCUGCC UCUCCUGA                                                                                    18

( 2 ) INFORMATION FOR SEQ ID NO:1126:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1126:

GGAACCUGUC CCUCCAGG                                                                                    18

( 2 ) INFORMATION FOR SEQ ID NO:1127:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1127:

UGAUCCAGAU CUGUCCUU                                                                                    18

( 2 ) INFORMATION FOR SEQ ID NO:1128:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1128:

CAGAUCUGUC CUUCGAUG                                                                                    18

( 2 ) INFORMATION FOR SEQ ID NO:1129:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1129:

AAAUUCUGUU CUUUAAAG                                                                                    18

( 2 ) INFORMATION FOR SEQ ID NO:1130:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1130:

GGAUACUGUU UUCAUUUU 18

( 2 ) INFORMATION FOR SEQ ID NO:1131:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1131:

GAACUCAGUU CUGGGCCA 18

( 2 ) INFORMATION FOR SEQ ID NO:1132:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1132:

AGAGACAGUC CCUGGAGC 18

( 2 ) INFORMATION FOR SEQ ID NO:1133:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1133:

CGAUGCUGUU UUUGAAGC 18

( 2 ) INFORMATION FOR SEQ ID NO:1134:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1134:

CUUCACAGUC GGAGUUUG 18

( 2 ) INFORMATION FOR SEQ ID NO:1135:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1135:

AGCAACAGCU GGUUUCAG 18

( 2 ) INFORMATION FOR SEQ ID NO:1136:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1136:

ACAGGCUGCU GCUUAGCU 18

( 2 ) INFORMATION FOR SEQ ID NO:1137:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1137:

GGCUGCUGCU UAGCUUGC         18

( 2 ) INFORMATION FOR SEQ ID NO:1138:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1138:

UGUGACAGAC GAGUGAUU         18

( 2 ) INFORMATION FOR SEQ ID NO:1139:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1139:

GCCAUCUCUU CCUUC         15

( 2 ) INFORMATION FOR SEQ ID NO:1140:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1140:

GAAGGAACUG AUGAGGCCGA AAGGCCGAAA GAUGGC         36

( 2 ) INFORMATION FOR SEQ ID NO:1141:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1141:

GCCAUCUCUU CCUUC         15

( 2 ) INFORMATION FOR SEQ ID NO:1142:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1142:

GAAGGAACUG AUGAGGGCCG AAAGGCCGAA AGAUGGCT         38

( 2 ) INFORMATION FOR SEQ ID NO:1143:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1143:

AUGCUGUUUU UGAAG     15

( 2 ) INFORMATION FOR SEQ ID NO:1144:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1144:

CUUCAAACUG AUGAGGCCGA AAGGCCGAAA CAGCAUT     37

( 2 ) INFORMATION FOR SEQ ID NO:1145:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1145:

CUGUUUUUGA AGAAU     15

( 2 ) INFORMATION FOR SEQ ID NO:1146:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1146:

AUUCUUCCUG AUGAGGCCGA AAGGCCGAAA AAACAGT     37

( 2 ) INFORMATION FOR SEQ ID NO:1147:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1147:

CUGUUUUUGA AGCAU     15

( 2 ) INFORMATION FOR SEQ ID NO:1148:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1148:

AUGCUUCCUG AUGAGGCCGA AAGGCCGAAA AAACAGT     37

( 2 ) INFORMATION FOR SEQ ID NO:1149:

( i ) SEQUENCE CHARACTERISTICS:

```
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1149:

CUUAUGAGGC  CGAAAGGCCG  AU                                                      2 2

( 2 ) INFORMATION FOR SEQ ID NO:1150:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1150:

CUGAUGAGGC  CGAAAGGCCG  AA                                                      2 2

( 2 ) INFORMATION FOR SEQ ID NO:1151:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1151:

AATGAAAACG  AGGTCCTTGC                                                          2 0
```

STROMELYSIN TARGETED RIBOZYMES

This application is a continuation-in-part of U.S. Ser. No. 08/354,920, filed Dec. 13, 1994, now abandoned, which is a continuation-in-part of U.S. Ser. No. 08/152,487, filed Nov. 12, 1993, now abandoned, which is a continuation-in-part of U.S. Ser. No. 07/989,848, filed Dec. 7, 1992, now abandoned.

BACKGROUND OF THE INVENTION

This invention relates to methods for inhibition of osteoarthritis, in particular, inhibition of genetic expression which leads to a reduction or elimination of extracellular matrix digestion by matrix metalloproteinases.

There are several types of arthritis, with osteoarthritis and rheumatoid arthritis being predominant. Osteoarthritis is a slowly progressive disease characterized by degeneration of articular cartilage with proliferation and remodeling of subchondral bone. It presents with a clinical picture of pain, deformity, and loss of joint motion. Rheumatoid arthritis is a chronic systemic inflammatory disease. Rheumatoid arthritis may be mild and relapsing or severe and progressive, leading to joint deformity and incapacitation.

Arthritis is the major contributor to functional impairment among the older population. It is the major cause of disability and accounts for a large proportion of the hospitalizations and health care expenditures of the elderly. Arthritis is estimated to be the principal cause of total incapacitation for about one million persons aged 55 and older and is thought to be an important contributing cause for about one million more.

Estimating the incidence of osteoarthritis is difficult for several reasons. First, osteoarthritis is diagnosed objectively on the basis of reading radiographs, but many people with radiologic evidence of disease have no obvious symptoms. Second, the estimates of prevalence are based upon clinical evaluations because radiographic data is not available for all afflicted joints. In the NHANESI survey of 1989, data were based upon a thorough musculoskeletal evaluation during which any abnormalities of the spine, knee, hips, and peripheral joints were noted as well as other specific diagnoses. Based on these observations, 12% of the U.S. population between 25 and 74 years of age have osteoarthritis.

It is generally agreed that rheumatoid arthritis has a world-wide distribution and affects all racial and ethnic groups. The exact prevalence in the U.S. is unknown but has been estimated to range between 0.5% and 1.5%. Rheumatoid arthritis occurs at all age levels and generally increases in prevalence with advancing age. It is 2–3 times more prevalent in women than in men and peak incidence occurs between 40–60 years of age. In addition to immunological factors, environmental, occupational and psychosocial factors have been studied for potential etiologic roles in the disease.

The extracellular matrix of multicellular organisms plays an important role in the formation and maintenance of tissues. The meshwork of the extracellular matrix is deposited by resident cells and provides a framework for cell adhesion and migration, as well as a permeability barrier in cell-cell communication. Connective tissue turnover during normal growth and development or under pathological conditions is thought to be mediated by a family of neutral metalloproteinases, which are zinc-containing enzymes that require calcium for full activity. The regulation of metalloproteinase expression is cell-type specific and may vary among species.

The best characterized of the matrix metalloproteinases, interstitial collagenase (MMP-1), is specific for collagen types I, II, and III. MMP-1 cleaves all three chains of the triple helix at a single point initiating sequential breakdown of the interstitial collagens. Interstitial collagenase activity has been observed in rheumatoid synovial cells as well as in the synovial fluid of patients with inflammatory arthritis. Gelatinases (MMP-2) represent a subgroup of the metalloproteinases consisting of two distinct gene products; a 70 kDa gelatinase expressed by most connective tissue cells, and a 92 kDa gelatinase expressed by inflammatory phagocytes and tumor cells. The larger enzyme is expressed by macrophages, SV-40 transformed fibroblasts, and neutrophils. The smaller enzyme is secreted by H-ras transformed bronchial epithelial cells and tumor cells, as well as normal human skin fibroblasts. These enzymes degrade gelatin (denatured collagen) as well as native collagen type XI. Stromelysin (MMP-3) has a wide spectrum of action on molecules composing the extracellular matrix. It digests proteoglycans, fibronectin, laminin, type IV and IX collagens and gelatin, and can remove the N-terminal propeptide region from procollagen, thus activating the collagenase. It has been found in human cartilage extracts, rheumatoid synovial cells, and in the synovium and chondrocytes of joints in rats with collagen-induced arthritis.

Both osteoarthritis and rheumatoid arthritis are treated mainly with compounds that inhibit cytokine or growth-factor induced synthesis of the matrix metalloproteinases which are involved in the extracellular matrix destruction observed in these diseases. Current clinical treatments rely upon dexamethasone and retinoid compounds, which are potent suppressors of a variety of metalloproteinases. The global effects of dexamethasone and retinoid treatment upon gene expression in treated cells make the development of alternative therapies desirable, especially for long term treatments. Recently, it was shown that gamma-interferon suppressed lipopolysaccharide induced collagenase and stromelysin production in cultured macrophages. Also, tissue growth factor-β (TGF-β) has been shown to block epidermal growth factor (EGF) induction of stromelysin synthesis in vitro. Experimental protocols involving gene therapy approaches include the controlled expression of the metalloproteinase inhibitors TIMP-1 and TIMP-2. Of the latter three approaches, only γ-interferon treatment is currently feasible in a clinical application.

SUMMARY OF THE INVENTION

Applicant notes that the inhibition of collagenase and stromelysin production in the synovial membrane of joints can be accomplished using ribozymes and antisense molecules. Ribozyme treatment can be a partner to current treatments which primarily target immune cells reacting to pre-existing tissue damage. Early ribozyme or antisense treatment which reduces the collagenase or stromelysin-induced damage can be followed by treatment with the anti-inflammatories or retinoids, if necessary. In this manner, expression of the proteinases can be controlled at both transcriptional and translational levels. Ribozyme or antisense treatment can be given to patients expressing radiological signs of osteoarthritis prior to the expression of clinical symptoms. Ribozyme or antisense treatment can impact the expression of stromelysin without introducing the nonspecific effects upon gene expression which accompany treatment with the retinoids and dexamethasone. The ability of stromelysin to activate procollagenase indicates that a ribozyme or antisense molecule which reduces stromelysin expression can also be used in the treatment of both osteoarthritis (which is primarily a stromelysin-associated pathology) and rheumatoid arthritis (which is primarily related to enhanced collagenase activity).

While a number of cytokines and growth factors induce metalloproteinase activities during wound healing and tissue injury of a pre-osteoarthritic condition, these molecules are not preferred targets for therapeutic intervention. Primary emphasis is placed upon inhibiting the molecules which are responsible for the disruption of the extracellular matrix, because most people will be presenting radiologic or clinical symptoms prior to treatment. The most versatile of the metalloproteinases (the molecule which can do the most structural damage to the extracellular matrix, if not regulated) is stromelysin. Additionally, this molecule can activate procollagenase, which in turn causes further damage to the collagen backbone of the extracellular matrix. Under normal conditions, the conversion of prostromelysin to active stromelysin is regulated by the presence of inhibitors called TIMPs (tissue inhibitors of MMP). Because the level of TIMP in synovial cells exceeds the level of prostromelysin and stromelysin activity is generally absent from the synovial fluid associated with non-arthritic tissues, the toxic effects of inhibiting stromelysin activity in non-target cells should be negligible.

Thus, the invention features use of ribozymes or antisense molecules to treat or prevent arthritis, particularly osteoarthritis, e.g., by inhibiting the synthesis of the prostromelysin molecule in synovial cells, or by inhibition of other matrix metalloproteinases discussed above. Cleavage of targeted mRNAs (stromelysin mRNAs, including stromelysin 1, 2, and 3, and collagenase) expressed in macrophages, neutrophils and synovial cells represses the synthesis of the zymogen form of stromelysin, prostromelysin.

Those in the art will recognize the other potential targets discussed above are also suitable for treatment with ribozymes, which will reduce the risk or occurrence of pathologic degradation of the extracellular matrix such as the collagenase and gelatinase metalloproteinases, other proteinases which can activate the proenzyme forms of the metalloproteinases in synovial fluid or cartilaginous cells, cytokines or growth factors which activate the expression of the metalloproteinases and adhesion molecules which attract macrophage and neutrophils to the areas of tissue injury.

Ribozymes are RNA molecules having an enzymatic activity which is able to repeatedly cleave other separate RNA molecules in a nucleotide base sequence specific manner. It is said that such enzymatic RNA molecules can be targeted to virtually any RNA transcript and efficient cleavage has been achieved in vitro. Kim et al., 84 *Proc. Nat. Acad. of Sci. U.S.A.* 8788, 1987; Haseloff and Gerlach, 334 *Nature* 585, 1988; Cech, 260 *JAMA* 3030, 1988; and Jefferies et al., 17 *Nucleic Acid Research* 1371, 1989.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

By "enzymatic RNA molecule" it is meant an RNA molecule which has complementarity in a substrate binding region to a specified mRNA target, and also has an enzymatic activity which is active to specifically cleave that mRNA. That is, the enzymatic RNA molecule is able to intermolecularly cleave mRNA and thereby inactivate a target mRNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. For in vivo treatment, complementarity between 30 and 45 bases is preferred; although lower numbers are also useful.

By "complementary" is meant a nucleotide sequence that can form hydrogen bond(s) with other nucleotide sequence by either traditional Watson-Crick or other non-traditional types (for example Hoogsteen type) of base-paired interactions.

The enzymatic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, *Proc. Natl. Acad. Sci. U.S.A.*, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or *Neurospora* VS RNA. Examples of such hammerhead motifs are described by Rossi et al., 1992, *Aids Research and Human Retroviruses* 8, 183, of hairpin motifs by Hampel et al., EPA 0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, *Neurospora* VS RNA ribozyme motif is described by Collins (Saville and Collins, 1990 *Cell* 61, 685–696; Saville and Collins, 1991 *Proc. Natl. Acad. Sci. U.S.A.* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target stromelysin encoding mRNAs such that specific treatment of a disease or condition can be provided with either one or several enzymatic nucleic acids. Such enzymatic nucleic acid molecules can be delivered exogenously to specific cells as required. Alternatively, the ribozymes can be expressed from DNA or RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. U.S.A.*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. U.S.A.* 89, 10802–6; Chen et al., 1992 *Nucleic Acids Res.*, 20, 4581–9; Sarver et al., 1990 *Science* 247, 1222–1225). Those skilled in the art realize that any ribozyme can be expressed in eukaryotic cells from the appropriate DNA vector. The activity of such ribozymes can be augmented by their release from the primary transcript by a second ribozyme (Draper et al., PCT WO 93/23569, and Sullivan et al., PCT WO 94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856).

Ribozyme therapy, due to its exquisite specificity, is particularly well-suited to target mRNA encoding factors that contribute to disease pathology. Thus, ribozymes that cleave stromelysin mRNAs may represent novel therapeutics for the treatment of asthma.

Thus, in a first aspect, the invention features ribozymes that inhibit stromelysin production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target stromelysin encoding mRNAs, preventing translation and stromelysin protein accumulation. In the absence of the expression of the target gene, a therapeutic effect may be observed.

By "inhibit" is meant that the activity or level of stromelysin encoding mRNAs and protein is reduced below that observed in the absence of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of stromelysin activity in a cell or tissue. By "related" is meant that the inhibition of stromelysin mRNAs and thus reduction in the level of stromelysin activity will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers. In preferred embodiments, the ribozymes have binding arms which are complementary to the sequences in Tables II, III, IV, VI, VIII and IX. Examples of such ribozymes are shown in Tables V, VII, VIII and IX. Examples of such ribozymes consist essentially of sequences defined in these Tables.

By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit stromelysin activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

This class of chemicals exhibits a high degree of specificity for cleavage of the intended target mRNA. Consequently, the ribozyme agent will only affect cells expressing that particular gene, and will not be toxic to normal tissues.

The invention can be used to treat or prevent (prophylactically) osteoarthritis or other pathological conditions which are mediated by metalloproteinase activation. The preferred administration protocol is in vivo administration to reduce the level of stromelysin activity.

Thus, in the first aspect, the invention features an enzymatic RNA molecule (or ribozyme) which cleaves mRNA associated with development or maintenance of an arthritic condition, e.g., mRNA encoding stromelysin, and in particular, those mRNA targets disclosed in the tables below, which include both hammerhead and hairpin target sites. In each case the site is flanked by regions to which appropriate substrate binding arms can be synthesized and an appropriate hammerhead or hairpin motif can be added to provide enzymatic activity, by methods described herein and known in the art. For example, referring to FIG. 1, arms I and III are modified to be specific substrate-binding arms, and arm II remains essentially as shown.

Ribozymes that cleave stromelysin mRNAs represent a novel therapeutic approach to arthritic disorders like osteoarthritis. The invention features use of ribozymes to treat osteoarthritis, e.g., by inhibiting the synthesis of prostromelysin molecule in synovial cells or by the inhibition of matrix metalloproteinases. Applicant indicates that ribozymes are able to inhibit the secretion of stromelysin and that the catalytic activity of the ribozymes is required for their inhibitory effect. Those of ordinary skill in the art, will find that it is clear from the examples described that other ribozymes that cleave stromelysin encoding mRNAs may be readily designed and are within the invention.

In preferred embodiments, the enzymatic RNA molecule is formed in a hammerhead motif, but may also be formed in the motif of a hairpin, hepatitis delta virus, group I intron or RNAseP-like RNA (in association with an RNA guide sequence). Examples of such hammerhead motifs are described by Rossi et al., 8 *Aids Research and Human Retroviruses* 183, 1992, of hairpin motifs by Hampel et al., "RNA Catalyst for Cleaving Specific RNA Sequences", filed Sep. 20, 1989, which is a continuation-in-part of U.S. Ser. No. 07/247,100, filed Sep. 20, 1988; Hampel and Tritz, 28 *Biochemistry* 4929, 1989; and Hampel et al., 18 *Nucleic Acids Research* 299, 1990, and an example of the hepatitis delta virus motif is described by Perrotta and Been, 31 *Biochemistry*, 16, 1992, of the RNAseP motif by Guerrier-Takada, et al., 35 *Cell* 849, 1983, and of the group I intron by Cech et al., U.S. Pat. No. 4,987,071. All the publications are hereby incorporated by reference herein. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In a second related aspect, the invention features a mammalian cell which includes an enzymatic RNA molecule as described above. Preferably, the mammalian cell is a human cell.

In a third related aspect, the invention features an expression vector which includes nucleic acid encoding an enzymatic RNA molecule described above, located in the vector, e.g., in a manner which allows expression of that enzymatic RNA molecule within a mammalian cell.

In a fourth related aspect, the invention features a method for treatment of an arthritic condition by administering to a patient an enzymatic RNA molecule as described above.

The invention provides a class of chemical cleaving agents which exhibit a high degree of specificity for the mRNA causative of an arthritic condition. Such enzymatic RNA molecules can be delivered exogenously or endogenously to infected cells. In the preferred hammerhead motif the small size (less than 40 nucleotides, preferably between 32 and 36 nucleotides in length) of the molecule allows the cost of treatment to be reduced.

The enzymatic RNA molecules of this invention can be used to treat arthritic or prearthritic conditions. Such treatment can also be extended to other related genes in nonhuman primates. Affected animals can be treated at the time of arthritic risk detection, or in a prophylactic manner. This timing of treatment will reduce the chance of further arthritic damage.

Other features and advantages of the invention will be apparent from the following description of the preferred embodiments thereof, and from the claims.

DESCRIPTION OF THE PREFERRED EMBODIMENTS

The drawing will first briefly be described.

Drawing

Figure 2A:
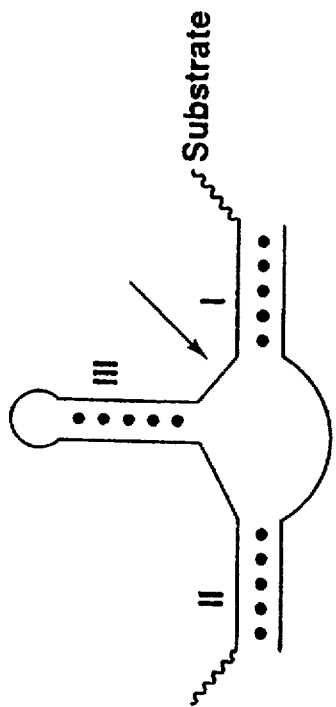
FIG. 2a is a diagrammatic representation of the hammerhead ribozyme domain known in the art.
Figure 2B:
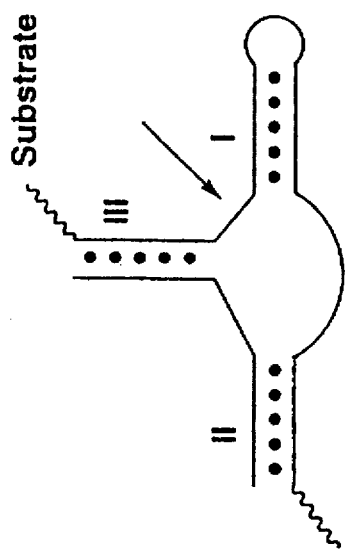
FIG. 2b is a diagrammatic representation of the hammerhead ribozyme as divided by Uhlenbeck (1987,*Nature*, 327, 596–600) into a substrate and enzyme portion.
Figure 2C:
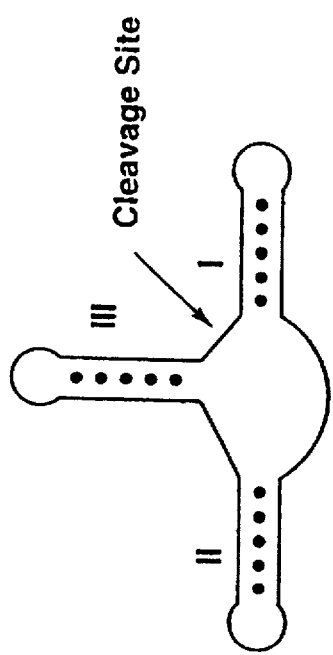
Figure 2D:
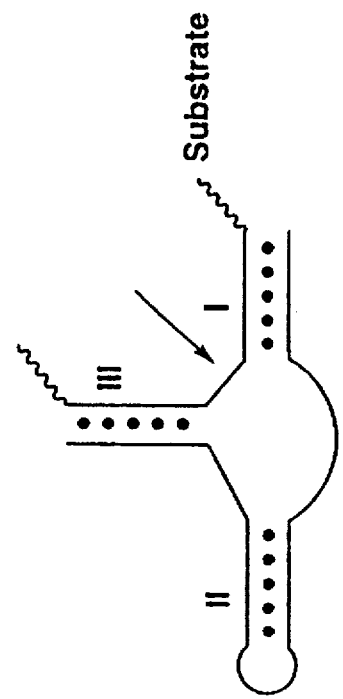

FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

Figure 3:
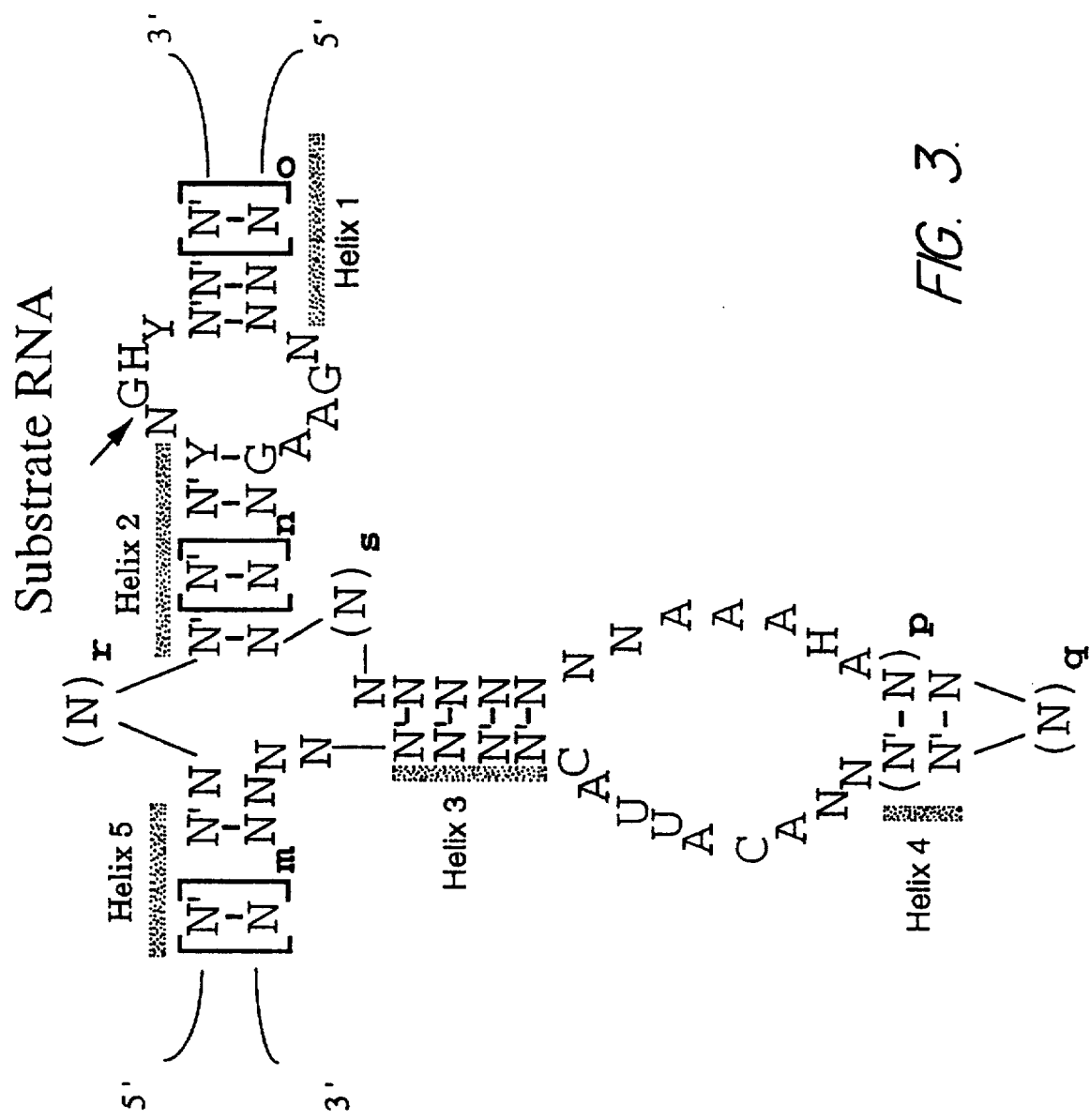

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H, refers to bases A, U or C. Y refers to pyrimidine bases. "'" refers to a chemical bond.

Figure 4:
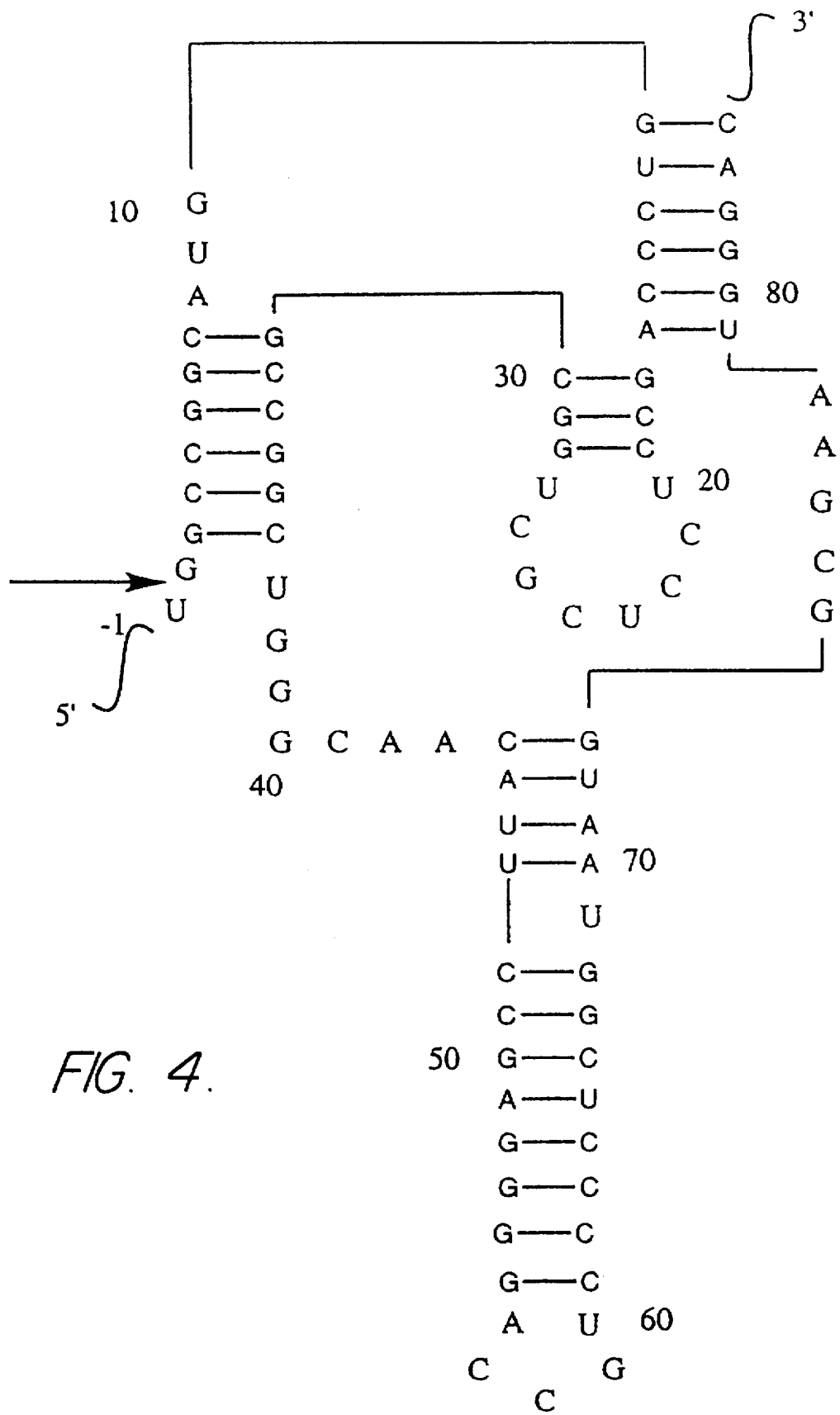

FIG. 4 is a representation of the general structure of the hepatitis delta virus ribozyme domain known in the art.

Figure 5:
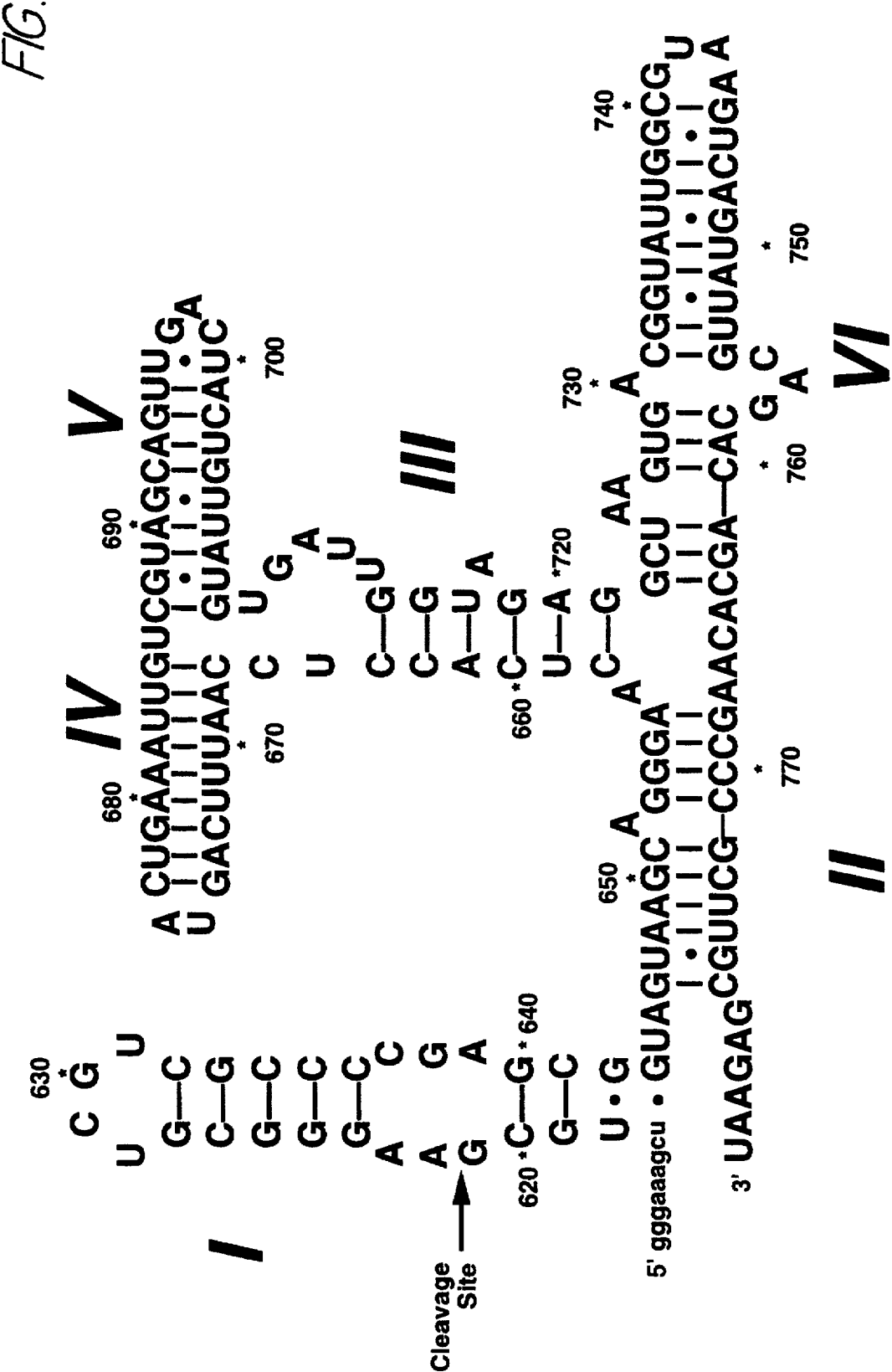

FIG. 5 is a representation of the general structure of the self-cleaving VS RNA ribozyme domain.

Figure 6:
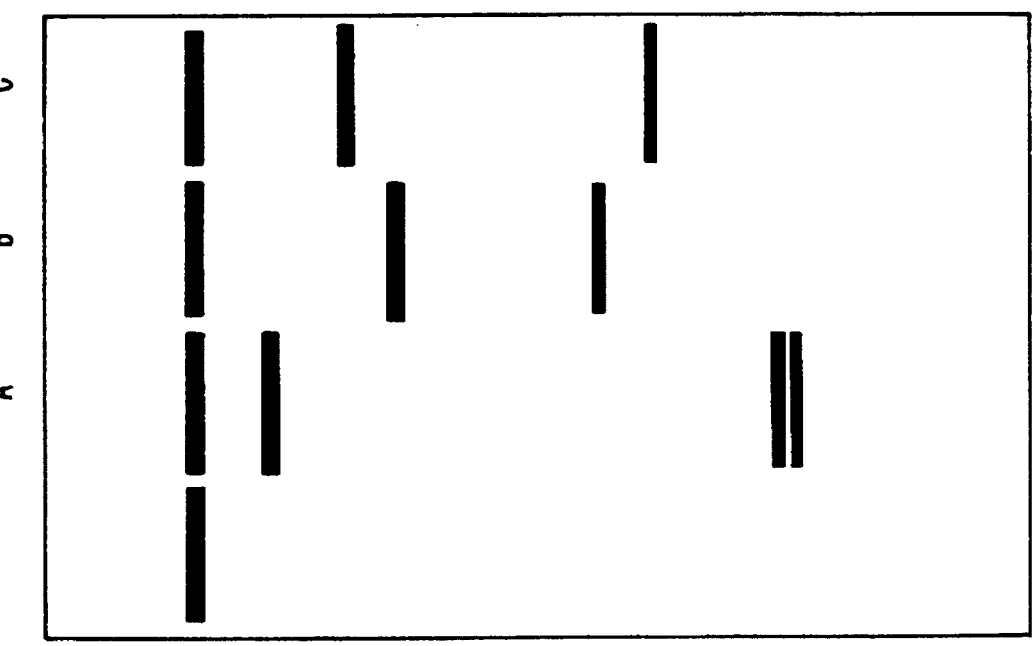
Figure 6:
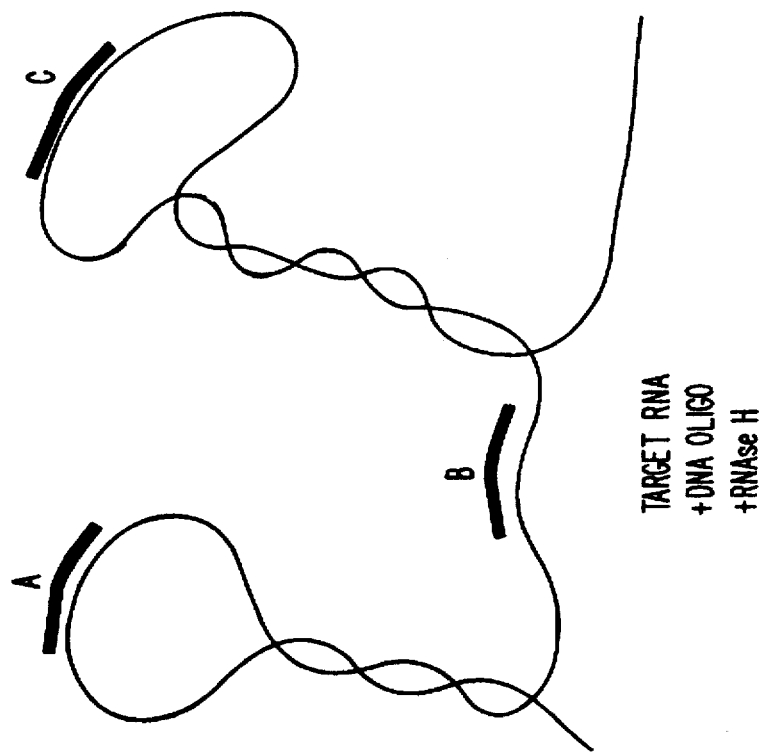

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
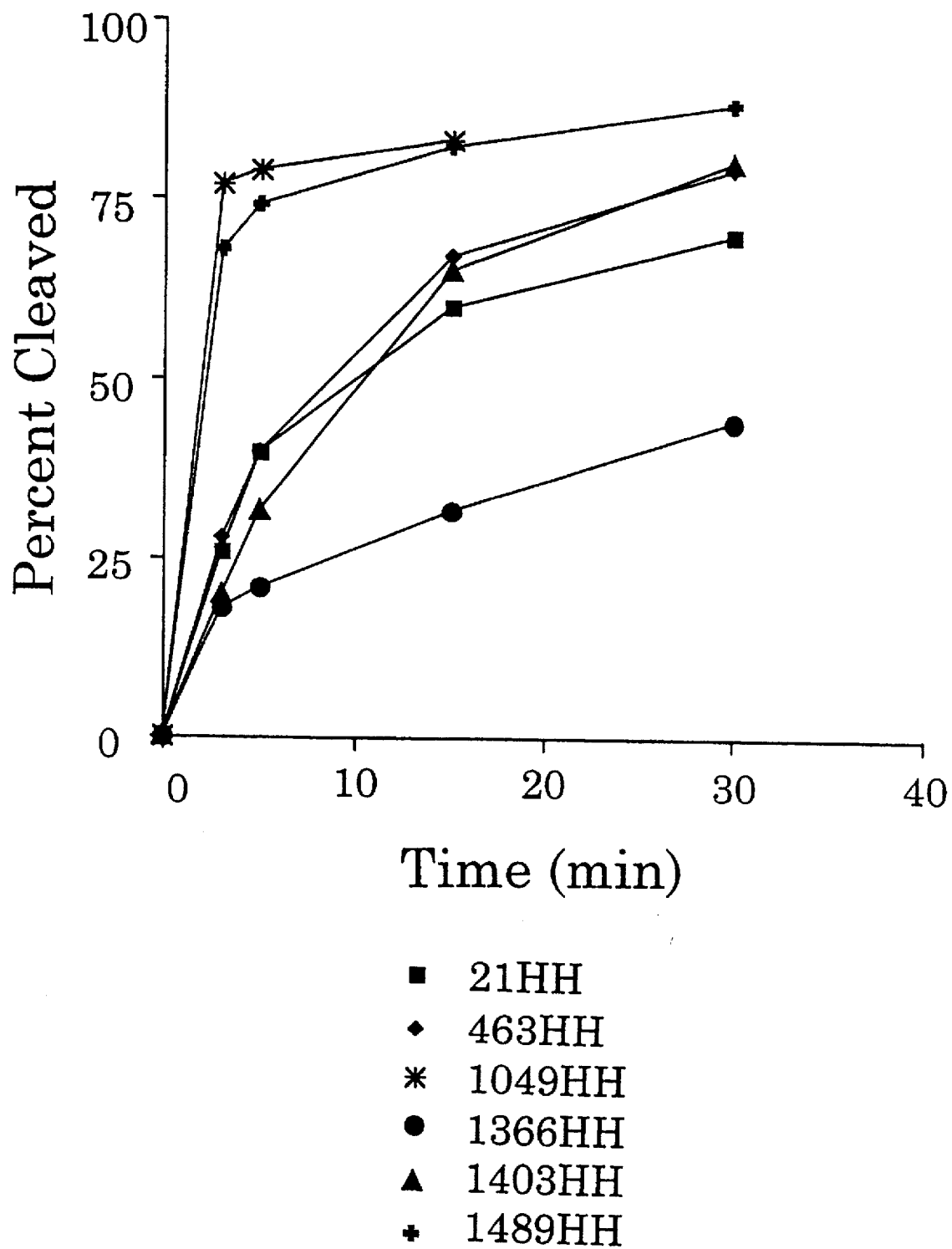

FIG. 7 shows in vitro cleavage of stromelysin mRNA by HH ribozymes.

Figure 8:
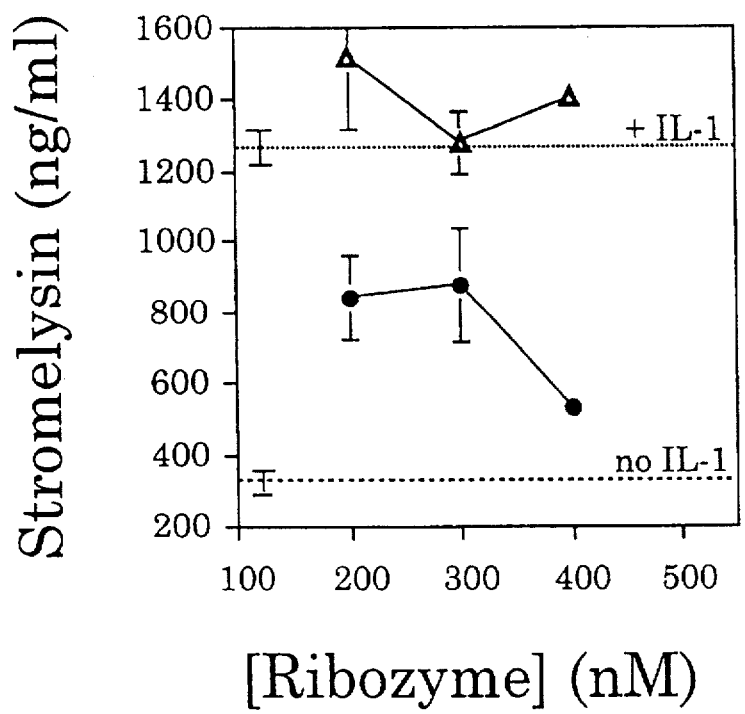

FIG. 8 shows inhibition of stromelysin expression by 21HH ribozyme in HS-27 fibroblast cell line.

Figure 9:
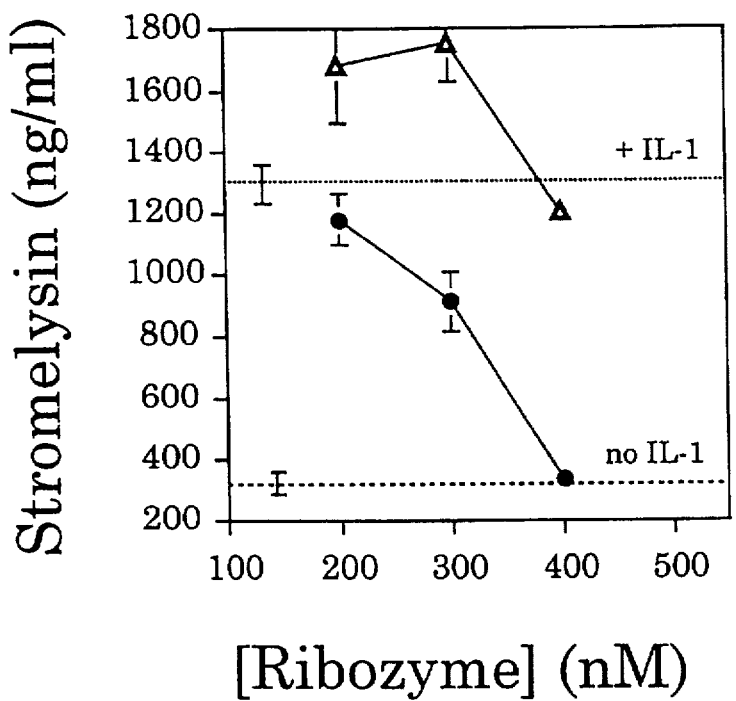

FIG. 9 shows inhibition of stromelysin expression ribozyme in HS-27 fibroblast cell line.

Figure 10:
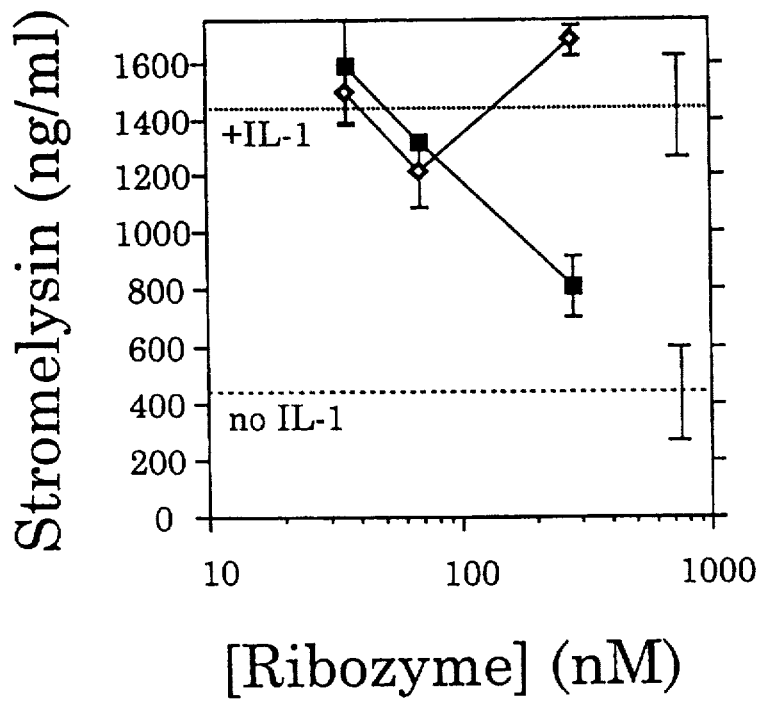

FIG. 10 shows inhibition of stromelysin expression by 1049HH ribozyme in HS-27 fibroblast cell line.

Figure 11:
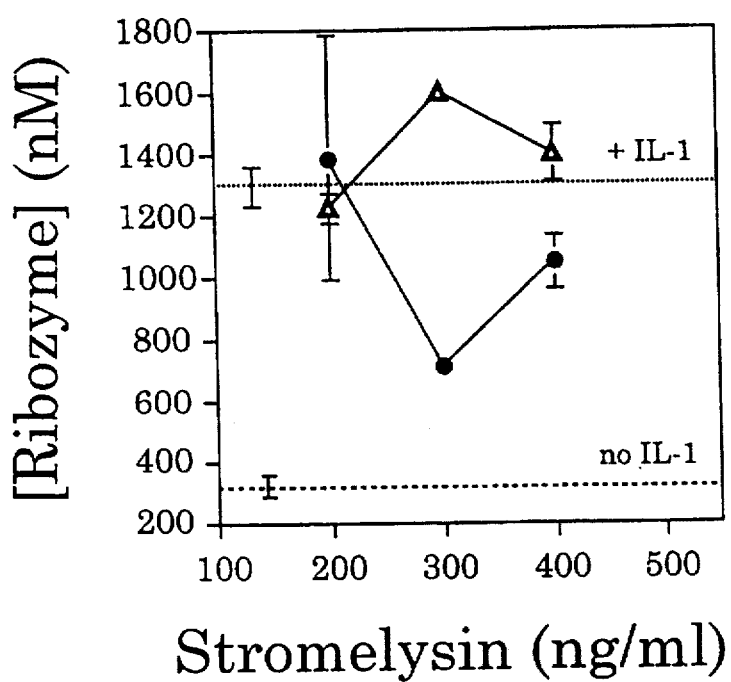

FIG. 11 shows inhibition of stromelysin expression by 1366HH ribozyme in HS-27 fibroblast cell line.

Figure 12:
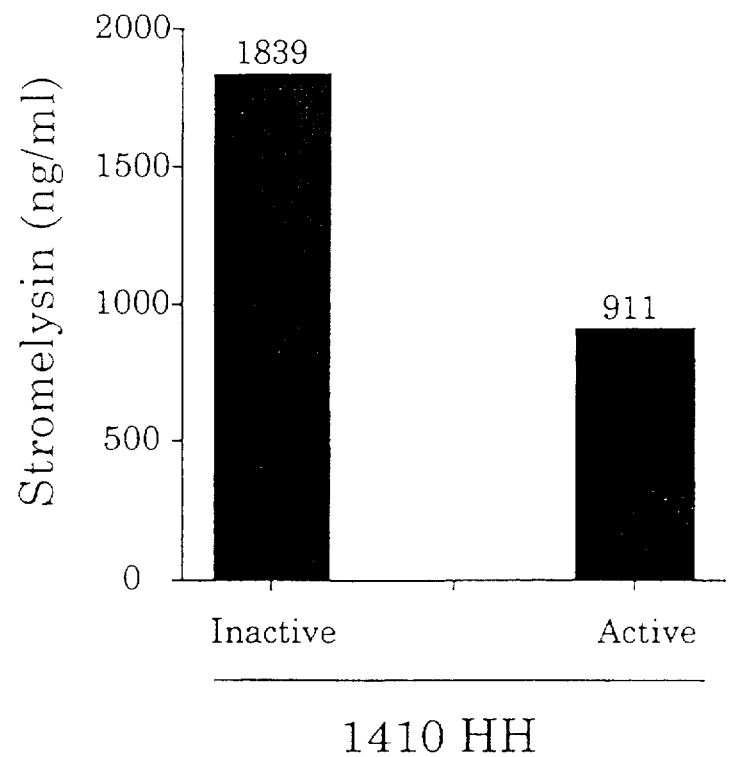

FIG. 12 shows inhibition of stromelysin expression by 1410HH ribozyme in HS-27 fibroblast cell line.

Figure 13:
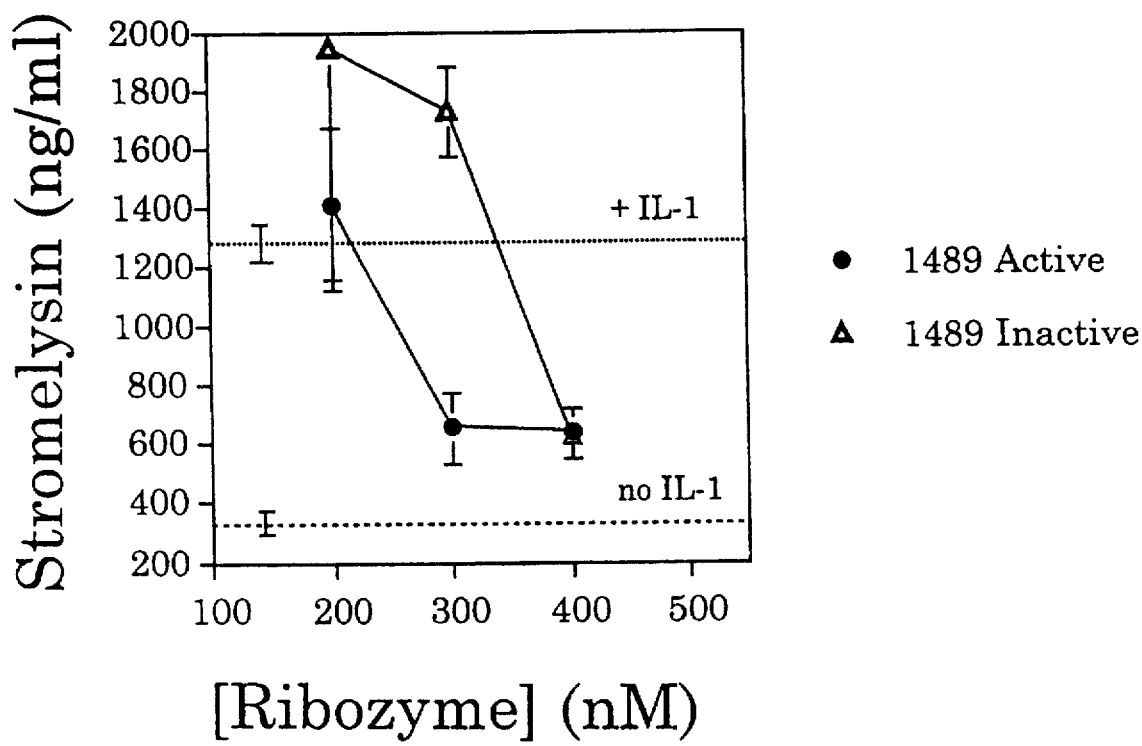

FIG. 13 shows inhibition of stromelysin expression by 1489HH ribozyme in HS-27 fibroblast cell line.

Figure 14:
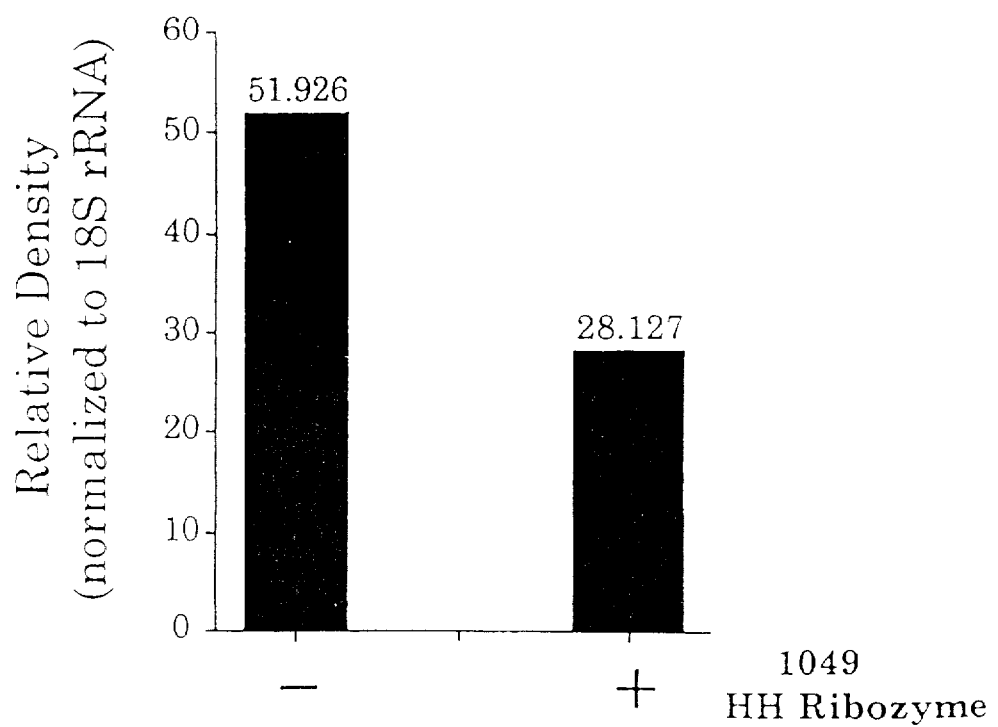

FIG. 14 shows 1049HH ribozyme-mediated reduction in the level of stromelysin mRNA in rabbit knee.

Figure 15:
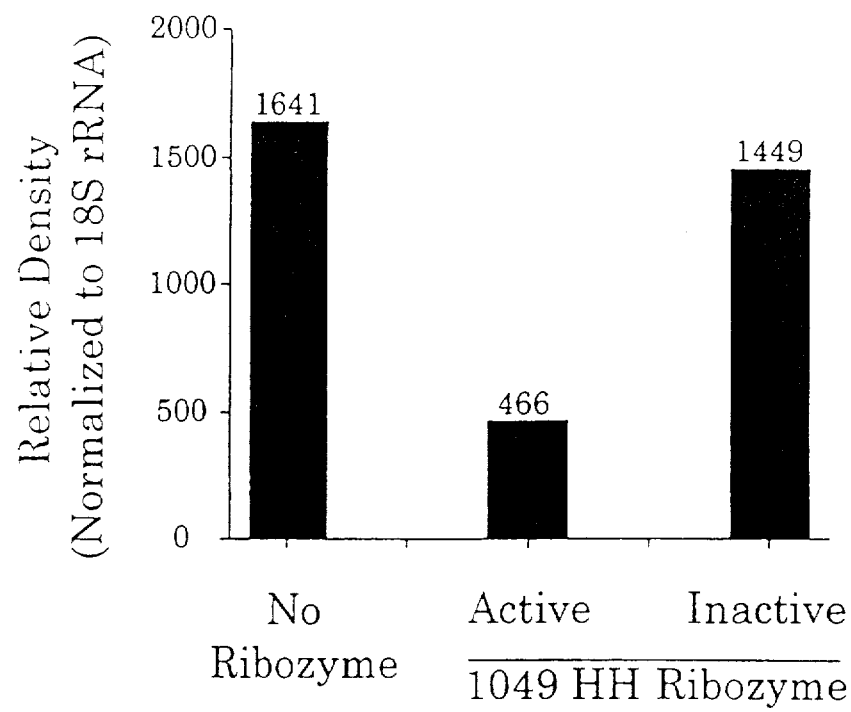

FIG. 15 shows 1049HH ribozyme-mediated reduction in the level of stromelysin mRNA in rabbit knee.

Figure 16:
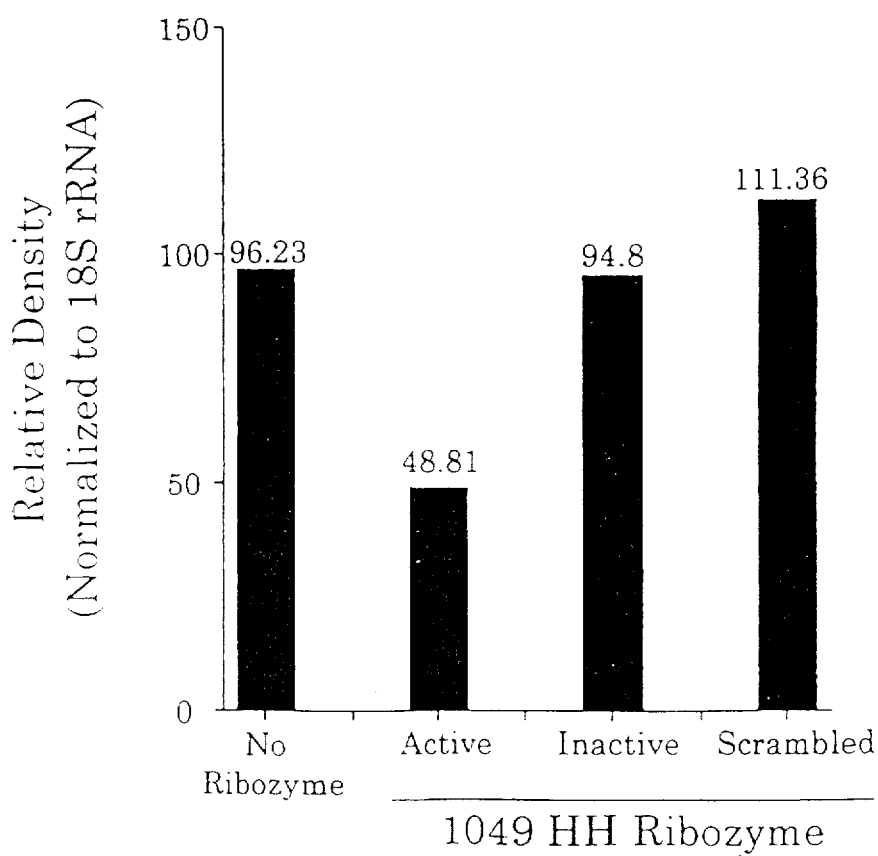

FIG. 16 shows 1049HH ribozyme-mediated reduction in the level of stromelysin mRNA in rabbit knee.

Figure 17A:
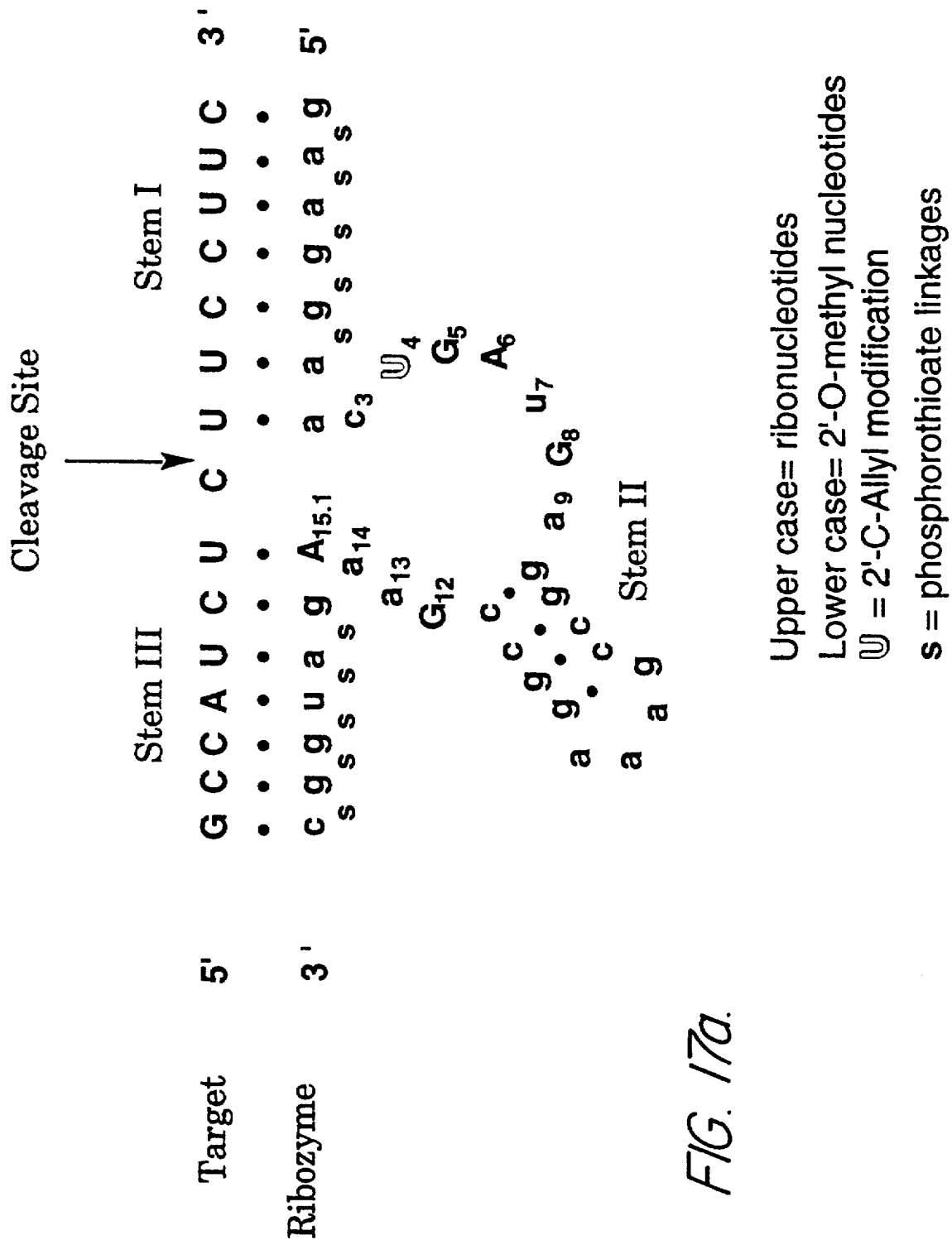
Figure 17B:
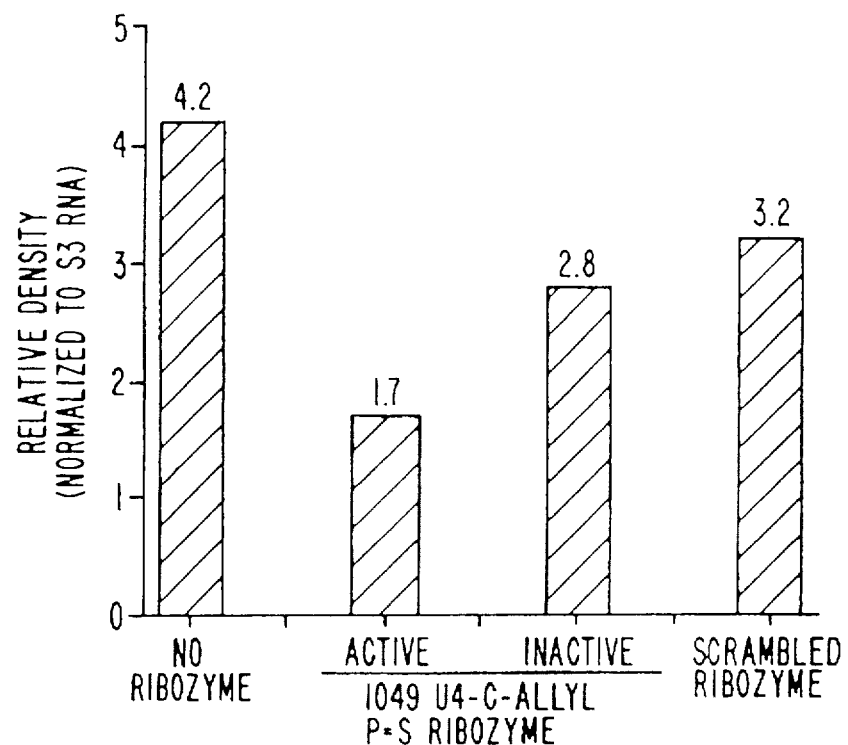

FIG. 17 shows the effect of phosphorthioate substitutions on the catalytic activity of 1049 2'-C-allyl HH ribozyme. A) diagrammatic representation of 1049 hammerhead ribozyme•substrate complex. 1049 U4-C-allyl P=S ribozyme represents a hammerhead containing ribose residues at five positions. The remaining 31 nucleotide positions contain 2'-hydroxyl group substitutions, wherein 30 nucleotides contain 2'-O-methyl substitutions and one nucleotide (U4) contains 2'-C-allyl substitution. Additionally, five nucleotides within the ribozyme, at the 5' and 3' termini, contain phosphorothioate substitutions. B) shows the ability of ribozyme described in FIG. 17A to decrease the level of stromelysin RNA in rabbit knee.

Figure 18:
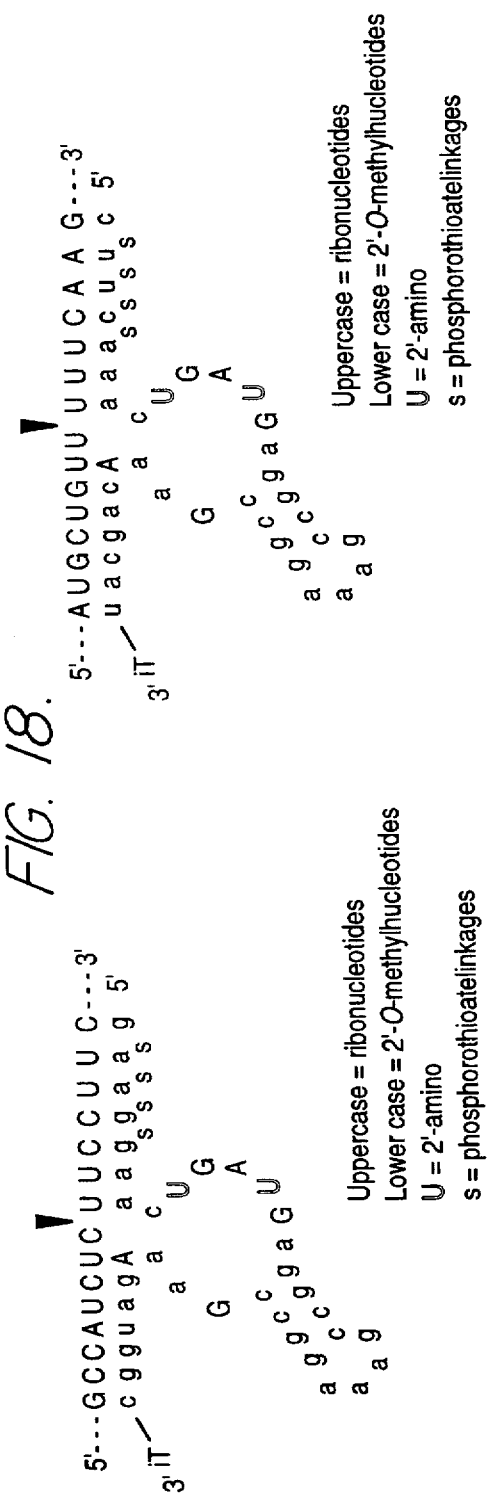

FIG. 18 is a diagrammatic representation of chemically modified ribozymes targeted against stromelysin RNA. 1049 2'-amino P=S Ribozyme represents a hammerhead containing ribose residues at five positions. The remaining 31 nucleotide positions contain 2'-hydroxyl group substitutions, wherein 29 nucleotides contain 2'-O-methyl substitutions and two nucleotides (U4 and U7) contain 2'-amino substitution. Additionally, the 3' end of this ribozyme contains a 340 —3' linked inverted T and four nucleotides at the 5' termini contain phosphorothioate substitutions. Arrowhead indicates the site of RNA cleavage (site 1049). 1363 2'-Amino P=S, Human and Rabbit 1366 2'-Amino P=S ribozymes are identical to the 1049 2'-amino P=S ribozyme except that they are targeted to sites 1363 and 1366 within stromelysin RNAs.

Figure 19:
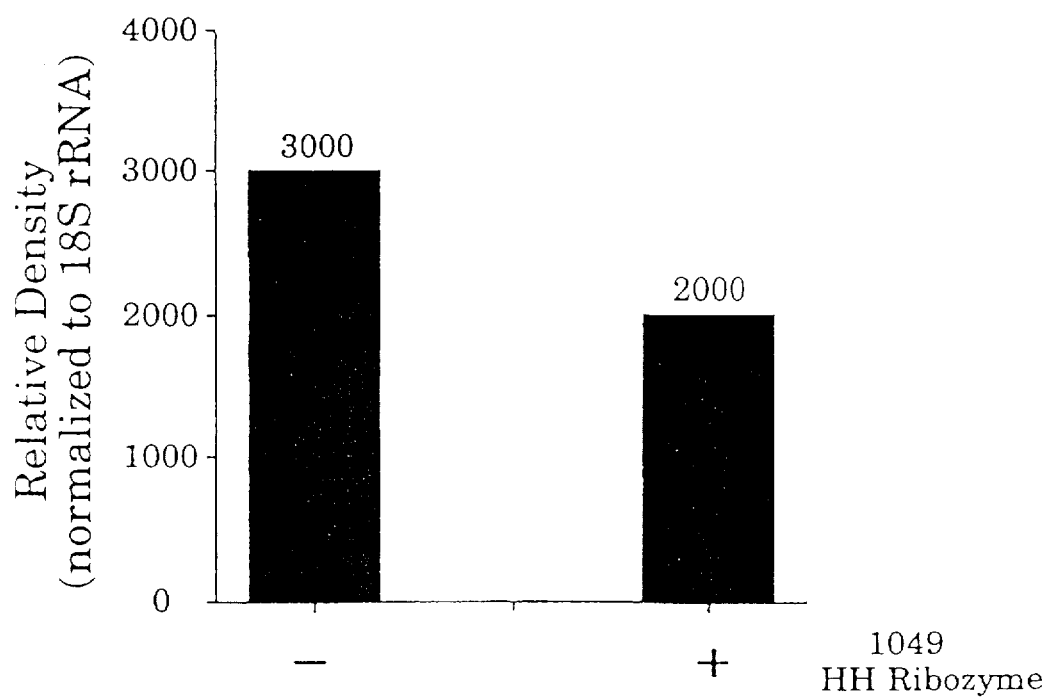

FIG. 19 shows 1049 2'-amino P=S ribozyme-mediated reduction in the level of stromelysin mRNA in rabbit knee.

Figure 20:
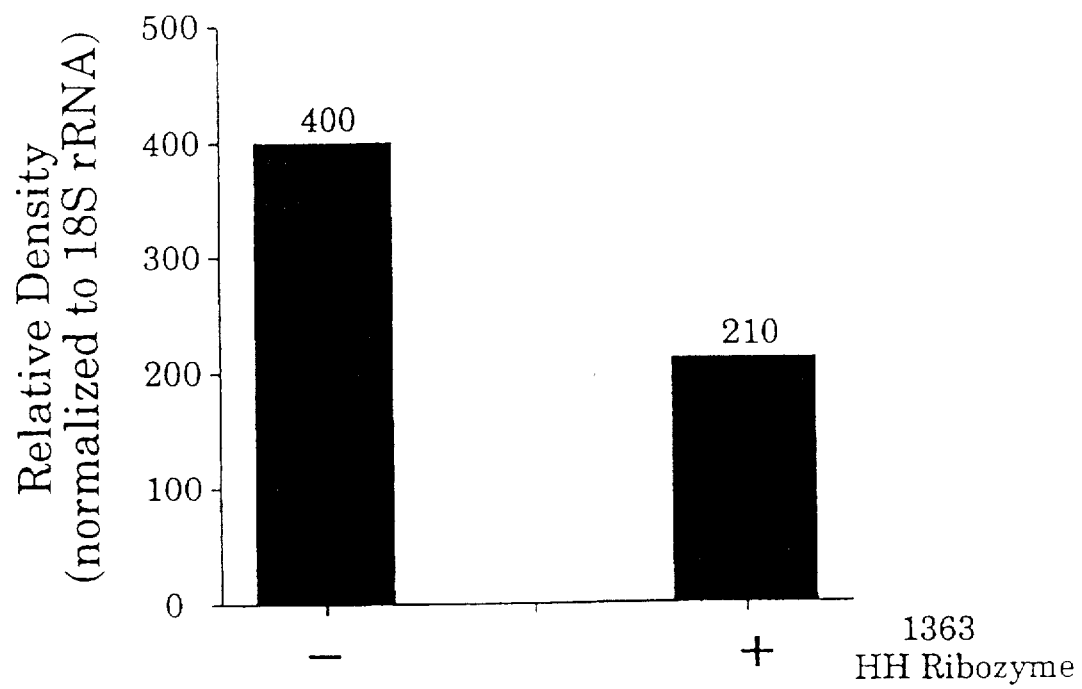

FIG. 20 shows 1363 2'-amino P=S ribozyme-mediated reduction in the level of stromelysin mRNA in rabbit knee.

Figure 21:
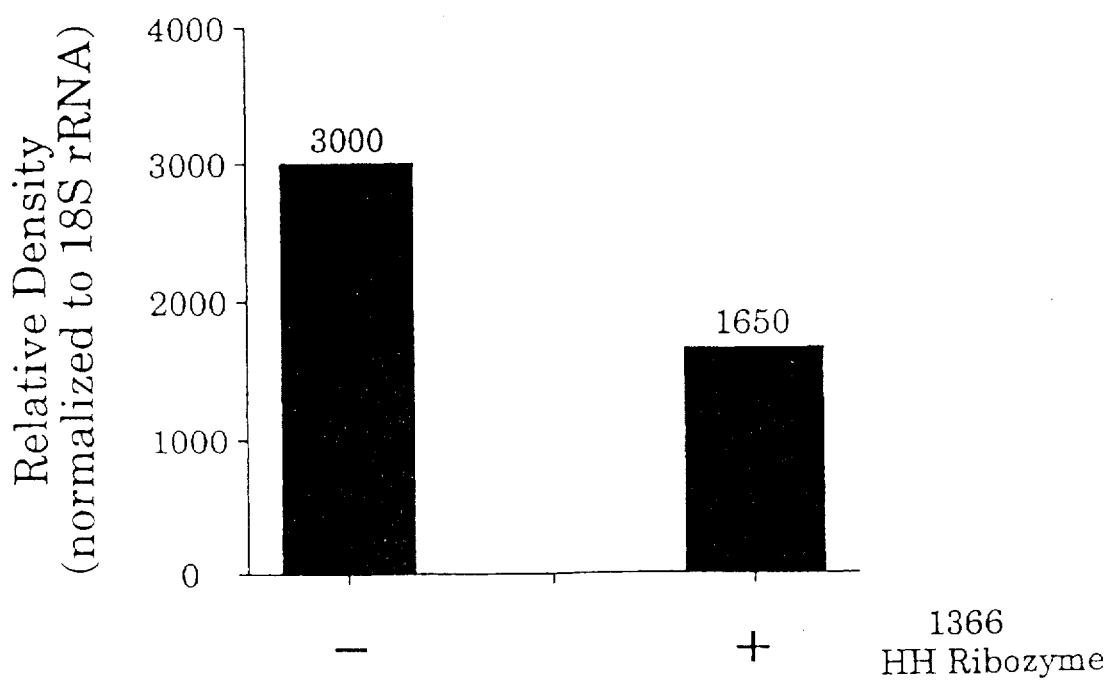

FIG. 21 shows 1366 2'-amino P=S ribozyme-mediated reduction in the level of stromelysin mRNA in rabbit knee.

RIBOZYMES

Ribozymes of this invention block to some extent stromelysin expression and can be used to treat disease or diagnose such disease. Ribozymes are delivered to cells in culture and to cells or tissues in animal models of osteoarthritis (Hembry et al., 1993 *Am. J. Pathol.* 143, 628). Ribozyme cleavage of stromelysin encoding mRNAs in these systems may prevent inflammatory cell function and alleviate disease symptoms.

TARGET SITES

Targets for useful ribozymes can be determined as disclosed in Draper et al supra, Sullivan et al., supra, as well as by Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to mouse and human RNA are provided, those in the art will recognize that the equivalent human RNA targets described can be used as described below. Thus, the same target may be used, but binding arms suitable for targeting human RNA sequences are present in the ribozyme. Such targets may also be selected as described below.

The sequence of human and rabbit stromelysin mRNA were screened for accessible sites using a computer folding algorithm. Potential hammerhead or hairpin ribozyme cleavage sites were identified. These sites are shown in Tables II, III, IV, VI, VIII and IX (All sequences are 5' to 3' in the tables.). While rabbit and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, rabbit targeted ribozymes are useful to test efficacy of action of the ribozyme prior to testing in humans. The nucleotide base position is noted in the Tables as that site to be cleaved by the designated type of ribozyme.

Hammerhead or hairpin ribozymes are designed that could bind and are individually analyzed by computer folding (Jaeger et al., 1989 *Proc. Natl. Acad. Sci. U.S.A.*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application No. 07/883,849 filed on May 1, 1992, entitled "Assay for ribozyme target site", hereby incorporated by reference herein. Briefly, DNA oligonucleotides representing potential hammerhead or hairpin ribozyme cleavage sites are synthesized. A polymerase chain reaction is used to generate a substrate for T7 RNA polymerase transcription from human or rabbit stromelysin cDNA clones. Labeled RNA transcripts are synthesized in vitro from the two templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a Phosphor Imaging system. From these data, hammerhead ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7845–7854 and in Scaringe et al., 1990 *Nucleic Acids Res.*, 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.*, 20, 3252). Hairpin ribozymes are synthesized in two parts and annealed to reconstruct the active ribozyme (Chowrira and Burke, 1992 *Nucleic Acids Res.*, 20, 2835–2840). All ribozymes are modified extensively to enhance stability by modification with nuclease resistant groups, for example, 2'-amino, 2'-C-allyl, 2'-flouro, 2'-o-methyl, 2'-H (for a review see Usman and Cedergren, 1992 *TIBS* 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

The sequences of the chemically synthesized ribozymes useful in this study are shown in Tables V, VII, VIII and IX. Those in the art will recognize that these sequences are representative only of many more such sequences where the enzymatic portion of the ribozyme (all but the binding arms) is altered to affect activity. For example, stem loop II sequence of hammerhead ribozymes listed in Tables V and VII (5'-GGCCGAAAGGCC-3') can be altered (substitution, deletion and/or insertion) to contain any sequence provided, a minimum of two base-paired stem structure can form. Similarly, stem-loop IV sequence of hairpin ribozymes listed in Tables VI and VII (5'-CACGUUGUG-3') can be altered (substitution, deletion and/or insertion) to contain any sequence provided, a minimum of two base-paired stem structure can form. The sequences listed in Tables V, VII, VIII and IX may be formed of ribonucleotides or other nucleotides or non-nucleotides. Such ribozymes are equivalent to the ribozymes described specifically in the Tables.

OPTIMIZING RIBOZYME ACTIVITY

Ribozyme activity can be optimized as described by Stinchcomb et al. supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al., U.S. patent application No. 07/829,729, Sproat, European Patent Application 92110298.4 and U.S. Pat. No. 5,334,711 and Jennings et al., WO 94/13688 which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U.S.A.*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. U.S.A.*, 89, 10802–6; Chen et al., 1992 *Nucleic Acids Res.*, 20, 4581–9; Yu et al., 1993 *Proc. Natl. Acad. Sci. U.S.A.*, 90, 6340–4; L'Huillier et al., 1992 *EMBO J.* 11, 4411–8; Lisziewicz et al., 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral or alphavirus vectors).

In a preferred embodiment of the invention, a transcription unit expressing a ribozyme that cleaves stromelysin RNA is inserted into a plasmid DNA vector or an adenovirus DNA virus or adeno-associated virus (AAV) vector. Both viral vectors have been used to transfer genes to the lung and both vectors lead to transient gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

EXAMPLE 1

Stromelysin Hammerhead Ribozymes

By engineering ribozyme motifs applicant has designed several ribozymes directed against stromelysin mRNA sequences. These ribozymes are synthesized with modifications that improve their nuclease resistance. The ability of ribozymes to cleave stromelysin target sequences in vitro is evaluated.

The ribozymes are tested for function in vivo by analyzing stromelysin expression levels. Ribozymes are delivered to cells by incorporation into liposomes, by complexing with cationic lipids, by microinjection, and/or by expression from DNA/RNA vectors. Stromelysin expression is monitored by biological assays, ELISA, by indirect immunofluoresence, and/or by FACS analysis. Stromelysin mRNA levels are assessed by Northern analysis, RNAse protection, primer extension analysis and/or quantitative RT-PCR. Ribozymes that block the induction of stromelysin activity and/or stromelysin mRNA by more than 50% are identified.

Ribozymes targeting selected regions of mRNA associated with arthritic disease are chosen to cleave the target RNA in a manner which preferably inhibits translation of the RNA. Genes are selected such that inhibition of translation will preferably inhibit cell replication, e.g., by inhibiting production of a necessary protein or prevent production of an undesired protein, e.g., stromelysin. Selection of effective target sites within these critical regions of mRNA may entail testing the accessibility of the target RNA to hybridization with various oligonucleotide probes. These studies can be performed using RNA or DNA probes and assaying accessibility by cleaving the hybrid molecule with RNAseH (see below and McSwiggen, Assay for Ribozyme Target Site Accessibility, U.S. Ser. No. 07/884,073, filed May 14, 1992, hereby incorporated by reference herein). Alternatively, such a study can use ribozyme probes designed from secondary structure predictions of the mRNAs, and assaying cleavage products by polyacrylamide gel electrophoresis (PAGE), to detect the presence of cleaved and uncleaved molecules.

Figure 1:
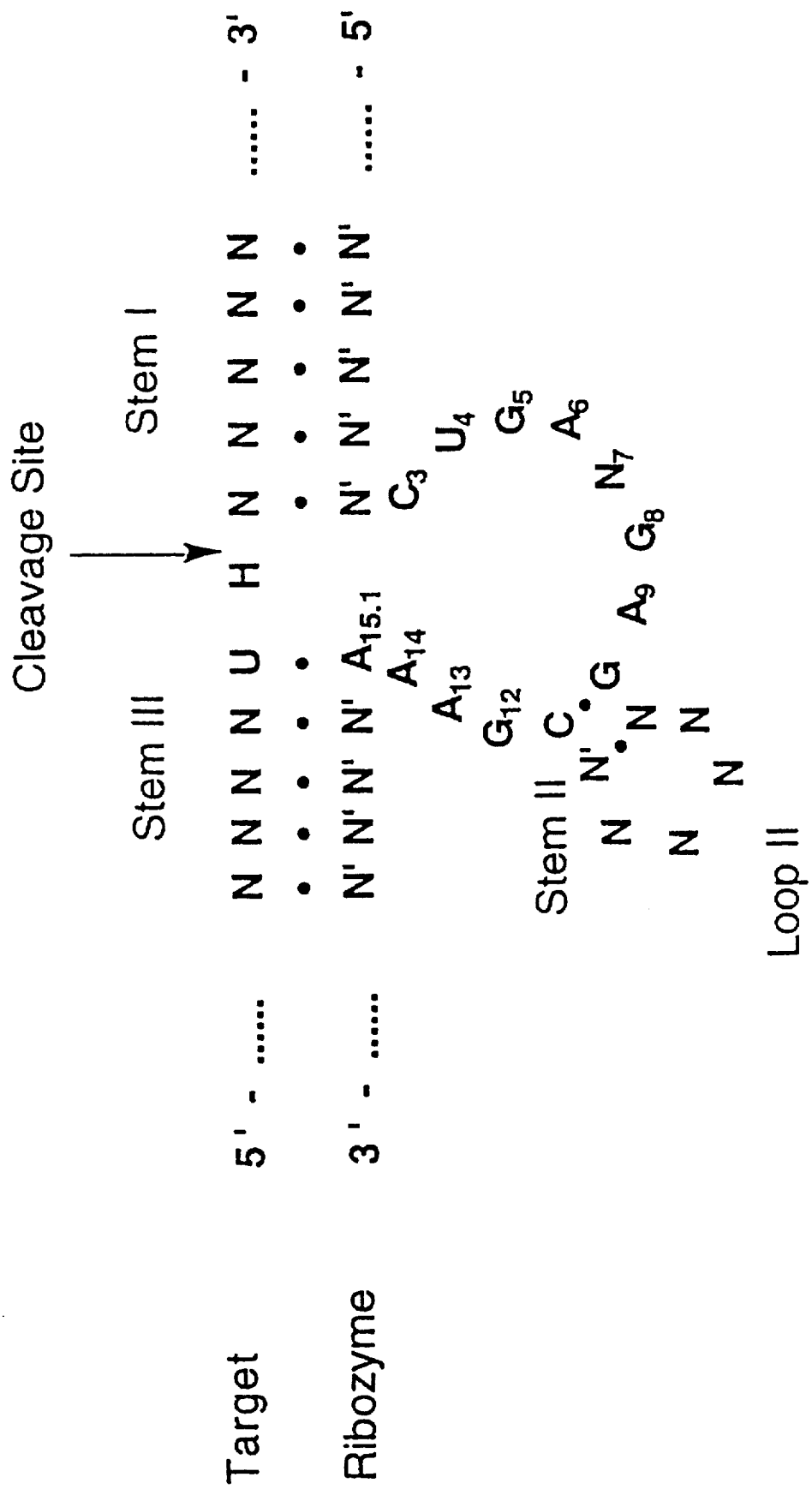
FIG. 1 is a diagrammatic representation of the hammerhead ribozyme domain known in the art. Stem II can be ≧2 base-pairs long.

In addition, potential ribozyme target sites within the rabbit stromelysin mRNA sequence (1795 nucleotides) were located and aligned with the human target sites. Because the rabbit stromelysin mRNA sequence has an 84% sequence identity with the human sequence, many ribozyme target sites are also homologous. Thus, the rabbit has potential as an appropriate animal model in which to test ribozymes that are targeted to human stromelysin but have homologous or nearly homologous cleavage sites on rabbit stromelysin mRNA as well (Tables II–VI, VIII & IX). Thirty of the 316 UH sites in the rabbit sequence are identical with the corresponding site in the human sequence with respect to at least 14 nucleotides surrounding the potential ribozyme cleavage sites. The nucleotide in the RNA substrate that is immediately adjacent (5') to the cleavage site is unpaired in the ribozyme-substrate complex (see FIG. 1) and is consequently not included in the comparison of human and rabbit potential ribozyme sites. In choosing human ribozyme target sites for continued testing, the presence of identical or nearly identical sites in the rabbit sequence is considered.

EXAMPLE 2

Superior Sites

Potential ribozyme target sites were subjected to further analysis using computer folding programs (Mulfold or a Macintosh-based version of the following program, LRNA (Zucker (1989) *Science* 244:48), to determine if 1) the target site is substantially single-stranded and therefore predicted to be available for interaction with a ribozyme, 2) if a ribozyme designed to that site is predicted to form stem II but is generally devoid of any other intramolecular base pairing, and 3) if the potential ribozyme and the sequence flanking both sides of the cleavage site together are predicted to interact correctly. The sequence of Stem II can be altered to maintain a stem at that position but minimize intramolecular basepairing with the ribozyme's substrate binding arms. Based on these minimal criteria, and including all the sites that are identical in human and rabbit stromelysin mRNA sequence, a subset of 66 potential superior ribozyme target sites was chosen (as first round targets) for continued analysis. These are SEQ. ID. NOS.: 34, 35, 37, 47, 54, 57, 61, 63, 64, 66, 76, 77, 79, 87, 88, 96, 97, 98, 99, 100, 107, 110, 121, 126, 128, 129, 133, 140, 146, 148, 151, 162, 170, 179, 188, 192, 194, 196, 199, 202, 203, 207, 208, 218, 220, 223, 224, 225, 227, 230, 232, 236, 240, 245, 246, 256, 259, 260, 269, 280, 281, 290, 302, 328, 335 and 353 (see Table III).

EXAMPLE 3

Accessible Sites

To determine if any or all of these potential superior sites might be accessible to a ribozyme directed to that site, an RNAse H assay is carried out (described in more detail in McSwiggen, U.S. Ser. Nos. 07/883,849 and 07/884,073 both filed May 14, 1992 and hereby incorporated by reference herein). Using this assay, the accessibility of a potential ribozyme target site to a DNA oligonucleotide probe can be assessed without having to synthesize a ribozyme to that particular site. If the complementary DNA oligonucleotide is able to hybridize to the potential ribozyme target site then RNAse H, which has the ability to cleave the RNA of a DNA/RNA hybrid, will be able to cleave the target RNA at that particular site. Specific cleavage of the target RNA by RNAse H is an indication that that site is "open" or "accessible" to oligonucleotide binding and thus predicts that the site will also be open for ribozyme binding. By comparing the relative amount of specific RNAse H cleavage products that are generated for each DNA oligonucleotide/site, potential ribozyme sites can be ranked according to accessibility.

To analyze target sites using the RNAse H assay, DNA oligonucleotides (generally 13–15 nucleotides in length) that are complementary to the potential target sites are synthesized. Body-labeled substrate RNAs (either full-length RNAs or ~500–600 nucleotide subfragments of the entire RNA) are prepared by in vitro transcription in the presence of a $^{32}$P-labeled nucleotide. Unincorporated nucleotides are removed from the $^{32}$P-labeled substrate RNA by spin chromatography on a G-50 Sephadex column and used without further purification. To carry out the assay, the $^{32}$P-labeled substrate RNA is pre-incubated with the specific DNA oligonucleotide (1 μM and 0.1 μM final concentration) in 20 mM Tris-HCl, pH 7.9, 100 mM KCl, 10 mM MgCl$_2$, 0.1 mM EDTA, 0.1 mM DTT at 37° C. for 5 minutes. An excess of RNAse H (0.8 units/10 μl reaction) is added and the incubation is continued for 10 minutes. The reaction is quenched by the addition of an equal volume of 95% formamide, 20 mM EDTA, 0.05% bromophenol blue and 0.05% xylene cyanol FF after which the sample is heated to 95° C. for 2 minutes, quick chilled and loaded onto a denaturing polyacrylamide gel. RNAse H-cleaved RNA products are separated from uncleaved RNA on denaturing polyacrylamide gels, visualized by autoradiography and the amount of cleavage product is quantified.

RNAse H analysis on the 66 potential ribozyme sites (round 1) was carried out and those DNA oligonucleotides/sites that supported the most RNAse H cleavage were determined. These assays were carried out using full-length human and rabbit stromelysin RNA as substrates. Results determined on human stromelysin RNA indicated that 23 of the 66 sites supported a high level of RNAse H cleavage, and an additional 13 supported a moderate level of RNAse H cleavage. Twenty-two sites were chosen from among these two groups for continued study. Two of the criteria used for making this choice were 1) that the particular site supported at least moderate RNAse H cleavage on human stromelysin RNA and 2) that the site have two or fewer nucleotide differences between the rabbit and the human stromelysin sequence. RNAse H accessibility on rabbit stromelysin RNA was determined, but was not used as a specific criteria for these choices. Those DNA oligonucleotides that are not totally complementary to the rabbit sequence may not be good indicators of the relative amount of RNAse H cleavage, possibly because the mismatch leads to less efficient hybridization of the DNA oligonucleotide to the mismatched RNA substrate and therefore less RNAse H cleavage is seen.

EXAMPLE 4

Analysis of Ribozymes

Ribozymes were then synthesized to 22 sites (Table V) predicted to be accessible as judged the RNAse H assay. Eleven of these 22 sites are identical to the corresponding rabbit sites. The 22 sites are SEQ. ID, NOS.: 34, 35, 57, 125, 126, 127, 128, 129, 140, 162, 170, 179, 188, 223, 224, 236, 245, 246, 256, 259, 260, 281. The 22 ribozymes were chemically synthesized with recognition arms of either 7 nucleotides or 8 nucleotides, depending on which ribozyme alone and ribozyme-substrate combinations were predicted by the computer folding program (Mulfold) to fold most correctly. After synthesis, ribozymes are either purified by HPLC or gel purified.

These 22 ribozymes were then tested for their ability to cleave both human and rabbit full-length stromelysin RNA. Full-length, body-labeled stromelysin RNA is prepared by in vitro transcription in the presence of [$\alpha$-$^{32}$P]CTP, passed over a G 50 Sephadex column by spin chromatography and used as substrate RNA without further purification. Assays are performed by prewarming a 2× concentration of purified ribozyme in ribozyme cleavage buffer (50 mM Tris-HCl, pH 7.5 at 37° C., 10 mM MgCl$_2$) and the cleavage reaction is initiated by adding the 2× ribozyme mix to an equal volume of substrate RNA (maximum of 1–5 nM) that has also been prewarmed in cleavage buffer. As an initial screen, assays are carried out for 1 hour at 37° C. using a final concentration of 1 µM and 0.1 µM ribozyme, i.e., ribozyme excess. The reaction is quenched by the addition of an equal volume of 95% formamide, 20 mM EDTA, 0.05% bromophenol blue and 0.05% xylene cyanol FF after which the sample is heated to 95° C. for 2 minutes, quick chilled and loaded onto a denaturing polyacrylamide gel. Full-length substrate RNA and the specific RNA products generated by ribozyme cleavage are visualized on an autoradiograph of the gel.

Of the 22 ribozymes tested, 21 were able to cleave human and rabbit substrate RNA in vitro in a site-specific manner. In all cases, RNA cleavage products of the appropriate lengths were visualized. The size of the RNA was judged by comparison to molecular weight standards electrophoresed in adjacent lanes of the gel. The fraction of substrate RNA cleaved during a ribozyme reaction can be used as an assessment of the activity of that ribozyme in vitro. The activity of these 22 ribozymes on full-length substrate RNA ranged from approximately 10% to greater than 95% of the substrate RNA cleaved in the ribozyme cleavage assay using 1 µM ribozyme as described above. A subset of seven of these ribozymes was chosen for continued study. These seven ribozymes (denoted in Table V) were among those with the highest activity on both human and rabbit stromelysin RNA. Five of these seven sites have sequence identity between human and rabbit stromelysin RNAs for a minimum of 7 nucleotides in both directions flanking the cleavage site. These sites are 883, 947, 1132, 1221 and 1410. and the ribozymes are SEQ. ID. NOS.: 368, 369, 370, 371, 372, 373, and 374.

EXAMPLE 5

Arm Length Tests

In order to test the effect of arm length variations on the cleavage activity of a ribozyme to a particular site in vitro, ribozymes to these seven sites were designed that had alterations in the binding arm lengths. For each site, a complete set of ribozymes was synthesized that included ribozymes with binding arms of 6 nucleotides, 7 nucleotides, 8 nucleotides, 10 nucleotides and 12 nucleotides, i.e., 5 ribozymes to each site. These ribozymes were gel-purified after synthesis and tested in ribozyme cleavage assays as described above.

After analysis of the 35 ribozymes, five ribozymes with varied arm lengths to each of these seven sites, it was clear that two ribozymes were the most active in vitro. These two ribozymes had seven nucleotide arms directed against human sequence cleavage sites of nucleotide 617 and nucleotide 820. These are referred to as RZ 617H 7/7 and RZ 820H 7/7 denoting the human (H) sequence cleavage site (617 or 820) and the arm length on the 5' and 3' side of the ribozyme molecule.

EXAMPLE 6

Testing the Efficacy of Ribozymes in Cell Culture

The two most active ribozymes in vitro (RZ 617H 7/7 and RZ 820H 7/7) were then tested for their ability to cleave stromelysin mRNA in the cell. Primary cultures of human or rabbit syncvial fibroblasts were used in these experiments. For these efficacy tests, ribozymes with 7 nucleotide arms were synthesized with 2' O-methyl modifications on the 5 nucleotides at the 5' end of the molecule and on the 5 nucleotides at the 3' end of the molecule. For comparison, ribozymes to the same sites but with 12 nucleotide arms (RZ 617H 12/12 and RZ 820H 12/12) were also synthesized with the 2' O methyl modifications at the 5 positions at the end of both binding arms. Inactive ribozymes that contain 2 nucleotide changes in the catalytic core region were also prepared for use as controls. The catalytic core in the inactive ribozymes is C U U̲A̲ U G A G G C C G A A A G G C C G A U̲versus CUG̲AUGAGGCCGAAAGGCCGAA̲ in the active ribozymes. The inactive ribozymes show no cleavage activity in vitro when measured on full-length RNA in the typical ribozyme cleavage assay at a 1 µM concentration for 1 hour.

The general assay was as follows: Fibroblasts, which produce stromelysin, are serum-starved overnight and ribozymes or controls are offered to the cells the next day. Cells are maintained in serum-free media. The ribozyme can be applied to the cells as free ribozyme, or in association with various delivery vehicles such as cationic lipids (including Transfectam™, Lipofectin™ and Lipofectamine™), conventional liposomes, non-phospholipid liposomes or biodegradable polymers. At the time of ribozyme addition, or up to 3 hours later, Interleukin-1α

(typically 20 units/ml) can be added to the cells to induce a large increase in stromelysin expression. The production of stromelysin can then be monitored over a time course, usually up to 24 hours.

If a ribozyme is effective in cleaving stromelysin mRNA within a cell, the amount of stromelysin mRNA will be decreased or eliminated. A decrease in the level of cellular stromelysin mRNA, as well as the appearance of the RNA products generated by ribozyme cleavage of the full-length stromelysin mRNA, can be analyzed by methods such as Northern blot analysis, RNAse protection assays and/or primer extension assays. The effect of ribozyme cleavage of cellular stromelysin mRNA on the production of the stromelysin protein can also be measured by a number of assays. These include the ELISA (Enzyme-Linked Immuno Sorbent Assay) and an immunofluorescence assay described below. In addition, functional assays have been published that monitor stromelysin's enzymatic activity by measuring degradation of its primary substrate, proteoglycan.

EXAMPLE 7

Analysis of Stromelysin Protein

Stromelysin secreted into the media of Interleukin-1α-induced human synovial fibroblasts was measured by ELISA using an antibody that recognizes human stromelysin. Where present, a Transfectam™-ribozyme complex (0.15 µM ribozyme final concentration) was offered to 2–4×10⁵ serum-starved cells for 3 hours prior to induction with Interleukin-1α. The Transfectam™ was prepared according to the manufacturer (Promega Corp.) except that 1:1 (w/w) dioleoyl phosphatidylethanolamine was included. The Transfectam™-ribozyme complex was prepared in a 5:1 charge ratio. Media was harvested 24 hours after the addition of Interleukin-1α. The control (NO RZ) is Transfectam™ alone applied to the cell. Inactive ribozymes, with 7 nucleotide arms or 12 nucleotide arms have the two inactivating changes to the catalytic core that are described above. Cell samples were prepared in duplicate and the assay was carried out on several dilutions of the conditioned media from each sample. Results of the ELISA are presented below as a percent of stromelysin present vs. the control (NO RZ) which is set at 100%.

|  | RZ TARGET SITE | |
| --- | --- | --- |
| TREATMENT | 617H | 820H |
| RZ 7/7 | 06.83 | 07.05 |
| RZ 12/12 | 18.47 | 33.90 |
| INACTIVE RZ 7/7 | 100 | 100 |
| INACTIVE RZ 12/12 | 100 | 100 |
| NO RZ CONTROL | 100 | 100 |

The results above clearly indicate that treatment with active ribozyme, either RZ 617H 7/7 and RZ 820H 7/7, has a dramatic effect on the amount of stromelysin secreted by the cells. When compared to untreated, control cells or cells treated with inactive ribozymes, the level of stromelysin was decreased by approximately 93%. Ribozymes to the same sites, but synthesized with 12 nucleotide binding arms, were also efficacious, causing a decrease in stromelysin to ~66 to ~81% of the control. In previous in vitro ribozyme cleavage assays, RZ 617H 7/7 and RZ 820H 7/7 had better cleavage activity on full-length RNA substrates than ribozymes with 12 nucleotide arms directed to the same sites (617H 12/12 and RZ 820H 12/12).

EXAMPLE 8

Immunofluorescent Assay

An alternative method of stromelysin detection is to visualize stromelysin protein in the cells by immunofluorescence. For this assay, cells are treated with monensin to prevent protein secretion from the cell. The stromelysin retained by the cells after monensin addition can then be visualized by immunofluorescence using either conventional or confocal microscopy. Generally, cells were serum-starved overnight and treated with ribozyme the following day for several hours. Monensin was then added and after ~5–6 hours, monensin-treated cells were fixed and permeabilized by standard methods and incubated with an antibody recognizing human stromelysin. Following an additional incubation period with a secondary antibody that is conjugated to a fluorophore, the cells were observed by microscopy. A decrease in the amount of fluorescence in ribozyme-treated cells, compared to cells treated with inactive ribozymes or media alone, indicates that the level of stromelysin protein has been decreased due to ribozyme treatment.

As visualized by the immunofluorescence technique described above, treatment of human synovial fibroblasts with either RZ 617H 7/7 or RZ 820H 7/7 (final concentrations of 1.5 µM free ribozyme or 0.15 µM ribozyme complexed with Transfectam™ resulted in a significant decrease in fluorescence, and therefore stromelysin protein, when compared with controls. Controls consisted of treating with media or Transfectam™ alone. Treatment of the cells with the corresponding inactive ribozymes with two inactivating changes in the catalytic core resulted in immunofluorescence similar to the controls without ribozyme treatment.

Rabbit synovial fibroblasts were also treated with RZ 617H 7/7 or RZ 820H 7/7, as well as with the two corresponding ribozymes (RZ 617R 7/7 or RZ 820R 7/7) that each have the appropriate one nucleotide change to make them completely complementary to the rabbit target sequence. Relative to controls that had no ribozyme treatment, immunofluorescence in Interleukin-1α-induced rabbit synovial fibroblasts was visibly decreased by treatment with these four ribozymes, whether specific for rabbit or human mRNA sequence. For the immunofluorescence study in rabbit synovial fibroblasts, the antibody to human stromelysin was used.

EXAMPLE 9

Ribozyme Cleavage of Cellular RNA

The following method was used in this example.
Primer extension assay:

The primer extension assay was used to detect full-length RNA as well as the 3' ribozyme cleavage products of the RNA of interest. The method involves synthesizing a DNA primer (generally ~20 nucleotides in length) that can hybridize to a position on the RNA that is downstream (3') of the putative ribozyme cleavage site. Before use, the primer was labeled at the 5' end with $^{32}$P[ATP] using T4 polynucleotide kinase and purified from a gel. The labeled primer was then incubated with a population of nucleic acid isolated from a cellular lysate by standard procedures. The reaction buffer was 50 mM Tris-HCl, pH 8.3, 3 mM MgCl$_2$, 20 mM KCl, and 10 mM DTT. A 30 minute extension reaction follows, in which all DNA primers that have hybridized to the RNA were substrates for reverse transcriptase, an enzyme that will add nucleotides to the 3' end of the DNA primer using the RNA as a template. Reverse transcriptase was obtained from Life Technologies and is used essentially as suggested by the manufacturer. Optimally, reverse transcriptase will extend the DNA primer, forming cDNA, until the end of the RNA substrate is reached. Thus, for ribozyme-cleaved RNA substrates, the cDNA product will be shorter than the resulting cDNA product of a full-length, or uncleaved RNA substrate. The differences in size of the $^{32}$P-labeled cDNAs produced by extension can then be discriminated by electrophoresis on a denaturing polyacrylamide gel and visualized by autoradiography.

Strong secondary structure in the RNA substrate can, however, lead to premature stops by reverse transcriptase. This background of shorter cDNAs is generally not a problem unless one of these prematurely terminated products electrophoreses in the expected position of the ribozyme-cleavage product of interest. Thus, 3' cleavage products are easily identified based on their expected size and their absence from control lanes. Strong stops due to secondary structure in the RNA do, however, cause problems in trying to quantify the total full-length and cleaved RNA present. For this reason, only the relative amount of cleavage can easily be determined.

The primer extension assay was carried out on RNA isolated from cells that had been treated with Transfectam™-complexed RZ 617H 7/7, RZ 820H 7/7, RZ 617H 12/12 and RZ 820H 12/12. Control cells had been treated with Transfectam™ alone. Primer extensions on RNA from cells treated with the Transfectam™ complexes of the inactive versions of these four ribozymes were also prepared. The 20 nucleotide primer sequence is 5' AATGAAAAC-GAGGTCCTTGC 3' and it is complementary to a region about 285 nucleotides downstream of ribozyme site 820. For ribozymes to site 617, the cDNA length for the 3' cleavage product is 488 nucleotides, for 820 the cDNA product is 285 nucleotides. Full-length cDNA will be 1105 nucleotides in length. Where present, 1 ml of 0.15 μM ribozyme was offered to ~2–3×10$^5$ serum-starved human synovial fibroblasts. After 3 hours, 20 units/ml Interleukin-1α was added to the cells and the incubation continued for 24 hours.

$^{32}$P-labeled cDNAs of the correct sizes for the 3' products were clearly visible in lanes that contained RNA from cells that had been treated with active ribozymes to sites 617 and 820. Ribozymes with 7 nucleotide arms were judged to be more active than ribozymes with 12 nucleotide arms by comparison of the relative amount of 3' cleavage product visible. This correlates well with the data obtained by ELISA analysis of the conditioned media from these same samples. In addition, no cDNAs corresponding to the 3' cleavage products were visible following treatment of the cells with any of the inactive ribozymes.

To insure that ribozyme cleavage of the RNA substrate was not occurring during the preparation of the cellular RNA or during the primer extension reaction itself, several controls have been carried out. One control was to add body-labeled stromelysin RNA, prepared by in vitro transcription, to the cellular lysate. This lysate was then subjected to the typical RNA preparation and primer extension analysis except that non-radioactive primer was used. If ribozymes that are present in the cell at the time of cell lysis are active under any of the conditions during the subsequent analysis, the added, body-labeled stromelysin RNA will become cleaved. This, however, is not the case. Only full-length RNA was visible by gel analysis, no ribozyme cleavage products were present. This is evidence that the cleavage products detected in RNA from ribozyme-treated cells resulted from ribozyme cleavage in the cell, and not during the subsequent analysis.

EXAMPLE 10

RNAse Protection Assay

By RNAse protection analysis, both the 3' and the 5' products generated by ribozyme cleavage of the substrate RNA in a cell can be identified. The RNAse protection assay is carried out essentially as described in the protocol provided with the Lysate Ribonuclease Protection Kit (United States Biochemical Corp.) The probe for RNAse protection is an RNA that is complementary to the sequence surrounding the ribozyme cleavage site. This "antisense" probe RNA is transcribed in vitro from a template prepared by the polymerase chain reaction in which the 5' primer was a DNA oligonucleotide containing the T7 promoter sequence. The probe RNA is body labeled during transcription by including $^{32}$P[CTP] in the reaction and purified away from unincorporated nucleotide triphosphates by chromatography on G-50 Sephadex. The probe RNA (100,000 to 250,000 cpms) is allowed to hybridize overnight at 37° C. to the RNA from a cellular lysate or to RNA purified from a cell lysate. After hybridization, RNAse T$_1$ and RNAse A are added to degrade all single-stranded RNA and the resulting products are analyzed by gel electrophoresis and autoradiography. By this analysis, full-length, uncleaved target RNA will protect the full-length probe. For ribozyme-cleaved target RNAs, only a portion of the probe will be protected from RNAse digestion because the cleavage event has occurred in the region to which the probe binds. This results in two protected probe fragments whose size reflects the position at which ribozyme cleavage occurs and whose sizes add up to the size of the full-length protected probe.

RNAse protection analysis was carried out on cellular RNA isolated from rabbit synovial fibroblasts that had been treated either with active or inactive ribozyme. The ribozymes tested had 7 nucleotide arms specific to the rabbit sequence but corresponding to human ribozyme sites 617 and 820 (i.e. RZ 617R 7/7, RZ 820R 7/7). The inactive ribozymes to the same sites also had 7 nucleotide arms and included the two inactivating changes described above. The inactive ribozymes were not active on full-length rabbit stromelysin RNA in a typical 1 hour ribozyme cleavage reaction in vitro at a concentration of 1 μM. For all samples, one ml of 0.15 μM ribozyme was administered as a Transfectam™ complex to serum-starved cells. Addition of Interleukin-1α followed 3 hours later and cells were harvested after 24 hours. For samples from cells treated with either active ribozyme tested, the appropriately-sized probe fragments representing ribozyme cleavage products were visible. For site 617, two fragments corresponding to 125 and 297 nucleotides were present, for site 820 the two fragments were 328 and 94 nucleotides in length. No protected probe fragments representing RNA cleavage products were visible in RNA samples from cells that not been treated with any ribozyme, or in cells that had received the inactive ribozymes. Full-length protected probe (422 nucleotides in length) was however visible, indicating the presence of full-length, uncleaved stromelysin RNA in these samples.

Delivery of Free and Transfectam-Complexed Ribozymes to Fibroblasts

Ribozymes can be delivered to fibroblasts complexed to a cationic lipid or in free form. To deliver free ribozyme, an appropriate dilution of stock ribozyme (final concentration is usually 1.5 μM) is made in serum-free medium; if a radioactive tracer is to be used (i.e., $^{32}$P), the specific activity of the ribozyme is adjusted to 800–1200 cpm/pmol. To deliver ribozyme complexed with the cationic lipid Transfectam, the lipid is first prepared as a stock solution containing 1/1 (w/w) dioleoylphosphatidylcholine (DOPE). Ribozyme is mixed with the Transfectam/DOPE mixture at a ⅕ (RZ/TF) charge ratio; for a 36-mer ribozyme, this is a 45-fold molar excess of Transfectam (Transfectam has 4 positive charges per molecule). After a 10 min incubation at room temperature, the mixture is diluted and applied to cells, generally at a ribozyme concentration of 0.15 µM. For $^{32}$P experiments, the specific activity of the ribozyme is the same as for the free ribozyme experiments.

After 24 hour, about 30% of the offered Transfectam-ribozyme cpm's are cell-associated (in a nuclease-resistant manner). Of this, about 10–15% of the cpm's represent intact ribozyme; this is about 20–25 million ribozymes per cell. For the free ribozyme, about 0.6% of the offered dose is cell-associated after 24 hours. Of this, about 10–15% is intact; this is about 0.6–0.8 million ribozymes per cell.

EXAMPLE 11

In vitro Cleavage of Stromelysin mRNA by HH Ribozymes

In order to screen for additional HH ribozyme cleavage sites, ribozymes, targeted against some of the sites listed in example 2 and Table 3, were synthesized. These ribozymes were extensively modified such that: 5' terminal nucleotides contain phosphorothioate substitutions; except for five ribose residues in the catalytic core, all the other 2'-hydroxyl groups within the ribozyme were substituted with either 2'-O-methyl groups or 2'-C-allyl modifications. The aforementioned modifications are meant to be non-limiting modifications. Those skilled in the art will recognize that other embodiments can be readily generated using the techniques known in the art.

These ribozymes were tested for their ability to cleave RNA substrates in vitro. Referring to FIG. 7, in vitro RNA cleavage by HH ribozymes targeted to sites 21, 463, 1049, 1366, 1403, 1410 and 1489 (SEQ. ID. NOS. 35, 98, 202, 263, 279, 281 and 292 respectively) was assayed at 37° C. Substrate RNAs were 5' end-labeled using [γ-$^{32}$P]ATP and T4 polynucleotide kinase enzyme. In a standard cleavage reaction under "ribozyme excess" conditions, ~1 nM substrate RNA and 40 nM ribozyme were denatured separately by heating to 90° C. for 2 min followed by snap cooling on ice for 10 min. The substrate and the ribozyme reaction mixtures were renatured in a buffer containing 50 mM Tris-HCl, pH 7.5 and 10 mM MgCl$_2$ at 37° C. for 10 min. Cleavage reaction was initiated by mixing the ribozyme and the substrate RNA and incubating at 37° C. Aliquots of 5 µl were taken at regular intervals of time and the reaction quenched by mixing with an equal volume of formamide stop mix. The samples were resolved on a 20% polyacrylamide/urea gel.

A plot of percent RNA substrate cleaved as a function of time is shown in FIG. 7. The plot shows that all six HH ribozymes cleaved the target RNA efficiently. Some HH ribozymes were, however, more efficient than others (e.g., 1049HH cleaves faster than 1366HH).

Ribozyme Efficacy Assay in Cultured HS-27 Cells (Used in the Following Examples):

Ribozymes were assayed on either human foreskin fibroblasts(HS-27) cell line or primary human synovial fibroblasts (HSF). All cells were plated the day before the assay in media containing 10% fetal bovine serum in 24 well plates at a density of 5×10$^4$ cells/well. At 24 hours after plating, the media was removed from the wells and the monolayers were washed with Dulbeccos phosphate buffered saline (PBS). The cells were serum starved for 24 h by incubating the cells in media containing 0.5% fetal bovine serum (FBS; 1 ml/well). Ribozyme/lipid complexes were prepared as follows: Ribozymes and LipofectAMINE were diluted separately in serum-free DMEM plus 20 mM Hepes pH 7.3 to 2× final concentration, then equal volumes were combined, vortexed and incubated at 37° C. for 15 minutes. The charge ratio of LipofectAmine: ribozyme was 3:1. Cells were washed twice with PBS containing Ca$^{2+}$ and Mg$^{2+}$. Cells were then treated the ribozyme/lipid complexes and incubated at 37° C. for 1.5 hours. FBS was then added to a final concentration of 10%. Two hours after FBS addition, the ribozyme containing solution was removed and 0.5 ml DMEM containing 50 u/ml IL-1, 10% FBS, 20 mM Hepes pH 7.3 added. Supernatants were harvested 16 hours after IL-1 induction and assayed for stromelysin expression by ELISA. Polyclonal antibody against Matrix Metalloproteinase 3 (Biogenesis, NH) was used as the detecting antibody and anti-stromelysin monoclonal antibody was used as the capturing antibody in the sandwich ELISA (Maniatis et al., supra) to measure stromelysin expression.

EXAMPLE 12

Ribozyme-Mediated Inhibition of Stromelysin Expression in Human Fibroblast Cells Referring to FIGS. 8 through 13, HH ribozymes, targeted to sites 21, 463, 1049, 1366, 1403, 1410 and 1489 within human stromelysin-1 mRNA, were transfected into HS-27 fibroblast or HSF cell line as described above. Catalytically inactive ribozymes that contain 2 nucleotide changes in the catalytic core region were also synthesized for use as controls. The catalytic core in the inactive ribozymes was C U U A U G A G G C C G A A A G G C C G A U versus CU GAUGAGGCCGAAAGGCCGAA in the active ribozymes. The inactive ribozymes show no cleavage activity in vitro when measured on full-length RNA in the typical ribozyme cleavage assay at a 1 µM concentration for 1 hour. Levels of stromelysin protein were measured using a sensitive ELISA protocol as described above. +IL-1 in the figures mean that cells were treated with IL-1 to induce the expression of stromelysin expression. -IL-1 means that the cells were not treated. FIGS. 8 through 14 show the dramatic reduction in the levels of stromelysin protein expressed in cells that were transfected with active HH ribozymes. This decrease in the level of stromelysin production is over and above some non-specific inhibition seen in cells that were transfected with catalytically inactive ribozymes. There is on an average a greater than 50% inhibition in stromelysin production (in cells transfected with active HH ribozymes) when compared with control cells that were transfected with inactive ribozymes. These results suggest that the reduction in stromelysin production in HS-27 cells is mediated by sequence-specific cleavage of human stromelysin-1 mRNA by catalytically active HH ribozymes. Reduction in stromelysin protein production in cells transfected with catalytically inactive ribozymes may be due to some "antisense effect" caused by binding of the inactive ribozyme to the target RNA and physically preventing translation.

EXAMPLE 13

Ribozyme-mediated Inhibition of Stromelysin Expression in Rabbit Knee

In order to extend the ribozyme efficacy in cell culture, applicant has chosen to use rabbit knee as a reasonable animal model to study ribozyme-mediated inhibition of rabbit stromelysin protein expression. Applicant selected a HH ribozyme (1049HH), targeted to site 1049 within human stromelysin-1 mRNA, for animal studies because site 1049 is 100% identical to site 1060 (Tables III and VI) within rabbit stromelysin mRNA. This has enabled applicant to compare the efficacy of the same ribozyme in human as well as in rabbit systems.

Male New Zealand White Rabbits (3–4 Kg) were anaesthetized with ketamine-HCl/xylazine and injected intraarticularly (I.T.) in both knees with 100 µg ribozyme (e.g., SEQ. ID. NO. 202) in 0.5 ml phosphate buffered saline (PBS) or PBS alone (Controls). The IL-1 (human recombinant IL-1α, 25 ng) was administered I.T., 24 hours following the ribozyme administration. Each rabbit received IL-1 in one knee and PBS alone in the other. The synovium was harvested 6 hours post IL-1 infusion, snap frozen in liquid nitrogen, and stored at −80° C. Total RNA is extracted with TRIzol reagent (GIBCO BRL, Gaithersburg, Md.), and was analyzed by Northern-blot analysis and/or RNase-protection assay. Briefly, 0.5 µg cellular RNA was separated on 1.0% agarose/formaldehyde gel and transferred to Zeta-Probe GT nylon membrane (Bio-Rad, Hercules, Calif.) by capillary transfer for ~16 hours. The blots were baked for two hours and then pre-hybridized for 2 hours at 65° C. in 10 ml Church hybridization buffer (7% SDS, 500 mM phosphate, 1 mM EDTA, 1% Bovine Serum Albumin). The blots were hybridized at 65° C. for ~16 hours with $10^6$ cpm/ml of full length $^{32}$P-labeled complementary RNA (cRNA) probes to rabbit stromelysin mRNA (cRNA added to the pre-hybridization buffer along with 100 µl 10 mg/ml salmon sperm DNA). The blot was rinsed once with 5% SDS, 25 mM phosphate, 1 mM EDTA and 0.5% BSA for 10 min at room temperature. This was followed by two washes (10 min each wash) with the same buffer at 65° C., which was then followed by two washes (10 min each wash) at 65° C. with 1% SDS, 25 mM phosphate and 1 mM EDTA. The blot was autoradiographed. The blot was reprobed with a 100 nt cRNA probe to 18S rRNA as described above. Following autoradiography, the stromelysin expression was quantified on a scanning densitometer, which is followed by normalization of the data to the 18S rRNA band intensities.

As shown in FIGS. 14–16, catalytically active 1049HH ribozyme mediates a decrease in the expression of stromelysin expression in rabbit knees. The inhibition appears to be sequence-specific and ranges from 50–70%.

EXAMPLE 14

Phosphorothioate-substituted Ribozymes Inhibit Stromelysin Expression in Rabbit Knee Ribozymes containing four phosphorothioate linkages at the 5' termini enhance ribozyme efficacy in mammalian cells. Referring to FIG. 17, applicant has designed and synthesized hammerhead ribozymes targeted to site 1049 within stromelysin RNA, wherein, the ribozymes contain five phosphorothioate linkages at their 5' and 3' termini. Additionally, these ribozymes contain 2'-O-methyl substitutions at 30 nucleotide positions, 2'-C-allyl substitution at U4 position and 2'-OH at five positions (FIG. 17A). As described above, these ribozymes were administered to rabbit knees to test for ribozyme efficacy. The 1049 U4-C-allyl P=S active ribozyme shows greater than 50% reduction in the level of stromelysin RNA in rabbit knee. Catalytically inactive version of the 1049 U4-C-allyl P=S ribozyme shows ~30% reduction in the level of stromelysin RNA.

Referring to FIG. 18, applicant has also designed and synthesized hammerhead ribozymes targeted to three distinct sites within stromelysin RNA, wherein, the ribozymes contain four phosphorothioate linkages at their 5' termini. Additionally, these ribozymes contain 2'-O-methyl substitutions at 29 nucleotide positions, 2'-amino substitutions at U4 and U7 positions and 2'-OH at five positions. As described above, these ribozymes were administered to rabbit knees to test for ribozyme efficacy. As shown in FIGS. 18, 19 and 20, ribozymes targeted to sites 1049, 1363 and 1366 are all efficacious in rabbit knee. All three ribozymes decreased the level of stromelysin RNA in rabbit knee by about 50%.

Sequences and chemical modifications described in FIGS. 17 and 18 are meant to be non-limiting examples. Those skilled in the art will recognize that similar embodiments with other ribozymes and ribozymes containing other chemical modifications can be readily generated using techniques known in the art and are within the scope of the present invention.

Applicant has shown that chemical modifications, such as 6-methyl U and abasic (nucleotide containing no base) moieties can be substituted at certain positions within the ribozyme, for example U4 and U7 positions, without significantly effecting the catalytic activity of the ribozyme. Similarly, 340 —3' linked abasic inverted ribose moieties can be used to protect the 3' ends of ribozymes in place of an inverted T without effecting the activity of the ribozyme.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.
RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)
Hairpin Ribozyme Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Cleavage of target RNAs recently demonstrated.

TABLE I-continued

Characteristics of Ribozymes

Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Size: ~144 nucleotides (at present)

TABLE I-continued

Characteristics of Ribozymes

Cleavage of target RNAs recently demonstrated.
Sequence requirements not fully determined.
Binding sites and structural requirements not fully determined.
Only 1 known member of this class. Found in Neurospora VS RNA (FIG. 5).

TABLE II

Ribozyme Target Sequence

| nt Position | Sequence | SEQ. ID. NO. |
| --- | --- | --- |
| 20 | UAGAGCUAAGUAAAGCCAG | ID. NO. 01 |
| 126 | ACACCAGCAUGAA | ID. NO. 02 |
| 147 | AGAAAUAUCUAGA | ID. NO. 03 |
| 171 | ACCUCAAAAAAGAUGUGAAACAGU | ID. NO. 04 |
| 240 | AAAUGCAGAAGUUC | ID. NO. 05 |
| 287 | GACACUCUGGAGGUGAUGCGCAAGCCCAGGUGU | ID. NO. 06 |
| 327 | CUGAUGUUGGUCACUUCAGAAC | ID. NO. 07 |
| 357 | GCAUCCCGAAGUGGAGGAAAACCCACCUUACAU | ID. NO. 08 |
| 402 | AUUAUACACCAGAUUUGCCAAAAGAUG | ID. NO. 09 |
| 429 | CUGUUGAUUCUGCUGUUGAGA | ID. NO. 10 |
| 455 | CUGAAAGUCUGGGAAGAGGUGA | ID. NO. 11 |
| 513 | CUGAUAUAAUGA | ID. NO. 12 |
| 592 | UGCCUAUGCCCC | ID. NO. 13 |
| 624 | AUGCCCACUUUGAUGAUGAUGAACAAUGGACA | ID. NO. 14 |
| 679 | AUUUCUCGUUGCUGCUCAUG | ID. NO. 15 |
| 725 | CACUCAGCCAACACUGA | ID. NO. 16 |
| 801 | AAGAUGAUAUAAAUGGCAUUCAGUCC | ID. NO. 17 |
| 827 | CUCUAUGGACCUCCCCCUGACUCCCCU | ID. NO. 18 |
| 859 | CCCCCUGGUACCCA | ID. NO. 19 |
| 916 | UCCUGCUUUGUCCUUUGAUGCUGUCAGCAC | ID. NO. 20 |
| 958 | AAUCCUGAUCUUUAAAGA | ID. NO. 21 |
| 975 | CAGGCACUUUUGGCGCAAAUCCC | ID. NO. 22 |
| 1018 | AUUGCAUUUGAUCUCUUCAUUUUGGCCAUC | ID. NO. 23 |
| 1070 | GCAUAUGAAGUUA | ID. NO. 24 |
| 1203 | AAAUCGAUGCAGCCAUUUCUGA | ID. NO. 25 |
| 1274 | UUUGAUGAGAAGAGAAAUUCCAUGGAGC | ID. NO. 26 |
| 1302 | CAGGCUUUCCCAAGCAAAUAGCUGAAGAC | ID. NO. 27 |
| 1420 | CCCAAAUGCAAAG | ID. NO. 28 |
| 1485 | AUGUAGAAGGCACAAUAUGGGCACUUUAAA | ID. NO. 29 |
| 1623 | UCUUGCCGGUCAUUUUUAUGUUAU | ID. NO. 30 |
| 1665 | GCUGCUGCUUAGC | ID. NO. 31 |
| 1733 | CAACAGACAAGUGACUGUAUCU | ID. NO. 32 |
| 1769 | CUUAUUUAAUA | ID. NO. 33 |

TABLE III

Human Stromelysin HH Target Sequence

| nt. Position | Target Sequence | Seq. ID. NO. |
| --- | --- | --- |
| 10 | GCAAGGCAUA GAGACAACAUAGAGC | ID. NO. 34 |
| 21 | GCAUAGAGACAACAUA GAGC-UAAGUAAAGCC | ID. NO. 35 |
| 27 | AGACAACAUAGAGCUA AGUAAAGC-CAGUGGA | ID. NO. 36 |
| 31 | AACAUAGAGCUAAGUA AAGCCAGUG-GAAAUG | ID. NO. 37 |
| 53 | GUGGAAAUGAAGAGUC UUCCAAUC-CUACUGU | ID. NO. 38 |
| 55 | GGAAAUGAAGAGUCUU CCAAUC-CUACUGUUG | ID. NO. 39 |
| 56 | GAAAUGAAGAGUCUUC CAAUC-CUACUGUUGC | ID. NO. 40 |
| 61 | GAAGAGUCUUCCAAUC CUACUG-UUGCUGUGC | ID. NO. 41 |
| 64 | GAGUCUUCCAAUCCUA CUGUUGCU-GUGCGUG | ID. NO. 42 |

TABLE III-continued

Human Stromelysin HH Target Sequence

| nt. Position | Target Sequence | Seq. ID. NO. |
|---|---|---|
| 69 | UUCCAAUCCUACUGUU GCUGUGCGUGGCAGU | ID. NO. 43 |
| 85 | GCUGUGCGUGGCAGUU UGCUCAGCCUAUCCA | ID. NO. 44 |
| 86 | CUGUGCGUGGCAGUUU GCUCAGCCUAUCCAU | ID. NO. 45 |
| 90 | GCGUGGCAGUUUGCUC AGCCUAUCCAUUGGA | ID. NO. 46 |
| 96 | CAGUUUGCUCAGCCUA UCCAUUGGAUGGAGC | ID. NO. 47 |
| 98 | GUUUGCUCAGCCUAUC CAUUGGAUGGAGCUG | ID. NO. 48 |
| 102 | GCUCAGCCUAUCCAUU GGAUGGAGCUGCAAG | ID. NO. 49 |
| 142 | CACCAGCAUGAACCUU GUUCAGAAAUAUCUA | ID. NO. 50 |
| 145 | CAGCAUGAACCUUGUU CAGAAAUAUCUAGAA | ID. NO. 51 |
| 146 | AGCAUGAACCUUGUUC AGAAAUAUCUAGAAA | ID. NO. 52 |
| 153 | ACCUUGUUCAGAAAUA UCUAGAAAACUACUA | ID. NO. 53 |
| 155 | CUUGUUCAGAAAUAUC UAGAAAACUACUACG | ID. NO. 54 |
| 157 | UGUUCAGAAAUAUCUA GAAAACUACUACGAC | ID. NO. 55 |
| 165 | AAUAUCUAGAAAACUA CUACGACCUCAAAAA | ID. NO. 56 |
| 168 | AUCUAGAAAACUACUA CGACCUCAAAAAAGA | ID. NO. 57 |
| 175 | AAACUACUACGACCUC AAAAAAGAUGUGAAA | ID. NO. 58 |
| 195 | AAGAUGUGAAACAGUU UGUUAGGAGAAAGGA | ID. NO. 59 |
| 196 | AGAUGUGAAACAGUUU GUUAGGAGAAAGGAC | ID. NO. 60 |
| 199 | UGUGAAACAGUUUGUU AGGAGAAAGGACAGU | ID. NO. 61 |
| 200 | GUGAAACAGUUUGUUA GGAGAAAGGACAGUG | ID. NO. 62 |
| 218 | AGAAAGGACAGUGGUC CUGUUGUUAAAAAAA | ID. NO. 63 |
| 223 | GGACAGUGGUCCUGUU GUUAAAAAAAUCCGA | ID. NO. 64 |
| 226 | CAGUGGUCCUGUUGUU AAAAAAAUCCGAGAA | ID. NO. 65 |
| 227 | AGUGGUCCUGUUGUUA AAAAAAUCCGAGAAA | ID. NO. 66 |
| 235 | UGUUGUUAAAAAAAUC CGAGAAAUGCAGAAG | ID. NO. 67 |
| 252 | GAGAAAUGCAGAAGUU CCUUGGAUUGGAGGU | ID. NO. 68 |
| 253 | AGAAAUGCAGAAGUUC CUUGGAUUGGAGGUG | ID. NO. 69 |
| 256 | AAUGCAGAAGUUCCUU GGAUUGGAGGUGACG | ID. NO. 70 |
| 261 | AGAAGUUCCUUGGAUU GGAGGUGACGGGGAA | ID. NO. 71 |
| 285 | CGGGGAAGCUGGACUC CGACACUCUGGAGGU | ID. NO. 72 |
| 293 | CUGGACUCCGACACUC UGGAGGUGAUGCGCA | ID. NO. 73 |
| 325 | GCCCAGGUGUGGAGUU CCUGAUGUUGGUCAC | ID. NO. 74 |
| 326 | CCCAGGUGUGGAGUUC CUGAUGUUGGUCACU | ID. NO. 75 |
| 334 | UGGAGUUCCUGAUGUU GGUCACUUCAGAACC | ID. NO. 76 |
| 338 | GUUCCUGAUGUUGGUC ACUUCAGAACCUUUC | ID. NO. 77 |
| 342 | CUGAUGUUGGUCACUU CAGAACCUUUCCUGG | ID. NO. 78 |
| 343 | UGAUGUUGGUCACUUC AGAACCUUUCCUGGC | ID. NO. 79 |
| 351 | GUCACUUCAGAACCUU UCCUGGCAUCCGAA | ID. NO. 80 |
| 352 | UCACUUCAGAACCUUU CCUGGCAUCCGAAG | ID. NO. 81 |
| 353 | CACUUCAGAACCUUUC CUGGCAUCCGAAGU | ID. NO. 82 |

TABLE III-continued

Human Stromelysin HH Target Sequence

| nt. Position | Target Sequence | Seq. ID. NO. |
|---|---|---|
| 361 | AACCUUUCCUGGCAUC CCGAAGUG-GAGGAAA | ID. NO. 83 |
| 385 | GAGGAAAACCCACCUU ACAUACAG-GAUUGUG | ID. NO. 84 |
| 386 | AGGAAAACCCACCUUA CAUACAGGA-UUGUGA | ID. NO. 85 |
| 390 | AAACCCACCUUACAUA CAGGAUU-GUGAAUUA | ID. NO. 86 |
| 397 | CCUUACAUACAGGAUU GUGAA-UUAUACACCA | ID. NO. 87 |
| 404 | UACAGGAUUGUGAAUU AUACACCA-GAUUUGC | ID. NO. 88 |
| 405 | ACAGGAUUGUGAAUUA UACACCAGA-UUUGCC | ID. NO. 89 |
| 407 | AGGAUUGUGAAUUAUA CACCAGA-UUUGCCAA | ID. NO. 90 |
| 416 | AAUUAUACACCAGAUU UGCCAAAA-GAUGCUG | ID. NO. 91 |
| 417 | AUUAUACACCAGAUUU GCCAAAA-GAUGCUGU | ID. NO. 92 |
| 433 | GCCAAAAGAUGCUGUU GAUUCUGCU-GUUGAG | ID. NO. 93 |
| 437 | AAAGAUGCUGUUGAUU CUGCUG-UUGAGAAAG | ID. NO. 94 |
| 438 | AAGAUGCUGUUGAUUC UGCUG-UUGAGAAAGC | ID. NO. 95 |
| 445 | UGUUGAUUCUGCUGUU GAGAAAGCU-CUGAAA | ID. NO. 96 |
| 455 | GCUGUUGAGAAAGCUC UGAAAGU-CUGGGAAG | ID. NO. 97 |
| 463 | GAAAGCUCUGAAAGUC UGGGAAGAG-GUGACU | ID. NO. 98 |
| 479 | UGGGAAGAGGUGACUC CACUCACA-UUCUCCA | ID. NO. 99 |
| 484 | AGAGGUGACUCCACUC ACAUUCUC-CAGGCUG | ID. NO. 100 |
| 489 | UGACUCCACUCACAUU CUCCAGGCU-GUAUGA | ID. NO. 101 |
| 490 | GACUCCACUCACAUUC UCCAGGCU-GUAUGAA | ID. NO. 102 |
| 492 | CUCCACUCACAUUCUC CAGGCU-GUAUGAAGG | ID. NO. 103 |
| 501 | CAUUCUCCAGGCUGUA UGAAG-GAGAGGCUGA | ID. NO. 104 |
| 518 | GAAGGAGAGGCUGAUA UAAUGAUCU-CUUUUG | ID. NO. 105 |
| 520 | AGGAGAGGCUGAUAUA AUGAUCUCU-UUUGCA | ID. NO. 106 |
| 526 | GGCUGAUAUAAUGAUC UCUUUUG-CAGUUAGA | ID. NO. 107 |
| 528 | CUGAUAUAAUGAUCUC UUUUGCAG-UUAGAGA | ID. NO. 108 |
| 530 | GAUAUAAUGAUCUCUU UUGCAGUUA-GAGAAC | ID. NO. 109 |
| 531 | AUAUAAUGAUCUCUUU UGCAGUUA-CAGAACA | ID. NO. 110 |
| 532 | UAUAAUGAUCUCUUUU GCAGUUA-GAGAACAU | ID. NO. 111 |
| 538 | GAUCUCUUUUGCAGUU AGAGAA-CAUGGAGAC | ID. NO. 112 |
| 539 | AUCUCUUUUGCAGUUA GAGAACAUG-GAGACU | ID. NO. 113 |
| 555 | GAGAACAUGGAGACUU UUACCCUU-UUGAUGG | ID. NO. 114 |
| 556 | AGAACAUGGAGACUUU UACCCUU-UUGAUGGA | ID. NO. 115 |
| 557 | GAACAUGGAGACUUUU ACCCUU-UUGAUGGAC | ID. NO. 116 |
| 558 | AACAUGGAGACUUUUA CCCUU-UUGAUGGACC | ID. NO. 117 |
| 563 | GGAGACUUUUACCCUU UUGAUGGAC-CUGGAA | ID. NO. 118 |
| 564 | GAGACUUUUACCCUUU UGAUGGAC-CUGGAAA | ID. NO. 119 |
| 565 | AGACUUUUACCCUUUU GAUGGAC-CUGGAAAU | ID. NO. 120 |
| 583 | UGGACCUGGAAAUGUU UUGGC-CCAUGCCUAU | ID. NO. 121 |
| 584 | GGACCUGGAAAUGUUU UGGC-CCAUGCCUAUG | ID. NO. 122 |

TABLE III-continued

Human Stromelysin HH Target Sequence

| nt. Position | Target Sequence | Seq. ID. NO. |
|---|---|---|
| 585 | GACCUGGAAAUGUUUU GGCCCAUGC-CUAUGC | ID. NO. 123 |
| 597 | UUUUGGCCCAUGCCUA UGC-CCCUGGGCCAGG | ID. NO. 124 |
| 616 | CCCUGGGCCAGGGAUU AAUG-GAGAUGCCCAC | ID. NO. 125 |
| 617 | CCUGGGCCAGGGAUUA AUG-GAGAUGCCCACU | ID. NO. 126 |
| 633 | AUGGAGAUGCCCACUU UGAUGAUGAUGAACA | ID. NO. 127 |
| 634 | UGGAGAUGCCCACUUU GAUGAUGAUGAACAA | ID. NO. 128 |
| 662 | CAAUGGACAAAGGAUA CAACAGG-GACCAAUU | ID. NO. 129 |
| 677 | ACAACAGGGACCAAUU UAUUUCUCG-UUGCUG | ID. NO. 130 |
| 678 | CAACAGGGACCAAUUU AUUUCUCG-UUGCUGC | ID. NO. 131 |
| 679 | AACAGGGACCAAUUUA UUUCUCG-UUGCUGCU | ID. NO. 132 |
| 681 | CAGGGACCAAUUUAUU UCUCG-UUGCUGCUCA | ID. NO. 133 |
| 682 | AGGGACCAAUUUAUUU CUCG-UUGCUGCUCAU | ID. NO. 134 |
| 683 | GGGACCAAUUUAUUUC UCG-UUGCUGCUCAUG | ID. NO. 135 |
| 685 | GACCAAUUUAUUUCUC GUUGCUGCU-CAUGAA | ID. NO. 136 |
| 688 | CAAUUUAUUUCUCGUU GCUGCU-CAUGAAAUU | ID. NO. 137 |
| 695 | UUUCUCGUUGCUGCUC AUGAAAUUG-GCCACU | ID. NO. 138 |
| 703 | UGCUGCUCAUGAAAUU GGCCACUC-CCUGGGU | ID. NO. 139 |
| 711 | AUGAAAUUGGCCACUC CCUGGGUCU-CUUUCA | ID. NO. 140 |
| 719 | GGCCACUCCCUGGGUC UCUUUCACU-CAGCCA | ID. NO. 141 |
| 721 | CCACUCCCUGGGUCUC UUUCACU-CAGCCAAC | ID. NO. 142 |
| 723 | ACUCCCUGGGUCUCUU UCACUCAGC-CAACAC | ID. NO. 143 |
| 724 | CUCCCUGGGUCUCUUU CACUCAGC-CAACACU | ID. NO. 144 |
| 725 | UCCCUGGGUCUCUUUC ACUCAGCCAA-CACUG | ID. NO. 145 |
| 729 | UGGGUCUCUUUCACUC AGCCAA-CACUGAAGC | ID. NO. 146 |
| 746 | GCCAACACUGAAGCUU UGAUGUAC-CCACUCU | ID. NO. 147 |
| 747 | CCAACACUGAAGCUUU GAUGUAC-CCACUCUA | ID. NO. 148 |
| 753 | CUGAAGCUUUGAUGUA CCCACUCUAU-CACUC | ID. NO. 149 |
| 760 | UUUGAUGUACCCACUC UAUCACU-CACUCACA | ID. NO. 150 |
| 762 | UGAUGUACCCACUCUA UCACUCACU-CACAGA | ID. NO. 151 |
| 764 | AUGUACCCACUCUAUC ACUCACUCA-CAGACC | ID. NO. 152 |
| 768 | ACCCACUCUAUCACUC ACUCACAGAC-CUGAC | ID. NO. 153 |
| 772 | ACUCUAUCACUCACUC ACAGAC-CUGACUCGG | ID. NO. 154 |
| 785 | CUCACAGACCUGACUC GGUUCCGCCU-GUCUC | ID. NO. 155 |
| 789 | CAGACCUGACUCGGUU CCGCCUGUCU-CAAGA | ID. NO. 156 |
| 790 | AGACCUGACUCGGUUC CGCCUGUCU-CAAGAU | ID. NO. 157 |
| 798 | CUCGGUUCCGCCUGUC UCAA-GAUGAUAUAAA | ID. NO. 158 |
| 800 | CGGUUCCGCCUGUCUC AAGAUGAUAUAAAUG | ID. NO. 159 |
| 809 | CUGUCUCAAGAUGAUA UAAAUGGCA-UUCAGU | ID. NO. 160 |
| 811 | GUCUCAAGAUGAUAUA AAUGGCAUU-CAGUCC | ID. NO. 161 |
| 820 | UGAUAUAAAUGGCAUU CAGUCCCUC-UAUGGA | ID. NO. 162 |

TABLE III-continued

Human Stromelysin HH Target Sequence

| nt. Position | Target Sequence | Seq. ID. NO. |
|---|---|---|
| 821 | GAUAUAAAUGGCAUUC AGUCCCUC-UAUGGAC | ID. NO. 163 |
| 825 | UAAAUGGCAUUCAGUC CCUCUAUG-GACCUCC | ID. NO. 164 |
| 829 | UGGCAUUCAGUCCCUC UAUGGACCUC-CCCCU | ID. NO. 165 |
| 831 | GCAUUCAGUCCCUCUA UGGACCUC-CCCCUGA | ID. NO. 166 |
| 839 | UCCCUCUAUGGACCUC CCCCUGACUC-CCCUG | ID. NO. 167 |
| 849 | GACCUCCCCUGACUC CCCUGAGAC-CCCCCU | ID. NO. 168 |
| 868 | UGAGACCCCCUGGUA CCCACGGAAC-CUGUC | ID. NO. 169 |
| 883 | ACCCACGGAACCUGUC CCUCCAGAAC-CUGGG | ID. NO. 170 |
| 887 | ACGGAACCUGUCCCUC CAGAACCUGG-GACGC | ID. NO. 171 |
| 917 | CCAGCCAACUGUGAUC CUGCUUUGUC-CUUUG | ID. NO. 172 |
| 923 | AACUGUGAUCCUGCUU UGUCCU-UUGAUGCUG | ID. NO. 173 |
| 924 | ACUGUGAUCCUGCUUU GUCCU-UUGAUGCUGU | ID. NO. 174 |
| 927 | GUGAUCCUGCUUUGUC CUUUGAUGCUGUCAG | ID. NO. 175 |
| 930 | AUCCUGCUUUGUCCUU UGAUGCUGU-CAGCAC | ID. NO. 176 |
| 931 | UCCUGCUUUGUCCUUU GAUGCUGU-CAGCACU | ID. NO. 177 |
| 940 | GUCCUUUGAUGCUGUC AGCACU-CUGAGGGGA | ID. NO. 178 |
| 947 | GAUGCUGUCAGCACUC UGAGGG-GAGAAAUCC | ID. NO. 179 |
| 961 | UCUGAGGGGAGAAAUC CUGAUCU-UUAAAGAC | ID. NO. 180 |
| 967 | GGGAGAAAUCCUGAUC UUUAAAGA-CAGGCAC | ID. NO. 181 |
| 969 | GAGAAAUCCUGAUCUU UAAAGACAG-GCACUU | ID. NO. 182 |
| 970 | AGAAAUCCUGAUCUUU AAAGACAG-GCACUUU | ID. NO. 183 |
| 971 | GAAAUCCUGAUCUUUA AAGACAG-GCACUUUU | ID. NO. 184 |
| 984 | UUAAAGACAGGCACUU UUGGCG-CAAAUCCCU | ID. NO. 185 |
| 985 | UAAAGACAGGCACUUU UGGCG-CAAAUCCCUC | ID. NO. 186 |
| 986 | AAAGACAGGCACUUUU GGCG-CAAAUCCCUCA | ID. NO. 187 |
| 996 | ACUUUUGGCGCAAAUC CCUCAG-GAAGCUUGA | ID. NO. 188 |
| 1000 | UUGGCGCAAAUCCCUC AGGAAGCU-UGAACCU | ID. NO. 189 |
| 1009 | AUCCCUCAGGAAGCUU GAACCUGAA-UUGCAU | ID. NO. 190 |
| 1020 | AGCUUGAACCUGAAUU GCAU-UUGAUCUCUUC | ID. NO. 191 |
| 1025 | GAACCUGAAUUGCAUU UGAUCUCU-UCAUUUU | ID. NO. 192 |
| 1026 | AACCUGAAUUGCAUUU GAUCUCU-UCAUUUUG | ID. NO. 193 |
| 1030 | UGAAUUGCAUUUGAUC UCUUCAU-UUUGGCCA | ID. NO. 194 |
| 1032 | AAUUGCAUUUGAUCUC UUCAUUUUG-GCCAUC | ID. NO. 195 |
| 1034 | UUGCAUUUGAUCUCUU CAUUUUGGC-CAUCUC | ID. NO. 196 |
| 1035 | UGCAUUUGAUCUCUUC AUUUUGGC-CAUCUCU | ID. NO. 197 |
| 1038 | AUUUGAUCUCUUCAUU UUGGCCAU-CUCUUCC | ID. NO. 198 |
| 1039 | UUUGAUCUCUUCAUUU UGGCCAUCU-CUUCCU | ID. NO. 199 |
| 1040 | UUGAUCUCUUCAUUUU GGCCAUCU-CUUCCUU | ID. NO. 200 |
| 1047 | CUUCAUUUUGGCCAUC UCUUCCUU-CAGGCGU | ID. NO. 201 |
| 1049 | UCAUUUUGGCCAUCUC UUCCUUCAG-GCGUGG | ID. NO. 202 |

TABLE III-continued

Human Stromelysin HH Target Sequence

| nt. Position | Target Sequence | Seq. ID. NO. |
|---|---|---|
| 1051 | AUUUUGGCCAUCUCUU CCUUCAG-GCGUGGAU | ID. NO. 203 |
| 1052 | UUUUGGCCAUCUCUUC CUUCAG-GCGUGGAUG | ID. NO. 204 |
| 1055 | UGGCCAUCUCUUCCUU CAGGCGUG-GAUGCCG | ID. NO. 205 |
| 1056 | GGCCAUCUCUUCCUUC AGGCGUG-GAUGCCGC | ID. NO. 206 |
| 1074 | GCGUGGAUGCCGCAUA UGAAGUUAC-UAGCAA | ID. NO. 207 |
| 1081 | UGCCGCAUAUGAAGUU ACUAGCAAG-GACCUC | ID. NO. 208 |
| 1082 | GCCGCAUAUGAAGUUA CUAGCAAG-GACCUCG | ID. NO. 209 |
| 1085 | GCAUAUGAAGUUACUA GCAAGGAC-CUCGUUU | ID. NO. 210 |
| 1095 | UACUAGCAAGGACCUC GUUUCAU-UUUUAAA | ID. NO. 211 |
| 1099 | UAGCAAGGACCUCGUU UUCAU-UUUUAAAGGA | ID. NO. 212 |
| 1100 | AGCAAGGACCUCGUUU UCAU-UUUUAAAGGAA | ID. NO. 213 |
| 1101 | GCAAGGACCUCGUUUU CAU-UUUUAAAGGAAA | ID. NO. 214 |
| 1102 | CAAGGACCUCGUUUUC AUU-UUUAAAGGAAAU | ID. NO. 215 |
| 1105 | GGACCUCGUUUUCAUU UUUAAAG-GAAAUCAA | ID. NO. 216 |
| 1106 | GACCUCGUUUUCAUUU UUAAAG-GAAAUCAAU | ID. NO. 217 |
| 1107 | ACCUCGUUUUCAUUUU UAAAG-GAAAUCAAUU | ID. NO. 218 |
| 1108 | CCUCGUUUUCAUUUUU AAAGGAAAU-CAAUUC | ID. NO. 219 |
| 1109 | CUCGUUUUCAUUUUUA AGGAAAU-CAAUUCU | ID. NO. 220 |
| 1118 | AUUUUUAAAGGAAAUC AAUU-CUGGGCCAUCA | ID. NO. 221 |
| 1122 | UUAAAGGAAAUCAAUU CUGGGCCAU-CAGAGG | ID. NO. 222 |
| 1123 | UAAAGGAAAUCAAUUC UGGGCCAU-CAGAGGA | ID. NO. 223 |
| 1132 | UCAAUUCUGGGCCAUC AGAG-GAAAUGAGGUA | ID. NO. 224 |
| 1147 | CAGAGGAAAUGAGGUA CGAGCUG-GAUACCCA | ID. NO. 225 |
| 1158 | AGGUACGAGCUGGAUA CCCAAGAG-GCAUCCA | ID. NO. 226 |
| 1171 | AUACCCAAGAGGCAUC CACACCCUAG-GUUUC | ID. NO. 227 |
| 1180 | AGGCAUCCACACCCUA GGUUUCCCUC-CAACC | ID. NO. 228 |
| 1184 | AUCCACACCCUAGGUU UCCCUCCAAC-CGUGA | ID. NO. 229 |
| 1185 | UCCACACCCUAGGUUU CCCUCCAAC-CGUGAG | ID. NO. 230 |
| 1186 | CCACACCCUAGGUUUC CUCCAAC-CGUGAGG | ID. NO. 231 |
| 1190 | ACCCUAGGUUUCCCUC CAACCGUGAG-GAAAA | ID. NO. 232 |
| 1207 | AACCGUGAGGAAAAUC GAUGCAGC-CAUUUCU | ID. NO. 233 |
| 1219 | AAUCGAUGCAGCCAUU UCUGAUAAG-GAAAAG | ID. NO. 234 |
| 1220 | AUCGAUGCAGCCAUUU CUGAUAAG-GAAAAGA | ID. NO. 235 |
| 1221 | UCGAUGCAGCCAUUUC UGAUAAG-GAAAAGAA | ID. NO. 236 |
| 1226 | GCAGCCAUUUCUGAUA AGGAAAA-GAACAAAA | ID. NO. 237 |
| 1245 | AAAAGAACAAAACAUA UUUCUUU-GUAGAGGA | ID. NO. 238 |
| 1247 | AAGAACAAAACAUAUU UCUUUGUA-GAGGACA | ID. NO. 239 |
| 1248 | AGAACAAAACAUAUUU CUUUGUA-GAGGACAA | ID. NO. 240 |
| 1249 | GAACAAAACAUAUUUC UUUGUAGAG-GACAAA | ID. NO. 241 |
| 1251 | ACAAAACAUAUUUCUU UGUAGAGGA-CAAAUA | ID. NO. 242 |

TABLE III-continued

Human Stromelysin HH Target Sequence

| nt. Position | Target Sequence | Seq. ID. NO. |
|---|---|---|
| 1252 | CAAAACAUAUUUCUUU GUAGAGGA-CAAAUAC | ID. NO. 243 |
| 1255 | AACAUAUUUCUUUGUA GAGGA-CAAAUACUGG | ID. NO. 244 |
| 1266 | UUGUAGAGGACAAAUA CUGGAGA-UUUGAUGA | ID. NO. 245 |
| 1275 | ACAAAUACUGGAGAUU UGAUGAGAA-GAGAAA | ID. NO. 246 |
| 1276 | CAAAUACUGGAGAUUU GAUGAGAA-GAGAAAU | ID. NO. 247 |
| 1292 | GAUGAAGAGAAAUU CCAUGGAGC-CAGGCU | ID. NO. 248 |
| 1293 | AUGAGAAGAGAAAUUC CAUGGAGC-CAGGCUU | ID. NO. 249 |
| 1308 | CCAUGGAGCCAGGCUU UCCCAAG-CAAAUAGC | ID. NO. 250 |
| 1309 | CAUGGAGCCAGGCUUU CCCAAG-CAAAUAGCU | ID. NO. 251 |
| 1310 | AUGGAGCCAGGCUUUC CCAAG-CAAAUAGCUG | ID. NO. 252 |
| 1321 | CUUUCCCAAGCAAAUA GCUGAAGACU-UUCCA | ID. NO. 253 |
| 1332 | AAAUAGCUGAAGACUU UCCAGGGA-UUGACUC | ID. NO. 254 |
| 1333 | AAUAGCUGAAGACUUU CCAGGGA-UUGACUCA | ID. NO. 255 |
| 1334 | AUAGCUGAAGACUUUC CAGGGA-UUGACUCAA | ID. NO. 256 |
| 1342 | AGACUUUCCAGGGAUU GACUCAAA-GAUUGAU | ID. NO. 257 |
| 1347 | UUCCAGGGAUUGACUC AAAGA-UUGAUGCUGU | ID. NO. 258 |
| 1354 | GAUUGACUCAAAGAUU GAUGCUGU-UUUUGAA | ID. NO. 259 |
| 1363 | AAAGAUUGAUGCUGUU UUUGAA-GAAUUUGGG | ID. NO. 260 |
| 1364 | AAGAUUGAUGCUGUUU UUGAAGAAU-UUGGGU | ID. NO. 261 |
| 1365 | AGAUUGAUGCUGUUUU UGAAGAAU-UUGGGUU | ID. NO. 262 |
| 1366 | GAUUGAUGCUGUUUUU GAAGAAU-UUGGGUUC | ID. NO. 263 |
| 1374 | CUGUUUUUGAAGAAUU UGGGUUCU-UUUAUUU | ID. NO. 264 |
| 1375 | UGUUUUUGAAGAAUUU GGGUUCU-UUUAUUUC | ID. NO. 265 |
| 1380 | UUGAAGAAUUUGGGUU CUUUUAUUU-CUUUAC | ID. NO. 266 |
| 1381 | UGAAGAAUUUGGGUUC UUUUAUUU-CUUUACU | ID. NO. 267 |
| 1383 | AAGAAUUUGGGUUCUU UUAUUUCU-UUACUGG | ID. NO. 268 |
| 1384 | AGAAUUUGGGUUCUUU UAUUUCU-UUACUGGA | ID. NO. 269 |
| 1385 | GAAUUUGGGUUCUUUU AUUUCU-UUACUGGAU | ID. NO. 270 |
| 1386 | AAUUUGGGUUCUUUUA UUUCU-UUACUGGAUG | ID. NO. 271 |
| 1388 | UUUGGGUUCUUUUAUU UCUUUACUG-GAUCUU | ID. NO. 272 |
| 1389 | UUGGGUUCUUUUAUUU CUUUACUG-GAUCUUC | ID. NO. 273 |
| 1390 | UGGGUUCUUUUAUUUC UUUACUG-GAUCUUCA | ID. NO. 274 |
| 1392 | GGUUCUUUUAUUUCUU UACUG-GAUCUUCACA | ID. NO. 275 |
| 1393 | GUUCUUUUAUUUCUUU ACUGGAUCU-UCACAG | ID. NO. 276 |
| 1394 | UUCUUUUAUUUCUUUA CUGGAUCU-UCACAGU | ID. NO. 277 |
| 1401 | AUUUCUUUACUGGAUC UUCACAG-UUGGAGUU | ID. NO. 278 |
| 1403 | UUCUUUACUGGAUCUU CACAGUUG-GAGUUUG | ID. NO. 279 |
| 1404 | UCUUUACUGGAUCUUC ACAGUUG-GAGUUUGA | ID. NO. 280 |
| 1410 | CUGGAUCUUCACAGUU GGAGU-UUGACCCAAA | ID. NO. 281 |
| 1416 | CUUCACAGUUGGAGUU UGAC-CCAAAUGCAAA | ID. NO. 282 |

TABLE III-continued

Human Stromelysin HH Target Sequence

| nt. Position | Target Sequence | Seq. ID. NO. |
|---|---|---|
| 1417 | UUCACAGUUGGAGUUU GAC-CCAAAUGCAAAG | ID. NO. 283 |
| 1448 | AAAGUGACACACACUU UGAA-GAGUAACAGCU | ID. NO. 284 |
| 1449 | AAGUGACACACACUUU GAAGAGUAA-CAGCUG | ID. NO. 285 |
| 1457 | CACACUUUGAAGAGUA ACAGCUG-GCUUAAUU | ID. NO. 286 |
| 1468 | GAGUAACAGCUGGCUU AAUUG-UUGAAAGAGA | ID. NO. 287 |
| 1469 | AGUAACAGCUGGCUUA AUUG-UUGAAAGAGAU | ID. NO. 288 |
| 1472 | AACAGCUGGCUUAAUU GUUGAAA-GAGAUAUG | ID. NO. 289 |
| 1475 | AGCUGGCUUAAUUGUU GAAA-GAGAUAUGUAG | ID. NO. 290 |
| 1485 | AUUGUUGAAAGAGAUA UGUAGAAG-GCACAAU | ID. NO. 291 |
| 1489 | UUGAAAGAGAUAUGUA GAAGGCA-CAAUAUGG | ID. NO. 292 |
| 1501 | UGUAGAAGGCACAAUA UGGGCACU-UUAAAUG | ID. NO. 293 |
| 1510 | CACAAUAUGGGCACUU UAAAUGAAGCUAAUA | ID. NO. 294 |
| 1511 | ACAAUAUGGGCACUUU AAAUGAAGC-UAAUAA | ID. NO. 295 |
| 1512 | CAAUAUGGGCACUUUA AAUGAAGC-UAAUAAU | ID. NO. 296 |
| 1522 | ACUUUAAAUGAAGCUA AUAAUUCU-UCACCUA | ID. NO. 297 |
| 1525 | UUAAAUGAAGCUAAUA AUUCUUCAC-CUAAGU | ID. NO. 298 |
| 1528 | AAUGAAGCUAAUAAUU CUUCAC-CUAAGUCUC | ID. NO. 299 |
| 1529 | AUGAAGCUAAUAAUUC UUCAC-CUAAGUCUCU | ID. NO. 300 |
| 1531 | GAAGCUAAUAAUUCUU CACCUAAGU-CUCUGU | ID. NO. 301 |
| 1532 | AAGCUAAUAAUUCUUC ACCUAAGU-CUCUGUG | ID. NO. 302 |
| 1537 | AAUAAUUCUUCACCUA AGUCUCU-GUGAAUUG | ID. NO. 303 |
| 1541 | AUUCUUCACCUAAGUC UCUGUGAA-UUGAAAU | ID. NO. 304 |
| 1543 | UCUUCACCUAAGUCUC UGUGAA-UUGAAAUGU | ID. NO. 305 |
| 1551 | UAAGUCUCUGUGAAUU GAAAUG-UUCGUUUUC | ID. NO. 306 |
| 1559 | UGUGAAUUGAAAUGUU CGUUUCUC-CUGCCU | ID. NO. 307 |
| 1560 | GUGAAUUGAAAUGUUC GUUUCUC-CUGCCUG | ID. NO. 308 |
| 1563 | AAUUGAAAUGUUCGUU UUCUCCUGC-CUGUGC | ID. NO. 309 |
| 1564 | AUUGAAAUGUUCGUUU UCUCCUGC-CUGUGCU | ID. NO. 310 |
| 1565 | UUGAAAUGUUCGUUUU CUCCUGCCU-GUGCUG | ID. NO. 311 |
| 1566 | UGAAAUGUUCGUUUUC UCCUGCCU-GUGCUGU | ID. NO. 312 |
| 1568 | AAAUGUUCGUUUUCUC CUGCCU-GUGCUGUGA | ID. NO. 313 |
| 1586 | GCCUGUGCUGUGACUC GAGUCACACU-CAAGG | ID. NO. 314 |
| 1591 | UGCUGUGACUCGAGUC ACACU-CAAGGGAACU | ID. NO. 315 |
| 1597 | GACUCGAGUCACACUC AAGGGAACU-UGAGCG | ID. NO. 316 |
| 1607 | ACACUCAAGGGAACUU GAGCGUGAAUCUGUA | ID. NO. 317 |
| 1618 | AACUUGAGCGUGAAUC UGUAUCU-UGCCGGUC | ID. NO. 318 |
| 1622 | UGAGCGUGAAUCUGUA UCUUGCCG-GUCAUUU | ID. NO. 319 |
| 1624 | AGCGUGAAUCUGUAUC UUGCCGGU-CAUUUUU | ID. NO. 320 |
| 1626 | CGUGAAUCUGUAUCUU GCCGGUCAU-UUUUAU | ID. NO. 321 |
| 1633 | CUGUAUCUUGCCGGUC AUUUUAUG-UUAUUA | ID. NO. 322 |

TABLE III-continued

Human Stromelysin HH Target Sequence

| nt. Position | Target Sequence | Seq. ID. NO. |
|---|---|---|
| 1636 | UAUCUUGCCGGUCAUU UUUAUGUUA-UUACAG | ID. NO. 323 |
| 1637 | AUCUUGCCGGUCAUUU UUAUGUUA-UUACAGG | ID. NO. 324 |
| 1638 | UCUUGCCGGUCAUUUU UAUGUUA-UUACAGGG | ID. NO. 325 |
| 1639 | CUUGCCGGUCAUUUUU AUGUUAUUA-CAGGGC | ID. NO. 326 |
| 1640 | UUGCCGGUCAUUUUUA UGUUAUUA-CAGGGCA | ID. NO. 327 |
| 1644 | CGGUCAUUUUUAUGUU AUUA-CAGGGCAUUCA | ID. NO. 328 |
| 1645 | GGUCAUUUUUAUGUUA UUA-CAGGGCAUUCAA | ID. NO. 329 |
| 1647 | UCAUUUUUAUGUUAUU ACAGGGCA-UUCAAAU | ID. NO. 330 |
| 1648 | CAUUUUUAUGUUAUUA CAGGGCAUU-CAAAUG | ID. NO. 331 |
| 1657 | GUUAUUACAGGGCAUU CAAAUGGGCUGCUGC | ID. NO. 332 |
| 1658 | UUAUUACAGGGCAUUC AAAUGGGCUGCUGCU | ID. NO. 333 |
| 1674 | AAAUGGGCUGCUGCUU AGCUUGCAC-CUUGUC | ID. NO. 334 |
| 1675 | AAUGGGCUGCUGCUUA GCUUGCAC-CUUGUCA | ID. NO. 335 |
| 1679 | GGCUGCUGCUUAGCUU GCACCUUGU-CACAUA | ID. NO. 336 |
| 1686 | GCUUAGCUUGCACCUU GUCACAUA-GAGUGAU | ID. NO. 337 |
| 1689 | UAGCUUGCACCUUGUC ACAUA-GAGUGAUCUU | ID. NO. 338 |
| 1694 | UGCACCUUGUCACAUA GAGUGAUCU-UUCCCA | ID. NO. 339 |
| 1702 | GUCACAUAGAGUGAUC UUUCCCAA-GAGAAGG | ID. NO. 340 |
| 1704 | CACAUAGAGUGAUCUU UCCCAA-GAGAAGGGG | ID. NO. 341 |
| 1705 | ACAUAGAGUGAUCUUU CCCAA-GAGAAGGGGA | ID. NO. 342 |
| 1706 | CAUAGAGUGAUCUUUC CCAA-GAGAAGGGGAA | ID. NO. 343 |
| 1727 | AGAAGGGGAAGCACUC GUGUGCAA-CAGACAA | ID. NO. 344 |
| 1751 | CAGACAAGUGACUGUA UCUGUGUA-GACUAUU | ID. NO. 345 |
| 1753 | GACAAGUGACUGUAUC UGUGUAGAC-UAUUUG | ID. NO. 346 |
| 1759 | UGACUGUAUCUGUGUA GACUAU-UUGCUUAUU | ID. NO. 347 |
| 1764 | GUAUCUGUGUAGACUA UUUGCUUAU-UUAAUA | ID. NO. 348 |
| 1766 | AUCUGUGUAGACUAUU UGCUUAU-UUAAUAAA | ID. NO. 349 |
| 1767 | UCUGUGUAGACUAUUU GCUUAU-UUAAUAAAG | ID. NO. 350 |
| 1771 | UGUAGACUAUUUGCUU AUUUAAUAAAGACGA | ID. NO. 351 |
| 1772 | GUAGACUAUUUGCUUA UUUAAUAAA-GACGAU | ID. NO. 352 |
| 1774 | AGACUAUUUGCUUAUU UAAUAAA-GACGAUUU | ID. NO. 353 |
| 1775 | GACUAUUUGCUUAUUU AAUAAAGAC-GAUUUG | ID. NO. 354 |
| 1776 | ACUAUUUGCUUAUUUA AUAAAGAC-GAUUUGU | ID. NO. 355 |
| 1779 | AUUUGCUUAUUUAAUA AAGACGA-UUUGUCAG | ID. NO. 356 |
| 1788 | UUUAAUAAAGACGAUU UGUCAGUU-GUUUU | ID. NO. 357 |
| 1789 | UUAAUAAAGACGAUUU GUCAGUUGU-UUU | ID. NO. 358 |
| 1792 | AUAAAGACGAUUUGUC AGUUGUUUU | ID. NO. 359 |

TABLE IV

Human Stromelysin HP Target Sequence

| nt. Position | Target Sequence | Seq. ID. NO. |
|---|---|---|
| 66 | CUACU GUU GCUGUGCGUGGCAGU | ID. NO. 360 |
| 82 | UGGCA GUU UGCUCAGCCUAUCCA | ID. NO. 361 |
| 192 | AAACA GUU UGUUAGGAGAAAGGA | ID. NO. 362 |
| 430 | AUGCU GUU GAUUCUGCUGUUGAG | ID. NO. 363 |
| 442 | CUGCU GUU GAGAAAGCUCUGAAA | ID. NO. 364 |
| 775 | UCACA GAC CUGACUCGGUUCCGC | ID. NO. 365 |
| 1360 | AUGCU GUU UUUGAAGAAUUGGG | ID. NO. 366 |
| 1407 | UCACA GUU GGAGUUUGACCCAAA | ID. NO. 367 |

TABLE V

Human HH Ribozyme Sequence

| nt. Position | Ribozyme Sequence | Seq. ID. |
|---|---|---|
| 10 | GUUGUCUC CUGAAGAGCACGAAAGUGCGAA AUGCCUUG | ID. NO. 375 |
| 21 | UUAGCUC CUGAUGAGGCCGAAAGGCCGAA AUGUUGU | ID. NO. 376 |
| 168 | GAGGUCG CUGAUGAGGCCGAAAGGCCGAA AGUAGUU | ID. NO. 377 |
| 616 | CUCCAUU CUGAUGAGGCCGAAAGGCCGAA AUCCCUG | ID. NO. 378 |
| 617 | UCUCCAU CUGAUGAGGCCGAAAGGCCGAA AAUCCCU | ID. NO. 379 |
| 633 | CAUCAUCA CUGAAGAGCACGAAAGUGCGAA AGUGGGCA | ID. NO. 380 |
| 634 | UCAUCAUC CUGAAGAGCACGAAAGUGCGAA AAGUGGGC | ID. NO. 381 |
| 662 | CCUGUUG CUGAUGAGGCCGAAAGGCCGAA AUCCUUU | ID. NO. 382 |
| 711 | ACCCAGG CUGAUGAGGCCGAAAGGCCGAA AGUGGCC | ID. NO. 383 |
| 820 | GGGACUG CUGAUGAGGCCGAAAGGCCGAA AUGCCAU | ID. NO. 384 |
| 883 | UCUGGAGG CUGAAGAGCACGAAAGUGCGAA ACAGGUUC | ID. NO. 385 |
| 947 | CCCCUCA CUGAUGAGGCCGAAAGGCCGAA AGUGCUG | ID. NO. 386 |
| 996 | CCUGAGG CUGAUGAGGCCGAAAGGCCGAA AUUUGCG | ID. NO. 387 |
| 1123 | UGGCCCA CUGAUGAGGCCGAAAGGCCGAA AAUUGAU | ID. NO. 388 |
| 1132 | UUUCCUCU CUGAUGAGCACGAAAGUGCGAA AUGGCCCA | ID. NO. 389 |
| 1221 | CCUUAUCA CUGAAGAGCACGAAAGUGCGAA AAAUGGCU | ID. NO. 390 |
| 1266 | UCUCCAG CUGAUGAGGCCGAAAGGCCGAA AUUUGUC | ID. NO. 391 |
| 1275 | UCUCAUCA CUGAAGAGCACGAAAGUGCGAA AUCUCCAG | ID. NO. 392 |
| 1334 | AUCCCUG CUGAUGAGGCCGAAAGGCCGAA AAAGUCU | ID. NO. 393 |
| 1354 | CAGCAUC CUGAUGAGGCCGAAAGGCCGAA AUCUUUG | ID. NO. 394 |
| 1363 | UCUUCAAA CUGAUGAGCACGAAAGUGCGAA ACAGCAUC | ID. NO. 395 |
| 1410 | AAACUCC CUGAUGAGGCCGAAAGGCCGAA ACUGUGA | ID. NO. 396 |

TABLE VI

Rabbit Stromelysin HH Ribozyme Target Sequence

| nt. | Target Sequence | Seq. ID No. | nt. | Target Sequence | Seq. ID No. |
|---|---|---|---|---|---|
| 18 | CAAGGCAU C AAGACAGC | 397 | 345 | CCUGAUGU U GGUCACUU | 437 |
| 29 | GACAGCAU A GAGCUGAG | 398 | 349 | AUGUUGGU C ACUUCAGU | 438 |
| 39 | AGCUGAGU A AAGCCAAU | 399 | 353 | UGGUCACU U CAGUACCU | 439 |
| 61 | UGAAAACU C UUCCAACC | 400 | 354 | GGUCACUU C AGUACCUU | 440 |
| 63 | AAAACUCU U CCAACCCU | 401 | 358 | ACUUCAGU A CCUUCCCU | 441 |
| 64 | AAACUCUU C CAACCCUG | 402 | 362 | CAGUACCU U CCCUGGCA | 442 |
| 75 | ACCCUGCU A CUGCUGUG | 403 | 363 | AGUACCUU C CCUGGCAC | 443 |
| 93 | GUGGCGCU U UGCUCAGC | 404 | 391 | CAAAAACU C ACCUAACU | 444 |
| 94 | UGGCGCUU U GCUCAGCC | 405 | 396 | ACUCACCU A ACUUACAG | 445 |
| 98 | GCUUUGCU C AGCCUAUC | 406 | 400 | ACCUAACU U ACAGGAUU | 446 |
| 104 | CUCAGCCU A UCCACUGG | 407 | 401 | CCUAACUU A CAGGAUUG | 447 |
| 106 | CAGCCUAU C CACUGGAU | 408 | 408 | UACAGGAU U GUGAAUUA | 448 |
| 122 | UGGAGCCU C AAGGGAUG | 409 | 415 | UUGUGAAU U ACACACCG | 449 |
| 153 | AUGGACCU U CUUCAGCA | 410 | 416 | UGUGAAUU A CACACCGG | 450 |
| 154 | UGGACCUU C UUCAGCAA | 411 | 427 | CACCGGAU C UGCCAAGA | 451 |
| 156 | GACCUUCU U CAGCAAUA | 412 | 444 | GAUGCUGU U GAUGCUGC | 452 |
| 157 | ACCUUCUU C AGCAAUAU | 413 | 456 | GCUGCCAU U GAGAAAGC | 453 |
| 164 | UCAGCAAU A UCUGGAAA | 414 | 466 | AGAAAGCU C UGAAGGUC | 454 |
| 166 | AGCAAUAU C UGGAAAAC | 415 | 474 | CUGAAGGU C UGGGAGGA | 455 |
| 176 | GGAAAACU A CUACAACC | 416 | 490 | AGGUGACU C CACUCACG | 456 |
| 179 | AAACUACU A CAACCUUG | 417 | 495 | ACUCCACU C ACGUUCUC | 457 |
| 186 | UACAACCU U GAAAAGA | 418 | 500 | ACUCACGU U CUCCAGGA | 458 |
| 206 | GAAACAGU U UGUUAAAA | 419 | 501 | CUCACGUU C UCCAGGAA | 459 |

TABLE VI-continued

Rabbit Stromelysin HH Ribozyme Target Sequence

| nt. | Target Sequence | Seq. ID No. | nt. | Target Sequence | Seq. ID No. |
|---|---|---|---|---|---|
| 207 | AAACAGUU U GUUAAAAG | 420 | 503 | CACGUUCU C CAGGAAGU | 460 |
| 210 | CAGUUUGU U AAAAGAAA | 421 | 512 | CAGGAAGU A UGAAGGAG | 461 |
| 211 | AGUUUGUU A AAAGAAAG | 422 | 531 | GCUGACAU A AUGAUCUC | 462 |
| 226 | AGGACAGU A GUCCUGUU | 423 | 537 | AUAAUGAU C UCUUUUGG | 463 |
| 229 | ACAGUAGU C CUGUUGUU | 424 | 539 | AAUGAUCU C UUUUGGAG | 464 |
| 234 | AGUCCUGU U GUUAAAAA | 425 | 541 | UGAUCUCU U UUGGAGUC | 465 |
| 237 | CCUGUUGU U AAAAAAAU | 426 | 542 | GAUCUCUU U UGGAGUCC | 466 |
| 238 | CUGUUGUU A AAAAAAUC | 427 | 543 | AUCUCUUU U GGAGUCCG | 467 |
| 246 | AAAAAAAU C CAAGAAAU | 428 | 549 | UUUGGAGU C CAAGAACA | 468 |
| 263 | GCAGAAGU U CCUUGGCU | 429 | 565 | AUGGAGAU U UUAUUCCU | 469 |
| 264 | CAGAAGUU C CUUGGCUU | 430 | 566 | UGGAGAUU U UAUUCCUU | 470 |
| 267 | AAGUUCCU U GGCUUGGA | 431 | 567 | GGAGAUUU U AUUCCUUU | 471 |
| 272 | CCUUGGCU U GGAGGUGA | 432 | 568 | GAGAUUUU A UUCCUUUU | 472 |
| 296 | GCUGGACU C CAACACCC | 433 | 570 | GAUUUUAU U CCUUUUGA | 473 |
| 315 | GAGGUGAU A CGCAAGCC | 434 | 571 | AUUUUAUU C CUUUUGAU | 474 |
| 336 | UGUGGCGU U CCUGAUGU | 435 | 574 | UUAUUCCU U UUGAUGGA | 475 |
| 337 | GUGGCGUU C CUGAUGUU | 436 | 575 | UAUUCCUU U UGAUGGAC | 476 |
| 576 | AUUCCUUU U GAUGGACC | 477 | 905 | UCCAGGAU C UGGGACCC | 526 |
| 594 | GGAAAUGU U UUGGCUCA | 478 | 918 | ACCCCAGU C AUGUGUGA | 527 |
| 595 | GAAAUGUU U UGGCUCAU | 479 | 928 | UGUGUGAU C CAGAUCUG | 528 |
| 596 | AAAUGUUU U GGCUCAUG | 480 | 934 | AUCCAGAU C UGCCUUC | 529 |
| 601 | UUUUGGCU C AUGCUUAU | 481 | 938 | AGAUCUGU C CUUCGAUG | 530 |
| 607 | CUCAUGCU U AUGCACCU | 482 | 941 | UCUGUCCU U CGAUGCAA | 531 |
| 608 | UCAUGCUU A UGCACCUG | 483 | 942 | CUGUCCUU C GAUGCAAU | 532 |
| 627 | CAGGCAAU U AAUGGAGA | 484 | 951 | GAUGCAAU C AGCACUCU | 533 |
| 628 | CAGGAAUU A AUGGAGAU | 485 | 958 | UCAGCACU C UGAGGGGA | 534 |
| 644 | UGCCCACU U GAUGAUG | 486 | 972 | GGAGAAAU U CUGUUCUU | 535 |
| 645 | GCCCACUU U GAUGAUGA | 487 | 973 | GAGAAAUU C UGUUCUUU | 536 |
| 673 | CAAAGGAU A CAACAGGA | 488 | 977 | AAUUCUGU U CUUUAAAG | 537 |
| 688 | GAACCAAU U UAUUCCUU | 489 | 978 | AUUCUGUU C UUUAAAGA | 538 |
| 689 | AACCAAUU U AUUCCUUG | 490 | 980 | UCUGUUCU U UAAAGACA | 539 |
| 690 | ACCAAUUU A UUCCUUGU | 491 | 981 | CUGUUCUU U AAAGACAG | 540 |
| 692 | CAAUUUAU U CCUUGUUG | 492 | 982 | UGUUCUUU A AAGACAGG | 541 |
| 693 | AAUUUAUU C CUUGUUGC | 493 | 992 | AGACAGGU A UUUCUGGC | 542 |
| 696 | UUAUUCCU U GUUGCUGC | 494 | 994 | ACAGGUAU U UCUGGCGC | 543 |
| 699 | UUCCUUGU U GCUGCUCA | 495 | 995 | CAGGUAUU U CUGGCGCA | 544 |
| 706 | UUGCUGCU A UGAGCGCAA | 496 | 996 | AGGUAUUU C UGGCGCAA | 545 |
| 714 | CAUGAGCU U GGCCACUC | 497 | 1007 | GCGCAAGU C CCUCAGGA | 546 |
| 722 | UGGCCACU C CCUGGGUC | 498 | 1011 | AAGUCCCU C AGGAUUCU | 547 |
| 730 | CCCUGGGU C UGUUUCAC | 499 | 1017 | CUCAGGAU U CUCGAACC | 548 |
| 734 | GGGUCUGU U UCACUCGG | 500 | 1018 | UCAGGAUU C UCGAACCU | 549 |
| 735 | GGUCUGUU U CACUCGGC | 501 | 1020 | AGGAUUCU C GAACCUGA | 550 |
| 736 | GUCUGUUU C ACUCGGCC | 502 | 1031 | ACCUGAGU U CAUUUGA | 551 |
| 740 | GUUUCACU C GGCCAACC | 503 | 1032 | CCUGAGUU U CAUUUGAU | 552 |
| 764 | CCUGAGUGU U CCCAGUCU | 504 | 1033 | CUGAGUUU C AUUUGAUC | 553 |
| 771 | UACCCAGU C UACAACGC | 505 | 1036 | AGUUUCAU U UGAUCUCU | 554 |
| 773 | CCCAGUCU A CAACGCCU | 506 | 1037 | GUUUCAUU U GAUCUCUU | 555 |
| 782 | CAACGCCU U CACAGACC | 507 | 1041 | CAUUUGAU C UCUUCAUU | 556 |
| 783 | AACGCCUU C ACAGACCU | 508 | 1043 | UUUGAUCU C UUCAUUCU | 557 |
| 800 | GGCCCGGU U CCGCCUUU | 509 | 1045 | UGAUCUCU U CAUUCUGG | 558 |
| 801 | GCCCGGUU C CGCCUUUC | 510 | 1046 | GAUCUCUU C AUUCUGGC | 559 |
| 807 | UUCCGCCU U UCUCAAGA | 511 | 1049 | CUCUUCAU U CUGGCCAU | 560 |
| 808 | UCCGCCUU U CUCAAGAU | 512 | 1050 | UCUUCAUU C UGGCCAUC | 561 |
| 809 | CCGCCUUU C UCAAGAUG | 513 | 1058 | CUGGCCAU C UCUUCCUU | 562 |
| 811 | GCCUUUCU C AAGAUGAU | 514 | 1060 | GGCCAUCU C UUCCUUCA | 563 |
| 831 | GAUGGCAU C CAAUCCCU | 515 | 1062 | CCAUCUCU U CCUUCAGC | 564 |
| 836 | CAUCCAAU C CCUCUAUG | 516 | 1063 | CAUCUCUU C CUUCAGCA | 565 |
| 840 | CAAUCCCU C UAUGGACC | 517 | 1066 | CUCUUCCU U CAGCAGUG | 566 |
| 842 | AUCCCUCU A UGGACCGG | 518 | 1067 | UCUUCCUU C AGCAGUGG | 567 |
| 860 | CCCUGCCU C UCCUGAUA | 519 | 1085 | UGCUGCAU A UGAAGUUA | 568 |
| 862 | CUGCCUCU C CUGAUAAC | 520 | 1092 | UAUGAAGU U AUUAGCAGG | 569 |
| 868 | CUCCUGAU A ACUCUGGA | 521 | 1093 | AUGAAGUU A UUAGCAGG | 570 |
| 872 | UGAUAACU C UGGAGUGC | 522 | 1095 | GAAGUUAU U AGCAGGGA | 571 |
| 883 | GAGUGCCU A UGGAACCU | 523 | 1096 | AAGUUAUU A GCAGGGAU | 572 |
| 894 | GAACCUGU A CCUCCAGG | 524 | 1105 | GCAGGGAU A CUGUUUUC | 573 |
| 898 | CUGUCCCU C CAGGAUCU | 525 | 1110 | GAUACUGU U UCAUUUU | 574 |
| 1111 | AUACUGUU U CAUUUUU | 575 | 1374 | GAUGCUGU U UUGAAGC | 624 |
| 1112 | UACUGUUU U CAUUUUUA | 576 | 1375 | AUGCUGUU U UGAAGCA | 625 |
| 1113 | ACUGUUUU C AUUUUUAA | 577 | 1376 | UGCUGUUU U GAAGCAU | 626 |
| 1116 | GUUUUCAU U UUUAAGG | 578 | 1377 | GCUGUUUU U GAAGCAUU | 627 |
| 1117 | UUUUCAUU U UUAAAGGA | 579 | 1385 | UGAAGCAU U UGGGUUUU | 628 |
| 1118 | UUUCAUUU U UAAAGGAA | 580 | 1386 | GAAGCAUU U GGGUUUUU | 629 |
| 1119 | UUCAUUUU U AAAGGAAC | 581 | 1391 | AUUUGGGU U UUCUAUUU | 630 |
| 1120 | UCAUUUUU A AAGGAACU | 582 | 1392 | UUUGGGUU U UUCUAUUU | 631 |

TABLE VI-continued

Rabbit Stromelysin HH Ribozyme Target Sequence

| nt. | Target Sequence | Seq. ID No. | nt. | Target Sequence | Seq. ID No. |
|---|---|---|---|---|---|
| 1129 | AAGGAACU C AGUUCUGG | 583 | 1393 | UUGGGUUU U UCUAUUUC | 632 |
| 1133 | AACUCAGU U CUGGGCCA | 584 | 1394 | UGGGUUUU U CUAUUUCU | 633 |
| 1134 | ACUCAGUU C UGGGCCAU | 585 | 1395 | GGGUUUUU C UAUUUCUU | 634 |
| 1143 | UGGGCCAU U AGAGGAAA | 586 | 1397 | GUUUUUCU A UUUCUUCA | 635 |
| 1144 | GGGCCAUU A GAGGAAAU | 587 | 1399 | UUUUCUAU U UCUUCAGU | 636 |
| 1158 | AAUGAGGU A CAAGCUGG | 588 | 1400 | UUUCUAUU U CUUCAGUG | 637 |
| 1168 | AAGCUGGU U ACCCAAGA | 589 | 1401 | UUCUAUUU C UUCAGUGG | 638 |
| 1169 | AGCUGGUU A CCCAAGAA | 590 | 1403 | CUAUUUCU U CAGUGGAU | 639 |
| 1182 | AGAAGCAU C CACACCCU | 591 | 1404 | UAUUUCUU C AGUGGAUC | 640 |
| 1195 | CCCUGGGU U UCCCUUCA | 592 | 1412 | CAGUGGAU C UUCACAGU | 641 |
| 1196 | CCUGGGUU U CCCUUCAA | 593 | 1414 | GUGGAUCU U CACAGUCG | 642 |
| 1197 | CUGGGUUU C CCUUCAAC | 594 | 1415 | UGGAUCUU C ACAGUCGG | 643 |
| 1201 | GUUUCCCU U CAACCAUA | 595 | 1421 | UUCACAGU C GGAGUUUG | 644 |
| 1202 | UUUCCCUU C AACCAUAA | 596 | 1427 | GUCGGAGU U UGACCCAA | 645 |
| 1209 | UCAACCAU A AGAAAAAU | 597 | 1428 | UCGGAGUU U GACCCAAA | 646 |
| 1218 | AGAAAAAU U GAUGCUGC | 598 | 1458 | ACACAUGU U UUGAAGAG | 647 |
| 1230 | GCUGCCAU U UCUGAUAA | 599 | 1459 | CACAUGUU U UGAAGAGC | 648 |
| 1231 | CUGCCAUU U CUGAUAAG | 600 | 1460 | ACAUGUUU U GAAGAGCA | 649 |
| 1232 | UGCCAUUU C UGAUAAGG | 601 | 1478 | CAGCUGGU U UCAGUGUU | 650 |
| 1237 | UUUCUGAU A AGGAAAGG | 602 | 1479 | AGCUGGUU U CAGUGUUA | 651 |
| 1256 | GAAAACAU C UUCUUUG | 603 | 1480 | GCUGGUUU C AGUGUUAG | 652 |
| 1259 | AACAUACU U CUUUGUGG | 604 | 1486 | UUCAGUGU U AGGAGGGG | 653 |
| 1260 | ACAUACUU C UUUGUGGA | 605 | 1487 | UCAGUGUU A GGAGGGGU | 654 |
| 1262 | AUACUUCU U UGUGGAAG | 606 | 1498 | AGGGGUGU A UAGAAGGC | 655 |
| 1263 | UACUUCUU U GUGGAAGA | 607 | 1500 | GGGUGUAU A GAAGGCAC | 656 |
| 1277 | AGACAAAU A CUGGAGGU | 608 | 1519 | AUGAAUGU U UUAAAUGA | 657 |
| 1286 | CUGGAGGU U UGAUGAGA | 609 | 1520 | UGAAUGUU U UAAAUGAA | 658 |
| 1287 | UGGAGGUU U GAUGAGAA | 610 | 1521 | GAAUGUUU U AAAUGAAC | 659 |
| 1304 | GAGACAGU C CCUGGAGC | 611 | 1522 | AAUGUUUU A AAUGAACC | 660 |
| 1319 | GCCAGGCU U UCCCAGAC | 612 | 1532 | AUGAACCU A AUUGUUCA | 661 |
| 1320 | CCAGGCUU U CCCAGACA | 613 | 1535 | AACCUAAU U GUUCAACA | 662 |
| 1321 | CAGGCUUU C CCAGACAU | 614 | 1538 | CUAAUUGU U CAACACUU | 653 |
| 1330 | CCAGACAU U AGCAGAA | 615 | 1539 | UAAUUGUU C AACACUUA | 664 |
| 1332 | AGACAUAU A GCAGAAGA | 616 | 1546 | UCAACACU U AGGACUUU | 665 |
| 1343 | AGAAGACU U UCCAGGAA | 617 | 1547 | CAACACUU A GGACUUUG | 666 |
| 1344 | GAAGACUU U CCAGGAAU | 618 | 1553 | UUAGGACU U UGUGAGUU | 667 |
| 1345 | AAGACUUU C CAGGAAUU | 619 | 1554 | UAGGACUU U GUGAGUUU | 668 |
| 1353 | CCAGGAAU U AAUCCAAA | 620 | 1561 | UUGUGAGU U GAAGUGGC | 669 |
| 1354 | CAGGAAUU A AUCCAAAG | 621 | 1571 | AAGUGGCU C AUUUCUC | 670 |
| 1357 | GAAUUAAU C CAAAGAUC | 622 | 1574 | UGGCUCAU U UUCUCCUG | 671 |
| 1365 | CCAAAGAU C GAUGCUGU | 623 | 1575 | GGCUCAUU U UCUCCUGC | 672 |
| 1576 | GCUCAUUU U CUCCUGCA | 673 | | | |
| 1577 | CUCAUUUU C UCCUGCAU | 674 | | | |
| 1579 | CAUUUUCU C CUGCAUAU | 675 | | | |
| 1586 | UCCUGCAU A UGCUGUGA | 676 | | | |
| 1602 | AUGGGAAU C UCGAGCAU | 677 | | | |
| 1604 | GGGAAUCU C GAGCAUGA | 678 | | | |
| 1620 | AACUGUGU A UCUAACUG | 679 | | | |
| 1622 | CUGUGUAU C UAACUGGA | 680 | | | |
| 1624 | GUGUAUCU A ACUGGACU | 681 | | | |
| 1633 | ACUGGACU U UGCACAUC | 682 | | | |
| 1634 | CUGGACUU U GCACAUCG | 683 | | | |
| 1641 | UUGCACAU C GUUACGGG | 684 | | | |
| 1644 | CACAUCGU U ACGGUGU | 685 | | | |
| 1645 | ACAUCGUU A CGGGUGUU | 686 | | | |
| 1653 | ACGGGUGU U CAAACAGG | 687 | | | |
| 1654 | CGGGUGUU C AAACAGGC | 688 | | | |
| 1670 | CUGCUGCU U AGCUUGCA | 689 | | | |
| 1671 | UGCUGCUU A GCUUGCAC | 690 | | | |
| 1675 | GCUUAGCU U GCACUUGA | 691 | | | |
| 1681 | CUUGCACU U GAUCACAU | 692 | | | |
| 1685 | CACUUGAU C ACAUGGAA | 693 | | | |
| 1701 | AGGGAGCU U CCACGAGA | 694 | | | |
| 1702 | GGGAGCUU C CACGAGAC | 695 | | | |
| 1720 | GGGGAAGU A CUCAUGUG | 696 | | | |
| 1723 | GAAGUACU C AUGUGUGA | 697 | | | |
| 1744 | CGAGUGAU U GUGUCUAU | 698 | | | |
| 1749 | GAUUGUGU C UAUGUGGA | 699 | | | |
| 1751 | UUGUGUCU A UGUGGAUU | 700 | | | |
| 1759 | AUGUGGAU U AUUUGCCC | 701 | | | |
| 1760 | UGUGGAUU A UUUGCCCA | 702 | | | |
| 1762 | UGGAUUAU U UGCCCAUU | 703 | | | |
| 1763 | GGAUUAUU U GCCCAUUA | 704 | | | |
| 1770 | UUGCCCAU U AUUUAAUA | 705 | | | |

TABLE VI-continued

Rabbit Stromelysin HH Ribozyme Target Sequence

| nt. | Target Sequence | Seq. ID No. | nt. | Target Sequence | Seq. ID No. |
|---|---|---|---|---|---|
| 1771 | UGCCCAUU A UUUAAUAA | 706 | | | |
| 1773 | CCCAUUAU U UAAUAAAG | 707 | | | |
| 1774 | CCAUUAUU U AAUAAAGA | 708 | | | |
| 1775 | CAUUAUUU A AUAAAGAG | 709 | | | |
| 1778 | UAUUUAAU A AAGAGGAU | 710 | | | |
| 1787 | AAGAGGAU U UGUCAAUU | 711 | | | |

TABLE VII

Rabbit Stromelysin HH Ribozyme Sequence

| nt. Position | Ribozyme Sequence | Sequence ID No. |
|---|---|---|
| 18 | GCUGUCUU CUGAUGAGGCCGAAAGGCCGAA AUGCCUUG | 712 |
| 29 | CUCAGCUC CUGAUGAGGCCGAAAGGCCGAA AUGCUGUC | 713 |
| 39 | AUUGGCUU CUGAUGAGGCCGAAAGGCCGAA ACUCAGCU | 714 |
| 61 | GGUUGGAA CUGAUGAGGCCGAAAGGCCGAA AGUUUUCA | 715 |
| 63 | AGGGUUGG CUGAUGAGGCCGAAAGGCCGAA AGAGUUUU | 716 |
| 64 | CAGGGUUG CUGAUGAGGCCGAAAGGCCGAA AAGAGUUU | 717 |
| 75 | CACAGCAG CUGAUGAGGCCGAAAGGCCGAA AGCAGGGU | 718 |
| 93 | GCUGAGCA CUGAUGAGGCCGAAAGGCCGAA AGCGCCAC | 719 |
| 94 | GGCUGAGC CUGAUGAGGCCGAAAGGCCGAA AAGCGCCA | 720 |
| 98 | GAUAGGCU CUGAUGAGGCCGAAAGGCCGAA AGCAAAGC | 721 |
| 104 | CCAGUGGA CUGAUGAGGCCGAAAGGCCGAA AGGCUGAG | 722 |
| 106 | AUCCAGUG CUGAUGAGGCCGAAAGGCCGAA AUAGGCUG | 723 |
| 122 | CAUCCCUU CUGAUGAGGCCGAAAGGCCGAA AGGCUCCA | 724 |
| 153 | UGCUGAAG CUGAUGAGGCCGAAAGGCCGAA AGGUCCAU | 725 |
| 154 | UUGCUGAA CUGAUGAGGCCGAAAGGCCGAA AAGGUCCA | 726 |
| 156 | UAUUGCUG CUGAUGAGGCCGAAAGGCCGAA AGAAGGUC | 727 |
| 157 | AUAUUGCU CUGAUGAGGCCGAAAGGCCGAA AAGAAGGU | 728 |
| 164 | UUUCCAGA CUGAUGAGGCCGAAAGGCCGAA AUUGCUGA | 729 |
| 166 | GUUUUCCA CUGAUGAGGCCGAAAGGCCGAA AUAUUGCU | 730 |
| 176 | GGUUGUAG CUGAUGAGGCCGAAAGGCCGAA AGUUUUCC | 731 |
| 179 | CAAGGUUG CUGAUGAGGCCGAAAGGCCGAA AGUAGUUU | 732 |
| 186 | UCUUUUUC CUGAUGAGGCCGAAAGGCCGAA AGGUUGUA | 733 |
| 206 | UUUUAACA CUGAUGAGGCCGAAAGGCCGAA ACUGUUUC | 734 |
| 207 | CUUUUAAC CUGAUGAGGCCGAAAGGCCGAA AACUGUUU | 735 |
| 210 | UUUCUUUU CUGAUGAGGCCGAAAGGCCGAA ACAAACUG | 736 |
| 211 | CUUUCUUU CUGAUGAGGCCGAAAGGCCGAA AACAAACU | 737 |
| 226 | AACAGGAC CUGAUGAGGCCGAAAGGCCGAA ACUGUCCU | 738 |
| 229 | AACAACAG CUGAUGAGGCCGAAAGGCCGAA ACUACUGU | 739 |
| 234 | UUUUUAAC CUGAUGAGGCCGAAAGGCCGAA ACAGGACU | 740 |
| 237 | AUUUUUUU CUGAUGAGGCCGAAAGGCCGAA ACAACAGG | 741 |
| 238 | GAUUUUUU CUGAUGAGGCCGAAAGGCCGAA AACAACAG | 742 |
| 246 | AUUUCUUG CUGAUGAGGCCGAAAGGCCGAA AUUUUUUU | 743 |
| 263 | AGCCAAGG CUGAUGAGGCCGAAAGGCCGAA ACUUCUGC | 744 |
| 264 | AAGCCAAG CUGAUGAGGCCGAAAGGCCGAA AACUUCUG | 745 |
| 267 | UCCAAGCC CUGAUGAGGCCGAAAGGCCGAA AGGAACUU | 746 |
| 272 | UCACCUCC CUGAUGAGGCCGAAAGGCCGAA AGCCAAGG | 747 |
| 296 | GGGUGUUG CUGAUGAGGCCGAAAGGCCGAA AGUCCAGC | 748 |
| 315 | GGCUUGCG CUGAUGAGGCCGAAAGGCCGAA AUCACCUC | 749 |
| 336 | ACAUCAGG CUGAUGAGGCCGAAAGGCCGAA ACGCCACA | 750 |
| 337 | AACAUCAG CUGAUGAGGCCGAAAGGCCGAA AACGCCAC | 751 |
| 345 | AAGUGACC CUGAUGAGGCCGAAAGGCCGAA ACAUCAGG | 752 |
| 349 | ACUGAAGU CUGAUGAGGCCGAAAGGCCGAA ACCAACAU | 753 |
| 353 | AGGUACUG CUGAUGAGGCCGAAAGGCCGAA AGUGACCA | 754 |
| 354 | AAGGUACU CUGAUGAGGCCGAAAGGCCGAA AAGUGACC | 755 |
| 358 | AGGGAAGG CUGAUGAGGCCGAAAGGCCGAA ACUGAAGU | 756 |
| 362 | UGCCAGGG CUGAUGAGGCCGAAAGGCCGAA AGGUACUG | 757 |
| 363 | GUGCCAGG CUGAUGAGGCCGAAAGGCCGAA AAGGUACU | 758 |
| 391 | AGUUAGGU CUGAUGAGGCCGAAAGGCCGAA AGUUUUG | 759 |
| 396 | CUGUAAGU CUGAUGAGGCCGAAAGGCCGAA AGGUGAGU | 760 |
| 400 | AAUCCUGU CUGAUGAGGCCGAAAGGCCGAA AGUUAGGU | 761 |
| 401 | CAAUCCUG CUGAUGAGGCCGAAAGGCCGAA AAGUUAGG | 762 |
| 408 | UAAUUCAC CUGAUGAGGCCGAAAGGCCGAA AUCCUGUA | 763 |
| 415 | CGGUGUGU CUGAUGAGGCCGAAAGGCCGAA AUUCACAA | 764 |
| 416 | CCGGUGUG CUGAUGAGGCCGAAAGGCCGAA AAUUCACA | 765 |
| 427 | UCUUGGCA CUGAUGAGGCCGAAAGGCCGAA AUCCGGUG | 766 |
| 444 | GCAGCAUC CUGAUGAGGCCGAAAGGCCGAA ACAGCAUC | 767 |
| 456 | GCUUUCUC CUGAUGAGGCCCAAAGGCCGAA AUGGCAGC | 768 |
| 466 | GACCUUCA CUGAUGAGGCCGAAAGGCCGAA AGCUUUCU | 769 |

TABLE VII-continued

Rabbit Stromelysin HH Ribozyme Sequence

| nt. Position | Ribozyme Sequence | Sequence ID No. |
| --- | --- | --- |
| 474 | UCCUCCCA CUGAUGAGGCCGAAAGGCCGAA ACCUUCAG | 770 |
| 490 | CGUGAGUG CUGAUGAGGCCGAAAGGCCGAA AGUCACCU | 771 |
| 495 | GAGAACGU CUGAUGAGGCCGAAAGGCCGAA AGUGGAGU | 772 |
| 500 | UCCUGGAG CUGAUGAGGCCGAAAGGCCGAA ACGUGAGU | 773 |
| 501 | UUCCUGGA CUGAUGAGGCCGAAAGGCCGAA AACGUGAG | 774 |
| 503 | ACUUCCUG CUGAUGAGGCCGAAAGGCCGAA AGAACGUG | 775 |
| 512 | CUCCUUCA CUGAUGAGGCCGAAAGGCCGAA ACUUCCUG | 776 |
| 531 | GAGAUCAU CUGAUGAGGCCGAAAGGCCGAA AUGUCAGC | 777 |
| 537 | CCAAAAGA CUGAUGAGGCCGAAAGGCCGAA AUCAUUAU | 778 |
| 539 | CUCCAAAA CUGAUGAGGCCGAAAGOCCGAA AGAUCAUU | 779 |
| 541 | GACUCCAA CUGAUGAGGCCGAAACGCCGAA AGAGAUCA | 780 |
| 542 | GGACUCCA CUGAUGAGGCCGAAAGGCCGAA AAGAGAUC | 781 |
| 543 | CGGACUCC CUGAUGAGGCCGAAAGGCCGAA AAAGAGAU | 782 |
| 549 | UGUUCUCG CUGAUGAGGCCGAAAGGCCGAA ACUCCAAA | 783 |
| 565 | AGGAAUAA CUGAUGAGGCCGAAAGGCCGAA AUCUCCAU | 784 |
| 566 | AAGGAAUA CUGAUGAGGCCGAAAGGCCGAA AAUCUCCA | 785 |
| 567 | AAAGGAAU CUGAUGAGGCCGAAAGGCCGAA AAAUCUCC | 786 |
| 568 | AAAAGGAA CUGAUGAGGCCGAAAGGCCGAA AAAAUCUC | 787 |
| 570 | UCAAAAGG CUGAUGAGGCCGAAAGGCCGAA AUAAAAUC | 788 |
| 571 | AUCAAAAG CUGAUGAGGCCGAAAGGCCGAA AAUAAAAU | 789 |
| 574 | UCCAUCAA CUGAUGAGGCCGAAAGGCCGAA AGGAAUAA | 790 |
| 575 | GUCCAUCA CUGAUGAGGCCGAAAGGCCGAA AAGGAAUA | 791 |
| 576 | GGUCCAUC CUGAUGAGGCCGAAAGGCCGAA AAAGGAAU | 792 |
| 594 | UGAGCCAA CUGAUGAGGCCGAAAGGCCGAA ACAUUUCC | 793 |
| 595 | AUGAGCCA CUGAUGAGGCCGAAAGGCCGAA AACAUUUC | 794 |
| 596 | CAUGAGCC CUGAUGAGGCCGAAAGGCCGAA AAACAUUU | 795 |
| 601 | AUAAGCAU CUGAUGAGGCCGAAAGGCCGAA AGCCAAAA | 796 |
| 607 | AGGUGCAU CUGAUGAGGCCGAAAGGCCGAA AGCAUGAG | 797 |
| 608 | CAGGUGCA CUGAUGAGGCCGAAAGGCCGAA AAGCAUGA | 798 |
| 627 | UCUCCAUU CUGAUGAGGCCGAAAGGCCGAA AUUCCUGG | 799 |
| 628 | AUCUCCAU CUGAUGAGGCCGAAAGGCCGAA AAUUCCUG | 800 |
| 644 | CAUCAUCA CUGAUGAGGCCGAAAGGCCGAA AGUGGGCA | 801 |
| 645 | UCAUCAUC CUGAUGAGGCCGAAAGGCCGAA AAGUGGGC | 802 |
| 673 | UCCUGUUG CUGAUGAGGCCGAAAGGCCGAA AUCCUUUG | 803 |
| 688 | AAGGAAUA CUGAUGAGGCCGAAAGGCCGAA AUUGGUUC | 804 |
| 689 | CAAGGAAU CUGAUGAGGCCGAAAGGCCGAA AAUUGGUU | 805 |
| 690 | ACAAGGAA CUGAUGAGGCCGAAAGGCCGAA AAAUUGGU | 806 |
| 692 | CAACAAGG CUGAUGAGGCCGAAAGGCCGAA AUAAAUUG | 807 |
| 693 | GCAACAAG CUGAUGAGGCCGAAAGGCCGAA AAUAAAUU | 808 |
| 696 | GCAGCAAC CUGAUGAGGCCGAAAGGCCGAA AGGAAUAA | 809 |
| 699 | UGAGCAGC CUGAUGAGGCCGAAAGGCCGAA ACAAGGAA | 810 |
| 706 | AAGCUCAU CUGAUGAGGCCGAAAGGCCGAA AGCAGCAA | 811 |
| 714 | GAGUGGCC CUGAUGAGGCCGAAAGGCCGAA AGCUCAUG | 812 |
| 722 | GACCCAGG CUGAUGAGGCCGAAAGGCCGAA AGUGGCCA | 813 |
| 730 | GUGAAACA CUGAUGAGGCCGAAAGGCCGAA ACCCAGGG | 814 |
| 734 | CCGAGUGA CUGAUGAGGCCGAAAGGCCGAA ACAGACCC | 815 |
| 735 | GCCGAGUG CUGAUGAGGCCGAAAGGCCGAA AACAGACC | 816 |
| 736 | GGCCGAGU CUGAUGAGGCCGAAAGGCCGAA AAACAGAC | 817 |
| 740 | GGUUGGCC CUGAUGAGGCCGAAAGGCCGAA AGUGAAAC | 818 |
| 764 | AGACUGGG CUGAUGAGGCCGAAAGGCCGAA ACAUCAGC | 819 |
| 771 | GCGUUGUA CUGAUGAGGCCGAAAGGCCGAA ACUGGGUA | 820 |
| 773 | AGGCGUUG CUCAUGAGGCCGAAAGGCCGAA AGACUGGG | 821 |
| 782 | GGUCUGUG CUGAUGAGGCCGAAAGGCCGAA AGGCGUUG | 822 |
| 783 | AGGUCUGU CUGAUGAGGCCGAAAGGCCGAA AAGGCGUU | 823 |
| 800 | AAAGGCGG CUGAUGAGGCCGAAAGGCCGAA ACCGGGCC | 824 |
| 801 | GAAAGGCG CUGAUGAGGCCGAAAGGCCGAA AACCGGGC | 825 |
| 807 | UCUUGAGA CUGAUGAGGCCGAAAGGCCGAA AGGCGGAA | 826 |
| 808 | AUCUUGAG CUGAUGAGGCCGAAAGGCCGAA AAGGCGGA | 827 |
| 809 | CAUCUUGA CUGAUGAGGCCGAAAGGCCGAA AAAGGCGG | 828 |
| 811 | AUCAUCUU CUGAUGAGGCCGAAAGGCCGAA AGAAAGGC | 829 |
| 831 | AGGGAUUG CUGAUGAGGCCGAAAGGCCGAA AUGCCAUC | 830 |
| 836 | CAUAGAGG CUGAUGAGGCCGAAAGGCCGAA AUUGGAUG | 831 |
| 840 | GGUCCAUA CUGAUGAGGCCGAAAGGCCGAA AGGGAUUG | 832 |
| 842 | CCGGUCCA CUGAUGAGGCCGAAAGGCCGAA AGAGGGAU | 833 |
| 860 | UAUCAGGA CUGAUGAGGCCGAAAGGCCGAA AGGCAGGG | 834 |
| 862 | GUUAUCAG CUGAUGAGGCCGAAAGGCCGAA AGAGGCAG | 835 |
| 868 | UCCAGAGU CUGAUGAGGCCGAAAGGCCGAA AUCAGGAG | 836 |
| 872 | GCACUCCA CUGAUGAGGCCGAAAGGCCGAA AGUUAUCA | 837 |
| 883 | AGGUUCCA CUGAUGAGGCCGAAAGGCCGAA AGGCACUC | 838 |
| 894 | CCUGGAGG CUGAUGAGGCCGAAAGGCCGAA ACAGGUUC | 839 |
| 898 | AGAUCCUG CUGAUGAGGCCGAAAGGCCGAA AGGGACAG | 840 |
| 905 | GGGUCCCA CUGAUGAGGCCGAAAGGCCGAA AUCCUGGA | 841 |
| 918 | UCACACAU CUGAUGAGGCCGAAAGGCCGAA ACUGGGGU | 842 |
| 928 | CAGAUCUG CUGAUGAGGCCGAAAGGCCGAA AUCACACA | 843 |

TABLE VII-continued

Rabbit Stromelysin HH Ribozyme Sequence

| nt. Position | Ribozyme Sequence | Sequence ID No. |
|---|---|---|
| 934 | GAAGGACA CUGAUGAGGCCGAAAGGCCGAA AUCUGGAU | 844 |
| 938 | CAUCGAAG CUGAUGAGGCCGAAAGGCCGAA ACAGAUCU | 845 |
| 941 | UUGCAUCG CUGAUGAGGCCGAAAGGCCGAA AGGACAGA | 846 |
| 942 | AUUGCAUC CUGAUGAGGCCGAAAGGCCGAA AAGGACAG | 847 |
| 951 | AGAGUGCU CUGAUGAGGCCGAAAGGCCGAA AUUGCAUC | 848 |
| 958 | UCCCCUCA CUGAUGAGGCCGAAAGGCCGAA AGUGCUGA | 849 |
| 972 | AAGAACAG CUGAUGAGGCCGAAAGGCCGAA AUUUCUCC | 850 |
| 973 | AAAGAACA CUGAUGAGGCCGAAAGGCCGAA AAUUUCUC | 851 |
| 977 | CUUUAAAG CUGAUGAGGCCGAAAGGCCGAA ACAGAAUU | 852 |
| 978 | UCUUUAAA CUGAUGAGGCCGAAAGGCCGAA AACAGAAU | 853 |
| 980 | UGUCUUUA CUGAUGAGGCCGAAAGGCCGAA AGAACAGA | 854 |
| 981 | CUGUCUUU CUGAUGAGGCCGAAAGGCCGAA AAGAACAG | 855 |
| 982 | CCUGUCUU CUGAUGAGGCCGAAAGGCCGAA AAAGAACA | 856 |
| 992 | GCCAGAAA CUGAUGAGGCCGAAAGGCCGAA ACCUGUCU | 857 |
| 994 | GCGCCAGA CUGAUGAGGCCGAAAGGCCGAA AUACCUGU | 588 |
| 995 | UGCGCCAG CUGAUGAGGCCGAAAGGCCGAA AAUACCUG | 859 |
| 996 | UUGCGCCA CUGAUGAGGCCGAAAGGCCGAA AAAUACCU | 860 |
| 1007 | UCCUGAGG CUGAUGAGGCCGAAAGGCCGAA ACUUGCGC | 861 |
| 1011 | AGAAUCCU CUGAUGAGGCCGAAAGGCCGAA AGGGACUU | 862 |
| 1017 | GGUUCGAG CUGAUGAGGCCGAAAGGCCGAA AUCCUGAG | 863 |
| 1018 | AGGUUCGA CUGAUGAGGCCGAAAGGCCGAA AAUCCUGA | 864 |
| 1020 | UCAGGUUC CUGAUGAGGCCGAAAGGCCGAA AGAAUCCU | 865 |
| 1031 | UCAAAUGA CUGAUGAGGCCGAAAGGCCGAA ACUCAGGU | 866 |
| 1032 | AUCAAAUG CUGAUGAGGCCGAAAGGCCGAA AACUCAGG | 867 |
| 1033 | GAUCAAAU CUGAUGAGGCCGAAAGGCCGAA AAACUCAG | 868 |
| 1036 | AGAGAUCA CUGAUGAGGCCGAAAGGCCGAA AUGAAACU | 869 |
| 1037 | AAGAGAUC CUGAUGAGGCCGAAAGGCCGAA AAUGAAAC | 870 |
| 1041 | AAUGAAGA CUGAUGAGGCCGAAAGGCCGAA AUCAAAUG | 871 |
| 1043 | AGAAUGAA CUGAUGAGGCCGAAAGGCCGAA AGAUCAAA | 872 |
| 1045 | CCAGAAUG CUGAUGAGGCCGAAAGGCCGAA AGAGAUCA | 873 |
| 1046 | GCCAGAAU CUGAUGAGGCCGAAAGGCCGAA AAGAGAUC | 874 |
| 1049 | AUGGCCAG CUGAUGAGGCCGAAAGGCCGAA AUGAAGAG | 875 |
| 1050 | GAUGGCCA CUGAUGAGGCCGAAAGGCCGAA AAUGAAGA | 876 |
| 1058 | AAGGAAGA CUGAUGAGGCCGAAAGGCCGAA AUGGCCAG | 877 |
| 1060 | UGAAGGAA CUGAUGAGGCCGAAAGGCCGAA AGAUGGCC | 878 |
| 1062 | GCUGAAGG CUGAUGAGGCCGAAAGGCCGAA AGAGAUGG | 879 |
| 1063 | UGCUGAAG CUGAUGAGGCCGAAAGGCCGAA AAGAGAUG | 880 |
| 1066 | CACUGCUG CUGAUGAGGCCGAAAGGCCGAA AGGAAGAG | 881 |
| 1067 | CCACUGCU CUGAUGAGGCCGAAAGGCCGAA AAGGAAGA | 882 |
| 1085 | UAACUUCA CUGAUGAGGCCGAAAGGCCGAA AUGCAGCA | 883 |
| 1092 | CUGCUAAU CUGAUGAGGCCGAAAGGCCGAA ACUUCAUA | 884 |
| 1093 | CCUGCUAA CUGAUGAGGCCGAAAGGCCGAA AACUUCAU | 885 |
| 1095 | UCCCUGCU CUGAUGAGGCCGAAAGGCCGAA AUAACUUC | 886 |
| 1096 | AUCCCUGC CUGAUGAGGCCGAAAGGCCGAA AAUAACUU | 887 |
| 1105 | GAAAACAG CUGAUGAGGCCGAAAGGCCGAA AUCCCUGC | 888 |
| 1110 | AAAAUGAA CUGAUGAGGCCGAAAGGCCGAA ACAGUAUC | 889 |
| 1111 | AAAAAUGA CUGAUGAGGCCGAAAGGCCGAA AACAGUAU | 890 |
| 1112 | UAAAAAUG CUGAUGAGGCCGAAAGGCCGAA AAACAGUA | 891 |
| 1113 | UUAAAAAU CUGAUGAGGCCGAAAGGCCGAA AAAACAGU | 892 |
| 1116 | CCUUUAAA CUGAUGAGGCCGAAAGGCCGAA AUGAAAAC | 893 |
| 1117 | UCCUUUAA CUGAUGAGGCCGAAAGGCCGAA AAUGAAAA | 894 |
| 1118 | UUCCUUUA CUGAUGAGGCCGAAAGGCCGAA AAAUGAAA | 895 |
| 1119 | GUUCCUUU CUGAUGAGGCCGAAAGGCCGAA AAAAUGAA | 896 |
| 1120 | AGUUCCUU CUGAUGAGGCCGAAAGGCCGAA AAAAAUGA | 897 |
| 1129 | CCAGAACU CUGAUGAGGCCGAAAGGCCGAA AGUUCCUU | 898 |
| 1133 | UGGCCCAG CUGAUGAGGCCGAAAGGCCGAA ACUGAGUU | 899 |
| 1134 | AUGGCCCA CUGAUGAGGCCGAAAGGCCGAA AACUGAGU | 900 |
| 1143 | UUUCCUCU CUGAUGAGGCCGAAAGGCCGAA AUGGCCCA | 901 |
| 1144 | AUUUCCUC CUGAUGAGGCCGAAAGGCCGAA AAUGGCCC | 902 |
| 1158 | CCAGCUUG CUGAUGAGGCCGAAAGGCCGAA ACCUCAUU | 903 |
| 1168 | UCUUGGGU CUGAUGAGGCCGAAAGGCCGAA ACCAGCUU | 904 |
| 1169 | UUCUUGGG CUGAUGAGGCCGAAAGGCCGAA AACCAGCU | 905 |
| 1182 | AGGGUGUG CUGAUGAGGCCGAAAGGCCGAA AUGCUUCU | 906 |
| 1195 | UGAAGGGA CUGAUGAGGCCGAAAGGCCGAA ACCCAGGG | 907 |
| 1196 | UUGAAGGG CUGAUGAGGCCGAAAGGCCGAA AACCCAGG | 908 |
| 1197 | GUUGAAGG CUGAUGAGGCCGAAAGGCCGAA AAACCCAG | 909 |
| 1201 | UAUGGUUG CUGAUGAGGCCGAAAGGCCGAA AGGGAAAC | 910 |
| 1202 | UUAUGGUU CUGAUGAGGCCGAAAGGCCGAA AAGGGAAA | 911 |
| 1209 | AUUUUUCU CUGAUGAGGCCGAAAGGCCGAA AUGGUUGA | 912 |
| 1218 | GCAGCAUC CUGAUGAGGCCGAAAGGCCGAA AUUUUUCU | 913 |
| 1230 | UUAUCAGA CUGAUGAGGCCGAAAGGCCGAA AUGGCAGC | 914 |
| 1231 | CUUAUCAG CUGAUGAGGCCGAAAGGCCGAA AAUGGCAG | 915 |
| 1232 | CCUUAUCA CUGAUGAGGCCGAAAGGCCGAA AAAUGGCA | 916 |
| 1237 | CCUUUCCU CUGAUGAGGCCGAAAGGCCGAA AUCAGAAA | 917 |

TABLE VII-continued

Rabbit Stromelysin HH Ribozyme Sequence

| nt. Position | Ribozyme Sequence | Sequence ID No. |
|---|---|---|
| 1256 | CAAAGAAG CUGAUGAGGCCGAAAGGCCGAA AUGUUUC | 918 |
| 1259 | CCACAAAG CUGAUGAGGCCGAAAGGCCGAA AGUAUGUU | 919 |
| 1260 | UCCACAAA CUGAUGAGGCCGAAAGGCCGAA AAGUAUGU | 920 |
| 1262 | CUUCCACA CUGAUGAGGCCGAAAGGCCGAA AGAAGUAU | 921 |
| 1263 | UCUUCCAC CUGAUGAGGCCGAAAGGCCGAA AAGAAGUA | 922 |
| 1277 | ACCUCCAG CUGAUGAGGCCGAAAGGCCGAA AUUUGUCU | 923 |
| 1286 | UCUCAUCA CUGAUGAGGCCGAAAGGCCGAA ACCUCCAG | 924 |
| 1287 | UUCUCAUC CUGAUGAGGCCGAAAGGCCGAA AACCUCCA | 925 |
| 1304 | GCUCCAGG CUGAUGAGGCCGAAAGGCCGAA ACUGUCUC | 926 |
| 1319 | GUCUGGGA CUGAUGAGGCCGAAAGGCCGAA AGCCUGGC | 927 |
| 1320 | UGUCUGGG CUGAUGAGGCCGAAAGGCCGAA AAGCCUGG | 928 |
| 1321 | AUGUCUGG CUGAUGAGGCCGAAAGGCCGAA AAAGCCUG | 929 |
| 1330 | UUCUGCUA CUGAUGAGGCCGAAAGGCCGAA AUGUCUGG | 930 |
| 1332 | UCUUCUGC CUGAUGAGGCCGAAAGGCCGAA AUAUGUCU | 931 |
| 1343 | UUCCUGGA CUGAUGAGGCCGAAAGGCCGAA AGUCUUCU | 932 |
| 1344 | AUUCCUGG CUGAUGAGGCCGAAAGGCCGAA AAGUCUUC | 933 |
| 1345 | AAUUCCUG CUGAUGAGGCCGAAAGGCCGAA AAAGUCUU | 934 |
| 1353 | UUUGGAUU CUGAUGAGGCCGAAAGGCCGAA AUUCCUGG | 935 |
| 1354 | CUUUGGAU CUGAUGAGGCCGAAAGGCCGAA AAUUCCUG | 936 |
| 1357 | GAUCUUUG CUGAUGAGGCCGAAAGGCCGAA AUUAAUUC | 937 |
| 1365 | ACAGCAUC CUGAUGAGGCCGAAAGGCCGAA AUCUUUGG | 938 |
| 1374 | GCUUCAAA CUGAUGAGGCCGAAAGGCCGAA ACAGCAUC | 939 |
| 1375 | UGCUUCAA CUGAUGAGGCCGAAAGGCCGAA AACAGCAU | 940 |
| 1376 | AUGCUUCA CUGAUGAGGCCGAAAGGCCGAA AAACAGCA | 941 |
| 1377 | AAUGCUUC CUGAUGAGGCCGAAAGGCCGAA AAAACAGC | 942 |
| 1385 | AAAACCCA CUGAUGAGGCCGAAAGGCCGAA AUGCUUCA | 943 |
| 1386 | AAAAACCC CUGAUGAGGCCGAAAGGCCGAA AAUGCUUC | 944 |
| 1391 | AAUAGAAA CUGAUGAGGCCGAAAGGCCGAA ACCCAAAU | 945 |
| 1392 | AAAUAGAA CUGAUGAGGCCGAAAGGCCGAA AACCCAAA | 946 |
| 1393 | GAAAUAGA CUGAUGAGGCCGAAAGGCCGAA AAACCCAA | 947 |
| 1394 | AGAAAUAG CUGAUGAGGCCGAAAGGCCGAA AAAACCCA | 948 |
| 1395 | AAGAAAUA CUGAUGAGGCCGAAAGGCCGAA AAAAACCC | 949 |
| 1397 | UGAAGAAA CUGAUGAGGCCGAAAGGCCGAA AGAAAAAC | 950 |
| 1399 | ACUGAAGA CUGAUGAGGCCGAAAGGCCGAA AUAGAAAA | 951 |
| 1400 | CACUGAAG CUGAUGAGGCCGAAAGGCCGAA AAUAGAAA | 952 |
| 1401 | CCACUGAA CUGAUGAGGCCGAAAGGCCGAA AAAUAGAA | 953 |
| 1403 | AUCCACUG CUGAUGAGGCCGAAAGGCCGAA AGAAAUAG | 954 |
| 1404 | GAUCCACU CUGAUGAGGCCGAAAGGCCGAA AAGAAAUA | 955 |
| 1412 | ACUGUGAA CUGAUGAGGCCGAAAGGCCGAA AUCCACUG | 956 |
| 1414 | CGACUGUG CUGAUGAGGCCGAAAGGCCGAA AGAUCCAC | 957 |
| 1415 | CCGACUGU CUGAUGAGGCCGAAAGGCCGAA AAGAUCCA | 958 |
| 1421 | CAAACUCC CUGAUGAGGCCGAAAGGCCGAA ACUGUGAA | 959 |
| 1427 | UUGGGUCA CUGAUGAGGCCGAAAGGCCGAA ACUCCGAC | 960 |
| 1428 | UUUGGGUC CUGAUGAGGCCGAAAGGCCGAA AACUCCGA | 961 |
| 1458 | CUCUUCAA CUGAUGAGGCCGAAAGGCCGAA ACAUGUGU | 962 |
| 1459 | GCUCUUCA CUGAUGAGGCCGAAAGGCCGAA AACAUGUG | 963 |
| 1460 | UGCUCUUC CUGAUGAGGCCGAAAGGCCGAA AAACAUGU | 964 |
| 1478 | AACACUGA CUGAUGAGGCCGAAAGGCCGAA ACCAGCUG | 965 |
| 1479 | UAACACUG CUGAUGAGGCCGAAAGGCCGAA AACCAGCU | 966 |
| 1480 | CUAACACU CUGAUGAGGCCGAAAGGCCGAA AAACCAGC | 967 |
| 1486 | CCCCUCCU CUGAUGAGGCCGAAAGGCCGAA ACACUGAA | 968 |
| 1487 | ACCCCUCC CUGAUGAGGCCGAAAGGCCGAA AACACUGA | 969 |
| 1498 | GCCUUCUA CUGAUGAGGCCGAAAGGCCGAA ACACCCCU | 970 |
| 1500 | GUGCCUUC CUGAUGAGGCCGAAAGGCCGAA AUACACCC | 971 |
| 1519 | UCAUUUAA CUGAUGAGGCCGAAAGGCCGAA ACAUUCAU | 972 |
| 1520 | UUCAUUUA CUGAUGAGGCCGAAAGGCCGAA AACAUUCA | 973 |
| 1521 | GUUCAUUU CUGAUGAGGCCGAAAGGCCGAA AAACAUUC | 974 |
| 1522 | GGUUCAUU CUGAUGAGGCCGAAAGGCCGAA AAAACAUU | 975 |
| 1532 | UGAACAAU CUGAUGAGGCCGAAAGGCCGAA AGGUUCAU | 976 |
| 1535 | UGUUGAAC CUGAUGAGGCCGAAAGGCCGAA AUUAGGUU | 977 |
| 1538 | AAGUGUUG CUGAUGAGGCCGAAAGGCCGAA ACAAUUAG | 978 |
| 1539 | UAAGUGUU CUGAUGAGGCCGAAAGGCCGAA AACAAUUA | 979 |
| 1546 | AAAGUCCU CUGAUGAGGCCGAAAGGCCGAA AGUGUUGA | 980 |
| 1547 | CAAAGUCC CUGAUGAGGCCGAAAGGCCGAA AAGUGUUG | 981 |
| 1553 | AACUCACA CUGAUGAGGCCGAAAGGCCGAA AGUCCUAA | 982 |
| 1554 | CAACUCAC CUGAUGAGGCCGAAAGGCCGAA AAGUCCUA | 983 |
| 1561 | GCCACUUC CUGAUGAGGCCGAAAGGCCGAA ACUCACAA | 984 |
| 1571 | GAGAAAAU CUGAUGAGGCCGAAAGGCCGAA AGCCACUU | 985 |
| 1574 | CAGGAGAA CUGAUGAGGCCGAAAGGCCGAA AUGAGCCA | 986 |
| 1575 | GCAGGAGA CUGAUGAGGCCGAAAGGCCGAA AAUGAGCC | 987 |
| 1576 | UGCAGGAG CUGAUGAGGCCGAAAGGCCGAA AAAUGAGC | 988 |
| 1577 | AUGCAGGA CUGAUGAGGCCGAAAGGCCGAA AAAAUGAG | 989 |
| 1579 | AUAUGCAG CUGAUGAGGCCGAAAGGCCGAA AGAAAAUG | 990 |
| 1586 | UCACAGCA CUGAUGAGGCCGAAAGGCCGAA AUGCAGGA | 991 |

TABLE VII-continued

Rabbit Stromelysin HH Ribozyme Sequence

| nt. Position | Ribozyme Sequence | Sequence ID No. |
|---|---|---|
| 1602 | AUGCUCGA CUGAUGAGGCCGAAAGGCCGAA AUUCCCAU | 992 |
| 1604 | UCAUGCUC CUGAUGAGGCCGAAAGGCCGAA AGAUUCCC | 993 |
| 1620 | CAGUUAGA CUGAUGAGGCCGAAAGGCCGAA ACACAGUU | 994 |
| 1622 | UCCAGUUA CUGAUGAGGCCGAAAGGCCGAA AUACACAG | 995 |
| 1624 | AGUCCAGU CUGAUGAGGCCGAAAGGCCGAA AGAUACAC | 996 |
| 1633 | GAUGUGCA CUGAUGAGGCCGAAAGGCCGAA AGUCCAGU | 997 |
| 1634 | CGAUGUGC CUGAUGAGGCCGAAAGGCCGAA AAGUCCAG | 998 |
| 1641 | CCCGUAAC CUGAUGAGGCCGAAAGGCCGAA AUGUGCAA | 999 |
| 1644 | ACACCCGU CUGAUGAGGCCGAAAGGCCGAA ACGAUGUG | 1000 |
| 1645 | AACACCCG CUGAUGAGGCCGAAAGGCCGAA AACGAUGU | 1001 |
| 1653 | CCUGUUUG CUGAUGAGGCCGAAAGGCCGAA ACACCCGU | 1002 |
| 1654 | GCCUGUUU CUGAUGAGGCCGAAAGGCCGAA AACACCCG | 1003 |
| 1670 | UGCAAGCU CUGAUGAGGCCGAAAGGCCGAA AGCAGCAG | 1004 |
| 1671 | GUGCAAGC CUGAUGAGGCCGAAAGGCCGAA AAGCAGCA | 1005 |
| 1675 | UCAAGUGC CUGAUGAGGCCGAAAGGCCGAA AGCUAAGC | 1006 |
| 1681 | AUGUGAUC CUGAUGAGGCCGAAAGGCCGAA AGUGCAAG | 1007 |
| 1685 | UUCCAUGU CUGAUGAGGCCGAAAGGCCGAA AUCAAGUG | 1008 |
| 1701 | UCUCGUGG CUGAUGAGGCCGAAAGGCCGAA AGCUCCCU | 1009 |
| 1702 | GUCUCGUG CUGAUGAGGCCGAAAGGCCGAA AAGCUCCC | 1010 |
| 1720 | CACAUGAG CUGAUGAGGCCGAAAGGCCGAA ACUUCCCC | 1011 |
| 1723 | UCACACAU CUGAUGAGGCCGAAAGGCCGAA AGUACUUC | 1012 |
| 1744 | AUAGACAC CUGAUGAGGCCGAAAGGCCGAA AUCACUCG | 1013 |
| 1749 | UCCACAUA CUGAUGAGGCCGAAAGGCCGAA ACACAAUC | 1014 |
| 1751 | AAUCCACA CUGAUGAGGCCGAAAGGCCGAA AGACACAA | 1015 |
| 1759 | GGGCAAAU CUGAUGAGGCCGAAAGGCCGAA AUCCACAU | 1016 |
| 1760 | UGGGCAAA CUGAUGAGGCCGAAAGGCCGAA AAUCCACA | 1017 |
| 1762 | AAUGGGCA CUGAUGAGGCCGAAAGGCCGAA AUAAUCCA | 1018 |
| 1763 | UAAUGGGC CUGAUGAGGCCGAAAGGCCGAA AAUAAUCC | 1019 |
| 1770 | UAUUAAAU CUGAUGAGGCCGAAAGGCCGAA AUGGGCAA | 1020 |
| 1771 | UUAUUAAA CUGAUGAGGCCGAAAGGCCGAA AAUGGGCA | 1021 |
| 1773 | CUUUAUUA CUGAUGAGGCCGAAAGGCCGAA AUAAUGGG | 1022 |
| 1774 | UCUUUAUU CUGAUGAGGCCCAAAGGCCGAA AAUAAUGG | 1023 |
| 1775 | CUCUUUAU CUGAUGAGGCCGAAAGGCCGAA AAAUAAUG | 1024 |
| 1778 | AUCCUCUU CUGAUGAGGCCGAAAGGCCGAA AUUAAAUA | 1025 |
| 1787 | AAUUGACA CUGAUGAGGCCGAAAGGCCGAA AUCCUCUU | 1026 |

TABLE VIII

Human Stromelysin Hairpin Ribozyme and Target Sequences

| nt. | Ribozyme | SEQ ID NO. | Substrate | SEQ ID NO. |
|---|---|---|---|---|
| 66 | CGCACAGCAGAAAGUAGGAACCAGAGAAACACGUUGUGGUACAUUACCUGGUA | 1027 | UCCUACUGUUGCUGUGCG | 1054 |
| 82 | GCUGAGCAAGAAGCCACGACCAGAGAAACACGUUGUGGUACAUUACCUGGUA | 1028 | CGUGGCAGUUGCUGCUCAGC | 1055 |
| 91 | AAUGGAUAAGAAGAGCAAACCAGAGAAACACGUUGUGGUACAUUACCUGGUA | 1029 | UUGCUCAGCCUAUCCAUU | 1056 |
| 192 | UCCUAAGAAGUUUCAACCAGAGAAACACGUUGUGGUACAUUACCUGGUA | 1030 | UGAAACAGUUUGUUAGGA | 1057 |
| 220 | UUUUUAACAGAAGGACCAACCAGAGAAACACGUUGUGGUACAUUACCUGGUA | 1031 | UGGUCCUGUGUGUUAAAA | 1058 |
| 328 | UGACCACAGAAGGAACUACCAGAGAAACACGUUGUGGUACAUUACCUGGUA | 1032 | AGUACCUGAUGUUGGUCA | 1059 |
| 412 | UUUGGCAAAGAAGGUGUAACCAGAGAAACACGUUGUGGUACAUUACCUGGUA | 1033 | UACACCAGAUUUGCCAAA | 1060 |
| 430 | GCAGAAUCAGAAGCUCUACCAGAGAAACACGUUGUGGUACAUUACCUGGUA | 1034 | AGAUGCUGUUGAUUCUGC | 1061 |
| 439 | UUCUCAACAGAAGAAUCAACCAGAGAAACACGUUGUGGUACAUUACCUGGUA | 1035 | UGAUUCUGUUGUUGAGAA | 1062 |
| 442 | GCUUUCUCAGAAGCAGAAAACCAGAGAAACACGUUGUGGUACAUUACCUGGUA | 1036 | UUCUGCUGUUGAGAAAGC | 1063 |
| 691 | AUUUCAUGAGAAGCAACGACCAGAGAAACACGUUGUGGUACAUUACCUGGUA | 1037 | CGUUGCUGCAUGAAAU | 1064 |
| 775 | CGAGUCAGAAGAAGUGAGAACCAGAGAAACACGUUGUGGUACAUUACCUGGUA | 1038 | ACUCACAGACCUGACUCG | 1065 |
| 780 | GGAACCGAAGAAGCUGACCAGAGAAACACGUUGUGGUACAUUACCUGGUA | 1039 | CAGACCUGACUCGGUUCC | 1066 |
| 786 | ACAGGCGGAAGAAGAGUCAACCAGAGAAACACGUUGUGGUACAUUACCUGGUA | 1040 | UGACUCGGUUCCGCCUGU | 1067 |
| 791 | UUGAGACAAGAAGAACCGACCAGAGAAACACGUUGUGGUACAUUACCUGGUA | 1041 | CGGUUCCGCCUGUCUCAA | 1068 |
| 795 | CAUCUUGAAGAAGGGCGGAACCAGAGAAACACGUUGUGGUACAUUACCUGGUA | 1042 | UCCGCCUGUCUCAAGAUG | 1069 |
| 822 | CAUAGAGGAAGAAAUGCACCAGAGAAACACGUUGUGGUACAUUACCUGGUA | 1043 | GCAUUCAGUCCCUCUAUG | 1070 |
| 844 | ACAGGCGGAAGAAGAGUCAACCAGAGAAACACGUUGUGGUACAUUACCUGGUA | 1044 | UCCCCCUGACUCCCCUGA | 1071 |
| 880 | UCAGGGGAGAAGAAGGUUCCACCAGAGAAACACGUUGUGGUACAUUACCUGGUA | 1045 | GGAACCUGUCCCUCCAGA | 1072 |
| 919 | AAGGACAAAGAAGGAUCAACCAGAGAAACACGUUGUGGUACAUUACCUGGUA | 1046 | UGAUCCUGCUUUGUCCUU | 1073 |
| 963 | CUUUAAAGAGAAGAUUUACCAGAGAAACACGUUGUGGUACAUUACCUGGUA | 1047 | AAAUCCUGAUCUUUAAAG | 1074 |
| 1360 | UCUUCAAAAGAAGCAUCAACCAGAGAAACACGUUGUGGUACAUUACCUGGUA | 1048 | UGAUGCUGUUUUGAAGA | 1075 |
| 1407 | CAAACUCCAGAAGUGAAGUUACUACCAGAGAAACACGUUGUGGUACAUUACCUGGUA | 1049 | CUUCACAGUUGGAGUUUG | 1076 |
| 1460 | AUUAAGCCAGAAGUUACUACCAGAGAAACACGUUGUGGUACAUUACCUGGUA | 1050 | AGUAACAGCUGCCUUAAU | 1077 |
| 1570 | ACAGCACAAGAAGAAAGCCAGAGAAACACGUUGUGGUACAUUACCUGGUA | 1051 | UUCUCCUGCCUGUGCUGU | 1078 |
| 1667 | AGCUAAGCAGAAGCCCAUACCAGAGAAACACGUUGUGGUACAUUACCUGGUA | 1052 | AUGGGCUGCUGCUUAGCU | 1079 |
| 1670 | GCAAGCUAAGCAGCCACCAGAAACACCAGAGAAACACGUUGUGGUACAUUACCUGGUA | 1053 | GGCUGCUGCUUAGCUUGC | 1080 |

TABLE IX

Rabbit Hairpin Ribozyme and Target Sequences

| nt. | Ribozyme Sequence | Sequence ID No. | Substrate | Sequence ID No. |
|---|---|---|---|---|
| 77 | CCACGCACAGAAGUAGCAACCAGAGAAACACACGUUGUGGUACAUUACCUGGUA | 1081 | UGCUACUGCUGUGCGUGG | 1110 |
| 99 | AGUGGAUAAGAAGAGCAAACCAGAGAAACACACGUUGUGGUACAUUACCUGGUA | 1082 | UUGCUCAGCCUAUCCACU | 1111 |
| 203 | UUUUAACAAGAAGUUUCAACCAGAGAAACACACGUUGUGGUACAUUACCUGGUA | 1083 | UGAAACAGUUGUUAAAA | 1112 |
| 231 | UUUUUAACCAGAAGGACUAACCAGAGAAACACACGUUGUGGUACAUUACCUGGUA | 1084 | UAGUCCUGUGUUUAAAA | 1113 |
| 339 | UGACCAGAAGGAACGACCAGAGAAACACACGUUGUGGUACAUUACCUGGUA | 1085 | CGUUCCUGAUGUUGGUCA | 1114 |
| 423 | CUUGGCAGAAGGUGUGACCAGAGAAACACACGUUGUGGUACAUUACCUGGUA | 1086 | CACACCGAUCUGCCAAG | 1115 |
| 441 | GCAGCAUCAGAAGCAUCUACCAGAGAAACACACGUUGUGGUACAUUACCUGGUA | 1087 | AGAUGCUGUUGAUGCUGC | 1116 |
| 702 | AGCUCAUGAGAAGAACAACCAGAGAAACACACGUUGUGGUACAUUACCUGGUA | 1088 | UGUUGCUGCAUGAGCU | 1117 |
| 731 | CCGAGUGAAGAAGACCCA ACCAGAGAAACACACGUUGUGGUACAUUACCUGGUA | 1089 | UGGGUCUGUUUCACUCGG | 1118 |
| 758 | CUGGGUACAGAAGCGCUACCAGAGAAACACACGUUGUGGUACAUUACCUGGUA | 1090 | AAGCGCUGAUGUACCCAG | 1119 |
| 768 | GCGUUGUAAGAAGGGUACACCAGAGAAACACACGUUGUGGUACAUUACCUGGUA | 1091 | GUACCCAGUCUACAACGC | 1120 |
| 786 | CGGGCCAGAGAAGUGAAGACCAGAGAAACACACGUUGUGGUACAUUACCUGGUA | 1092 | CUUCACAGACCUGGCCCG | 1121 |
| 797 | AAAGGCGGAGAAGGGCCAACCAGAGAAACACACGUUGUGGUACAUUACCUGGUA | 1093 | UGGCCCGGUCCGUCCGCUUU | 1122 |
| 802 | UUGAGAAAAGAAGAACCGACCAGAGAAACACACGUUGUGGUACAUUACCUGGUA | 1094 | CGGUUCCGCCUUUCUCAA | 1123 |
| 849 | GAGGCAGGAGAAGGUCCAACCAGAGAAACACACGUUGUGGUACAUUACCUGGUA | 1095 | UGGACCGGCCCCUGCCUC | 1124 |
| 855 | UCAGGAGGAGAAGGGGCCACCAGAGAAACACACGUUGUGGUACAUUACCUGGUA | 1096 | GGCCCUGCCUCUCCUGA | 1125 |
| 891 | CCUGGAGGAGAAGGUUCCACCAGAGAAACACACGUUGUGGUACAUUACCUGGUA | 1097 | GGAACCUGUCCCUCCAGG | 1126 |
| 930 | AAGGACAGAGAAGGAUCAACCAGAGAAACACACGUUGUGGUACAUUACCUGGUA | 1098 | UGAUCCAGAUCUGUCCUU | 1127 |
| 935 | CAUCGAAGAGAAGAUCUGACCAGAGAAACACACGUUGUGGUACAUUACCUGGUA | 1099 | CAGAUCUGUCCUUCGAUG | 1128 |
| 974 | CUUUAAAAGAGAAGAAUUACCAGAGAAACACACGUUGUGGUACAUUACCUGGUA | 1100 | AAAUUCUGUUCUUUAAAG | 1129 |
| 1107 | AAAUGAAAGAAGUAUCCACCAGAGAAACACACGUUGUGGUACAUUACCUGGUA | 1101 | GGAUACUGUUUUCAUUUU | 1130 |
| 1130 | UGGCCCAGAGAAGAGUCUACCAGAGAAACACACGUUGUGGUACAUUACCUGGUA | 1102 | GAACUCAGUUCUGGGCCA | 1131 |
| 1301 | GCUCCAGAGAAGUCUCUACCAGAGAAACACACGUUGUGGUACAUUACCUGGUA | 1103 | AGAACAGUCCCUGGAGC | 1132 |
| 1371 | GCUUCAAAAGAAGCAUCGACCAGAGAAACACACGUUGUGGUACAUUACCUGGUA | 1104 | CGAUGCUGUUUUGAAGC | 1133 |
| 1418 | CAAACUCCAGAAGUGAAGACCAGAGAAACACACGUUGUGGUACAUUACCUGGUA | 1105 | CUUCACAGUCGGAGUUUG | 1134 |
| 1471 | CUGAAACCAGAAGUUGCUACCAGAGAAACACACGUUGUGGUACAUUACCUGGUA | 1106 | AGCAACAGCUGGUUUCAG | 1135 |
| 1663 | AGCUAAGCAGAAGCCUGUACCAGAGAAACACACGUUGUGGUACAUUACCUGGUA | 1107 | ACAGGCUGCUGCUUAGCU | 1136 |
| 1666 | GCAAGCUAAGAAGCAGCACCAGAGAAACACACGUUGUGGUACAUUACCUGGUA | 1108 | GGCUGCUGCUUAGCUUGC | 1137 |
| 1733 | AAUCACUCAGAAGUCACAACCAGAGAAACACACGUUGUGGUACAUUACCUGGUA | 1109 | UGUGACAGACGUGAUU | 1138 |

We claim:

1. An enzymatic RNA molecule which specifically cleaves stromelysin RNA.

2. The enzymatic RNA molecule of claim 1, which specifically cleaves target RNA having a sequence selected from a group consisting of SEQ. ID. NOS. 1, 3–27, 29–359, wherein said enzymatic RNA molecule is in a hammerhead motif.

3. An enzymatic RNA molecule of claim 1, which specifically cleaves target mRNA having a sequence selected from SEQ. ID. NOS. 360–367 and 1054–1080 wherein said enzymatic RNA molecule is in a hairpin motif.

4. The enzymatic RNA molecule of claim 1, which specifically cleaves target mRNA having a sequence selected from SEQ. ID. NOS. 1–33, wherein said enzymatic RNA molecule is in a hepatitis delta virus motif.

5. The enzymatic RNA molecule of claim 2, which specifically cleaves target mRNA having a sequence selected from SEQ. ID. NOS. 34, 35, 37, 47, 54, 57, 61, 63, 64, 66, 76, 77, 79, 87, 88, 96, 97, 98, 99, 100, 107, 110, 121, 126, 128, 129, 133, 140, 146, 148, 151, 162, 170, 179, 188, 192, 194, 196, 199, 202, 203, 207, 208, 218, 220, 223, 224, 225, 227, 230, 232, 236, 240, 245, 246, 256, 259, 260, 269, 280, 281, 290, 302, 328, 335 and 353.

6. The enzymatic RNA molecule of claim 2, which specifically cleaves target mRNA having a sequence selected from SEQ. ID. NOS. 34, 35, 57, 125, 126, 127, 128, 129, 140, 162, 170, 179, 188, 223, 224, 236, 245, 246, 256, 259, 260, and 281.

7. The enzymatic RNA molecule of claim 2, which specifically cleaves target mRNA having a sequence selected from SEQ. ID. NOS. 35, 98, 202, 263, 272, and 292.

8. The enzymatic RNA molecule of claim 1, wherein said enzymatic RNA molecule is in a hammerhead motif.

9. The enzymatic RNA molecule of claim 1, wherein said enzymatic RNA molecule is in a hairpin, hepatitis Delta virus, group I intron, VS RNA, or RNAseP RNA motif.

10. The enzymatic RNA molecule of any of claims 4, 8, 9, 1, 2, or 3, wherein said enzymatic RNA molecule comprises between 5 and 23 bases complementary to said mRNA.

11. The enzymatic RNA molecule of any of claims 4, 8, 9, 1, 2 or 3, wherein said enzymatic RNA molecule comprises between 10 and 18 bases complementary to said mRNA.

12. The enzymatic RNA molecule of any of claims 4, 8, 9, 1, 2, or 3, wherein said enzymatic RNA molecule comprises between 30 and 45 bases complementary to said mRNA.

13. A mammalian cell including an enzymatic RNA molecule of any of claims 4, 8, 9, 1, 2 or 3 in vitro.

14. The cell of claim 13, wherein said cell is a human cell.

15. An expression vector including nucleic acid encoding the enzymatic nucleic acid molecule of any of claims 4, 8, 9, 1, 2 or 3, in a manner which allow expression of that enzymatic RNA molecule within a mammalian cell in vitro.

16. The enzymatic RNA molecule of any of claims 8 or 2, wherein said enzymatic RNA molecule comprises at least five ribose residues, and wherein said enzymatic RNA comprises a 2'-C-allyl modification at position No. 4 of said enzymatic RNA molecule, and wherein said enzymatic RNA molecule comprises at least ten 2'-O-methyl modifications.

17. The enzymatic RNA molecule of any of claims 8 or 2, wherein said enzymatic RNA molecule comprises at least five ribose residues, and wherein said enzymatic RNA comprises a 2'-amino modification at position No. 4 and/or at position No. 7 of said enzymatic RNA molecule, wherein said enzymatic RNA molecule comprises at least ten 2'-O-methyl modifications.

18. The enzymatic RNA molecule of any of claims 8 or 2, wherein said enzymatic RNA molecule comprises at least five ribose residues, and wherein said enzymatic RNA molecule comprises non-nucleotide substitution at position No. 4 and/or at position No. 7 of said enzymatic RNA molecule, wherein said enzymatic RNA molecule comprises at least ten 2'-O-methyl modifications.

19. The enzymatic RNA molecule of any of claims 8 or 2, wherein said enzymatic RNA molecule comprises at least five ribose residues, and wherein said enzymatic RNA molecule acid comprises 6-methyl uridine substitutions at position No. 4 and/or at position No. 7 of the said enzymatic RNA molecule, wherein said enzymatic RNA molecule comprises at least ten 2'-O-methyl modifications.

20. The enzymatic RNA molecule of any one of claims 4, 8, 9, 16, 17–19, 21–25, wherein said enzymatic RNA molecule comprises phosphorothioate linkages at at least three 5' terminal nucleotides.

21. The enzymatic RNA molecule of any of claims 8 or 2, wherein said hammerhead motif comprises a stem II region of length greater than or equal to two base-pairs.

22. The enzymatic RNA molecule of any of claims 9 or 3, wherein said hairpin motif comprises a stem IV region of length greater than or equal to two base-pairs.

23. The enzymatic RNA molecule of any one of claims 4, 8, 9, 1, 2 or 3, wherein said enzymatic RNA molecule comprises a 3'—3' linked inverted ribose moiety at its 3' end.

24. The enzymatic RNA molecule of any one of claims 4, 8, 9, 1, 2 or 3, wherein said enzymatic RNA molecule comprises a 3'—3' linked inverted thymidine moiety at its 3' end.

25. The enzymatic RNA molecule of any one of claims 4, 8, 9, 1, 2 or 3, wherein said enzymatic RNA molecule molecule comprises a 240 —3' linked inverted ribose or thymidine moiety at its 3' end.

26. The enzymatic RNA molecule of any one of claims 4, 8, 9, 1, 2 or 3, wherein said enzymatic RNA molecule comprises a 5'-end modification.

27. The enzymatic RNA molecule of any one of claims 4, 8, 9, 1, 2, or 3, wherein said enzymatic RNA molecule comprises at least on 2'-O-methyl sugar modification.

28. The enzymatic RNA molecule of any one of claims 4, 8, 9, 1, 2 or 3, wherein said enzymatic RNA molecule comprised at least one phosphorothioate group.

29. The enzymatic RNA molecule of claim 16, wherein said enzymatic RNA molecule comprises a stem II region of length greater than or equal to two base-pairs.

30. The enzymatic RNA molecule of claim 16, wherein said enzymatic RNA molecule comprises a 3'—3' linked inverted ribose moiety at its 3' end.

31. The enzymatic RNA molecule of claim 16, wherein said enzymatic RNA molecule further comprises a 3'—3' linked inverted thymidine moiety at its 3' end.

32. The enzymatic RNA molecule of any one of claim 16, wherein said enzymatic RNA molecule comprises a 240 —3' linked inverted ribose or thymidine moiety at its 3' end.

33. The enzymatic RNA molecule of claim 16, wherein said enzymatic RNA molecule comprises a 5'-end modification.

34. The enzymatic RNA molecule of claim 16, wherein said enzymatic RNA molecule comprises phosphorothioate linkages at at least three 5' terminal nucleotides.

35. The enzymatic RNA molecule of claims 17, wherein said enzymatic RNA molecule comprises a stem II region of greater than or equal to two base-pairs.

36. The enzymatic RNA molecule of claim 17, wherein said enzymatic RNA molecule comprises a 3'—3' linked inverted ribose moiety at its 3' end.

37. The enzymatic RNA molecule of claim 17, wherein said enzymatic RNA molecule comprises a 3'—3' linked inverted thymidine moiety at its 3' end.

38. The enzymatic RNA molecule of claim 17, wherein said enzymatic RNA molecule comprises a 240 —3' linked inverted ribose or thymidine moiety at its 3' end.

39. The enzymatic RNA molecule of claim 17, wherein said enzymatic RNA molecule comprises a 5'-end modification.

40. The enzymatic RNA molecule of claim 17, wherein said enzymatic RNA molecule comprises phosphorothioate linkages at at least three 5' terminal nucleotides.

41. The enzymatic RNA molecule of claim 18, wherein said enzymatic RNA molecule comprises a 5'-end modification.

42. The enzymatic RNA molecule of claim 18, wherein said enzymatic RNA molecule comprises a stem II region of length greater than or equal to two base-pairs.

43. The enzymatic RNA molecule of claim 18, wherein said enzymatic RNA molecule comprises a 3'—3' linked inverted ribose moiety at its 3' end.

44. The enzymatic RNA molecule of claim 18, wherein said enzymatic RNA molecule comprises a 3'—3' linked inverted thymidine moiety at its 3' end.

45. The enzymatic RNA molecule of any one of claim 18, wherein said enzymatic RNA molecule comprises a 240 —3' linked inverted ribose or thymidine moiety at its 3' end.

46. The enzymatic RNA molecule of claim 18, wherein said enzymatic RNA molecule comprise phosphorothioate linkages at at least three 5' terminal nucleotides.

47. The enzymatic RNA molecule of claim 18, wherein said enzymatic RNA molecule comprises a 5'-end modification.

48. The enzymatic RNA molecule of claim 19, wherein said enzymatic RNA molecule comprises a stem II region of length greater than or equal to two base-pairs.

49. The enzymatic RNA molecule of claim 19, wherein said enzymatic RNA molecule comprises a 3'—3' linked inverted ribose moiety at its 3' end.

50. The enzymatic RNA molecule of claim 19, wherein said enzymatic RNA molecule comprises a 3'—3' linked inverted thymidine moiety at its 3' end.

51. The enzymatic RNA molecule of any one of claim 19, wherein said enzymatic RNA molecule comprises a 240 —3' linked inverted ribose or thymidine moiety at its 3' end.

52. The enzymatic RNA molecule of claim 19, wherein said enzymatic RNA molecule comprises phosphorothioate linkages at at least three 5' terminal nucleotides.

53. The enzymatic RNA molecule of claim 2, wherein the enzymatic RNA molecule specifically cleaves the RNA sequence defined as SEQ ID NO. 34.

54. The enzymatic RNA molecule of claim 2, wherein said enzymatic RNA molecule specifically cleaves the RNA sequence defined as SEQ ID NO. 35.

55. The enzymatic RNA molecule of claim 2, wherein said enzymatic RNA molecule specifically cleaves the RNA sequence defined as SEQ ID NO. 37.

56. The enzymatic RNA molecule of claim 2, wherein said enzymatic RNA molecule specifically cleaves the RNA sequence defined as SEQ ID NO. 47.

57. The enzymatic RNA molecule of claim 2, wherein said enzymatic RNA molecule specifically cleaves the RNA sequence defined as SEQ ID NO. 54.

58. The enzymatic RNA molecule of claim 2, wherein said enzymatic RNA molecule specifically cleaves the RNA sequence defined as SEQ ID NO. 57.

59. The enzymatic RNA molecule of claim 2, wherein said enzymatic RNA molecule specifically cleaves the RNA sequence defined as SEQ ID NO. 61.

60. The enzymatic RNA molecule of claim 2, wherein said enzymatic RNA molecule specifically cleaves the RNA sequence defined as SEQ ID NO. 63.

61. The enzymatic RNA molecule of claim 2, wherein said enzymatic RNA molecule specifically cleaves the RNA sequence defined as SEQ ID NO. 64.

62. The enzymatic RNA molecule of claim 2, wherein said enzymatic RNA molecule specifically cleaves the RNA sequence defined as SEQ ID NO. 66.

63. The enzymatic RNA molecule of claim 2, wherein said enzymatic RNA molecule specifically cleaves the RNA sequence defined as SEQ ID NO. 68.

64. The enzymatic RNA molecule of claim 2, wherein said enzymatic RNA molecule specifically cleaves the RNA sequence defined as SEQ ID NO. 76.

65. The enzymatic RNA molecule of claim 2, wherein said enzymatic RNA molecule specifically cleaves the RNA sequence defined as SEQ ID NO. 77.

66. The enzymatic RNA molecule of claim 2, wherein said enzymatic RNA molecule specifically cleaves the RNA sequence defined as SEQ ID NO. 79.

67. The enzymatic RNA molecule of claim 2, wherein said enzymatic RNA molecule specifically cleaves the RNA sequence defined as SEQ ID NO. 87.

68. The enzymatic RNA molecule of claim 2, wherein said enzymatic RNA molecule specifically cleaves the RNA sequence defined as SEQ ID NO. 88.

69. The enzymatic RNA molecule of claim 2, wherein said enzymatic RNA molecule specifically cleaves the RNA sequence defined as SEQ ID NO. 96.

70. The enzymatic RNA molecule of claim 2, wherein said enzymatic RNA molecule specifically cleaves the RNA sequence defined as SEQ-ID NO. 97.

71. The enzymatic RNA molecule of claim 2, wherein said enzymatic RNA molecule specifically cleaves the RNA sequence defined as SEQ ID NO. 98.

72. The enzymatic RNA molecule of claim 2, wherein said enzymatic RNA molecule specifically cleaves the RNA sequence defined as SEQ ID NO 99.

73. The enzymatic RNA molecule of claim 2, wherein said enzymatic RNA molecule specifically cleaves the RNA sequence defined as SEQ ID NO 100.

74. The enzymatic RNA molecule of claim 2, wherein said enzymatic RNA molecule specifically cleaves the RNA sequence defined as SEQ ID NO 107.

75. The enzymatic RNA molecule of claim 2, wherein said enzymatic RNA molecule specifically cleaves the RNA sequence defined as SEQ ID NO 110.

76. The enzymatic RNA molecule of claim 2, wherein said enzymatic RNA molecule specifically cleaves the RNA sequence defined as SEQ ID NO 121.

77. The enzymatic RNA molecule of claim 2, wherein said enzymatic RNA molecule specifically cleaves the RNA sequence defined as SEQ ID NO 125.

78. The enzymatic RNA molecule of claim 2, wherein said enzymatic RNA molecule specifically cleaves the RNA sequence defined as SEQ ID NO. 126.

79. The enzymatic RNA molecule of claim 2, wherein said enzymatic RNA molecule specifically cleaves the RNA sequence defined as SEQ ID NO. 127.

80. The enzymatic RNA molecule of claim 2, wherein said enzymatic RNA molecule specifically cleaves the RNA sequence defined as SEQ ID NO. 128.

81. The enzymatic RNA molecule of claim 2, wherein said enzymatic RNA molecule specifically cleaves the RNA sequence defined as SEQ ID NO. 129.

82. The enzymatic RNA molecule of claim 2, wherein said enzymatic RNA molecule specifically cleaves the RNA sequence defined as SEQ ID NO. 133.

83. The enzymatic RNA molecule of claim 2, wherein said enzymatic RNA molecule specifically cleaves the RNA sequence defined as SEQ ID NO. 140.

84. The enzymatic RNA molecule of claim 2, wherein said enzymatic RNA molecule specifically cleaves the RNA sequence defined as SEQ ID NO. 146.

85. The enzymatic RNA molecule of claim 2, wherein said enzymatic RNA molecule specifically cleaves the RNA sequence defined as SEQ ID NO. 148.

86. The enzymatic RNA molecule of claim 2, wherein said enzymatic RNA molecule specifically cleaves the RNA sequence defined as SEQ ID NO. 151.

87. The enzymatic RNA molecule of claim 2, wherein said enzymatic RNA molecule specifically cleaves the RNA sequence defined as SEQ ID NO. 162.

88. The enzymatic RNA molecule of claim 2, wherein said enzymatic RNA molecule specifically cleaves the RNA sequence defined as SEQ ID NO. 169.

89. The enzymatic RNA molecule of claim 2, wherein said enzymatic RNA molecule specifically cleaves the RNA sequence defined as SEQ ID NO. 170.

90. The enzymatic RNA molecule of claim 2, wherein said enzymatic RNA molecule specifically cleaves the RNA sequence defined as SEQ ID NO. 179.

91. The enzymatic RNA molecule of claim 2, wherein said enzymatic RNA molecule specifically cleaves the RNA sequence defined as SEQ ID NO. 188.

92. The enzymatic RNA molecule of claim 2, wherein said enzymatic RNA molecule specifically cleaves the RNA sequence defined as SEQ ID NO. 192.

93. The enzymatic RNA molecule of claim 2, wherein said enzymatic RNA molecule specifically cleaves the RNA sequence defined as SEQ ID NO. 193.

94. The enzymatic RNA molecule of claim 2, wherein said enzymatic RNA molecule specifically cleaves the RNA sequence defined as SEQ ID NO. 194.

95. The enzymatic RNA molecule of claim 2, wherein sad enzymatic RNA molecule specifically cleaves the RNA sequence defined as SEQ ID NO. 196.

96. The enzymatic RNA molecule of claim 2, wherein said enzymatic RNA molecule specifically cleaves the RNA sequence defined as SEQ ID NO. 199.

97. The enzymatic RNA molecule of claim 2, wherein said enzymatic RNA molecule specifically cleaves the RNA sequence defined as SEQ ID NO. 202.

98. The enzymatic RNA molecule of claim 2, wherein said enzymatic RNA molecule specifically cleaves the RNA sequence defined as SEQ ID NO. 203.

99. The enzymatic RNA molecule of claim 2, wherein said enzymatic RNA molecule specifically cleaves the RNA sequences defined as SEQ ID NO. 207.

100. The enzymatic RNA molecule of claim 2, wherein said enzymatic RNA molecule specifically cleaves the RNA sequence defined as SEQ ID NO. 208.

101. The enzymatic RNA molecule of claim 2, wherein said enzymatic RNA molecule specifically cleaves the RNA sequence defined as SEQ ID NO. 218.

102. The enzymatic RNA molecule of claim 2, wherein said enzymatic RNA molecule specifically cleaves the RNA sequence defined as SEQ ID NO. 220.

103. The enzymatic RNA molecule of claim 2, wherein said enzymatic RNA molecule specifically cleaves the RNA sequence defined as SEQ ID NO. 223.

104. The enzymatic RNA molecule of claim 2, wherein said enzymatic RNA molecule specifically cleaves the RNA sequence defined as SEQ ID NO. 224.

105. The enzymatic RNA molecule of claim 2, wherein said enzymatic RNA molecule specifically cleaves the RNA sequences defined as SEQ ID NO. 225.

106. The enzymatic RNA molecule of claim 2, wherein said enzymatic RNA molecule specifically cleaves the RNA sequence defined as SEQ ID NO. 227.

107. The enzymatic RNA molecule of claim 2, wherein said enzymatic RNA molecule specifically cleaves the RNA sequence defined as SEQ ID NO. 230.

108. The enzymatic RNA molecule of claim 2, wherein said enzymatic RNA molecule specifically cleaves the RNA sequence defined as SEQ ID NO. 232.

109. The enzymatic RNA molecule of claim 2, wherein said enzymatic RNA molecule specifically cleaves the RNA sequence defined as SEQ ID NO. 236.

110. The enzymatic RNA molecule of claim 2, wherein said enzymatic RNA molecule specifically cleaves the RNA sequence defined as SEQ ID NO. 240.

111. The enzymatic RNA molecule of claim 2, wherein said enzymatic RNA molecule specifically cleaves the RNA sequence defined as SEQ ID NO. 245.

112. The enzymatic RNA molecule of claim 2, wherein said enzymatic RNA molecule specifically cleaves the RNA sequence defined as SEQ ID NO. 246.

113. The enzymatic RNA molecule of claim 2, wherein said enzymatic RNA molecule specifically cleaves the RNA sequence defined as SEQ ID NO. 256.

114. The enzymatic RNA molecule of claim 2, wherein said enzymatic RNA molecule specifically cleaves the RNA sequence defined as SEQ ID NO. 259.

115. The enzymatic RNA molecule of claim 2, wherein said enzymatic RNA molecule specifically cleaves the RNA sequence defined as SEQ ID NO. 260.

116. The enzymatic RNA molecule of claim 2, wherein said enzymatic RNA molecule specifically cleaves the RNA sequence defined as SEQ ID NO. 263.

117. The enzymatic RNA molecule of claim 2, wherein said enzymatic RNA molecule specifically cleaves the RNA sequence defined as SEQ ID NO. 269.

118. The enzymatic RNA molecule of claim 2, wherein said enzymatic RNA molecule specifically cleaves the RNA sequence defined as SEQ ID NO. 279.

119. The enzymatic RNA molecule of claim 2, wherein said enzymatic RNA molecule specifically cleaves the RNA sequence defined as SEQ ID NO. 280.

120. The enzymatic RNA molecule of claim 2, wherein said enzymatic RNA molecule specifically cleaves the RNA sequence defined as SEQ ID NO. 281.

121. The enzymatic RNA molecule of claim 2, wherein said enzymatic RNA molecule specifically cleaves the RNA sequence defined as SEQ ID NO. 290.

122. The enzymatic RNA molecule of claim 2, wherein said enzymatic RNA molecule specifically cleaves the RNA sequence defined as SEQ ID NO. 292.

123. The enzymatic RNA molecule of claim 2, wherein said enzymatic RNA molecule specifically cleaves the RNA sequence defined as SEQ ID NO. 302.

124. The enzymatic RNA molecule of claim 2, wherein said enzymatic RNA molecule specifically cleaves the RNA sequence defined as SEQ ID NO. 312.

125. The enzymatic RNA molecule of claim 2, wherein said enzymatic RNA molecule specifically cleaves the RNA sequence defined as SEQ ID NO. 328.

126. The enzymatic RNA molecule of claim 2, wherein said enzymatic RNA molecule specifically cleaves the RNA sequence defined as SEQ ID NO. 335.

127. The enzymatic RNA molecule of claim 2, wherein said enzymatic RNA molecule specifically cleaves the RNA sequence defined as SEQ ID NO. 336.

128. The enzymatic RNA molecule of claim 2, wherein said enzymatic RNA molecule specifically cleaves the RNA sequence defined as SEQ ID NO. 350.

129. The enzymatic RNA molecule of claim 2, wherein said enzymatic RNA molecule specifically cleaves the RNA sequence defined as SEQ ID NO. 353.

130. The enzymatic RNA molecule of claim 3, wherein said enzymatic RNA molecule specifically cleaves the RNA sequence defined as SEQ ID NO. 360.

131. The enzymatic RNA molecule of claim 3, wherein said enzymatic RNA molecule specifically cleaves the RNA sequence defined as SEQ ID NO. 361.

132. The enzymatic RNA molecule of claim 3, wherein said enzymatic RNA molecule specifically cleaves the RNA sequence defined as SEQ ID NO. 362.

133. The enzymatic RNA molecule of claim 3, wherein said enzymatic RNA molecule specifically cleaves the RNA sequence defined as SEQ ID NO. 363.

134. The enzymatic RNA molecule of claim 3, wherein said enzymatic RNA molecule specifically cleaves the RNA sequence defined as SEQ ID NO. 364.

135. The enzymatic RNA molecule of claim 3, wherein said enzymatic RNA molecule specifically cleaves the RNA sequence defined as SEQ ID NO. 365.

136. The enzymatic RNA molecule of claim 3, wherein said enzymatic RNA molecule specifically cleaves the RNA sequence defined as SEQ ID NO. 366.

137. The enzymatic RNA molecule of claim 3, wherein said enzymatic RNA molecule specifically cleaves the RNA sequence defined as SEQ ID NO. 367.

138. The enzymatic RNA molecule of claim 3, wherein said enzymatic RNA molecule specifically cleaves the RNA sequence defined as SEQ ID NO. 1054.

139. The enzymatic RNA molecule of claim 3, wherein said enzymatic RNA molecule specifically cleaves the RNA sequence defined as SEQ ID NO. 1055.

140. The enzymatic RNA molecule of claim 3, wherein said enzymatic RNA molecule specifically cleaves the RNA sequence defined as SEQ ID NO. 1056.

141. The enzymatic RNA molecule of claim 3, wherein said enzymatic RNA molecule specifically cleaves the RNA sequence defined as SEQ ID NO. 1057.

142. The enzymatic RNA molecule of claim 3, wherein said enzymatic RNA molecule specifically cleaves the RNA sequence defined as SEQ ID NO. 1058.

143. The enzymatic RNA molecule of claim 3, wherein said enzymatic RNA molecule specifically cleaves the RNA sequence defined as SEQ ID NO. 1059.

144. The enzymatic RNA molecule of claim 3, wherein said enzymatic RNA molecule specifically cleaves the RNA sequence defined as SEQ ID NO. 1060.

145. The enzymatic RNA molecule of claim 3, wherein said enzymatic RNA molecule specifically cleaves the RNA sequence defined as SEQ ID NO. 1061.

146. The enzymatic RNA molecule of claim 3, wherein said enzymatic RNA molecule specifically cleaves the RNA sequence defined as SEQ ID NO. 1062.

147. The enzymatic RNA molecule of claim 3, wherein said enzymatic RNA molecule specifically cleaves the RNA sequence defined as SEQ ID NO. 1063.

148. The enzymatic RNA molecule of claim 3, wherein said enzymatic RNA molecule specifically cleaves the RNA sequence defined as SEQ ID NO. 1064.

149. The enzymatic RNA molecule of claim 3, wherein said enzymatic RNA molecule specifically cleaves the RNA sequence defined as SEQ ID NO. 1065.

150. The enzymatic RNA molecule of claim 3, wherein said enzymatic RNA molecule specifically cleaves the RNA sequence defined as SEQ ID NO. 1066.

151. The enzymatic RNA molecule of claim 3, wherein said enzymatic RNA molecule specifically cleaves the RNA sequence defined as SEQ ID NO. 1067.

152. The enzymatic RNA molecule of claim 3, wherein said enzymatic RNA molecule specifically cleaves the RNA sequence defined as SEQ ID NO. 1068.

153. The enzymatic RNA molecule of claim 3, wherein said enzymatic RNA molecule specifically cleaves the RNA sequence defined as SEQ ID NO. 1069.

154. The enzymatic RNA molecule of claim 3, wheein said enzymatic RNA molecule specifically cleaves the RNA sequence defined as SEQ ID NOS. 1070.

155. The enzymatic RNA molecule of claim 3, wherein said enzymatic RNA molecule specifically cleaves the RNA sequence defined as SEQ ID NO. 1071.

156. The enzymatic RNA molecule of claim 3, wherein said enzymatic RNA molecule specifically cleaves the RNA sequence defined as SEQ ID NO. 1072.

157. The enzymatic RNA molecule of claim 3, wherein said enzymatic RNA molecule specifically cleaves the RNA sequence defined as SEQ ID NO. 1073.

158. The enzymatic RNA molecule of claim 3, wherein said enzymatic RNA molecule specifically cleaves the RNA sequence defined as SEQ ID NO. 1074.

159. The enzymatic RNA molecule of claim 3, wherein said enzymatic RNA molecule specifically cleaves the RNA sequence defined as SEQ ID NO. 1075.

160. The enzymatic RNA molecule of claim 3, wherein said enzymatic RNA molecule specifically cleaves the RNA sequence defined as SEQ ID NO. 1076.

161. The enzymatic RNA molecule of claim 3, wherein said enzymatic RNA molecule specifically cleaves the RNA sequence defined as SEQ ID NO. 1077.

162. The enzymatic RNA molecule of claim 3, wherein said enzymatic RNA molecule specifically cleaves the RNA sequence defined as SEQ ID NO. 1078.

163. The enzymatic RNA molecule of claim 3, wherein said enzymatic RNA molecule specifically cleaves the RNA sequence defined as SEQ ID NO. 1079.

164. The enzymatic RNA molecule of claim 3, wherein said enzymatic RNA molecule specifically cleaves the RNA sequence defined as SEQ ID NO. 1080.

165. The enzymatic RNA molecule of claim 8 wherein said enzymatic RNA molecule consists of any sequence selected from the group consisting of SEQ. ID NOS. 375–396.

166. The enzymatic RNA molecule of claim 9 wherein said enzymatic RNA molecule is in a hairpin motif and wherein said enzymatic RNA molecule consists of any sequence selected from the group consisting of SEQ. ID NOS. 1027–1053.

\* \* \* \* \*

UNITED STATES PATENT AND TRADEMARK OFFICE
CERTIFICATE OF CORRECTION

PATENT NO. : 5,612,215
DATED : March 18, 1997
INVENTOR(S) : Kenneth G. Draper, et al.

It is certified that error appears in the above-identified patent and that said Letters Patent is hereby corrected as shown below:

Column 8, Line 46: Delete " "" " and insert -- ----- --

Column 9, Line 1: After "expression" insert --by 463HH--

Column 9, Line 39: Delete " 340-3' " and insert -- 3'-3' --

Column 16, Line 41: Delete "syncvial" and insert --synovial--

Column 24, Line 26: Delete " 340-3' " and insert -- 3'-3'--

Column 35, Table III, Under the Heading "nt. Position", 9th entry down: Delete "1095" and insert --1096--

Claim 15, Column 438, Line 48: Delete "nucleic acid" and insert --RNA--

Claim 17, Column 438, Line 59: After "RNA" insert -- molecule--

Claim 19, Column 439, Line 7: Delete "acid"

Claim 20, Column 439, Line 12: After 17-19, insert -- 1-3, --

Claim 25, Column 439, Line 30: Delete " 240-3' " and insert -- 2'-3' --

Claim 32, Column 439, Line 51: Delete " 240-3' " and insert -- 2'-3' --

Claim 35, Column 439, Line 59: Delete "claims 17" and insert --claim 17--

Claim 38, Column 440, Line 2: Delete " 240-3' " and insert -- 2'-3' --

UNITED STATES PATENT AND TRADEMARK OFFICE
CERTIFICATE OF CORRECTION

PATENT NO. : 5,612,215
DATED : March 18, 1997
INVENTOR(S) : Kenneth G. Draper, et al.

It is certified that error appears in the above-identified patent and that said Letters Patent is hereby corrected as shown below:

Claim 45, Column 440, Line 24: Delete " 240-3' " and insert -- 2'-3' --

Claim 51, Column 440, Line 43: Delete " 240-3' " and insert -- 2'-3' --

Signed and Sealed this

Third Day of November, 1998

Attest:

Attesting Officer

BRUCE LEHMAN

Commissioner of Patents and Trademarks